(12) United States Patent
Cuero Rengifo et al.

(10) Patent No.: US 11,692,192 B2
(45) Date of Patent: Jul. 4, 2023

(54) ANTI-MICROBIAL AND UV-PROTECTIVE EXTRACTS AND METHODS OF MAKING AND USING THEREOF

(71) Applicant: BIOCAPITAL HOLDINGS, LLC, Houston, TX (US)

(72) Inventors: Raul Cuero Rengifo, Cypress, TX (US); Juliana Londoño Murillo, Manizales (CO)

(73) Assignee: BIOCAPITAL HOLDINGS, LLC, Houston, TX (US)

( * ) Notice: Subject to any disclaimer, the term of this patent is extended or adjusted under 35 U.S.C. 154(b) by 189 days.

(21) Appl. No.: 16/971,347

(22) PCT Filed: Feb. 22, 2019

(86) PCT No.: PCT/US2019/019075
§ 371 (c)(1),
(2) Date: Aug. 20, 2020

(87) PCT Pub. No.: WO2019/165163
PCT Pub. Date: Aug. 29, 2019

(65) Prior Publication Data
US 2021/0017525 A1 Jan. 21, 2021

Related U.S. Application Data

(60) Provisional application No. 62/754,291, filed on Nov. 1, 2018, provisional application No. 62/634,251, filed on Feb. 23, 2018.

(51) Int. Cl.
| | | |
|---|---|---|
| C12N 15/00 | (2006.01) | |
| C12N 15/52 | (2006.01) | |
| A61K 8/9728 | (2017.01) | |
| A01N 63/50 | (2020.01) | |
| C05F 11/00 | (2006.01) | |
| C12N 15/62 | (2006.01) | |
| C09D 5/16 | (2006.01) | |
| C09D 5/32 | (2006.01) | |
| C12N 9/02 | (2006.01) | |
| C12N 9/04 | (2006.01) | |
| C12N 9/20 | (2006.01) | |
| C12N 15/81 | (2006.01) | |
| C08G 18/32 | (2006.01) | |
| C08G 18/76 | (2006.01) | |
| A61K 8/99 | (2017.01) | |
| C08G 101/00 | (2006.01) | |
| C12N 15/70 | (2006.01) | |
| C07K 14/405 | (2006.01) | |
| C12N 9/64 | (2006.01) | |

(52) U.S. Cl.
CPC .............. *C12N 15/52* (2013.01); *A01N 63/50* (2020.01); *A61K 8/9728* (2017.08); *A61K 8/99* (2013.01); *C05F 11/00* (2013.01); *C08G 18/3218* (2013.01); *C08G 18/7671* (2013.01); *C09D 5/1637* (2013.01); *C09D 5/32* (2013.01); *C12N 9/0006* (2013.01); *C12N 9/0091* (2013.01); *C12N 9/20* (2013.01); *C12N 15/62* (2013.01); *C12N 15/81* (2013.01); *C12Y 101/01001* (2013.01); *C07K 14/405* (2013.01); *C07K 2319/00* (2013.01); *C08G 2101/00* (2013.01); *C12N 9/641* (2013.01); *C12N 15/70* (2013.01)

(58) Field of Classification Search
CPC .. C12Q 1/6806; C07K 2319/00; C12N 15/52; C12N 15/70; C12N 9/20; C12N 15/62; C12N 15/8213; C12Y 101/01001
USPC ........ 435/69.7, 257.2, 320.2, 44.4; 536/23.2, 536/23.1
See application file for complete search history.

(56) References Cited

U.S. PATENT DOCUMENTS

| | | |
|---|---|---|
| 5,744,340 A | 4/1998 | Fossetta et al. |
| 2009/0325240 A1 | 12/2009 | Daniell |
| 2010/0047224 A1 | 2/2010 | Geursten et al. |
| 2010/0173367 A1 | 7/2010 | Marner, II et al. |
| 2014/0244228 A1 | 8/2014 | Lee et al. |
| 2015/0218596 A1 | 8/2015 | Feldman et al. |

FOREIGN PATENT DOCUMENTS

| | | |
|---|---|---|
| WO | 2015017852 A1 | 2/2015 |
| WO | 2018213526 A2 | 11/2018 |
| WO | 2019055457 A1 | 3/2019 |

OTHER PUBLICATIONS

Devos et al., Proteins: Structure, Function and Genetics, 2000, vol. 41: 98-107.*

(Continued)

*Primary Examiner* — Robert B Mondesi
*Assistant Examiner* — Mohammad Y Meah
(74) *Attorney, Agent, or Firm* — Thomas | Horstemeyer, LLP

(57) ABSTRACT

Described herein are anti-microbial and UV-protective biological devices and extracts produced therefrom. The biological devices include microbial cells transformed with a DNA construct containing genes for producing proteins such as, for example, zinc-related protein/oxidase, silicatein, silaffin, and alcohol dehydrogenase. In some instances, the biological devices also include a gene for lipase. Methods for producing and using the devices are also described herein. Finally, compositions and methods for using the devices and extracts to kill microbial species or prevent microbial growth and to reduce or prevent UV-induced damage or exposure to materials, items, plants, and human and animal subjects are described herein. Also disclosed are biological devices producing polyactive carbohydrates and carbo sugars, as well as compositions and articles incorporating both extracts from these devices and the anti-microbial and UV-protective extracts.

26 Claims, 21 Drawing Sheets

Specification includes a Sequence Listing.

(56) References Cited

OTHER PUBLICATIONS

Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
International Search Report and Written Opinion for PCT/US2019/019075 dated May 8, 2019.

* cited by examiner

1.

T7 Promoter ⟹ Cellulose Synthase ⟹ Galactomannan's ⟹ Yellow Reporter + STOP ⟹ T7 Terminator Sub-cloned Device in pYES2 vector

2.

Gal1 Promoter from pYES2 ⟹ Cellulose Synthase ⟹ Galactomannan's ⟹ Yellow Reporter +
STOP ⟹ CYC1 Terminator from pYES2

Sub-cloned Device in pYES2 vector

3.

GAL1 Promoter from pYES2 ⟹ Cellulose Synthase ⟹ CYC1 terminator + Gal1 Prom ⟹
Galactomannan's ⟹ CYC1 terminator + Gal1 Prom ⟹ Yellow Reporter Sub-cloned Device in pYES2 vector

FIGURE 5B

```
                        SEQUENCE LISTING

<160> NUMBER OF SEQ ID NOS: 22

<210> SEQ ID NO 1
<211> LENGTH: 1493
<212> TYPE: DNA
<213> ORGANISM: Streptomyces zinciresistens

<400> SEQUENCE: 1
cctaggatga cagatcgttg tccaggtagg gatgctccac acttagcagt cattggagca      60
ggtccagctg gcttagcagc agcattagct gctgctgcta gaggtgttcg tgtaaccttg     120
ttggatgctg aaccagaagc aggaggccaa ttctatagac agccagcagc agctttacgt     180
gctagaaggc cacaagcatt acaccatcag tggcgtacct ttgccagatt gagacacgga     240
ttagccaggc acattgcagc aggtagagtt agacatgcta gagaacacca tgtttggttt     300
gctgagagag ctcctgatgg tggattcacc gttcatgctt tgactggtcc aggtagagga     360
gatccagcag aagtgagagc agatgcagtc ttgttggcaa ctggtggtca cgagactgtg     420
ttgccattcc caggttggac cttgccaggt gttgtcacag ctggaggtgc ccaagccatg     480
```

```
ttgaaggcag gtttagttac atctggcaac accgcagtcg tagctggtac tggtccattg        540
ttgttgccag tagctacagg tttagctgct gctggtgttg acgtaagagc attagtcgaa        600
agtgctgatc ctggtgcctt accaagacag gcacgtgctt tggcagctca acctggcaag        660
ttggctgaag gtgctttgta tgctggtcaa ttgttgaggc acagagtgcg tgtcttgact        720
agacacactg tcgttgaagc acatggtaca gagaggttgg aagcagttac tgttgcagcc        780
ttggatgcag gtgacgtac  tagacctggc actgctagaa gaatagcatg tgcaacttta        840
gctgtgggtc atggtatgtt gccacataca gacttggcag acgccttagg ctgccgttta        900
gcaggtccag cagttcatgc agatgatgaa caaagaactg atgttcctgg tgtgtgggca        960
gcaggagagt gtactggcgt aggtggtgca gctttgtctt tggctgaggg tcatatcgct       1020
ggcagaagtg cagcagccag attgttagga gcacctccag gtcccgacgc atggccagag       1080
gcagctagaa caagagcaag gttgagagct ttctccgctg tattggatgc tgtttacact       1140
cctcctcctg gttggggtga gagagtcacc gacgcaaccg ttgtatgcag gtgtgaagaa       1200
gttacagcag gtgcaatccg tgcttctgtg agggaattgg gagctggtga cgtacgtact       1260
gtaaagttgt tgactagagc tggcatggga tggtgtcagg gaagaatgtg tgctcctgct       1320
gtcgctggat tggcaggttg tgctttcact cctagtcgta gaccattcgc taggccagtg       1380
cctttgggag tgttggccag agctggtgaa gatgcaggtg gcgatggagg cagagctgag       1440
gatcaaggtg aaggagatgg acgtgctgct ggagcaggag gttgattaat taa            1493

<210> SEQ ID NO 2
<211> LENGTH: 1012
<212> TYPE: DNA
<213> ORGANISM: Suberites domuncula

<400> SEQUENCE: 2
ggcgcgccac catgcttgtc acagtggtag tactgggtct actggggttt gcttctgcag         60
cccagcccaa gtttgaattt gtagaagaat ggcagctgtg gaagtccact cactctaaga        120
tgtacgagtc acagttaatg gaactcgaaa gacatctgac gtggctctcc aataagaaat        180
atatcgagca acacaatgtc aactcacaca ttttcggttt tactctggca atgaaccagt        240
ttggagatct gagtgaattg gagtatgcta actatcttgg ccagtatcgc attgaggata        300
aaaaatctgg caactactca agacttttc agcgtgatcc tctacaggac tacccctgaag        360 ctgtagactg gagaaccaaa ggagctgtca cggctgtcaa ggaccaggga gactgtggtg        420
ctagctatgc tttcagtgct atgggtgctt ggagggtgc taatgcttta gccaagggaa        480
atgcagtatc tctcagtgaa cagaacatca ttgattgctc gattccttac ggtaaccacg        540
gttgtcatgg aggcaatatg tatgatgctt ttttgtatgt catcgctaac gagggggtcg        600
atcaggacag tgcatatcca tttgtaggaa agcaatccag ctgcaactat aatagtaaat        660
acaaaggtac atcaatgtcg gggatggtgt caatcaaaag tggtagtgag tctgacttac        720
aagcagctgt ttcaaacgtt ggccctgtat ctgttgctat tgatggtgct aacagtgcct        780
tcaggtttta ctacagtggt gtctatgact catcacgatg ctctagtagt agtcttaacc        840
acgcaatggt agtcactgga tacgatcat acaatggaa aaaatactgg ctggccaaga        900
atagctgggg aactaactgg ggtaacagtg ctatgtgat gatggctcgc aacaagtaca        960
accagtgtgg aattgctacc gatgcatctt atcccaccct ataagtttaa ac             1012

<210> SEQ ID NO 3
```

```
<211> LENGTH: 816
<212> TYPE: DNA
<213> ORGANISM: Cylindrotheca fulsiformis

<400> SEQUENCE: 3
ctcgaggcca ccatgaagct gaccgccatc tttccgcttc ttttcactgc tgtcgggtac      60
tgtgctgccc aaagcattgc tgacttggca gcagccaatc tcagcactga ggattccaag     120
tcagctcagc tcatctcagc agactcctcg gatgacgcat ctgattcctc tgtcgagtct     180
gtcgacgccg cctcctctga cgtctctggt tcctctgtcg aatctgtcga cgtctctggt     240
tcctctctgg aatccgttga cgtctctggt tcctctctgg agtccgtcga cgactccagt     300
gaggactccg aagaggaaga acttcgtatc ttgtcttcca agaaatccgg atcctactac     360
tcctacggca ccaagaagtc gggatcctac tcgggatact ccacaaagaa atccgcatcg     420
cgtcgcatct tgtcctccaa gaaatcggga tcctactcgg atattccac aaagaaatcc      480
ggatcgcgtc gcatcttgtc ctccaagaaa tcggatcct actcgggatc caagggttcc     540
aagcgtcgca tcttgtcctc caaaaaatcc ggatcctact cgggatccaa gggctccaag     600
cgtcgcaact tgtcctccaa gaaatccgga tcctactcgg gatccaaggg ttccaagcgt     660
cgcatcttgt cctccaaaaa atccggatcc tactcgggat ccagggctc caagcgtcgc      720
aacttgtcct ccaagaaatc cggatcctac tcgggatcca agggttccaa gcgtcgcatc     780
ttgtccgggg gtctcagagg ctccatgtaa ggtacc                               816

<210> SEQ ID NO 4
<211> LENGTH: 1059
<212> TYPE: DNA
<213> ORGANISM: Saccharomyces cerevisiae

<400> SEQUENCE: 4
ggtaccatgt ctattccaga aactcaaaaa gccattatct tctacgaatc caacggcaag      60
ttggagcata aggatatccc agttccaaag ccaaagccca acgaattgtt aatcaacgtc     120
aagtactctg gtgtctgcca caccgatttg cacgcttggc atggtgactg ccattgcca      180
actaagttac cattagttgg tggtcacgaa ggtgccggtg tcgttgtcgg catgggtgaa     240
aacgttaagg gctggaagat cggtgactac gccggtatca atggttgaa cggttcttgt      300
atggcctgtg aatactgtga attgggtaac gaatccaact gtcctcacgc tgacttgtca     360
ggttacaccc acgacggttc tttccaagaa tacgctaccg ctgacgctgt tcaagccgct     420
cacattcctc aaggtactga cttggctgaa gtcgcgccaa tcttgtgtgc tggtatcacc     480
gtatacaagg ctttgaagtc tgccaacttg agagcaggcc actgggcggc catttctggt     540
gctgctggtg gtctaggttc tttggctgtt caatatgcta aggcgatggg ttacagagtc     600
ttaggtattg atggtggtcc aggaaaggaa gaattgttta cctcgctcgg tggtgaagta     660
ttcatcgact tcaccaaaga gaaggacatt gttagcgcag tcgttaaggc taccaacggc     720
ggtgcccacg gtatcatcaa tgtttccgtt tccgaagccg ctatcgaagc ttctaccaga     780
tactgtaggg cgaacggtac tgttgtcttg gttggtttgc cagccggtgc aaagtgctcc     840
tctgatgtct tcaaccacgt tgtcaagtct atctccattg tcggctctta cgtggggaac     900
agagctgata ccagagaagc cttagatttc tttgccagag gtctagtcaa gtctccaata     960
aaggtagttg gcttatccag tttaccagaa atttacgaaa agatggagaa gggccaaatt    1020
gctggtagat acgttgttga cacttctaaa taactcgag                          1059
```

<210> SEQ ID NO 5
<211> LENGTH: 1215
<212> TYPE: DNA
<213> ORGANISM: Micrococcus sp. HL-2003

<400> SEQUENCE: 5

| | | | | | |
|---|---|---|---|---|---|
| atggtgttta | tcgtcaatct | tttctcctgc | accttatctg | aaaccacggt | tagctcaata | 60 |
| aaatctgaag | ctacggttag | ctcaacattt | actgccgtca | cggccctgca | attggtggct | 120 |
| gagggtaagt | tgcagtcggc | gaagggtttc | ggtggtggta | cgattcacta | cccaaccctc | 180 |
| gcggccgaag | caccctggtg | gacgccgggc | caaggccatg | gttacgaggc | gatcacctac | 240 |
| ggctggctgg | tcggcgaact | gctgcgccgc | gccgatgggc | gtgggcctgg | tctgttaggc | 300 |
| gctattgccg | tggttcctgg | ttacgtttct | tacgagaact | ctatcaagtg | gtggggaccg | 360 |
| cgtctggctt | cttggggctt | tgtcgttgca | cggccgttgg | gcctggactt | tcatgtgggc | 420 |
| ctggcggatg | aagagtttta | tcgtgttgcc | catatagcgc | gcagcaaagc | caatgcagca | 480 |
| ctagataaca | ttgctgatga | caccgtcggc | agtatagatc | taagcggtt | gggcgctatt | 540 |
| ggctggtcag | gtggcggcgg | cgcgcttaaa | ctggcaacgg | agcgcagcac | agtacgagcc | 600 |
| attttgacca | gtactaataa | acctgaatgg | cgacgcttcg | ataaattctt | atgtgcctgc | 660 |
| gaggatgacc | ggattgctga | gactaagaaa | tatgccaacg | cgttttataa | aaatgccgac | 720 |
| atgctcgaag | agttgacccg | tgaacacagt | atcgggccgg | ataaacatt | attgacacaa | 780 |
| actcggtttg | gcttggggtg | cttggatcaa | ccgcaagcag | gggttaaaat | tcattttgaa | 840 |
| gagtaccttg | atcaaaccca | tggatttatc | aatttgacgc | cagtttcaca | taaggcgaga | 900 |
| gcaaatctga | ttcagatgcc | taatgccaca | ttcggccttg | gcccgcgtgc | ttttgggcat | 960 |
| cctggtgcag | gtggatcggt | aggttttgcc | gaccccgaac | acgatgtagc | gtttggtttc | 1020 |
| gtgactaata | cattggggcc | ttatgtagtt | gagtttaaaa | gccgtcatcc | ctcatttat | 1080 |
| gcatataaag | atggattggt | gctgactgga | aatgacgtcg | actatgtgac | tgattactat | 1140 |
| gcaacaaagc | atgctgtaca | tttagatgat | ccacgtgcac | agaagttggt | cggaatattg | 1200 |
| gccggttgtc | tgtaa | | | | | 1215 |

<210> SEQ ID NO 6
<211> LENGTH: 3414
<212> TYPE: DNA
<213> ORGANISM: Saccharomyces cerevisiae

<400> SEQUENCE: 6

| | | | | | |
|---|---|---|---|---|---|
| aagcttgcca | ccatgagtga | tcaaaataat | cgatcgagaa | atgaatatca | ctcaaaccgg | 60 |
| aagaatgaac | cttcctatga | actccaaaat | gcacatagcg | ggctatttca | ctcttctaat | 120 |
| gaagaattaa | caaacaggaa | ccaaagatat | accaatcaaa | atgccagcat | gggttcattc | 180 |
| actccagtcc | aatctttgca | atttccagaa | caatctcagc | aaacaaatat | gctttataac | 240 |
| ggtgacgatg | caataataa | tactatcaat | gataacgaac | gagacatata | tggaggtttt | 300 |
| gtcaaccacc | atcgccagcg | tcccccacca | gcaactgcag | aatacaatga | cgttttaat | 360 |
| acgaatagtc | aacagctacc | gtcggaacat | caatacaata | acgtaccttc | atatccactt | 420 |
| ccttcgataa | atgtgattca | aaccactcca | gaactccatac | ataacggctc | acagactatg | 480 |
| gccacccca | tcgaaaggcc | cttctttaac | gaaaacgact | actattataa | taacaggaac | 540 |
| tctaggacgt | caccgagtat | tgcttctagt | agcgatggtt | atgcagatca | ggaagctagg | 600 |
| cccatttttgg | agcaacccaa | caataacatg | aatagcggta | atattcctca | ataccatgac | 660 |

-continued

```
caaccttttg gatacaacaa tggttaccat ggcctacagg caaaagatta ctatgacgat    720
ccggagggtg gttatattga tcagagagga gatgactatc agattaattc atatttgggt    780
agaaacggtg aaatggttga tccttacgat tatgaaaaca gtttaagaca tatgactcct    840
atggagcgta gagaatatct tcatgatgat agcagacccg taaacgatgg aaaagaagaa    900
ttagacagtg tgaaaagcgg ttactctcat agagacttgg gggaatatga caaggatgat    960
ttttcaaggg atgacgagta cgatgatctc aacactattg ataaattaca gtttcaagct   1020
aatggtgtac ctgcatcatc ctcggtgtct tctatcggat ctaaagaatc cgacataata   1080
gtaagcaatg ataacttaac cgcaaataga gcactaaaga gaagcggtac tgaaattagg   1140
aaattcaaac tttggaatgg taattttgtt ttcgattctc aatcagtaa gacgctattg    1200 gaccaatacg ctactacaac agaaaatgca aacactttac caaatgagtt taagtttatg   1260
agatatcaag cagttacttg cgaacctaat caacttgcag agaagaattt cacggtgagg   1320
cagttgaagt atttaactcc aagggaaacg gaattgatgc tagtagtcac aatgtataat   1380
gaagaccata tcctgttagg aagaactttg aaaggtatta tggacaatgt caaatatatg   1440
gtgaaaaaaa aaaattcaag cacttggggg ccggatgcat ggaaaaagat tgtcgtttgt   1500
atcatttcag atggtagatc caaaattaat gaacgctcgc tagcattact aagttcgtta   1560
ggttgttacc aggacgggtt tgctaaggat gaaattaatg aaaaaaaagt ggcaatgcat   1620
gtctacgaac atacgacaat gatcaacatc acaaatattt cggaatcaga ggtttcatta   1680
gaatgcaatc aaggtactgt tccaatacaa cttttgtttt gtttgaaaga gcaaaatcag   1740
aaaaaaatta actcacatag atgggcattt gaaggctttg cagaattact gcgtcccaat   1800
atcgttacat tgttagatgc tggtactatg ccaggtaaag attctattta ccagttatgg   1860
agagagttca ggaatccaaa tgttggtggc gcatgtggtg aaataagaac tgatttgggt   1920
aagagatttg taaagttgtt gaatcctta gttgcatcac agaatttcga atacaaaatg    1980
tccaatattt tagacaaaac aaccgagtct aactttggat ttattactgt tctaccgggg   2040
gcattctctg cgtataggtt tgaagctgtg agaggccaac cattacagaa gtacttttat   2100
ggtgaaatta tggaaaatga aggttttcat ttttttttctt ccaatatgta tcttgctgaa   2160
gatcgtattt tatgctttga agtggtcaca aaaaaaaatt gtaattggat tttgaaatac   2220
tgcagaagtt cttatgcttc aacagatgta ccggagaggg tccctgaatt tattcttcag   2280
aggaggcgtt ggttgaatgg ttcatttttt gctagtgtat attccttttg tcattttttac   2340 agagtctgga gcagtggtca taatattggt agaaaactcc ttttgacggt tgaatttttt   2400 tacctttttct tcaatacatt gatttcatgg ttttcattga gttcattttt cctagtcttt   2460
aggattctca ctgtttctat tgcactggca taccattcag catttaatgt gttgtccgtc   2520
atattcctgt ggctttatgg gatttgtacc ttatcaacat tcatactgtc attgggtaat   2580
aaacctaaaa gtactgagaa attttatgtt ctaacttgcg tcatttttgc ggtgatgatg   2640
atttacatga tattctgcag tatattcatg agtgtcaaat ccttccaaaa tatattgaaa   2700
aacgatacca tcagctttga gggtttgatt accacagagg ctttcaggga tattgttatc   2760
tctctgggct ccactattg tttgtaccta atcagttcaa ttatctattt gcagccatgg   2820
catatgttga caagttttat tcagtatatt ttattgagtc cttcttacat caatgttttg   2880
aatatctatg cattttgtaa tgtccacgac ttatcatggg gtacaaaggg tgcaatggca   2940
aatccgctgg gtaagattaa tactacagaa gatggtacgt tcaaaatgga agttctggtc   3000
tctagttcag agattcaagc aaactacgat aaatatttga aagttttaaa tgacttcgat   3060
```

| | | |
|---|---|---|
| ccaaaatcag aatctcggcc tactgagcca tcttatgatg aaaaaaagac tggctattat | 3120 | |
| gcaaacgtta gatctctcgt gattatcttt tgggtcatca caaatttcat catcgttgct | 3180 | |
| gttgtcttag aaaccggtgg gattgcagat tatattgcta tgaaatccat atcaactgat | 3240 | |
| gacactttag aaactgcaaa gaaggcggaa attcccttaa tgaccagtaa ggcctcaatt | 3300 | |
| tattttaatg taattttatg gttagttgca ttatcggcat taataaggtt cattggttgc | 3360 | |
| tcaatataca tgatagtaag gttttttaaa aaggttacat ttcgctaagg tacc | 3414 | |

<210> SEQ ID NO 7
<211> LENGTH: 1712
<212> TYPE: DNA
<213> ORGANISM: Saccharomyces cerevisiae

<400> SEQUENCE: 7

| | | |
|---|---|---|
| gaattcaagc ttatgtcact cctttacatc attcttctat tcacacaatt cttactactg | 60 | |
| ccaaccgatg cctttgatag gtctgctaac acaaatattg ctgtttattg gggtcaaaac | 120 | |
| tcagcaggaa cgcaagaatc cttagctact tactgtgaat cttctgatgc tgatattttc | 180 | |
| ctattatctt tcttgaacca atttccaacc cttggtttga actttgccaa cgcatgctct | 240 | |
| gatactttt ctgatggctt acttcactgc acccagattg ctgaagatat tgaaacttgc | 300 | |
| cagtccctag gaaagaaagt tctattatca ttaggtggtg catctggtag ctacctcttt | 360 | |
| tcagatgatt ctcaagcgga aacttttgca caaactttat gggatacttt cggtgaaggt | 420 | |
| acaggtgcca gtgagagacc atttgactca gcagtcgttg atggttttga ttttgatatt | 480 | |
| gaaaacaaca acgaagtagg ctatagtgcg ttagctacca agttaagaac tttgtttgcc | 540 | |
| gaaggtacaa agcaatatta cctttctgcc gcaccacaat gtccataccc ggatgcttct | 600 | |
| gttggtgact tgttggaaaa tgcagacatt gattttgcgt tcatccaatt ttacaataat | 660 | |
| tactgcagtg tgagtggtca attcaattgg gatacttggt taacctatgc tcaaactgta | 720 | |
| tccccaaata aaaatatcaa actgttctta ggtttacctg gttctgcttc tgctgctggc | 780 | |
| tctggttata tttctgacac ttctttattg gaatcaacta ttgcagatat tgcctcttca | 840 | |
| agttcttttg gtggtattgc gttatgggat gcatctcaag cctttccaa cgagctaaat | 900 | |
| ggtgaaccat atgttgagat tttgaagaat ttgctaacaa gtgctagcca gaccgccact | 960 | |
| actacagttg ccacctcaaa aacctcagca gcctcaactt catctgcttc aacttcatct | 1020 | |
| gcttcaactt ctcagaaaaa gaccacacaa tctacgacat ctacacaaag taaaagcaaa | 1080 | |
| gttactttat ctccaactgc aagcagcgct atcaaaacat caattactca aactacaaaa | 1140 | |
| acattgacga gtagcaccaa gacaaaatct agtctaggta ccaccacaac agagagcact | 1200 | |
| ttaaattcag ttgctatcac aagtatgaaa actactctat cttcccaaat aaccagtgct | 1260 | |
| gccttggtga cccctcaaac aactactact agcatagttt cttcggcccc aattcaaaca | 1320 | |
| gctatcacta gtactcttc gccagcaacg aagagttcct ctgtcgtttc cctacagaca | 1380 | |
| gctactacta gtacgctttc cccaacaacg accagtacaa gctcaggtag tacaagctca | 1440 | |
| ggtagtacaa gctcagacag tacagctcgt acattggcta agaattgaa tgctcaatat | 1500 | |
| gcggctggta aattgaacgg taaatctacc tgtactgaag gtgaaattgc atgctctgct | 1560 | |
| gatgggaagt tcgccgtttg tgatcatagc gcttgggttt acatggaatg tgcttctgga | 1620 | |
| accacatgtt atgcttatga ctccggcgac tcagtctata cccaatgtaa tttctcttat | 1680 | |
| ttggaaagca attactttta actcgaggat cc | 1712 | |

<210> SEQ ID NO 8
<211> LENGTH: 939
<212> TYPE: DNA
<213> ORGANISM: Saccharomyces cerevisiae

<400> SEQUENCE: 8

| | | | | | | |
|---|---|---|---|---|---|---|
| atgagaatac | aactaaatac | aattgatttg | caatgtatta | ttgcactttc | ctgtctgggg | 60 |
| caatttgttc | acgcggaagc | taatagggaa | gatttaaagc | agatagactt | tcaatttcct | 120 |
| gtattggaaa | gggcagctac | aaaaacgcct | tttccggatt | ggcttagtgc | atttaccggg | 180 |
| ttaaaagaat | ggcctgggtt | agatccacct | tatatacctt | tagatttcat | tgatttcagt | 240 |
| caaattccag | attataagga | atatgatcaa | aaccattgcg | acagtgttcc | aagggactcg | 300 |
| tgctctttcg | attgccatca | ctgcaccgaa | acgatgatg | tgtacacatg | ttccaaactt | 360 |
| tcccagacat | ttgacgatgg | tccttctgct | tccactacta | aattattgga | ccggttgaag | 420 |
| cataattcca | ccttcttcaa | tttaggtgtc | aatatagttc | aacatccaga | tatctatcaa | 480 |
| agaatgcaaa | aggagggaca | cttaatcggc | tcacatacct | ggtctcacgt | atatttgcca | 540 |
| aatgtatcga | atgaaaaaat | tatagctcaa | attgaatggt | ccatctgggc | gatgaatgct | 600 |
| actggcaacc | atacccccaa | atggttcaga | cctccatatg | gcggaataga | taatagagta | 660 |
| agagcaataa | caaggcaatt | tggcttacaa | gccgtcttat | gggatcacga | tactttgat | 720 |
| tggagcctcc | ttctcaatga | ttctgtcata | actgaacaag | aaattcttca | aaatgtaata | 780 |
| aactggaaca | agtcaggaac | cggattaata | ttagaacacg | attcaacgga | aaaaactgtc | 840 |
| gatcttgcca | ttaaaataaa | taagttgata | ggtgatgatc | aatcaacagt | ttctcattgt | 900 |
| gtcggcggaa | ttgattacat | aaaagaattc | ttgtcctaa | | | 939 |

<210> SEQ ID NO 9
<211> LENGTH: 2328
<212> TYPE: DNA
<213> ORGANISM: Pyropia yezoensis

<400> SEQUENCE: 9

| | | | | | | |
|---|---|---|---|---|---|---|
| ggatccggta | ccatggagac | tgttcgtcca | ggttgttttc | gtgctgttgt | ttctgttcca | 60 |
| ctgggtcgtc | tgacttactc | tttcctggtg | acggtcagc | cgaagtacaa | cccggactgt | 120 |
| ccgactctgg | ttaacgaagc | tggcgtgcgt | gtgaacgtac | gccacggtgg | ttctgacggt | 180 |
| gattgcgacg | gtgaagctga | cgaagaatgg | ggtaaaggtc | gtccaagccg | tgctcgtcgc | 240 |
| gtgctgagcc | aggtttctgg | cctggacctg | tactctcagc | actccaccag | cgacatcgtt | 300 |
| tctatgctgg | tgttccgttt | cttctacctg | gctatgattc | cagctggtgc | ctactacttc | 360 |
| ttctggctga | gcgttcgtgg | tggtaatcgc | caggctccag | tttgctgggt | ggtgttcgtt | 420 |
| atgagcgaaa | tcctgtctt | cgttagcgcg | ctgatttccc | tgtttggcat | gtggaagccg | 480 |
| atcaaacgtc | gttggcgctc | tctggacgct | ctgcgtccag | ctctgccagt | tgcagattgg | 540 |
| ccaactgtag | acgtgatcat | tgccactac | aaagaggaca | ccgaacagct | gcgtcagact | 600 |
| attcgtgcag | cgatgaaact | ggattaccca | gcccatctgc | tgcacattct | gattgccgac | 660 |
| gatggcttct | tccaaccctc | caagatggta | gagcgttctg | atattggtct | ggctctgtac | 720 |
| cagacctgtg | ttgaggaagc | gggttatgat | ccgctgctgg | aagaaaccat | gaatgaacgt | 780 |
| ggtctggttg | aacactatac | tgttaaggca | ggtgacgacc | tgccgcgtca | tgattgcgcg | 840 |
| gttgaagctc | accagttcga | gtttggtccg | tatggtgcgg | acatgtacgg | tccaggtgcc | 900 |
| ctgccacgtc | tgtccctggt | tgctcgtgtg | aagccggctg | acgctcacaa | caaggcaggc | 960 |

```
aacatcaaca acgtactgtc caactctaac gcagaaggta agattgttct gttcctggat    1020
gctgacatga agccggtaga atcttacctg ctgcgtgttc tgccactgat gctggaagag    1080
cagcgttccg atagcctgca gagccaactg atccaggcag aggacccaga gctgggtgct    1140
ggtacttcta agagctggca aatcaaccgt gacattggct tcgttggctg cccacaacgc    1200
ttcgcgaacg tatccggtga ccatccggat tactgtgctc accgtaacgc gatctactac    1260
gacggtatct gcactggtcg tgatggtttc ggtatgaccg acttcgttgg cactaacgcg    1320
tgttggcgtc gcgaagttct gaacgagatc ggtggcttcg tttatggtag cgtgactgaa    1380
gacaccctga ctagcaacga agttcatcgc cgtggctaca ttagccgcta cgctgacgaa    1440
gacctgtgct ggggtgaagc accagttacc gttgcagcag ctctgctgca gcgtcaacgt    1500
tgggctaaag gtgccatcat gaacggtatg cgtatcttca aggtgctgc taaagaacgc     1560 aaagaaatgc tgctgagccg tgagaaaccg tctgaactgt ctgagttcta cgcatatcgt    1620
cgtcagcagc gtaaaccaaa caacactttc gtttctacca tgttctggct ggattctact    1680
ctgtacccac tgctgggttg gggtgctttc ggttacgtgt tctgtgctat cttccacctg    1740
atcaccgctc aggcaccgat ctctccgacc tctactcaga gcctggctgg tgcgtttgtg    1800
acctactatc tgattcgtta cggtgcattc ttctctgcct tctatgaagt gaacatgacc    1860
gacgttctgc gctctcagca gtgttggttc tcttactcct tcgcccacac tgtgggtgta    1920
tgggatgctc tgtttggtgg tgccaagttt ggctgggttg ctaacactgg ccaacgtcat    1980
cgccgtagct ggctggaatg gttcaacatc ctgactctgg gtgctctgct gtccggcatt    2040
gtgtggcgtc tgttcgcgtt cattgttatc gaagaagcgt gttctccgta cgagaacttc    2100
ggtgctgttg cattcggcgg ttacgtagcg tggatgatgg ctccagttgc tctggttagc    2160
ctgaacgaac gcctgtcttc cgctgacgaa tccgagcgtg aaggtaaacc gatgccagtg    2220
ccgactccga tcatcgctgc tgccctgact atcctgggtg ttgtgttcct gtctggttgg    2280
gcaaacgctc gttgtggtat cgaagctcgc ggttaaaagc ttctcgag                 2328
```

<210> SEQ ID NO 10
<211> LENGTH: 1367
<212> TYPE: DNA
<213> ORGANISM: Oryza japonica

<400> SEQUENCE: 10

```
ctcgagaagc ttttagctgg tagtggagat cttagctttc acatccaggt tctctttatc     60
atcgatcggt ttggtagtct ggttgcgaac acgcttgatc ttcggagact ccaggccttt    120
gtgagcgaaa ccgtacagac gcagaacctg gttgtcagca agttgaacg cacgctccat     180 agaacgcaga caacgttcaa ccggatagtg gccgtaagaa ccgcacggtt tgcagcccac    240
gaagtgagtc acaaatggcc agcgttcgtc acccagacct gggtggtggt tttccatcat    300
ttcttcgtac ttatctacca gacctgccca gaagccgtgc aggtagtagc tgttttcgat    360
aaacactttg ttcatccact ctccttctg gctcagcagc aggtagatca gggcagactg     420
gtcatccgcc tcgaacgctg gacgacccct caggttcgcg tcagaatct tgcctgcttc      480 atcacggata aaccttttcg gacccatcgg ggccacgcg tccagcagat ccagggacca     540
ctggcagttg cggaacagga aggaaccggt gttcagagca atccaggaat gcttttcaaa    600
cagcagatcc tggtaaccgt gaataatcag gttgcgatcc tggtaacgag acagcggcag    660
ttcgaaagcc atgtcagtga acagtgcgtc gctgtccatc caccagatcc attcaacttc    720
```

| | |
|---|---|
| cgggtgagac agcatcaggc gacgcagcag tggcagtttc gcccagtagc ctgccagttc | 780 |
| ggtgtccagg tgtgccaggt tatgtacgat ctcgatacca tgcagacgac agtaatcaat | 840 |
| tttgttctta gtagttttca gcagatagtg atcacccagt gggttgtcgc atggacctgg | 900 |
| ctgggagcca gtcaccagca ggatacgcgg tttgccacca gccacagtgg acggaaagcc | 960 |
| tggattctga cgcagccaac gacgacgctg accatcccaa tcagaaatct ttggacccag | 1020 |
| tgcatagcgt tccactgcag atgcgtacgc tgcagcagcc tcagtagcgt tcagcgcggt | 1080 |
| cgcgttgaag ctgcctgcca gatcgcctgc agccgctgca tcgtcgtcgg caccaccgtc | 1140 |
| agagcggatc tcacgcagaa tgcgatcgat atcttcaacc gcctttgcac ctgccagagc | 1200 |
| gtctgcatcg gttggctggt ttggcaggct caggttcaga ccaatggtgc cacgcagtac | 1260 |
| cagaatagta accagaccac acagaacagt gatcttaacg ttgttgaagg tgcgatgaat | 1320 |
| cttacgagaa cgatgatggt gaccgtggga gctcagcgga gatgcac | 1367 |

<210> SEQ ID NO 11
<211> LENGTH: 1365
<212> TYPE: DNA
<213> ORGANISM: Medicago trunculata

<400> SEQUENCE: 11

| | |
|---|---|
| ctcgagaagc ttttacggct gcggatagtc aaacggcaga gaagaaacac cgttgtcacc | 60 |
| cagatcctta tgaacgaagc cgaatttgcg cataacctgg ttatctgcaa agttcagggc | 120 |
| tttcttcatg ccgttccagc aagcgtccgc agtgtacatt tcgttatact tgccagaaca | 180 |
| cggctgacag ccagtgaagt gagtcacgaa tggacgacgc cagctgcctt taccatagcc | 240 |
| tgcatctttc aggtattctt cacggataac accatacgct tcggatactt tctcagcgta | 300 |
| gcgacgacgc agtttcggtt ccaccttctc gatgtcctcg tatttcttgc tgatgttgga | 360 |
| gaaagtttcc acgatctctt cccagtaacc ttcgaagtag tattcgcctt ccaggtagat | 420 |
| tttatcaccc cacttctctt tctcgatggc gatcaggtat gccagaccgg tttgatcatc | 480 |
| agattccggg aagaacttgt ctttgaaagt gctacgcagg gtcttacccc attcttcgta | 540 |
| gtctggagac tgtggaccca tgccagccca tgcctccatg aagtccaggc tccattgaca | 600 |
| gttacgaatc aggaacacac ctgcgttcag accggtccag ctgcgtttct cgtggatcag | 660 |
| gtgtggccag ccgtgtacca ccaggttatg gtccttgtaa cgtttcagtg gcagcttgaa | 720 |
| atccatgtca gtgaacagcg catcgctatc cacccaccaa atccattcag cttctgggtg | 780 |
| agccatcata gcggctttca ctaccggata ctttgcccaa tacgcaaaca ttttcggatg | 840 |
| cagcagtgca ttgttgtaga agatgtcgta gccgtggatg cgggagtaat ctactttgtt | 900 |
| cttgaagaag cgcagcagca gatggtcacc aatcggattc ttacacgag acggttggga | 960 |
| gccagtcacc atcagcacgc gttctttgc acctgcagag aaagacgggt ggtgtttcag | 1020 |
| ccattcttca cgcttctcat cccagtcttc cagtttcacg gacatggtat attccatttc | 1080 |
| cggatcgtcg tagaaggtct ggtccggtgg gtcgaaacgc aggtccggag tagagtaaga | 1140 |
| tacaacattg ttcttatggc tcttcagagt caggttgtcg ttcgggatcg gattagtgaa | 1200 |
| agaggagaag cccaaaacca gcagcagtgc gctgaatgca ccacccagga acaggaaacc | 1260 |
| atcagacaga aagatgctgg aagatttgtt acgcgggatc ggtttcgcca tgatgctgct | 1320 |
| gaagtgagaa tgagacagtt cggtagtaac catggtaccg gatcc | 1365 |

<210> SEQ ID NO 12
<211> LENGTH: 1332

```
<212> TYPE: DNA
<213> ORGANISM: Cyamopsis tetragonoloba

<400> SEQUENCE: 12
ggatccggta ccatggcgaa gtttggtagc cgtaataagt ctccgaagtg gatctctaac      60
ggctgctgct tcctgctggg tgcctttact gctctgctgc tgctgtgggg tctgtgctcc     120
tttattatcc cgattccgaa caccgatccg aagctgaact ctgtagcgac ctctctgcgt     180
tctctgaact ccccgaagaa cccagcagct accctgccac cgaacctgca gcatgatcca     240
ccggatacta ctttctacga cgatccggaa acctcttata ctatggataa accgatgaag     300
aactgggacg agaaacgtaa ggaatggctg ctgcatcacc cgtccttcgg cgcagctgct     360
cgtgacaaga tcctgctggt aaccggttcc cagccgaaac gctgtcacaa cccgattggt     420
gatcacctgc tgctgcgttt ctttaagaac aaagtggatt actgccgtct gcataattac     480
gatatcatct ataacaacgc actgctgcac ccgaaaatga actcctattg ggctaagtac     540
ccagtgatcc gtgctgcaat gatggctcat ccggaagttg aatgggtgtg gtgggttgac     600
tctgacgctg tattcactga catggagttt aaactgccac tgaaacgcta taagaaccac     660
aatctggtgg tgcatggttg ggaaggtctg gtacgtctga accactcctg gactggtctg     720
aacgcaggtg tattcctgat ccgtaattgc caatggagcc tggagttcat ggatgtatgg     780
gttagcatgg gtccacaaac tccagaatac gagaaatggg gtgagcgtct gcgcgaaacc     840
ttcaaagata agttctgcc agactctgat gaccagactg cactggcata cctgatcgca     900
accgataaca agacacctg gcgtgagaaa atcttcctgg aaagcgagta ctacttcgaa     960
ggctattggc tggaaatcgt aaagacttac gagaacatct ccgaacgtta cgatgaagtt    1020
gaacgcaaag tagaaggtct gcgtcgtcgc cacgctgaga aggttagcga gaaatacggt    1080
gcaatgcgtg aagaatacct gaaagataac aaacgtcgtc cgttcatcac ccatttcact    1140
ggttgccagc cgtgcaacgg tcaccataac ccagcataca atgcgaacga ctgttggaat    1200
ggtatggaac gtgcactgaa ctttgcagat aaccagatcc tgcgtaccta cggttaccat    1260
cgtcagaatc tgctggacaa gtccgttctt ccactgccgt tcggttatcc agcagcttaa    1320
aagcttctcg ag                                                        1332

<210> SEQ ID NO 13
<211> LENGTH: 20
<212> TYPE: DNA
<213> ORGANISM: Artificial sequence
<220> FEATURE:
<223> OTHER INFORMATION: Synthetic construct

<400> SEQUENCE: 13
taatacgact cactataggg                                                  20

<210> SEQ ID NO 14
<211> LENGTH: 1386
<212> TYPE: DNA
<213> ORGANISM: Artificial sequence
<220> FEATURE:
<223> OTHER INFORMATION: Synthetic construct

<400> SEQUENCE: 14
ctcgaggaat tctcactgga acagcgcgtc actcgacagg ccattcttct ccagaatctc       60
ccgcaggcgc ttcagcgcct cgacctggat ctgacgaacc cgctcgcggg tcaggccgat      120
ttcctggccg acctcttcca gcgtgctgct ttcgtgaccg cgcaagccga agcggcgaat      180
```

```
caccacctca cgctgcttgt cggtgagttc cgtcagctgc tttcgctgag atcgtcatcc      240
tgcagcagct cgcacggatc ggtggggcga tcgtcggtga gcgtatccag cagggtcttg      300
tccgagtccg gaccaagaga gacgtctacc gaagtcaccc gttcgttcag gccgagcatg      360
cgcttgacct cggcgaccgg cttctccagc aggttggcga tttcttcggg tgaaggttcg      420
tggtcgagct tgtgggtcag ttcccgcgcc gcacgcaggt agacgttgag ctccttgacc      480
acatggatcg gcaagcgaat ggtccgggtc tggttcatga tggcccgctc gatggtctgg      540
cggatccacc aggtggcgta ggtcgagaac cggaatccgc gctccggatc gaacttctcc      600
acggcgcgga tcaggcctag gttgccttcc tcgatcaggt cgagcaggga cagtccgcga      660
ttgacatagc gccgggcgat cttcaccacc aaccgcaggt tgctctcgat catccgcttc      720
cgaccagcgg gatcgccctt ctgcgccaga cgagcgaagt ggacttcctc ttcgggcgtc      780
aacaggggcg agaaaccgat ttcgttgaga tacagctgcg ttgcgtccaa cgcgcgcgtg      840
tagtcgatgt gcttgtgttg tttggaagag aaggaagtgg tggcttttgg agttgcccgg      900
ggagaaggct gctcgtcggc agacgactcg tccagcatga tgccgggctc caggaggagc      960
acttcatcat cgtggtcaaa ctccggccct tctttttttga gtgccatgtc gttatcccctt     1020 gcatgagttc gactcaagcc cgggcgattc ctttcccgct ggacacgccc ggacccgctc     1080
acctacatga tgtgggcggg cgaactcccg gtcagcgacg tggcaaatat tgcagtggat     1140
cgacaggctt accctggcgg cgaatctcga agtgcagctt cacccgatcg gttcctgtgg     1200
agcccatctc ggcaatcgat tgccctacct tgacctgttg cccttcccgc accagcagcc     1260
tgcggttgtg accgtaggca ctcacgtagg tctcgttgtg tttgatgatg accaactcgc     1320
cgtagccccg caaaccacta ccggcgtata caacggtccc accagacgca gccaggtacc     1380
aagctt                                                                 1386
```

<210> SEQ ID NO 15
<211> LENGTH: 890
<212> TYPE: DNA
<213> ORGANISM: Artificial sequence
<220> FEATURE:
<223> OTHER INFORMATION: Synthetic construct

<400> SEQUENCE: 15

```
ggattcaaag aggagaaata ctagatggtg agcaagggcg aggagctgtt caccggggtg       60
gtgcccatcc tggtcgagct ggacggcgac gtaaacggcc acaagttcag cgtgtccggc      120
gagggcgagg gcgatgccac ctacggcaag ctgaccctga agttcatctg caccaccggc      180
aagctgcccg tgccctggcc caccctcgtg accaccttcg gctacggcct gcaatgcttc      240
gcccgctacc ccgaccacat gaagctgcac gacttcttca gtccgccat gcccgaaggc      300 tacgtccagg agcgcaccat cttcttcaag gacgacggca actacaagac ccgcgccgag      360
gtgaagttcg agggcgacac cctggtgaac cgcatcgagc tgaagggcat cgacttcaag      420
gaggacggca acatcctggg gcacaagctg gagtacaact acaacagcca caacgtctat      480
atcatggccg acaagcagaa gaacggcatc aaggtgaact tcaagatccg ccacaacatc      540
gaggacggca gcgtgcagct cgccgaccac taccagcaga acacccccat cggcgacggc      600
cccgtgctgc tgcccgacaa ccactacctg agctaccagt ccgccctgag caaagacccc      660
aacgagaagc gcgatcacat ggtcctgctg gagttcgtga ccgccgccgg gatcactctc      720
ggcatggacg agctgtacaa gtaataatac tagagccagg catcaaataa aacgaaaggc      780
tcagtcgaaa gactgggcct ttcgttttat ctgttgtttg tcggtgaacg ctctctacta      840
```

```
gagtcacact ggctcacctt cgggtgggcc tttctgcgtt tataaagctt            890
```

<210> SEQ ID NO 16
<211> LENGTH: 13637
<212> TYPE: DNA
<213> ORGANISM: Artificial sequence
<220> FEATURE:
<223> OTHER INFORMATION: Synthetic construct

<400> SEQUENCE: 16

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttccta ggatgacaga tcgttgtcca ggtagggatg    540
ctccacactt agcagtcatt ggagcaggtc agctggctt agcagcagca ttagctgctg    600
ctgctagagg tgttcgtgta accttgttgg atgctgaacc agaagcagga ggccaattct    660
atagacagcc agcagcagct ttacgtgcta aaggccaca agcattacac catcagtggc    720
gtacctttgc cagattgaga cacggattag ccaggcacat tgcagcaggt agagttagac    780
atgctagaga acaccatgtt tggtttgctg agagagctcc tgatggtgga ttcaccgttc    840
atgctttgac tggtccaggt agaggagatc cagcagaagt gagagcagat gcagtcttgt    900
tggcaactgg tggtcacgag actgtgttgc cattcccagg ttggaccttg ccaggtgttg    960
tcacagctgg aggtgcccaa gccatgttga aggcaggttt agttacatct ggcaacaccg   1020
cagtcgtagc tggtactggt ccattgttgt tgccagtagc tacaggttta gctgctgctg   1080
gtgttgacgt aagagcatta gtcgaaagtg ctgatcctgg tgccttacca agacaggcac   1140
gtgctttggc agctcaacct ggcaagttgg ctgaaggtgc tttgtatgct ggtcaattgt   1200
tgaggcacag agtgcgtgtc ttgactagac acactgtcgt tgaagcacat ggtacagaga   1260
ggttggaagc agttactgtt gcagccttgg atgcaggtgg acgtactaga cctggcactg   1320
ctagaagaat agcatgtgca actttagctg tgggtcatgg tatgttgcca catacagact   1380
tggcagacgc cttaggctgc cgtttagcag gtccagcagt tcatgcagat gatgaacaaa   1440
gaactgatgt tcctggtgtg tgggcagcag agagtgtac tggcgtaggt ggtgcagctt   1500
tgtctttggc tgagggtcat atcgctggca gaagtgcagc agccagattg ttaggagcac   1560
ctccaggtcc cgacgcatgg ccagaggcag ctagaacaag agcaaggttg agagcttttct   1620
ccgctgtatt ggatgctgtt tacactcctc ctcctggttg gggtgagaga gtcaccgacg   1680
caaccgttgt atgcaggtgt gaagaagtta cagcaggtgc aatccgtgct tctgtgaggg   1740
aattgggagc tggtgacgta cgtactgtaa agttgttgac tagagctggc atgggatggt   1800
gtcagggaag aatgtgtgct cctgctgtcg ctggattggc aggttgtgct ttcactccta   1860
gtcgtagacc attcgctagg ccagtgcctt gggagtgtt ggccagagct ggtgaagatg   1920
caggtggcga tggaggcaga gctgaggatc aaggtgaagg agatggacgt gctgctggag   1980
```

```
caggaggttg attaattaat catgtaatta gttatgtcac gcttacattc acgccctccc    2040
cccacatccg ctctaaccga aaaggaagga gttagacaac ctgaagtcta ggtccctatt    2100 tatttttta  tagttatgtt agtattaaga acgttattta tatttcaaat ttttcttttt    2160
tttctgtaca gacgcgtgta cgcatgtaac attatactga aaaccttgct tgagaaggtt    2220
ttgggacgct cgaaggcttt aatttgccgg attagaagcc gccgagcggg tgacagccct    2280
ccgaaggaag actctcctcc gtgcgtcctc gtcttcaccg gtcgcgttcc tgaaacgcag    2340
atgtgcctcg cgccgcactg ctccgaacaa taaagattct acaatactag cttttatggt    2400
tatgaagagg aaaaattggc agtaacctgg ccccacaaac cttcaaatga acgaatcaaa    2460
ttaacaacca taggatgata atgcgattag ttttttagcc ttatttctgg ggtaattaat    2520
cagcgaagcg atgattttg  atctattaac agatatataa atgcaaaaac tgcataacca    2580
ctttaactaa tactttcaac attttcggtt tgtattactt cttattcaaa tgtaataaaa    2640
gtatcaacaa aaaattgtta atatacctct atactttaac gtcaaggagg gcgcgccacc    2700
atgcttgtca cagtggtagt actgggtcta ctggggtttg cttctgcagc ccagcccaag    2760
tttgaatttg tagaagaatg gcagctgtgg aagtccactc actctaagat gtacgagtca    2820
cagttaatgg aactcgaaag acatctgacg tggctctcca ataagaaata tatcgagcaa    2880
cacaatgtca actcacacat tttcggtttt actctggcaa tgaaccagtt tggagatctg    2940
agtgaattgg agtatgctaa ctatcttggc cagtatcgca ttgaggataa aaaatctggc    3000
aactactcaa agacttttca gcgtgatcct ctacaggact accctgaagc tgtagactgg    3060
agaaccaaag gagctgtcac ggctgtcaag gaccagggag actgtggtgc tagctatgct    3120
ttcagtgcta tgggtgcttt ggagggtgct aatgctttag ccaagggaaa tgcagtatct    3180
ctcagtgaac agaacatcat tgattgctcg attccttacg gtaaccacgg ttgtcatgga    3240
ggcaatatgt atgatgcttt tttgtatgtc atcgctaacg aggggggtcga tcaggacagt    3300 gcatatccat ttgtaggaaa gcaatccagc tgcaactata atagtaaata caaaggtaca    3360
tcaatgtcgg ggatggtgtc aatcaaaagt ggtagtgagt ctgacttaca agcagctgtt    3420
tcaaacgttg gccctgtatc tgttgctatt gatggtgcta acagtgcctt caggttttac    3480
tacagtggtg tctatgactc atcacgatgc tctagtagta gtcttaacca cgcaatggta    3540
gtcactggat acggatcata caatgggaaa aaatactggc tggccaagaa tagctgggga    3600
actaactggg gtaacagtgg ctatgtgatg atggctcgca acaagtacaa ccagtgtgga    3660
attgctaccg atgcatctta tcccaccta  taagtttaaa ctcatgtaat tagttatgtc    3720
acgcttacat tcacgccctc ccccacatc  cgctctaacc gaaaaggaag gagttagaca    3780
acctgaagtc taggtcccta tttattttt  tatagtattg ttagtattaa gaacgttatt    3840
tatatttcaa attttctttt tttttctgta cagacgcgtg tacgcatgta acattatact    3900
gaaaaccttg cttgagaagg ttttgggacg ctcgaaggct ttaatttgcc ggattagaag    3960
ccgccgagcg ggtgacagcc ctccgaagga agactctcct ccgtgcgtcc tcgtcttcac    4020
cggtcgcgtt cctgaaacgc agatgtgcct cgcgccgcac tgctccgaac aataaagatt    4080
ctacaatact agcttttatg gttatgaaga ggaaaaattg gcagtaacct ggccccacaa    4140
accttcaaat gaacgaatca aattaacaac cataggatga taatgcgatt agttttttag    4200
ccttatttct ggggtaatta atcagcgaag cgatgatttt tgatctatta acagatatat    4260
aaatgcaaaa actgcataac cactttaact aatactttca acattttcgg tttgtattac    4320
ttcttattca aatgtaataa aagtatcaac aaaaaattgt taatatacct ctatacttta    4380
```

```
acgtcaagga gctcgaggcc accatgaagc tgaccgccat ctttccgctt cttttcactg   4440
ctgtcgggta ctgtgctgcc caaagcattg ctgacttggc agcagccaat ctcagcactg   4500
aggattccaa gtcagctcag ctcatctcag cagactcctc ggatgacgca tctgattcct   4560
ctgtcgagtc tgtcgacgcc gcctcctctg acgtctctgg ttcctctgtc gaatctgtcg   4620
acgtctctgg ttcctctctg gaatccgttg acgtctctgg ttcctctctg gagtccgtcg   4680
acgactccag tgaggactcc gaagaggaag aacttcgtat cttgtcttcc aagaaatccg   4740
gatcctacta ctcctacggc accaagaagt cgggatccta ctcgggatac tccacaaaga   4800
aatccgcatc gcgtcgcatc ttgtcctcca agaaatcggg atcctactcg ggatattcca   4860
caaagaaatc cggatcgcgt cgcatcttgt cctccaagaa atcgggatcc tactcgggat   4920
ccaagggttc caagcgtcgc atcttgtcct ccaaaaaatc cggatcctac tcgggatcca   4980
agggctccaa gcgtcgcaac ttgtcctcca gaaatccgg atcctactcg ggatccaagg   5040
gttccaagcg tcgcatcttg tcctccaaaa atccggatc ctactcggga tccaagggct   5100
ccaagcgtcg caacttgtcc tccaagaaat ccggatccta ctcgggatcc aagggttcca   5160
agcgtcgcat cttgtccggg gtctcagag gctccatgta aggtacctca tgtaattagt   5220
tatgtcacgc ttacattcac gccctccccc cacatccgct ctaaccgaaa aggaaggagt   5280
tagacaacct gaagtctagg tccctattta ttttttata gttatgttag tattaagaac   5340
gttatttata tttcaaattt ttcttttttt tctgtacaga cgcgtgtacg catgtaacat   5400
tatactgaaa accttgcttg agaaggtttt gggacgctcg aaggctttaa tttgccggat   5460
tagaagccgc cgagcgggtg acagccctcc gaaggaagac tctcctccgt gcgtcctcgt   5520
cttcaccggt cgcgttcctg aaacgcagat gtgcctcgcg ccgcactgct ccgaacaata   5580
aagattctac aatactagct tttatggtta tgaagaggaa aaattggcag taacctggcc   5640
ccacaaacct tcaaatgaac gaatcaaatt aacaaccata ggatgataat gcgattagtt   5700
ttttagcctt atttctgggg taattaatca gcgaagcgat gattttgat ctattaacag   5760 atatataaat gcaaaaactg cataaccact ttaactaata ctttcaacat tttcggtttg   5820
tattacttct tattcaaatg taataaaagt atcaacaaaa aattgttaat atacctctat   5880
actttaacgt caaggaggga tccatgtcta ttccagaaac tcaaaaagcc attatcttct   5940
acgaatccaa cggcaagttg gagcataagg atatcccagt tccaaagcca agcccaacg   6000 aattgttaat caacgtcaag tactctggtg tctgccacac cgatttgcac gcttggcatg   6060
gtgactggcc attgccaact aagttaccat tagttggtgg tcacgaaggt gccggtgtcg   6120
ttgtcggcat gggtgaaaac gttaagggct ggaagatcgg tgactacgcc ggtatcaaat   6180
ggttgaacgg ttcttgtatg gcctgtgaat actgtgaatt gggtaacgaa tccaactgtc   6240
ctcacgctga cttgtctggt tacacccacg acggttcttt ccaagaatac gctaccgctg   6300
acgctgttca agccgctcac attcctcaag gtactgactt ggctgaagtc gcgccaatct   6360
tgtgtgctgg tatcaccgta tacaaggctt tgaagtctgc caacttgaga gcaggccact   6420
gggcggccat ttctggtgct gctggtggtc taggttcttt ggctgttcaa tatgctaagg   6480
cgatgggtta cagagtctta ggtattgatg gtggtccagg aaaggaagaa ttgtttacct   6540
cgctcggtgg tgaagtattc atcgacttca ccaaagagaa ggacattgtt agcgcagtcg   6600
ttaaggctac caacggcggt gcccacggta tcatcaatgt ttccgtttcc gaagccgcta   6660
tcgaagcttc taccagatac tgtagggcga acggtactgt tgtcttggtt ggtttgccag   6720
```

```
ccggtgcaaa gtgctcctct gatgtcttca accacgttgt caagtctatc tccattgtcg    6780
gctcttacgt ggggaacaga gctgatacca gagaagcctt agatttcttt gccagaggtc    6840
tagtcaagtc tccaataaag gtagttggct tatccagttt accagaaatt tacgaaaaga    6900
tggagaaggg ccaaattgct ggtagatacg ttgttgacac ttctaaataa gaattctcat    6960
gtaattagtt atgtcacgct tacattcacg ccctccccccc acatccgctc taaccgaaaa    7020
ggaaggagtt agacaacctg aagtctaggt ccctatttat ttttttatag ttatgttagt    7080
attaagaacg ttatttatat ttcaaatttt tctttttttt ctgtacagac gcgtgtacgc    7140
atgtaacatt atactgaaaa ccttgcttga aaggttttg ggacgctcga aggctttaat    7200
ttgccggatt agaagccgcc gagcgggtga cagccctccg aaggaagact ctcctccgtg    7260
cgtcctcgtc ttcaccggtc gcgttcctga acgcagatg tgcctcgcgc cgcactgctc    7320
cgaacaataa agattctaca atactagctt ttatggttat gaagaggaaa aattggcagt    7380
aacctggccc cacaaacctt caaatgaacg aatcaaatta acaaccatag gatgataatg    7440
cgattagttt tttagcctta tttctggggt aattaatcag cgaagcgatg attttttgatc    7500 tattaacaga tatataaatg caaaaactgc ataaccactt taactaatac tttcaacatt    7560
ttcggtttgt attacttctt attcaaatgt aataaaagta tcaacaaaaa attgttaata    7620
tacctctata ctttaacgtc aaggaggcgg ccgccatggt gagcaagggc gaggagctgt    7680
tcaccggggt ggtgcccatc ctggtcgagc tggacggcga cgtaaacggc cacaagttca    7740
gcgtgtccgg cgagggcgag ggcgatgcca cctacggcaa gctgaccctg aagttcatct    7800
gcaccaccgg caagctgccc gtgccctggc ccaccctcgt gaccaccttc ggctacggcc    7860
tgcaatgctt cgcccgctac cccgaccaca tgaagctgca cgacttcttc aagtccgcca    7920
tgcccgaagg ctacgtccag gagcgcacca tcttcttcaa ggacgacggc aactacaaga    7980
cccgcgccga ggtgaagttc gagggcgaca ccctggtgaa ccgcatcgag ctgaagggca    8040
tcgacttcaa ggaggacggc aacatcctgg ggcacaagct ggagtacaac tacaacagcc    8100
acaacgtcta tatcatggcc gacaagcaga agaacggcat caaggtgaac ttcaagatcc    8160
gccacaacat cgaggacggc agcgtgcagc tcgccgacca ctaccagcag aacaccccca    8220
tcggcgacgg ccccgtgctg ctgcccgaca accactacct gagctaccag tccgccctga    8280
gcaaagaccc caacgagaag cgcgatcaca tggtcctgct ggagttcgtg accgccgccg    8340
ggatcactct cggcatggac gagctgtaca agtaatctag agggccgcat catgtaatta    8400
gttatgtcac gcttacattc acgccctccc cccacatccg ctctaaccga aaaggaagga    8460
gttagacaac ctgaagtcta ggtccctatt tatttttttta tagttatgtt agtattaaga    8520 acgttatttta tatttcaaat ttttctttttt tttctgtaca gacgcgtgta cgcatgtaac    8580
attatactga aaaccttgct tgagaaggtt ttgggacgct cgaaggcttt aatttgcggc    8640
cctgcattaa tgaatcggcc aacgcgcggg gagaggcggt ttgcgtattg ggcgctcttc    8700
cgcttcctcg ctcactgact cgctgcgctc ggtcgttcgg ctgcggcgag cggtatcagc    8760
tcactcaaag gcggtaatac ggttatccac agaatcaggg gataacgcag gaaagaacat    8820
gtgagcaaaa ggccagcaaa agcccaggaa ccgtaaaaag gccgcgttgc tggcgttttt    8880
ccataggctc cgcccccctg acgagcatca caaaaatcga cgctcaagtc agaggtggcg    8940
aaacccgaca ggactataaa gataccaggc gtttccccct ggaagctccc tcgtgcgctc    9000
tcctgttccg accctgccgc ttaccggata cctgtccgcc tttctccctt cgggaagcgt    9060
ggcgctttct catagctcac gctgtaggta tctcagttcg gtgtaggtcg ttcgctccaa    9120
```

```
gctgggctgt gtgcacgaac cccccgttca gcccgaccgc tgcgccttat ccggtaacta    9180
tcgtcttgag tccaacccgg taagacacga cttatcgcca ctggcagcag ccactggtaa    9240
caggattagc agagcgaggt atgtaggcgg tgctacagag ttcttgaagt ggtggcctaa    9300
ctacggctac actagaagga cagtatttgg tatctgcgct ctgctgaagc cagttacctt    9360
cggaaaaaga gttggtagct cttgatccgg caaacaaacc accgctggta gcggtggttt    9420
ttttgtttgc aagcagcaga ttacgcgcag aaaaaaagga tctcaagaag atcctttgat    9480
cttttctacg gggtctgacg ctcagtggaa cgaaaactca cgttaaggga ttttggtcat    9540
gagattatca aaaaggatct tcacctagat ccttttaaat taaaaatgaa gttttaaatc    9600
aatctaaagt atatatgagt aaacttggtc tgacagttac caatgcttaa tcagtgaggc    9660
acctatctca gcgatctgtc tatttcgttc atccatagtt gcctgactcc ccgtcgtgta    9720
gataactacg atacgggagc gcttaccatc tggccccagt gctgcaatga taccgcgaga    9780
cccacgctca ccggctccag atttatcagc aataaaccag ccagccggaa gggccgagcg    9840
cagaagtggt cctgcaactt tatccgcctc catccagtct attaattgtt gccgggaagc    9900
tagagtaagt agttcgccag ttaatagttt gcgcaacgtt gttggcattg ctacaggcat    9960
cgtggtgtca ctctcgtcgt ttggtatggc ttcattcagc tccggttccc aacgatcaag   10020
gcgagttaca tgatccccca tgttgtgcaa aaaagcggtt agctccttcg gtcctccgat   10080
cgttgtcaga agtaagttgg ccgcagtgtt atcactcatg gttatggcag cactgcataa   10140
ttctcttact gtcatgccat ccgtaagatg cttttctgtg actggtgagt actcaaccaa   10200
gtcattctga aatagtgta tgcggcgacc gagttgctct tgcccggcgt caatacggga   10260
taatagtgta tcacatagca gaactttaaa agtgctcatc attggaaaac gttcttcggg   10320
gcgaaaactc tcaaggatct taccgctgtt gagatccagt tcgatgtaac ccactcgtgc   10380
acccaactga tcttcagcat cttttacttt caccagcgtt tctgggtgag caaaaacagg   10440
aaggcaaaat gccgcaaaaa agggaataag ggcgacacgg aaatgttgaa tactcatact   10500 cttcctttt caatgggtaa taactgatat aattaaattg aagctctaat ttgtgagttt   10560
agtatacatg catttactta taatacagtt ttttagtttt gctggccgca tcttctcaaa   10620
tatgcttccc agcctgcttt tctgtaacgt tcaccctcta ccttagcatc ccttcccttt   10680
gcaaatagtc ctcttccaac aataataatg tcagatcctg tagagaccac atcatccacg   10740
gttctatact gttgacccaa tgcgtctccc ttgtcatcta aacccacacc gggtgtcata   10800
atcaaccaat cgtaaccttc atctcttcca cccatgtctc tttgagcaat aaagccgata   10860
acaaaatctt tgtcgctctt cgcaatgtca acagtaccct tagtatattc tccagtagat   10920
agggagccct tgcatgacaa ttctgctaac atcaaaaggc tctaggttc ctttgttact   10980 tcttctgccg cctgcttcaa accgctaaca atacctgggc ccaccacacc gtgtgcattc   11040
gtaatgtctg cccattctgc tattctgtat acacccgcag agtactgcaa tttgactgta   11100
ttaccaatgt cagcaaattt tctgtcttcg aagagtaaaa aattgtactt ggcggataat   11160
gcctttagcg gcttaactgt gccctccatg gaaaaatcag tcaagatatc cacatgtgtt   11220
tttagtaaac aaattttggg acctaatgct tcaactaact ccagtaattc cttggtggta   11280
cgaacatcca tgaagcaca caagtttgtt tgcttttcgt gcatgatatt aaatagcttg   11340
gcagcaacag gactaggatg agtagcagca cgttccttat atgtagcttt cgacatgatt   11400
tatcttcgtt tcctgcaggt ttttgttctg tgcagttggg ttaagaatac tgggcaattt   11460
```

```
catgtttctt caacactaca tatgcgtata tataccaatc taagtctgtg ctccttcctt   11520
cgttcttcct tctgttcgga gattaccgaa tcaaaaaaat ttcaaagaaa ccgaaatcaa   11580 aaaaagaat  aaaaaaaaaa tgatgaattg aattgaaaag ctagcttatc gatgataagc   11640
tgtcaaagat gagaattaat tccacggact atagactata ctagatactc cgtctactgt   11700
acgatacact tccgctcagg tccttgtcct ttaacgaggc cttaccactc ttttgttact   11760
ctattgatcc agctcagcaa aggcagtgtg atctaagatt ctatcttcgc gatgtagtaa   11820
aactagctag accgagaaag agactagaaa tgcaaaaggc acttctacaa tggctgccat   11880
cattattatc cgatgtgacg ctgcagcttc tcaatgatat tcgaatacgc tttgaggaga   11940
tacagcctaa tatccgacaa actgttttac agatttacga tcgtacttgt tacccatcat   12000
tgaattttga acatccgaac ctgggagttt tccctgaaac agatagtata tttgaacctg   12060
tataataata tatagtctag cgctttacgg aagacaatgt atgtatttcg gttcctggag   12120
aaactattgc atctattgca taggtaatct tgcacgtcgc atccccggtt cattttctgc   12180
gtttccatct tgcacttcaa tagcatatct ttgttaacga agcatctgtg cttcatttttg  12240 tagaacaaaa atgcaacgcg agagcgctaa ttttttcaaac aaagaatctg agctgcattt   12300
ttacagaaca gaaatgcaac gcgaaagcgc tatttttacca acgaagaatc tgtgcttcat   12360
ttttgtaaaa caaaaatgca acgcgacgag agcgctaatt tttcaaacaa agaatctgag   12420
ctgcattttt acgaacagaa atgcaacgc  gagagcgcta ttttaccaac aaagaatcta   12480
tacttctttt ttgttctaca aaaatgcatc ccgagagcgc tattttttcta caaagcatc   12540 ttagattact tttttctcc tttgtgcgct ctataatgca gtctcttgat aacttttttgc   12600 actgtaggtc cgttaaggtt agaagaaggc tactttggtg tctattttct cttccataaa   12660 aaagcctga ctccacttcc cgcgtttact gattactagc gaagctgcgg gtgcattttt   12720
tcaagataaa ggcatccccg attatattct ataccgatgt ggattgcgca ctttgtga    12780 acagaaagtg atagcgttga tgattcttca ttggtcagaa aattatgaac ggtttcttct   12840
attttgtctc tatatactac gtataggaaa tgtttacatt ttcgtattgt tttcgattca   12900
ctctatgaat agttcttact acaatttttt tgtctaaaga gtaatactag agataaacat   12960
aaaaaatgta gaggtcgagt ttagatgcaa gttcaaggag cgaaaggtgg atgggtaggt   13020 tatatagggga tatagcacag agatatatag caaagagata cttttgagca atgtttgtgg   13080
aagcggtatt cgcaatggga agctccaccc cggttgataa tcagaaaagc cccaaaaaca   13140
ggaagattgt ataagcaaat atttaaattg taaacgttaa tattttgtta aaattcgcgt   13200 taaattttg ttaaatcagc tcattttta acgaatagcc cgaaatcggc aaaatccctt     13260
ataaatcaaa agaatagacc gagatagggt tgagtgttgt tccagtttcc aacaagagtc   13320
cactattaaa gaacgtggac tccaacgtca aagggcgaaa aagggtctat cagggcgatg   13380
gcccactacg tgaaccatca ccctaatcaa gttttttggg gtcgaggtgc cgtaaagcag   13440
taaatcggaa gggtaaacgg atgcccccat ttagagcttg acggggaaag ccggcgaacg   13500
tggcgagaaa ggaagggaag aaagcgaaag gagcgggggc tagggcggtg ggaagtgtag   13560
gggtcacgct gggcgtaacc accacacccg ccgcgcttaa tggggcgcta cagggcgcgt   13620
ggggatgatc cactagt                                                  13637
```

<210> SEQ ID NO 17
<211> LENGTH: 15564
<212> TYPE: DNA
<213> ORGANISM: Artificial sequence
<220> FEATURE:
<223> OTHER INFORMATION: Synthetic construct

<400> SEQUENCE: 17

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttccta ggccaccatg gtgtttatcg tcaatctttt     540
ctcctgcacc ttatctgaaa ccacggttag ctcaataaaa tctgaagcta cggttagctc     600
aacatttact gccgtcacgg ccctgcaatt ggtggctgag ggtaagttgc agtcggcgaa     660
gggtttcggt ggtggtacga ttcactaccc aaccctcgcg gccgaagcac cctggtggac     720
gccgggccaa ggccatggtt acgaggcgat cacctacggc tggctggtcg gcgaactgct     780
gcgccgcgcc gatgggcgtg ggcctggtct gttaggcgct attgccgtgg ttcctggtta     840
cgtttcttac gagaactcta tcaagtggtg gggaccgcgt ctggcttctt ggggctttgt     900
cgttgcacgg ccgttgggcc tggactttca tgtgggcctg gcggatgaag agttttatcg     960
tgttgcccat atagcgcgca gcaaagccaa tgcagcacta gataacattg ctgatgacac    1020
cgtcggcagt atagatccta agcggttggg cgctattggc tggtcaggtg gcggcggcgc    1080
gcttaaactg gcaacggagc gcagcacagt acgagccatt ttgaccagta ctaataaacc    1140
tgaatggcga cgcttcgata aattcttatg tgcctgcgag gatgaccgga ttgctgagac    1200
taagaaatat gccaacgcgt tttataaaaa tgccgacatg ctcgaagagt tgacccgtga    1260
acacagtatc gggccggata aaacattatt gacacaaact cggtttggct tggggtgctt    1320
ggatcaaccg caagcagggg ttaaaattca ttttgaagag taccttgatc aaacccatgg    1380
atttatcaat ttgacgccag tttcacataa ggcgagagca atctgattc agatgcctaa     1440
tgccacattc ggccttggcc cgcgtgcttt tgggcatcct ggtgcaggtg gatcggtagg    1500
ttttgccgac cccgaacacg atgtagcgtt tggtttcgtg actaatacat tggggcctta    1560
tgtagttgag tttaaaagcc gtcatccctc attttatgca tataaagatg gattggtgct    1620
gactggaaat gacgtcgact atgtgactga ttactatgca acaaagcatg ctgtacattt    1680
agatgatcca cgtgcacaga gttggtcgg aatattggcc ggttgtctgt aacccgggtc     1740
atgtaattag ttatgtcacg cttacattca cgccctcccc ccacatccgc tctaaccgaa    1800
aaggaaggag ttagacaacc tgaagtctag gtccctattt atttttttat agttatgtta    1860
gtattaagaa cgttatttat atttcaaatt tttctttttt ttctgtacag acgcgtgtac    1920
gcatgtaaca ttatactgaa aaccttgctt gagaaggttt tgggacgctc gaaggcttta    1980
atttgccgga ttagaagccg ccgagcgggt gacagccctc cgaaggaaga ctctcctccg    2040
tgcgtcctcg tcttcaccgg tcgcgttcct gaaacgcaga tgtgcctcgc gccgcactgc    2100
tccgaacaat aaagattcta caatactagc ttttatggtt atgaagagga aaattggca    2160
gtaacctggc cccacaaacc ttcaaatgaa cgaatcaaat taacaaccat aggatgataa    2220
```

```
tgcgattagt tttttagcct tatttctggg gtaattaatc agcgaagcga tgattttttga    2280 tctattaaca gatatataaa tgcaaaaact gcataaccac tttaactaat actttcaaca    2340
ttttcggttt gtattacttc ttattcaaat gtaataaaag tatcaacaaa aaattgttaa    2400
tatacctcta tactttaacg tcaaggagcc gcggccacca tgacagatcg ttgtccaggt    2460
agggatgctc cacacttagc agtcattgga gcaggtccag ctggcttagc agcagcatta    2520
gctgctgctg ctagaggtgt tcgtgtaacc ttgttggatg ctgaaccaga agcaggaggc    2580
caattctata gacagccagc agcagcttta cgtgctagaa ggccacaagc attacaccat    2640
cagtggcgta cctttgccag attgagacac ggattagcca ggcacattgc agcaggtaga    2700
gttagacatg ctagagaaca ccatgtttgg tttgctgaga gagctcctga tggtggattc    2760
accgttcatg ctttgactgg tccaggtaga ggagatccag cagaagtgag agcagatgca    2820
gtcttgttgg caactggtgg tcacgagact gtgttgccat tcccaggttg gaccttgcca    2880
ggtgttgtca cagctggagg tgcccaagcc atgttgaagg caggtttagt tacatctggc    2940
aacaccgcag tcgtagctgg tactggtcca ttgttgttgc cagtagctac aggtttagct    3000
gctgctggtg ttgacgtaag agcattagtc gaaagtgctg atcctggtgc cttaccaaga    3060
caggcacgtg ctttggcagc tcaacctggc aagttggctg aaggtgcttt gtatgctggt    3120
caattgttga ggcacagagt gcgtgtcttg actagacaca ctgtcgttga agcacatggt    3180
acagagaggt tggaagcagt tactgttgca gccttggatg caggtggacg tactagacct    3240
ggcactgcta aagaatagc atgtgcaact ttagctgtgg gtcatggtat gttgccacat    3300
acagacttgg cagacgcctt aggctgccgt ttagcaggtc cagcagttca tgcagatgat    3360
gaacaaagaa ctgatgttcc tggtgtgtgg gcagcaggag agtgtactgg cgtaggtggt    3420
gcagctttgt ctttggctga gggtcatatc gctggcagaa gtgcagcagc cagattgtta    3480
ggagcacctc caggtcccga cgcatggcca gaggcagcta aacaagagc aaggttgaga    3540 gctttctccg ctgtattgga tgctgtttac actcctcctc ctggttgggg tgagagagtc    3600
accgacgcaa ccgttgtatg caggtgtgaa gaagttacag caggtgcaat ccgtgcttct    3660
gtgagggaat tgggagctgg tgacgtacgt actgtaaagt tgttgactag agctggcatg    3720
ggatggtgtc agggaagaat gtgtgctcct gctgtcgctg gattggcagg ttgtgctttc    3780
actcctagtc gtagaccatt cgctaggcca gtgccttttgg gagtgttggc cagagctggt    3840
gaagatgcag gtggcgatgg aggcagagct gaggatcaag gtgaaggaga tggacgtgct    3900
gctggagcag gaggttgatt aattaatcat gtaattagtt atgtcacgct acattcacg    3960 ccctccccc acatccgctc taaccgaaaa ggaaggagtt agacaacctg aagtctaggt    4020
ccctatttat ttttttatag ttatgttagt attaagaacg ttatttatat ttcaaatttt    4080 tcttttttt ctgtacagac gcgtgtacgc atgtaacatt atactgaaaa ccttgcttga    4140
gaaggttttg gacgctcga aggctttaat ttgccggatt agaagccgcc gagcgggtga    4200
cagccctccg aaggaagact ctcctccgtg cgtcctcgtc ttcaccggtc gcgttcctga    4260
aacgcagatg tgcctcgcgc cgcactgctc cgaacaataa agattctaca atactagctt    4320
ttatggttat gaagaggaaa aattggcagt aacctgccc cacaaaccctt caaatgaacg    4380 aatcaaatta acaaccatag gatgataatg cgattagtt tttagcctta tttctgggtg    4440
aattaatcag cgaagcgatg attttttgatc tattaacaga tatataaatg caaaaactgc    4500
ataaccactt taactaatac tttcaacatt ttcggttttgt attacttctt attcaaatgt    4560
aataaaagta tcaacaaaaa attgttaata tacctctata ctttaacgtc aaggagggcg    4620
```

```
cgccaccatg cttgtcacag tggtagtact gggtctactg gggtttgctt ctgcagccca    4680
gcccaagttt gaatttgtag aagaatggca gctgtggaag tccactcact ctaagatgta    4740
cgagtcacag ttaatggaac tcgaaagaca tctgacgtgg ctctccaata agaaatatat    4800
cgagcaacac aatgtcaact cacacatttt cggttttact ctggcaatga accagtttgg    4860
agatctgagt gaattggagt atgctaacta tcttggccag tatcgcattg aggataaaaa    4920
atctggcaac tactcaaaga cttttcagcg tgatcctcta caggactacc ctgaagctgt    4980
agactggaga accaaaggag ctgtcacggc tgtcaaggac cagggagact gtggtgctag    5040
ctatgctttc agtgctatgg gtgctttgga gggtgctaat gctttagcca agggaaatgc    5100
agtatctctc agtgaacaga acatcattga ttgctcgatt ccttacggta accacggttg    5160
tcatggaggc aatatgtatg atgctttttt gtatgtcatc gctaacgagg gggtcgatca    5220
ggacagtgca tatccatttg taggaaagca atccagctgc aactataata gtaaatacaa    5280
aggtacatca atgtcgggga tggtgtcaat caaaagtggt agtgagtctg acttacaagc    5340
agctgtttca aacgttggcc ctgtatctgt tgctattgat ggtgctaaca gtgccttcag    5400
gttttactac agtggtgtct atgactcatc acgatgctct agtagtagtc ttaaccacgc    5460
aatggtagtc actggatacg gatcatacaa tgggaaaaaa tactggctgg ccaagaatag    5520
ctggggaact aactgggta acagtggcta tgtgatgatg gctcgcaaca agtacaacca    5580
gtgtggaatt gctaccgatg catcttatcc caccctataa gtttaaactc atgtaattag    5640
ttatgtcacg cttacattca cgccctcccc ccacatccgc tctaaccgaa aggaaggag    5700 ttagacaacc tgaagtctag gtccctattt atttttttat agttatgtta gtattaagaa    5760
cgttatttat atttcaaatt tttcttttt ttctgtacag acgcgtgtac gcatgtaaca    5820
ttatactgaa aaccttgctt gagaaggttt tgggacgctc gaaggcttta atttgccgga    5880
ttagaagccg ccgagcgggt gacagccctc cgaaggaaga ctctcctccg tgcgtcctcg    5940
tcttcaccgg tcgcgttcct gaaacgcaga gtgcctcgc gccgcactgc tccgaacaat    6000
aaagattcta caatactagc ttttatggtt atgaagagga aaattggca gtaacctggc    6060 cccacaaacc ttcaaatgaa cgaatcaaat taacaaccat aggatgataa tgcgattagt    6120
tttttagcct tatttctggg gtaattaatc agcgaagcga tgattttga tctattaaca    6180 gatatataaa tgcaaaaact gcataaccac tttaactaat actttcaaca ttttcggttt    6240
gtattacttc ttattcaaat gtaataaaag tatcaacaaa aaattgttaa tatacctcta    6300
tactttaacg tcaaggagct cgaggccacc atgaagctga ccgccatctt ccgcttctt    6360 ttcactgctg tcgggtactg tgctgcccaa agcattgctg acttggcagc agccaatctc    6420
agcactgagg attccaagtc agctcagctc atctcagcag actcctcgga tgacgcatct    6480
gattcctctg tcgagtctgt cgacgccgcc tcctctgacg tctctggttc ctctgtcgaa    6540
tctgtcgacg tctctggttc ctctctggaa tccgttgacg tctctggttc ctctctggag    6600
tccgtcgacg actccagtga ggactccgaa gaggaagaac ttcgtatctt gtcttccaag    6660
aaatccggat cctactactc ctacggcacc aagaagtcgg gatcctactc gggatactcc    6720
acaaagaaat ccgcatcgcg tcgcatcttg tcctccaaga atcgggatc ctactcggga    6780 tattccacaa agaaatccgg atcgcgtcgc atcttgtcct ccaagaaatc gggatcctac    6840
tcgggatcca agggttccaa gcgtcgcatc ttgtcctcca aaaaatccgg atcctactcg    6900
ggatccaagg gctccaagcg tcgcaacttg tcctccaaga atccggatc ctactcggga    6960
```

-continued

```
tccaagggtt ccaagcgtcg catcttgtcc tccaaaaaat ccggatccta ctcgggatcc    7020
aagggctcca agcgtcgcaa cttgtcctcc aagaaatccg gatcctactc gggatccaag    7080
ggttccaagc gtcgcatctt gtccgggggt ctcagaggct ccatgtaagg tacctcatgt    7140
aattagttat gtcacgctta cattcacgcc ctcccccac atccgctcta accgaaaagg     7200
aaggagttag acaacctgaa gtctaggtcc ctatttattt ttttatagtt atgttagtat    7260
taagaacgtt atttatattt caaattttc ttttttttct gtacagacgc gtgtacgcat     7320
gtaacattat actgaaaacc ttgcttgaga aggttttggg acgctcgaag ctttaattt     7380 gccggattag aagccgccga gcgggtgaca gccctccgaa ggaagactct cctccgtgcg    7440
tcctcgtctt caccggtcgc gttcctgaaa cgcagatgtg cctcgcgccg cactgctccg    7500
aacaataaag attctacaat actagctttt atggttatga agaggaaaaa ttggcagtaa    7560
cctggcccca caaaccttca aatgaacgaa tcaaattaac aaccatagga tgataatgcg    7620
attagttttt tagccttatt ctggggtaa ttaatcagcg aagcgatgat ttttgatcta     7680
ttaacagata tataaatgca aaaactgcat aaccacttta actaatactt tcaacattt     7740 cggtttgtat tacttcttat tcaaatgtaa taaaagtatc aacaaaaat tgttaatata     7800 cctctatact ttaacgtcaa ggagggatcc atgtctattc cagaaactca aaaagccatt    7860
atcttctacg aatccaacgg caagttggag cataaggata tcccagttcc aaagccaaag    7920
cccaacgaat tgttaatcaa cgtcaagtac tctggtgtct gccacaccga tttgcacgct    7980
tggcatggtg actggccatt gccaactaag ttaccattag ttggtggtca cgaaggtgcc    8040
ggtgtcgttg tcggcatggg tgaaaacgtt aagggctgga agatcggtga ctacgccggt    8100
atcaaatggt tgaacggttc ttgtatggcc tgtgaatact gtgaattggg taacgaatcc    8160
aactgtcctc acgctgactt gtctggttac acccacgacg gttctttcca agaatacgct    8220
accgctgacg ctgttcaagc cgctcacatt cctcaaggta ctgacttggc tgaagtcgcg    8280
ccaatcttgt gtgctggtat caccgtatac aaggctttga gtctgccaa cttgagagca     8340 ggccactggg cggccatttc tggtgctgct ggtggtctag gttctttggc tgttcaatat    8400
gctaaggcga tgggttacag agtcttaggt attgatggtg gtccaggaaa ggaagaattg    8460
tttacctcgc tcggtggtga agtattcatc gacttcacca agagaaggaa cattgttagc    8520
gcagtcgtta aggctaccaa cggcggtgcc cacggtatca tcaatgtttc cgttccgaa     8580 gccgctatcg aagcttctac cagatactgt agggcgaacg gtactgttgt cttggttggt    8640
ttgccagccg gtgcaaagtg ctcctctgat gtcttcaacc acgttgtcaa gtctatctcc    8700
attgtcggct cttacgtggg gaacagagct gataccagag aagccttaga ttctttgcc    8760 agaggtctag tcaagtctcc aataaaggta gttggcttat ccagtttacc agaaattac     8820 gaaagatgg agaaggccaa aatgctggt agatacgttg ttgacacttc taaataagaa     8880
ttctcatgta attagttatg tcacgcttac attcacgccc tcccccaca tccgctctaa     8940 ccgaaaagga aggagttaga caacctgaag tctaggtccc tatttatttt tttatagtta    9000
tgttagtatt aagaacgtta tttatatttc aaatttttct ttttttctg tacagacgcg    9060 tgtacgcatg taacattata ctgaaaacct tgcttgagaa ggttttggga cgctcgaagg    9120
ctttaatttg ccggattaga agccgccgag cgggtgacag ccctccgaag gaagactctc    9180
ctccgtgcgt cctcgtcttc accggtcgcg ttcctgaaac gcagatgtgc ctcgcgccgc    9240
actgctccga acaataaaga ttctacaata ctagctttta tggttatgaa gaggaaaaat    9300
tggcagtaac ctggccccac aaaccttcaa atgaacgaat caaattaaca accataggat    9360
```

-continued

```
gataatgcga ttagttttt agccttattt ctggggtaat taatcagcga agcgatgatt    9420
tttgatctat taacagatat ataaatgcaa aaactgcata accactttaa ctaatacttt    9480
caacattttc ggtttgtatt acttcttatt caaatgtaat aaaagtatca acaaaaaatt    9540
gttaatatac ctctatactt taacgtcaag gaggcggccg ccatggtgag caagggcgag    9600
gagctgttca ccggggtggt gcccatcctg gtcgagctgg acggcgacgt aaacggccac    9660
aagttcagcg tgtccggcga gggcgagggc gatgccacct acggcaagct gaccctgaag    9720
ttcatctgca ccaccggcaa gctgcccgtg ccctggccca ccctcgtgac caccttcggc    9780
tacggcctgc aatgcttcgc ccgctacccc gaccacatga gctgcacga cttcttcaag    9840 tccgccatgc ccgaaggcta cgtccaggag cgcaccatct tcttcaagga cgacggcaac    9900
tacaagaccc gcgccgaggt gaagttcgag ggcgacaccc tggtgaaccg catcgagctg    9960
aagggcatcg acttcaagga ggacggcaac atcctggggc acaagctgga gtacaactac   10020
aacagccaca acgtctatat catggccgac aagcagaaga acggcatcaa ggtgaacttc   10080
aagatccgcc acaacatcga ggacggcagc gtgcagctcg ccgaccacta ccagcagaac   10140
acccccatcg gcgacggccc cgtgctgctg cccgacaacc actacctgag ctaccagtcc   10200
gccctgagca agacccccaa cgagaagcgc gatcacatgg tcctgctgga gttcgtgacc   10260
gccgccggga tcactctcgg catggacgag ctgtacaagt aatctagagg gccgcatcat   10320
gtaattagtt atgtcacgct tacattcacg ccctcccccc acatccgctc taaccgaaaa   10380
ggaaggagtt agacaacctg aagtctaggt ccctatttat tttttatag ttatgttagt    10440 attaagaacg ttatttatat ttcaaatttt tcttttttt ctgtacagac gcgtgtacgc    10500
atgtaacatt atactgaaaa ccttgcttga aaggttttg gacgctcga aggctttaat    10560 ttgcggccct gcattaatga atcggccaac gcgcgggag aggcggtttg cgtattgggc    10620
gctcttccgc ttcctcgctc actgactcgc tgcgctcggt cgttcggctg cggcgagcgg   10680
tatcagctca ctcaaaggcg gtaatacggt tatccacaga atcaggggat aacgcaggaa   10740
agaacatgtg agcaaaaggc cagcaaaagc ccaggaaccg taaaaaggcc gcgttgctgg   10800 cgttttttcca taggctccgc cccccctgacg agcatcacaa aaatcgacgc tcaagtcaga   10860
ggtggcgaaa cccgacagga ctataaagat accaggcgtt tcccctgga agctccctcg    10920 tgcgctctcc tgttccgacc ctgccgctta ccggatacct gtccgccttt ctcccttcgg   10980
gaagcgtggc gctttctcat agctcacgct gtaggtatct cagttcggtg taggtcgttc   11040
gctccaagct gggctgtgtg cacgaacccc ccgttcagcc cgaccgctgc gccttatccg   11100
gtaactatcg tcttgagtcc aacccggtaa gacacgactt atcgccactg gcagcagcca   11160
ctggtaacag gattagcaga gcgaggtatg taggcggtgc tacagagttc ttgaagtggt   11220
ggcctaacta cggctacact agaaggacag tatttggtat ctgcgctctg ctgaagccag   11280
ttaccttcgg aaaaagagtt ggtagctctt gatccggcaa acaaaccacc gctggtagcg   11340
gtggtttttt tgtttgcaag cagcagatta cgcgcagaaa aaaaggatct caagaagatc   11400
ctttgatctt ttctacgggg tctgacgctc agtggaacga aaactcacgt taagggattt   11460
tggtcatgag attatcaaaa aggatcttca cctagatcct tttaaattaa aaatgaagtt   11520
ttaaatcaat ctaaagtata tatgagtaaa cttggtctga cagttaccaa tgcttaatca   11580
gtgaggcacc tatctcagcg atctgtctat ttcgttcatc catagttgcc tgactcccg    11640 tcgtgtagat aactacgata cgggagcgct taccatctgg ccccagtgct gcaatgatac   11700
```

```
cgcgagaccc acgctcaccg gctccagatt tatcagcaat aaaccagcca gccggaaggg   11760
ccgagcgcag aagtggtcct gcaactttat ccgcctccat ccagtctatt aattgttgcc   11820
gggaagctag agtaagtagt tcgccagtta atagtttgcg caacgttgtt ggcattgcta   11880
caggcatcgt ggtgtcactc tcgtcgtttg gtatggcttc attcagctcc ggttcccaac   11940
gatcaaggcg agttacatga tcccccatgt tgtgcaaaaa agcggttagc tccttcggtc   12000
ctccgatcgt tgtcagaagt aagttggccg cagtgttatc actcatggtt atggcagcac   12060
tgcataattc tcttactgtc atgccatccg taagatgctt ttctgtgact ggtgagtact   12120
caaccaagtc attctgagaa tagtgtatgc ggcgaccgag ttgctcttgc ccggcgtcaa   12180
tacgggataa tagtgtatca catagcagaa ctttaaaagt gctcatcatt ggaaaacgtt   12240
cttcggggcg aaaactctca aggatcttac cgctgttgag atccagttcg atgtaaccca   12300
ctcgtgcacc caactgatct tcagcatctt ttactttcac cagcgtttct gggtgagcaa   12360
aaacaggaag gcaaaatgcc gcaaaaaagg gaataagggc gacacggaaa tgttgaatac   12420
tcatactctt ccttttcaa tgggtaataa ctgatataat taaattgaag ctctaatttg   12480
tgagtttagt atacatgcat ttacttataa tacagttttt tagttttgct ggccgcatct   12540
tctcaaatat gcttcccagc ctgcttttct gtaacgttca ccctctacct tagcatccct   12600
tccctttgca aatagtcctc ttccaacaat aataatgtca gatcctgtag agaccacatc   12660
atccacggtt ctatactgtt gacccaatgc gtctcccttg tcatctaaac ccacaccggg   12720
tgtcataatc aaccaatcgt aaccttcatc tcttccaccc atgtctcttt gagcaataaa   12780
gccgataaca aaatctttgt cgctcttcgc aatgtcaaca gtacccttag tatattctcc   12840
agtagatagg gagcccttgc atgacaattc tgctaacatc aaaaggcctc taggttcctt   12900
tgttacttct tctgccgcct gcttcaaacc gctaacaata cctgggccca ccacaccgtg   12960
tgcattcgta atgtctgccc attctgctat tctgtataca cccgcagagt actgcaattt   13020
gactgtatta ccaatgtcag caaatttct gtcttcgaag agtaaaaaat tgtacttggc   13080
ggataatgcc tttagcggct taactgtgcc ctccatggaa aaatcagtca agatatccac   13140
atgtgttttt agtaaacaaa ttttgggacc taatgcttca actaactcca gtaattcctt   13200
ggtggtacga acatccaatg aagcacacaa gtttgtttgc ttttcgtgca tgatattaaa   13260
tagcttggca gcaacaggac taggatgagt agcagcacgt tccttatatg tagctttcga   13320
catgatttat cttcgtttcc tgcaggtttt tgttctgtgc agttgggtta agaatactgg   13380
gcaatttcat gttcttcaa cactacatat gcgtatatat accaatctaa gtctgtgctc   13440
cttccttcgt tcttccttct gttcggagat taccgaatca aaaaaatttc aaagaaaccg   13500
aaatcaaaaa aaagaataaa aaaaaatga tgaattgaat tgaaaagcta gcttatcgat   13560
gataagctgt caaagatgag aattaattcc acggactata gactatacta gatactccgt   13620
ctactgtacg atacacttcc gctcaggtcc ttgtcctta acgaggcctt accactcttt   13680
tgttactcta ttgatccagc tcagcaaagg cagtgtgatc taagattcta tcttcgcgat   13740
gtagtaaaac tagctagacc gagaaagaga ctagaaatgc aaaaggcact tctacaatgg   13800
ctgccatcat tattatccga tgtgacgctg cagcttctca atgatattcg aatacgctttt   13860 gaggagatac agcctaatat ccgacaaact gttttacaga tttacgatcg tacttgttac   13920
ccatcattga attttgaaca tccgaacctg ggagttttcc ctgaaacaga tagtatattt   13980
gaacctgtat aataatatat agtctagcgc tttacggaag acaatgtatg tatttcggtt   14040
cctggagaaa ctattgcatc tattgcatag gtaatcttgc acgtcgcatc cccggttcat   14100
```

-continued

```
tttctgcgtt tccatcttgc acttcaatag catatctttg ttaacgaagc atctgtgctt    14160
cattttgtag aacaaaaatg caacgcgaga gcgctaattt ttcaaacaaa gaatctgagc    14220 tgcatttta cagaacagaa atgcaacgcg aaagcgctat tttaccaacg aagaatctgt    14280
gcttcatttt tgtaaaacaa aaatgcaacg cgacgagagc gctaattttt caaacaaaga    14340
atctgagctg catttttaca gaacagaaat gcaacgcgag agcgctattt taccaacaaa    14400
gaatctatac ttcttttttg ttctacaaaa atgcatcccg agagcgctat ttttctaaca    14460
aagcatctta gattactttt tttctccttt gtgcgctcta taatgcagtc tcttgataac    14520 ttttgcact gtaggtccgt taaggttaga agaaggctac tttggtgtct attttctctt    14580
ccataaaaaa agcctgactc cacttcccgc gtttactgat tactagcgaa gctgcgggtg    14640 catttttca agataaaggc atccccgatt atattctata ccgatgtgga ttgcgcatac    14700
tttgtgaaca gaaagtgata gcgttgatga ttcttcattg gtcagaaaat tatgaacggt    14760
ttcttctatt ttgtctctat atactacgta taggaaatgt ttacattttc gtattgtttt    14820
cgattcactc tatgaatagt tcttactaca attttttttgt ctaaagagta atactagaga    14880
taaacataaa aaatgtagag gtcgagttta gatgcaagtt caaggagcga aaggtggatg    14940
ggtaggttat atagggatat agcacagaga tatatagcaa agagatactt ttgagcaatg    15000
tttgtggaag cggtattcgc aatgggaagc tccaccccgg ttgataatca gaaaagcccc    15060
aaaaacagga agattgtata agcaaatatt taaattgtaa acgttaatat tttgttaaaa    15120
ttcgcgttaa attttgtta aatcagctca ttttttaacg aatagcccga aatcggcaaa    15180
atcccttata aatcaaaaga atagaccgag atagggttga gtgttgttcc agtttccaac    15240
aagagtccac tattaaagaa cgtggactcc aacgtcaaag ggcgaaaaag ggtctatcag    15300
ggcgatggcc cactacgtga accatcaccc taatcaagtt ttttgggtc gaggtgccgt    15360 aaagcagtaa atcggaaggg taacggatg cccccattta gagcttgacg gggaaagccg    15420
gcgaacgtgg cgagaaagga agggaagaaa gcgaaaggag cggggggctag ggcggtggga    15480 agtgtagggg tcacgctggg cgtaaccacc acacccgccg cgcttaatgg ggcgctacag    15540
ggcgcgtggg gatgatccac tagt                                         15564
```

<210> SEQ ID NO 18
<211> LENGTH: 14634
<212> TYPE: DNA
<213> ORGANISM: Artificial sequence
<220> FEATURE:
<223> OTHER INFORMATION: Synthetic construct

<400> SEQUENCE: 18

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240 ttagttttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttgcca ccatgagtga tcaaaataat cgatcgagaa     540
```

```
atgaatatca ctcaaaccgg aagaatgaac cttcctatga actccaaaat gcacatagcg    600
ggctatttca ctcttctaat gaagaattaa caaacaggaa ccaaagatat accaatcaaa    660
atgccagcat gggttcattc actccagtcc aatctttgca atttccagaa caatctcagc    720
aaacaaatat gctttataac ggtgacgatg caataataa tactatcaat gataacgaac    780
gagacatata tggaggtttt gtcaaccacc atcgccagcg tcccccacca gcaactgcag    840
aatacaatga cgtttttaat acgaatagtc aacagctacc gtcggaacat caatacaata    900
acgtaccttc atatccactt ccttcgataa atgtgattca aaccactcca gaactcatac    960
ataacggctc acagactatg gccaccccca tcgaaaggcc cttctttaac gaaaacgact   1020
actattataa taacaggaac tctaggacgt caccgagtat tgcttctagt agcgatggtt   1080
atgcagatca ggaagctagg cccatttttgg agcaacccaa caataacatg aatagcggta   1140
atattcctca ataccatgac caaccttttg gatacaacaa tggttaccat ggcctacagg   1200
caaaagatta ctatgacgat ccggagggtg gttatattga tcagagagga gatgactatc   1260
agattaattc atatttgggt agaaacggtg aaatggttga tccttacgat tatgaaaaca   1320
gtttaagaca tatgactcct atggagcgta gagaatatct tcatgatgat agcagacccg   1380
taaacgatgg aaaagaagaa ttagacagtg tgaaaagcgg ttactctcat agagacttgg   1440
gggaatatga caaggatgat tttcaaggg atgacgagta cgatgatctc aacactattg   1500
ataaattaca gtttcaagct aatggtgtac ctgcatcatc ctcggtgtct tctatcggat   1560
ctaaagaatc cgacataata gtaagcaatg ataacttaac cgcaaataga gcactaaaga   1620
gaagcggtac tgaaattagg aaattcaaac tttggaatgg taattttgtt ttcgattctc   1680
caatcagtaa gacgctattg gaccaatacg ctactacaac agaaaatgca aacactttac   1740
caaatgagtt taagttttatg agatatcaag cagttacttg cgaacctaat caacttgcag   1800
agaagaattt cacggtgagg cagttgaagt atttaactcc aagggaaacg gaattgatgc   1860
tagtagtcac aatgtataat gaagaccata tcctgttagg aagaactttg aaaggtatta   1920
tggacaatgt caaatatatg gtgaaaaaaa aaaattcaag cacttggggg ccggatgcat   1980
ggaaaaagat tgtcgtttgt atcatttcag atggtagatc caaaattaat gaacgctcgc   2040
tagcattact aagttcgtta ggttgttacc aggacgggtt tgctaaggat gaaattaatg   2100
aaaaaaaagt ggcaatgcat gtctacgaac atacgacaat gatcaacatc acaaatattt   2160
cggaatcaga ggtttcatta gaatgcaatc aaggtactgt tccaatacaa cttttgtttt   2220
gtttgaaaga gcaaaatcag aaaaaaatta actcacatag atgggcattt gaaggctttg   2280
cagaattact gcgtcccaat atcgttacat tgttagatgc tggtactatg ccaggtaaag   2340
attctattta ccagttatgg agagagttca ggaatccaaa tgttggtggc gcatgtggtg   2400
aaataagaac tgatttgggt aagagatttg taaagttgtt gaatccttta gttgcatcac   2460
agaatttcga atacaaaatg tccaatatt tagacaaaac aaccgagtct aactttggat   2520
ttattactgt tctaccgggg gcattctctg cgtataggtt tgaagctgtg agaggccaac   2580
cattacagaa gtacttttat ggtgaaatta tggaaaatga aggttttcat ttttttttctt   2640 ccaatatgta tcttgctgaa gatcgtattt tatgctttga agtggtcaca aaaaaaaatt   2700
gtaattggat tttgaaatac tgcagaagtt cttatgcttc aacagatgta ccggagaggg   2760
tccctgaatt tattcttcag aggaggcgtt ggttgaatgg ttcatttttt gctagtgtat   2820
attccttttg tcattttttac agagtctgga gcagtggtca taatattggt agaaaactcc   2880
ttttgacggt tgaatttttt taccttttct tcaatacatt gatttcatgg ttttcattga   2940
```

```
gttcattttt cctagtcttt aggattctca ctgtttctat tgcactggca taccattcag    3000
catttaatgt gttgtccgtc atattcctgt ggctttatgg gatttgtacc ttatcaacat    3060
tcatactgtc attgggtaat aaacctaaaa gtactgagaa attttatgtt ctaacttgcg    3120
tcatttttgc ggtgatgatg atttacatga tattctgcag tatattcatg agtgtcaaat    3180
ccttccaaaa tatattgaaa aacgatacca tcagctttga gggtttgatt accacagagg    3240
ctttcaggga tattgttatc tctctgggct ccacttattg tttgtaccta atcagttcaa    3300 ttatctatt gcagccatgg catatgttga caagtttat tcagtatatt ttattgagtc       3360
cttcttacat caatgttttg aatatctatg cattttgtaa tgtccacgac ttatcatggg    3420
gtacaaaggg tgcaatggca atccgctgg gtaagattaa tactacagaa gatggtacgt      3480
tcaaaatgga agttctggtc tctagttcag agattcaagc aaactacgat aaatatttga    3540
aagttttaaa tgacttcgat ccaaaatcag aatctcggcc tactgagcca tcttatgatg    3600
aaaaaaagac tggctattat gcaaacgtta gatctctcgt gattatcttt tgggtcatca    3660
caaatttcat catcgttgct gttgtcttag aaaccggtgg gattgcagat tatattgcta    3720
tgaaatccat atcaactgat gacactttag aaactgcaaa gaaggcggaa attcccttaa    3780
tgaccagtaa ggcctcaatt tattttaatg taattttatg gttagttgca ttatcggcat    3840
taataaggtt cattggttgc tcaatataca tgatagtaag gttttttaaa aaggttacat    3900
ttcgctaagg tacctcatgt aattagttat gtcacgctta cattcacgcc ctcccccac     3960 atccgctcta accgaaaagg aaggagttag acaacctgaa gtctaggtcc ctatttattt    4020
ttttatagtt atgttagtat taagaacgtt atttatattt caaattttc tttttttct      4080 gtacagacgc gtgtacgcat gtaacattat actgaaaacc ttgcttgaga aggttttggg    4140
acgctcgaag gctttaattt gccggattag aagccgccga gcgggtgaca gccctccgaa    4200
ggaagactct cctccgtgcg tcctcgtctt caccggtcgc gttcctgaaa cgcagatgtg    4260
cctcgcgccg cactgctccg aacaataaag attctacaat actagctttt atggttatga    4320
agaggaaaaa ttggcagtaa cctggcccca caaaccttca aatgaacgaa tcaaattaac    4380
aaccatagga tgataatgcg attagttttt tagcctatt tctggggtaa ttaatcagcg     4440
aagcgatgat ttttgatcta ttaacagata tataaatgca aaaactgcat aaccacttta    4500
actaatactt tcaacatttt cggtttgtat tacttcttat tcaaatgtaa taaaagtatc    4560
aacaaaaaat tgttaatata cctctatact ttaacgtcaa ggagggatcc gccaccatgt    4620
cactccttta catcattctt ctattcacac aattcttact actgccaacc gatgcctttg    4680
ataggtctgc taacacaaat attgctgttt attggggtca aaactcagca ggaacgcaag    4740
aatccttagc tacttactgt gaatcttctg atgctgatat tttcctatta tctttcttga    4800
accaatttcc aacccttggt ttgaactttg ccaacgcatg ctctgatact ttttctgatg    4860
gcttacttca ctgcacccag attgctgaag atattgaaac ttgccagtcc ctaggaagaa    4920
aagttctatt atcattaggt ggtgcatctg gtagctacct cttttcagat gattctcaag    4980
cggaaacttt tgcacaaact ttatgggata cttttcggtga aggtacaggt gccagtgaga    5040
gaccatttga ctcagcagtc gttgatggtt ttgattttga tattgaaaac aacaacgaag    5100
taggctatag tgcgttagct accaagttaa gaactttgtt tgccgaaggt acaaagcaat    5160 attaccttc tgccgcacca caatgtccat acccggatgc ttctgttggt gacttgttgg    5220
aaaatgcaga cattgatttt gcgttcatcc aatttttacaa taattactgc agtgtgagtg    5280
```

-continued

```
gtcaattcaa ttgggatact tggttaacct atgctcaaac tgtatcccca aataaaaata    5340
tcaaactgtt cttaggttta cctggttctg cttctgctgc tggctctggt tatatttctg    5400
acacttcttt attggaatca actattgcag atattgcctc ttcaagttct tttggtggta    5460
ttgcgttatg ggatgcatct caagcctttt ccaacgagct aaatggtgaa ccatatgttg    5520
agattttgaa gaatttgcta caagtgcta gccagaccgc cactactaca gttgccacct    5580
caaaaacctc agcagcctca acttcatctg cttcaacttc atctgcttca acttctcaga    5640
aaaagaccac acaatctacg acatctacac aaagtaaaag caaagttact ttatctccaa    5700
ctgcaagcag cgctatcaaa acatcaatta ctcaaactac aaaaacattg acgagtagca    5760
ccaagacaaa atctagtcta ggtaccacca aacagagag cactttaaat tcagttgcta    5820
tcacaagtat gaaaactact ctatcttccc aaataaccag tgctgccttg gtgaccctc    5880 aaacaactac tactagcata gtttcttcgg ccccaattca aacagctatc actagtactc    5940
tttcgccagc aacgaagagt tcttctgtcg tttccctaca gacagctact actagtacgc    6000
tttccccaac aacgaccagt acaagctcag gtagtacaag ctcaggtagt acaagctcag    6060
acagtacagc tcgtacattg gctaaagaat tgaatgctca atatgcggct ggtaaattga    6120
acggtaaatc tacctgtact gaaggtgaaa ttgcatgctc tgctgatggg aagttcgccg    6180
tttgtgatca tagcgcttgg gtttacatgg aatgtgcttc tggaaccaca tgttatgctt    6240
atgactccgg cgactcagtc tatacccaat gtaatttctc ttatttggaa agcaattact    6300
tttaattaat catgtaatta gttatgtcac gcttacattc acgccctccc cccacatccg    6360
ctctaaccga aaaggaagga gttagacaac ctgaagtcta ggtccctatt tattttttta    6420
tagttatgtt agtattaaga acgttattta tatttcaaat ttttcttttt tttctgtaca    6480
gacgcgtgta cgcatgtaac attatactga aaaccttgct tgagaaggtt ttgggacgct    6540
cgaaggcttt aatttgccgg attagaagcc gccgagcggg tgacagccct ccgaaggaag    6600
actctcctcc gtgcgtcctc gtcttcaccg gtcgcgttcc tgaaacgcag atgtgcctcg    6660
cgccgcactg ctccgaacaa taaagattct acaatactag ctttatggt tatgaagagg    6720 aaaaattggc agtaacctgg ccccacaaac cttcaaatga acgaatcaaa ttaacaacca    6780
taggatgata atgcgattag ttttttagcc ttatttctgg ggtaattaat cagcgaagcg    6840 atgattttg atctattaac agatatataa atgcaaaaac tgcataacca ctttaactaa    6900
tactttcaac attttcggtt tgtattactt cttattcaaa tgtaataaaa gtatcaacaa    6960
aaaattgtta atatacctct atactttaac gtcaaggagc tcgagatgag aatacaacta    7020
aatacaattg atttgcaatg tattattgca ctttcctgtc tggggcaatt tgttcacgcg    7080
gaagctaata gggaagattt aaagcagata gactttcaat ttcctgtatt ggaaagggca    7140
gctacaaaaa cgccttttcc ggattggctt agtgcattta ccgggttaaa agaatggcct    7200
gggttagatc caccttatat acctttagat ttcattgatt tcagtcaaat tccagattat    7260
aaggaatatg atcaaaacca ttgcgacagt gttccaaggg actcgtgctc tttcgattgc    7320
catcactgca ccgaacacga tgatgtgtac acatgttcca aactttccca gacatttgac    7380
gatggtcctt ctgcttccac tactaaatta ttggaccggt tgaagcataa ttccaccttc    7440
ttcaatttag gtgtcaatat agttcaacat ccagatatct atcaaagaat gcaaaaggag    7500
ggacacttaa tcggctcaca tacctggtct cacgtatatt tgccaaatgt atcgaatgaa    7560
aaaattatag ctcaaattga atggtccatc tgggcgatga atgctactgg caaccatacc    7620
cccaaatggt tcagacctcc atatggcgga atagataata gagtaagagc aataacaagg    7680
```

```
caatttggct tacaagccgt cttatgggat cacgatactt ttgattggag cctccttctc    7740
aatgattctg tcataactga acaagaaatt cttcaaaatg taataaactg aacaagtca     7800 ggaaccggat taatattaga acacgattca acggaaaaaa ctgtcgatct tgccattaaa    7860
ataaataagt tgataggtga tgatcaatca acagtttctc attgtgtcgg cggaattgat    7920
tacataaaag aattcttgtc ctaagaattc tcatgtaatt agttatgtca cgcttacatt    7980
cacgccctcc ccccacatcc gctctaaccg aaaaggaagg agttagacaa cctgaagtct    8040
aggtccctat ttatttttt atagttatgt tagtattaag aacgttattt atatttcaaa     8100
tttttctttt ttttctgtac agacgcgtgt acgcatgtaa cattatactg aaaaccttgc    8160
ttgagaaggt tttgggacgc tcgaaggctt taatttgccg gattagaagc cgccgagcgg    8220
gtgacagccc tccgaaggaa gactctcctc cgtgcgtcct cgtcttcacc ggtcgcgttc    8280
ctgaaacgca gatgtgcctc gcgccgcact gctccgaaca ataaagattc tacaatacta    8340
gcttttatgg ttatgaagag gaaaaattgg cagtaacctg gccccacaaa ccttcaaatg    8400
aacgaatcaa attaacaacc ataggatgat aatgcgatta gttttttagc cttatttctg    8460
gggtaattaa tcagcgaagc gatgattttt gatctattaa cagatatata aatgcaaaaa    8520
ctgcataacc actttaacta atactttcaa cattttcggt ttgtattact tcttattcaa    8580
atgtaataaa agtatcaaca aaaaattgtt aatataccct tatactttaa cgtcaaggag    8640
gcggccgcca tggtgagcaa gggcgaggag ctgttcaccg gggtggtgcc catcctggtc    8700
gagctggacg gcgacgtaaa cggccacaag ttcagcgtgt ccggcgaggg cgagggcgat    8760
gccacctacg gcaagctgac cctgaagttc atctgcacca ccggcaagct gcccgtgccc    8820
tggcccaccc tcgtgaccac cttcggctac ggcctgcaat gcttcgcccg ctaccccgac    8880
cacatgaagc tgcacgactt cttcaagtcc gccatgcccg aaggctacgt ccaggagcgc    8940
accatcttct tcaaggacga cggcaactac aagacccgcg ccgaggtgaa gttcgagggc    9000
gacaccctgg tgaaccgcat cgagctgaag ggcatcgact tcaaggagga cggcaacatc    9060
ctggggcaca gcctggagta caactacaac agccacaacg tctatatcat ggccgacaag    9120
cagaagaacg gcatcaaggt gaacttcaag atccgccaca acatcgagga cggcagcgtg    9180
cagctcgccg accactacca gcagaacacc cccatcggcg acggccccgt gctgctgccc    9240
gacaaccact acctgagcta ccagtccgcc ctgagcaaag cccccaacga gaagcgcgat    9300
cacatggtcc tgctggagtt cgtgaccgcc gccgggatca ctctcggcat ggacgagctg    9360
tacaagtaat aatctagagg gccgcatcat gtaattagtt atgtcacgct tacattcacg    9420
ccctcccccc acatccgctc taaccgaaaa ggaaggagtt agacaacctg aagtctaggt    9480
ccctatttat tttttatag ttatgttagt attaagaacg ttatttatat ttcaaatttt     9540
tctttttttt ctgtacagac gcgtgtacgc atgtaacatt atactgaaaa ccttgcttga    9600 gaaggtttg gacgctcga aggctttaat ttgcggccct gcattaatga atcggccaac      9660
gcgcggggag aggcggtttg cgtattgggc gctcttccgc ttcctcgctc actgactcgc    9720
tgcgctcggt cgttcggctg cggcgagcgg tatcagctca ctcaaaggcg gtaatacggt    9780
tatccacaga atcaggggat aacgcaggaa agaacatgtg agcaaaaggc cagcaaaagc    9840
ccaggaaccg taaaaaggcc gcgttgctgg cgttttttcca taggctccgc cccctgacg    9900 agcatcacaa aaatcgacgc tcaagtcaga ggtggcgaaa cccgacagga ctataaagat    9960
accaggcgtt tccccctgga agctccctcg tgcgctctcc tgttccgacc ctgccgctta   10020
```

```
ccggatacct gtccgccttt ctcccttcgg gaagcgtggc gctttctcat agctcacgct    10080
gtaggtatct cagttcggtg taggtcgttc gctccaagct gggctgtgtg cacgaaccct    10140
ccgttcagcc cgaccgctgc gccttatccg gtaactatcg tcttgagtcc aacccggtaa    10200
gacacgactt atcgccactg gcagcagcca ctggtaacag gattagcaga gcgaggtatg    10260
taggcggtgc tacagagttc ttgaagtggt ggcctaacta cggctacact agaaggacag    10320
tatttggtat ctgcgctctg ctgaagccag ttaccttcgg aaaaagagtt ggtagctctt    10380
gatccggcaa acaaaccacc gctggtagcg gtggtttttt tgtttgcaag cagcagatta    10440
cgcgcagaaa aaaaggatct caagaagatc ctttgatctt ttctacgggg tctgacgctc    10500
agtggaacga aaactcacgt taagggattt tggtcatgag attatcaaaa aggatcttca    10560
cctagatcct tttaaattaa aaatgaagtt ttaaatcaat ctaaagtata tatgagtaaa    10620
cttggtctga cagttaccaa tgcttaatca gtgaggcacc tatctcagcg atctgtctat    10680
ttcgttcatc catagttgcc tgactccccg tcgtgtagat aactacgata cgggagcgct    10740
taccatctgg ccccagtgct gcaatgatac cgcgagaccc acgctcaccg gctccagatt    10800
tatcagcaat aaaccagcca gccggaaggg ccgagcgcag aagtggtcct gcaactttat    10860
ccgcctccat ccagtctatt aattgttgcc gggaagctag agtaagtagt tcgccagtta    10920
atagtttgcg caacgttgtt ggcattgcta caggcatcgt ggtgtcactc tcgtcgtttg    10980
gtatggcttc attcagctcc ggttcccaac gatcaaggcg agttacatga tcccccatgt    11040
tgtgcaaaaa agcggttagc tccttcggtc ctccgatcgt tgtcagaagt aagttggccg    11100
cagtgttatc actcatggtt atggcagcac tgcataattc tcttactgtc atgccatccg    11160
taagatgctt ttctgtgact ggtgagtact caaccaagtc attctgagaa tagtgtatgc    11220
ggcgaccgag ttgctcttgc ccggcgtcaa tacgggataa tagtgtatca catagcagaa    11280
ctttaaaagt gctcatcatt ggaaaacgtt cttcggggcg aaaactctca aggatcttac    11340
cgctgttgag atccagttcg atgtaaccca ctcgtgcacc caactgatct tcagcatctt    11400
ttactttcac cagcgtttct gggtgagcaa aaacaggaag gcaaaatgcc gcaaaaaagg    11460
gaataagggc gacacggaaa tgttaatac tcatactctt ccttttcaa tgggtaataa    11520 ctgatataat taaattgaag ctctaatttg tgagtttagt atacatgcat ttacttataa    11580
tacagttttt tagttttgct ggccgcatct tctcaaatat gcttcccagc ctgcttttct    11640
gtaacgttca ccctctacct tagcatccct tccctttgca aatagtcctc ttccaacaat    11700
aataatgtca gatcctgtag agaccacatc atccacggtt ctatactgtt gacccaatgc    11760
gtctcccttg tcatctaaac ccacaccggg tgtcataatc aaccaatcgt aaccttcatc    11820
tcttccaccc atgtctcttt gagcaataaa gccgataaca aaatctttgt cgctcttcgc    11880
aatgtcaaca gtacccttag tatattctcc agtagatagg gagcccttgc atgacaattc    11940
tgctaacatc aaaaggcctc taggttcctt tgttacttct tctgccgcct gcttcaaacc    12000
gctaacaata cctgggccca ccacccgtg tgcattcgta atgtctgccc attctgctat    12060
tctgtataca cccgcagagt actgcaattt gactgtatta ccaatgtcag caaattttct    12120
gtcttcgaag agtaaaaat tgtacttggc ggataatgcc tttagcggct taactgtgcc    12180
ctccatggaa aaatcagtca agatatccac atgtgttttt agtaaacaaa ttttgggacc    12240
taatgcttca actaactcca gtaattcctt ggtggtacga acatccaatg aagcacacaa    12300
gtttgtttgc ttttcgtgca tgatattaaa tagcttggca gcaacaggac taggatgagt    12360
agcagcacgt tccttatatg tagctttcga catgatttat cttcgtttcc tgcaggtttt    12420
```

```
tgttctgtgc agttgggtta agaatactgg gcaatttcat gtttcttcaa cactacatat   12480
gcgtatatat accaatctaa gtctgtgctc cttccttcgt tcttccttct gttcggagat   12540
taccgaatca aaaaaatttc aaagaaaccg aaatcaaaaa aagaataaa aaaaaaatga    12600
tgaattgaat tgaaaagcta gcttatcgat gataagctgt caaagatgag aattaattcc   12660
acggactata gactatacta gatactccgt ctactgtacg atacacttcc gctcaggtcc   12720
ttgtccttta acgaggcctt accactcttt tgttactcta ttgatccagc tcagcaaagg   12780
cagtgtgatc taagattcta tcttcgcgat gtagtaaaac tagctagacc gagaaagaga   12840
ctagaaatgc aaaaggcact tctacaatgg ctgccatcat tattatccga tgtgacgctg   12900
cagcttctca atgatattcg aatacgcttt gaggagatac agcctaatat ccgacaaact   12960
gttttacaga tttacgatcg tacttgttac ccatcattga atttgaaca tccgaacctg    13020
ggagttttcc ctgaaacaga tagtatattt gaacctgtat aataatatat agtctagcgc   13080
tttacggaag acaatgtatg tatttcggtt cctggagaaa ctattgcatc tattgcatag   13140
gtaatcttgc acgtcgcatc cccggttcat tttctgcgtt tccatcttgc acttcaatag   13200
catatctttg ttaacgaagc atctgtgctt cattttgtag aacaaaaatg caacgcgaga   13260
gcgctaattt ttcaaacaaa gaatctgagc tgcatttta cagaacagaa atgcaacgcg    13320
aaagcgctat tttaccaacg aagaatctgt gcttcatttt tgtaaaacaa aaatgcaacg   13380
cgacgagagc gctaatttt caaacaaaga atctgagctg cattttaca gaacagaaat     13440
gcaacgcgag agcgctattt taccaacaaa gaatctatac ttcttttttg ttctacaaaa   13500
atgcatcccg agagcgctat ttttctaaca aagcatctta gattactttt tttctccttt   13560
gtgcgctcta taatgcagtc tcttgataac tttttgcact gtaggtccgt taaggttaga   13620
agaaggctac tttggtgtct attttctctt ccataaaaaa agcctgactc cacttcccgc   13680
gtttactgat tactagcgaa gctgcgggtg catttttca agataaaggc atccccgatt    13740
atattctata ccgatgtgga ttgcgcatac tttgtgaaca gaaagtgata gcgttgatga   13800
ttcttcattg gtcagaaaat tatgaacggt ttcttctatt ttgtctctat atactacgta   13860
taggaaatgt ttacatttc gtattgtttt cgattcactc tatgaatagt tcttactaca    13920
attttttgt ctaaagagta atactagaga taaacataaa aaatgtagag gtcgagttta    13980
gatgcaagtt caaggagcga aaggtggatg ggtaggttat atagggatat agcacagaga   14040
tatatagcaa agagatactt ttgagcaatg tttgtggaag cggtattcgc aatgggaagc   14100
tccacccegg ttgataatca gaaaagcccc aaaaacagga agattgtata agcaaatatt   14160
taaattgtaa acgttaatat tttgttaaaa ttcgcgttaa attttgtta aatcagctca    14220
ttttttaacg aatagcccga aatcggcaaa atcccttata aatcaaaaga atagaccgag   14280
ataggttga gtgttgttcc agtttccaac aagagtccac tattaaagaa cgtggactcc    14340
aacgtcaaag ggcgaaaaag ggtctatcag ggcgatggcc cactacgtga accatcaccc   14400
taatcaagtt ttttggggtc gaggtgccgt aaagcagtaa atcggaaggg taaacggatg   14460
cccccattta gagcttgacg gggaaagccg gcgaacgtgg cgagaaagga agggaagaaa   14520
gcgaaaggag cggggctag gcggtggga agtgtagggg tcacgctggg cgtaaccacc    14580
acacccgccg cgcttaatgg ggcgctacag ggcgcgtggg gatgatccac tagt          14634
```

<210> SEQ ID NO 19
<211> LENGTH: 16558
<212> TYPE: DNA

<213> ORGANISM: Artificial sequence
<220> FEATURE:
<223> OTHER INFORMATION: Synthetic construct

<400> SEQUENCE: 19

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagttttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttgcca ccatggtgtt tatcgtcaat cttttctcct    540
gcaccttatc tgaaaccacg gttagctcaa taaaatctga agctacggtt agctcaacat    600
ttactgccgt cacggccctg caattggtgg ctgagggtaa gttgcagtcg gcgaagggtt    660
tcggtggtgg tacgattcac tacccaaccc tcgcggccga agcaccctgg tggacgccgg    720
gccaaggcca tggttacgag gcgatcacct acggctggct ggtcggcgaa ctgctgcgcc    780
gcgccgatgg gcgtgggcct ggtctgttag gcgctattgc cgtggttcct ggttacgttt    840
cttacgagaa ctctatcaag tggtggggac cgcgtctggc ttcttggggc tttgtcgttg    900
cacggccgtt gggcctggac tttcatgtgg gcctggcgga tgaagagttt tatcgtgttg    960
cccatatagc gcgcagcaaa gccaatgcag cactagataa cattgctgat gacaccgtcg   1020
gcagtataga tcctaagcgg ttgggcgcta ttggctggtc aggtggcggc ggcgcgctta   1080
aactggcaac ggagcgcagc acagtacgag ccattttgac cagtactaat aaacctgaat   1140
ggcgacgctt cgataaattc ttatgtgcct gcgaggatga ccggattgct gagactaaga   1200
aatatgccaa cgcgttttat aaaaatgccg acatgctcga agagttgacc cgtgaacaca   1260
gtatcgggcc ggataaaaca ttattgacac aaactcggtt tggcttgggg tgcttggatc   1320
aaccgcaagc aggggttaaa attcattttg aagagtacct tgatcaaacc catggattta   1380
tcaatttgac gccagtttca cataaggcga gagcaaatct gattcagatg cctaatgcca   1440
cattcggcct tggcccgcgt gcttttgggc atcctggtgc aggtggatcg gtaggttttg   1500
ccgaccccga acacgatgta gcgtttggtt tcgtgactaa tcattgggg ccttatgtag   1560
ttgagtttaa aagccgtcat ccctcatttt atgcatataa agatggattg gtgctgactg   1620
gaaatgacgt cgactatgtg actgattact atgcaacaaa gcatgctgta catttagatg   1680
atccacgtgc acagaagttg gtcggaatat tggccggttg tctgtaaccc gggtaatcat   1740
gtaattagtt atgtcacgct tacattcacg ccctccccccc acatccgctc taaccgaaaa   1800
ggaaggagtt agacaacctg aagtctaggt ccctatttat ttttttatag ttatgttagt   1860
attaagaacg ttatttatat ttcaaatttt tctttttttt ctgtacagac gcgtgtacgc   1920
atgtaacatt atactgaaaa ccttgcttga aaggttttg ggacgctcga aggctttaat   1980
ttgccggatt agaagccgcc gagcgggtga cagccctccg aaggaagact ctcctccgtg   2040
cgtcctcgtc ttcaccggtc gcgttcctga aacgcagatg tgcctcgcgc cgcactgctc   2100
cgaacaataa agattctaca atactagctt ttatggttat gaagaggaaa aattggcagt   2160
aacctggccc cacaaaacctt caaatgaacg aatcaaatta caaccatag gatgataatg   2220
```

```
cgattagttt tttagcctta tttctggggt aattaatcag cgaagcgatg attttttgatc    2280 tattaacaga tatataaatg caaaaactgc ataaccactt taactaatac tttcaacatt    2340
ttcggtttgt attacttctt attcaaatgt aataaaagta tcaacaaaaa attgttaata    2400
tacctctata ctttaacgtc aaggaggcgc gccaccatga gtgatcaaaa taatcgatcg    2460
agaaatgaat atcactcaaa ccggaagaat gaaccttcct atgaactcca aaatgcacat    2520
agcgggctat ttcactcttc taatgaagaa ttaacaaaca ggaaccaaag atataccaat    2580
caaaatgcca gcatgggttc attcactcca gtccaatctt tgcaatttcc agaacaatct    2640
cagcaaacaa atatgcttta taacggtgac gatggcaata ataatactat caatgataac    2700
gaacgagaca tatatggagg ttttgtcaac caccatcgcc agcgtccccc accagcaact    2760
gcagaataca atgacgtttt taatacgaat agtcaacagc taccgtcgga acatcaatac    2820
aataacgtac cttcatatcc acttccttcg ataaatgtga ttcaaaccac tccagaactc    2880
atacataacg gctcacagac tatggccacc cccatcgaaa ggcccttctt taacgaaaac    2940
gactactatt ataataacag gaactctagg acgtcaccga gtattgcttc tagtagcgat    3000
ggttatgcag atcaggaagc taggcccatt ttggagcaac ccaacaataa catgaatagc    3060
ggtaatattc ctcaatacca tgaccaacct tttggataca acaatggtta ccatggccta    3120
caggcaaaag attactatga cgatccggag ggtggttata ttgatcagag aggagatgac    3180
tatcagatta attcatattt gggtagaaac ggtgaaatgg ttgatcctta cgattatgaa    3240
aacagtttaa gacatatgac tcctatggag cgtagagaat atcttcatga tgatagcaga    3300
cccgtaaacg atggaaaaga agaattagac agtgtgaaaa gcggttactc tcatagagac    3360
ttgggggaat atgacaagga tgattttca agggatgacg agtacgatga tctcaacact    3420
attgataaat tacagtttca agctaatggt gtacctgcat catcctcggt gtcttctatc    3480
ggatctaaag aatccgacat aatagtaagc aatgataact taaccgcaaa tagagcacta    3540
aagagaagcg gtactgaaat taggaaattc aaactttgga atggtaattt tgttttcgat    3600
tctccaatca gtaagacgct attggaccaa tacgctacta caacagaaaa tgcaaacact    3660
ttaccaaatg agtttaagtt tatgagatat caagcagtta cttgcgaacc taatcaactt    3720
gcagagaaga atttcacggt gaggcagttg aagtatttaa ctccaaggga acggaattg     3780 atgctagtag tcacaatgta taatgaagac catatcctgt taggaagaac tttgaaaggt    3840
attatggaca atgtcaaata tatggtgaaa aaaaaaaatt caagcacttg ggggccggat    3900
gcatggaaaa agattgtcgt ttgtatcatt tcagatggta gatccaaaat taatgaacgc    3960
tcgctagcat tactaagttc gttaggttgt taccaggacg ggtttgctaa ggatgaaatt    4020
aatgaaaaaa aagtggcaat gcatgtctac gaacatacga caatgatcaa catcacaaat    4080
atttcggaat cagaggtttc attagaatgc aatcaaggta ctgttccaat acaacttttg    4140
ttttgtttga agagcaaaa tcagaaaaaa attaactcac atagatgggc atttgaaggc    4200
tttgcagaat tactgcgtcc caatatcgtt acattgttag atgctggtac tatgccaggt    4260
aaagattcta tttaccagtt atggagagag ttcaggaatc aaatgttgg tggcgcatgt    4320 ggtgaaataa gaactgattt gggtaagaga tttgtaaagt tgttgaatcc tttagttgca    4380
tcacagaatt tcgaatacaa aatgtccaat attttagaca aaacaaccga gtctaacttt    4440
ggatttatta ctgttctacc gggggcattc tctgcgtata ggtttgaagc tgtgagaggc    4500
caaccattac agaagtactt ttatggtgaa attatggaaa atgaaggttt tcatttttt     4560
```

```
tcttccaata tgtatcttgc tgaagatcgt attttatgct ttgaagtggt cacaaaaaaa    4620
aattgtaatt ggattttgaa atactgcaga agttcttatg cttcaacaga tgtaccggag    4680
agggtccctg aatttattct tcagaggagg cgttggttga atggttcatt ttttgctagt    4740
gtatattcct tttgtcattt ttacagagtc tggagcagtg gtcataatat tggtagaaaa    4800
ctccttttga cggttgaatt ttttaccttt tcttcaata cattgatttc atggttttca     4860
ttgagttcat ttttcctagt ctttaggatt ctcactgttt ctattgcact ggcataccat    4920
tcagcattta atgtgttgtc cgtcatattc ctgtggcttt atgggatttg taccttatca    4980
acattcatac tgtcattggg taataaacct aaaagtactg agaaatttta tgttctaact    5040
tgcgtcattt ttgcggtgat gatgatttac atgatattct gcagtatatt catgagtgtc    5100
aaatccttcc aaaatatatt gaaaaacgat accatcagct ttgagggttt gattaccaca    5160
gaggctttca gggatattgt tatctctctg ggctccactt attgtttgta cctaatcagt    5220
tcaattatct atttgcagcc atggcatatg ttgacaagtt ttattcagta tattttattg    5280
agtccttctt acatcaatgt tttgaatatc tatgcatttt gtaatgtcca cgacttatca    5340
tggggtacaa agggtgcaat ggcaaatccg ctgggtaaga ttaatactac agaagatggt    5400
acgttcaaaa tggaagttct ggtctctagt tcagagatte aagcaaacta cgataaatat    5460
ttgaaagttt taaatgactt cgatccaaaa tcagaatctc ggcctactga gccatcttat    5520
gatgaaaaaa agactggcta tatgcaaac gttagatctc tcgtgattat cttttgggtc     5580
atcacaaatt tcatcatcgt tgctgttgtc ttagaaaccg gtgggattgc agattatatt    5640
gctatgaaat ccatatcaac tgatgacact ttagaaactg caaagaaggc ggaaattccc    5700
ttaatgacca gtaaggcctc aatttatttt aatgtaattt tatggttagt tgcattatcg    5760
gcattaataa ggttcattgg ttgctcaata tacatgatag taaggttttt taaaaaggtt    5820
acatttcgct aaggtaccte atgtaattag ttatgtcacg cttacattca cgccctcccc    5880
ccacatccgc tctaaccgaa aaggaaggag ttagacaacc tgaagtctag gtccctattt    5940
atttttttat agttatgtta gtattaagaa cgttatttat atttcaaatt tttctttttt    6000
ttctgtacag acgcgtgtac gcatgtaaca ttatactgaa aaccttgctt gagaaggttt    6060
tgggacgctc gaaggcttta atttgccgga ttagaagccg ccgagcgggt gacagccctc    6120
cgaaggaaga ctctcctccg tgcgtcctcg tcttcaccgg tcgcgttcct gaaacgcaga    6180
tgtgcctcgc gccgcactgc tccgaacaat aaagattcta caatactagc ttttatggtt    6240
atgaagagga aaaattggca gtaacctggc cccacaaacc ttcaaatgaa cgaatcaaat    6300
taacaaccat aggatgataa tgcgattagt tttttagcct tatttctggg gtaattaatc    6360
agcgaagcga tgattttga tctattaaca gatatataaa tgcaaaaact gcataaccac      6420
tttaactaat actttcaaca ttttcggttt gtattacttc ttattcaaat gtaataaaag    6480
tatcaacaaa aaattgttaa tatacctcta tactttaacg tcaaggaggg atccgccacc    6540
atgtcactcc tttacatcat tcttctattc acacaattct tactactgcc aaccgatgcc    6600
tttgataggt ctgctaacac aaatattgct gtttattggg gtcaaaactc agcaggaacg    6660
caagaatcct tagctactta ctgtgaatct tctgatgctg atattttcct attatctttc    6720
ttgaaccaat ttccaaccct tggtttgaac tttgccaacg catgctctga tacttttcct    6780
gatggcttac ttcactgcac ccagattgct gaagatattg aaacttgcca gtccctagga    6840
aagaaagttc tattatcatt aggtggtgca tctggtagct acctcttttc agatgattct    6900
caagcggaaa cttttgcaca aactttatgg gatacttcg gtgaaggtac aggtgccagt    6960
```

```
gagagaccat ttgactcagc agtcgttgat ggttttgatt ttgatattga aaacaacaac    7020
gaagtaggct atagtgcgtt agctaccaag ttaagaactt tgtttgccga aggtacaaag    7080
caatattacc tttctgccgc accacaatgt ccatacccgg atgcttctgt tggtgacttg    7140
ttggaaaatg cagacattga ttttgcgttc atccaatttt acaataatta ctgcagtgtg    7200
agtggtcaat tcaattggga tacttggtta acctatgctc aaactgtatc cccaaataaa    7260
aatatcaaac tgttcttagg tttacctggt tctgcttctg ctgctggctc tggttatatt    7320
tctgacactt ctttattgga atcaactatt gcagatattg cctcttcaag ttcttttggt    7380
ggtattgcgt tatgggatgc atctcaagcc ttttccaacg agctaaatgg tgaaccatat    7440
gttgagattt tgaagaattt gctaacaagt gctagccaga ccgccactac tacagttgcc    7500
acctcaaaaa cctcagcagc ctcaacttca tctgcttcaa cttcatctgc ttcaacttct    7560
cagaaaaaga ccacacaatc tacgacatct acacaaagta aaagcaaagt tactttatct    7620
ccaactgcaa gcagcgctat caaaacatca attactcaaa ctacaaaaac attgacgagt    7680
agcaccaaga caaaatctag tctaggtacc accacaacag agagcacttt aaattcagtt    7740
gctatcacaa gtatgaaaac tactctatct tcccaaataa ccagtgctgc cttggtgacc    7800
cctcaaacaa ctactactag catagtttct tcggccccaa ttcaaacagc tatcactagt    7860
actctttcgc cagcaacgaa gagttcttct gtcgtttccc tacagacagc tactactagt    7920
acgctttccc caacaacgac cagtacaagc tcaggtagta caagctcagg tagtacaagc    7980
tcagacagta cagctcgtac attggctaaa gaattgaatg ctcaatatgc ggctggtaaa    8040
ttgaacggta aatctacctg tactgaaggt gaaattgcat gctctgctga tgggaagttc    8100
gccgtttgtg atcatagcgc ttgggtttac atggaatgtg cttctggaac cacatgttat    8160
gcttatgact ccggcgactc agtctatacc caatgtaatt tctcttattt ggaaagcaat    8220
tacttttaat taatcatgta attagttatg tcacgcttac attcacgccc tccccccaca    8280
tccgctctaa ccgaaaagga aggagttaga caacctgaag tctaggtccc tatttatttt    8340
tttatagtta tgttagtatt aagaacgtta tttatatttc aaattttttct tttttttctg    8400 tacagacgcg tgtacgcatg taacattata ctgaaaacct tgcttgagaa ggttttggga    8460
cgctcgaagg ctttaatttg ccggattaga agccgccgag cgggtgacag ccctccgaag    8520
gaagactctc ctccgtgcgt cctcgtcttc accggtcgcg ttcctgaaac gcagatgtgc    8580
ctcgcgccgc actgctccga acaataaaga ttctacaata ctagctttta tggttatgaa    8640
gaggaaaaat tggcagtaac ctggccccac aaaccttcaa atgaacgaat caaattaaca    8700
accataggat gataatgcga ttagtttttt agccttattt ctggggtaat taatcagcga    8760
agcgatgatt tttgatctat taacagatat ataaatgcaa aaactgcata accactttaa    8820
ctaatacttt caacattttc ggtttgtatt acttcttatt caaatgtaat aaaagtatca    8880
acaaaaaatt gttaatatac ctctatactt taacgtcaag gagctcgaga tgagaataca    8940
actaaataca attgatttgc aatgtattat tgcactttcc tgtctggggc aatttgttca    9000
cgcggaagct aatagggaag atttaaagca gatagacttt caatttcctg tattggaaag    9060
ggcagctaca aaaacgcctt ttccggattg gcttagtgca tttaccgggt taaagaatg    9120 gcctgggtta gatccaccct tataccttt agatttcatt gatttcagtc aaattccaga    9180
ttataaggaa tatgatcaaa accattgcga cagtgttcca agggactcgt gctctttcga    9240
ttgccatcac tgcaccgaac acgatgatgt gtacacatgt tccaaacttt cccagacatt    9300
```

```
tgacgatggt ccttctgctt ccactactaa attattggac cggttgaagc ataattccac    9360
cttcttcaat ttaggtgtca atatagttca acatccagat atctatcaaa gaatgcaaaa    9420
ggagggacac ttaatcggct cacatacctg gtctcacgta tatttgccaa atgtatcgaa    9480
tgaaaaaatt atagctcaaa ttgaatggtc catctgggcg atgaatgcta ctggcaacca    9540
taccccaaa tggttcagac ctccatatgg cggaatagat aatagagtaa gagcaataac     9600
aaggcaattt ggcttacaag ccgtcttatg ggatcacgat acttttgatt ggagcctcct    9660
tctcaatgat tctgtcataa ctgaacaaga aattcttcaa aatgtaataa actggaacaa    9720
gtcaggaacc ggattaatat tagaacacga ttcaacggaa aaaactgtcg atcttgccat    9780
taaaataaat aagttgatag gtgatgatca atcaacagtt tctcattgtg tcggcggaat    9840
tgattacata aaagaattct tgtcctaaga attctcatgt aattagttat gtcacgctta    9900
cattcacgcc ctccccccac atccgctcta accgaaaagg aaggagttag acaacctgaa    9960
gtctaggtcc ctatttattt ttttatagtt atgttagtat taagaacgtt atttatattt   10020
caaattttc ttttttttct gtacagacgc gtgtacgcat gtaacattat actgaaaacc    10080
ttgcttgaga aggttttggg acgctcgaag gctttaattt gccggattag aagccgccga   10140
gcgggtgaca gccctccgaa ggaagactct cctccgtgcg tcctcgtctt caccggtcgc   10200
gttcctgaaa cgcagatgtg cctcgcgccg cactgctccg aacaataaag attctacaat   10260
actagctttt atggttatga agaggaaaaa ttggcagtaa cctggcccca caaaccttca   10320
aatgaacgaa tcaaattaac aaccatagga tgataatgcg attagttttt tagccttatt   10380
tctgggtaa ttaatcagcg aagcgatgat ttttgatcta ttaacagata tataaatgca    10440
aaaactgcat aaccacttta actaatactt tcaacatttt cggtttgtat tacttcttat   10500
tcaaatgtaa taaagtatc aacaaaaaat tgttaatata cctctatact ttaacgtcaa    10560
ggaggcggcc gccatggtga gcaagggcga ggagctgttc accggggtgg tgcccatcct   10620
ggtcgagctg gacggcgacg taaacggcca caagttcagc gtgtccggcg agggcgaggg   10680
cgatgccacc tacggcaagc tgaccctgaa gttcatctgc accaccggca agctgcccgt   10740
gccctggccc acccctcgtga ccaccttcgg ctacggcctg caatgcttcg cccgctaccc   10800
cgaccacatg aagctgcacg acttcttcaa gtccgccatg cccgaaggct acgtccagga   10860
gcgcaccatc ttcttcaagg acgacggcaa ctacaagacc cgcgccgagg tgaagttcga   10920
gggcgacacc ctggtgaacc gcatcgagct gaagggcatc gacttcaagg aggacggcaa   10980
catcctgggg cacaagctgg agtacaacta caacagccac aacgtctata tcatggccga   11040
caagcagaag aacggcatca aggtgaactt caagatccgc cacaacatcg aggacggcag   11100
cgtgcagctc gccgaccact accagcagaa caccccatc ggcgacggcc ccgtgctgct    11160
gcccgacaac cactacctga gctaccagtc cgccctgagc aaagacccca acgagaagcg   11220
cgatcacatg gtcctgctgg agttcgtgac cgccgcgggg atcactctcg gcatggacga   11280
gctgtacaag taataatcta gagggccgca tcatgtaatt agttatgtca cgcttacatt   11340
cacgccctcc ccccacatcc gctctaaccg aaaaggaagg agttagacaa cctgaagtct   11400
aggtccctat ttatttttt atagttatgt tagtattaag aacgttattt atatttcaaa    11460
tttttctttt ttttctgtac agacgcgtgt acgcatgtaa cattatactg aaaaccttgc   11520
ttgagaaggt tttgggacgc tcgaaggctt taatttgcgg ccctgcatta atgaatcggc   11580
caacgcgcgg ggagaggcgg tttgcgtatt gggcgctctt ccgcttcctc gctcactgac   11640
tcgctgcgct cggtcgttcg gctgcggcga gcggtatcag ctcactcaaa ggcggtaata   11700
```

```
cggttatcca cagaatcagg ggataacgca ggaaagaaca tgtgagcaaa aggccagcaa   11760
aagcccagga accgtaaaaa ggccgcgttg ctggcgtttt tccataggct ccgcccccct   11820
gacgagcatc acaaaaatcg acgctcaagt cagaggtggc gaaacccgac aggactataa   11880
agataccagg cgtttccccc tggaagctcc ctcgtgcgct ctcctgttcc gaccctgccg   11940
cttaccggat acctgtccgc ctttctccct tcgggaagcg tggcgctttc tcatagctca   12000
cgctgtaggt atctcagttc ggtgtaggtc gttcgctcca agctgggctg tgtgcacgaa   12060
ccccccgttc agcccgaccg ctgcgcctta tccggtaact atcgtcttga gtccaacccg   12120
gtaagacacg acttatcgcc actggcagca gccactggta acaggattag cagagcgagg   12180
tatgtaggcg gtgctacaga gttcttgaag tggtggccta actacggcta cactagaagg   12240
acagtatttg gtatctgcgc tctgctgaag ccagttacct tcggaaaaag agttggtagc   12300
tcttgatccg gcaaacaaac caccgctggt agcggtggtt ttttgtttg caagcagcag   12360 attacgcgca gaaaaaaagg atctcaagaa gatcctttga tcttttctac ggggtctgac   12420
gctcagtgga acgaaaactc acgttaaggg attttggtca tgagattatc aaaaaggatc   12480
ttcacctaga tccttttaaa ttaaaaatga agttttaaat caatctaaag tatatatgag   12540
taaacttggt ctgacagtta ccaatgctta atcagtgagg cacctatctc agcgatctgt   12600
ctatttcgtt catccatagt tgcctgactc cccgtcgtgt agataactac gatacgggag   12660
cgcttaccat ctggccccag tgctgcaatg ataccgcgag acccacgctc accggctcca   12720
gatttatcag caataaacca gccagccgga agggccgagc gcagaagtgg tcctgcaact   12780
ttatccgcct ccatccagtc tattaattgt tgccgggaag ctagagtaag tagttcgcca   12840
gttaatagtt tgcgcaacgt tgttggcatt gctacaggca tcgtggtgtc actctcgtcg   12900
tttggtatgg cttcattcag ctccggttcc caacgatcaa ggcgagttac atgatccccc   12960
atgttgtgca aaaagcggt tagctccttc ggtcctccga tcgttgtcag aagtaagttg   13020
gccgcagtgt tatcactcat ggttatggca gcactgcata attctcttac tgtcatgcca   13080
tccgtaagat gcttttctgt gactggtgag tactcaacca agtcattctg agaatagtgt   13140
atgcggcgac cgagttgctc ttgcccggcg tcaatacggg ataatagtgt atcacatagc   13200
agaactttaa aagtgctcat cattggaaaa cgttcttcgg ggcgaaaact ctcaaggatc   13260
ttaccgctgt tgagatccag ttcgatgtaa cccactcgtg cacccaactg atcttcagca   13320
tcttttactt tcaccagcgt ttctgggtga gcaaaaacag gaaggcaaaa tgccgcaaaa   13380
aagggaataa gggcgacacg gaaatgttga atactcatac tcttcctttt tcaatgggta   13440
ataactgata taattaaatt gaagctctaa tttgtgagtt tagtatacat gcatttactt   13500
ataatacagt tttttagttt tgctggccgc atcttctcaa atatgcttcc cagcctgctt   13560
ttctgtaacg ttcaccctct accttagcat cccttccctt tgcaaatagt cctcttccaa   13620
caataataat gtcagatcct gtagagacca catcatccac ggttctatac tgttgaccca   13680
atgcgtctcc cttgtcatct aaacccacac cgggtgtcat aatcaaccaa tcgtaacctt   13740
catctcttcc acccatgtct ctttgagcaa taaagccgat aacaaatct ttgtcgctct   13800 tcgcaatgtc aacagtaccc ttagtatatt ctccagtaga tagggagccc ttgcatgaca   13860
attctgctaa catcaaaagg cctctaggtt cctttgttac ttcttctgcc gcctgcttca   13920
aaccgctaac aatacctggg cccaccacac cgtgtgcatt cgtaatgtct gcccattctg   13980
ctattctgta tacacccgca gagtactgca atttgactgt attaccaatg tcagcaaatt   14040
```

```
ttctgtcttc gaagagtaaa aaattgtact tggcggataa tgcctttagc ggcttaactg    14100
tgccctccat ggaaaaatca gtcaagatat ccacatgtgt ttttagtaaa caaattttgg    14160
gacctaatgc ttcaactaac tccagtaatt ccttggtggt acgaacatcc aatgaagcac    14220
acaagtttgt ttgcttttcg tgcatgatat taaatagctt ggcagcaaca ggactaggat    14280
gagtagcagc acgttcctta tatgtagctt tcgacatgat ttatcttcgt ttcctgcagg    14340
tttttgttct gtgcagttgg gttaagaata ctgggcaatt tcatgttcct tcaacactac    14400
atatgcgtat atataccaat ctaagtctgt gctccttcct tcgttcttcc ttctgttcgg    14460
agattaccga atcaaaaaaa tttcaaagaa accgaaatca aaaaaagaa taaaaaaaaa    14520 atgatgaatt gaattgaaaa gctagcttat cgatgataag ctgtcaaaga tgagaattaa    14580
ttccacggac tatagactat actagatact ccgtctactg tacgatacac ttccgctcag    14640
gtccttgtcc tttaacgagg ccttaccact cttttgttac tctattgatc cagctcagca    14700
aaggcagtgt gatctaagat tctatcttcg cgatgtagta aaactagcta gaccgagaaa    14760
gagactagaa atgcaaaagg cacttctaca atggctgcca tcattattat ccgatgtgac    14820
gctgcagctt ctcaatgata ttcgaatacg cttgaggag atacagccta atatccgaca    14880
aactgtttta cagatttacg atcgtacttg ttacccatca ttgaattttg aacatccgaa    14940
cctgggagtt ttccctgaaa cagatagtat atttgaacct gtataataat atatagtcta    15000
gcgctttacg gaagacaatg tatgtatttc ggttcctgga gaaactattg catctattgc    15060
ataggtaatc ttgcacgtcg catccccggt tcattttctg cgtttccatc ttgcacttca    15120
atagcatatc tttgttaacg aagcatctgt gcttcatttt gtagaacaaa aatgcaacgc    15180
gagagcgcta atttttcaaa caaagaatct gagctgcatt tttacagaac agaaatgcaa    15240
cgcgaaagcg ctattttacc aacgaagaat ctgtgcttca tttttgtaaa acaaaaatgc    15300
aacgcgacga gagcgctaat ttttcaaaca aagaatctga gctgcatttt tacagaacag    15360
aaatgcaacg cgagagcgct attttaccaa caaagaatct atacttcttt tttgttctac    15420
aaaaatgcat cccgagagcg ctatttttct aacaaagcat cttagattac tttttttctc    15480
ctttgtgcgc tctataatgc agtctcttga taacttttg cactgtaggt ccgttaaggt    15540
tagaagaagg ctactttggt gtctattttc tcttccataa aaaaagcctg actccacttc    15600
ccgcgtttac tgattactag cgaagctgcg ggtgcatttt ttcaagataa aggcatcccc    15660
gattatattc tataccgatg tggattgcgc atactttgtg aacagaaagt gatagcgttg    15720
atgattcttc attggtcaga aaattatgaa cggtttcttc tattttgtct ctatatacta    15780
cgtataggaa atgtttacat tttcgtattg ttttcgattc actctatgaa tagttcttac    15840
tacaattttt ttgtctaaag agtaaatacta gagataaaca taaaaaatgt agaggtcgag    15900
tttagatgca agttcaagga gcgaaaggtg gatgggtagg ttatataggg atatagcaca    15960
gagatatata gcaaagagat acttttgagc aatgtttgtg gaagcggtat tcgcaatggg    16020
aagctccacc ccggttgata atcagaaaag ccccaaaaac aggaagattg tataagcaaa    16080
tatttaaatt gtaaacgtta atattttgtt aaaattcgcg ttaaattttt gttaaatcag    16140
ctcatttttt aacgaatagc ccgaaatcgg caaaatccct tataaatcaa agaatagac    16200 cgagataggg ttgagtgttg ttccagtttc caacaagagt ccactattaa agaacgtgga    16260
ctccaacgtc aaagggcgaa aaagggtcta tcagggcgat ggcccactac gtgaaccatc    16320
accctaatca agttttttgg ggtcgaggtg ccgtaaagca gtaaatcgga agggtaaacg    16380 gatgcccccca tttagagctt gacggggaaa gccggcgaac gtggcgagaa aggaagggaa    16440
```

<210> SEQ ID NO 20
<211> LENGTH: 11513
<212> TYPE: DNA
<213> ORGANISM: Artificial sequence
<220> FEATURE:
<223> OTHER INFORMATION: Synthetic construct

<400> SEQUENCE: 20

```
gaaagcgaaa ggagcggggg ctagggcggt gggaagtgta ggggtcacgc tgggcgtaac      16500
caccacaccc gccgcgctta atggggcgct acagggcgcg tggggatgat ccactagt       16558 acggattaga agccgccgag cgggtgacag ccctccgaag gaagactctc ctccgtgcgt        60
cctcgtcttc accggtcgcg ttcctgaaac gcagatgtgc ctcgcgccgc actgctccga       120
acaataaaga ttctacaata ctagctttta tggttatgaa gaggaaaaat tggcagtaac       180
ctggccccac aaaccttcaa atgaacgaat caaattaaca accataggat gataatgcga       240
ttagtttttt agccttattt ctggggtaat taatcagcga agcgatgatt tttgatctat       300
taacagatat ataaatgcaa aaactgcata accactttaa ctaatacttt caacattttc       360
ggtttgtatt acttcttatt caaatgtaat aaaagtatca acaaaaaatt gttaatatac       420
ctctatactt taacgtcaag gagaaaaaac cccggatcgg actactagca gctgtaatac       480
gactcactat agggaatatt aagcttacca tggagactgt tcgtccaggt tgttttcgtg       540
ctgttgtttc tgttccactg ggtcgtctga cttactcttt cctggtggac ggtcagccga       600
agtacaaccc ggactgtccg actctggtta acgaagctgg cgtgcgtgtg aacgtacgcc       660
acggtggttc tgacggtgat tgcgacggtg aagctgacga agaatggggt aaaggtcgtc       720
caagccgtgc tcgtcgcgtg ctgagccagg tttctggcct ggacctgtac tctcagcact       780
ccaccagcga catcgtttct atgctggtgt tccgtttctt ctacctggct atgattccag       840
ctggtgccta ctacttcttc tggctgagcg ttcgtggtgg taatcgccag gctccagttt       900
gctgggtggt gttcgttatg agcgaaatcc tgtctttcgt tagcgcgctg atttccctgt       960
ttggcatgtg gaagccgatc aaacgtcgtt ggcgctctct ggacgctctg cgtccagctc      1020
tgccagttgc agattggcca actgtagacg tgatcatttg ccactacaaa gaggacaccg      1080
aacagctgcg tcagactatt cgtgcagcga tgaaactgga ttacccagcc catctgctgc      1140
acattctgat tgccgacgat ggcttcttcc aacctccaa gatggtagag cgttctgata      1200
ttggtctggc tctgtaccag acctgtgttg aggaagcggg ttatgatccg ctgctggaag      1260
aaaccatgaa tgaacgtggt ctggttgaac actatactgt taaggcaggt gacgacctgc      1320
cgcgtcatga ttgcgcggtt gaagctcacc agttcgagtt tggtccgtat ggtgcggaca      1380
tgtacggtcc aggtgccctg ccacgtctgt ccctggttgc tcgtgtgaag ccggctgacg      1440
ctcacaacaa ggcaggcaac atcaacaacg tactgtccaa ctctaacgca gaaggtaaga      1500
ttgttctgtt cctggatgct gacatgaagc cggtagaatc ttacctgctg cgtgttctgc      1560
cactgatgct ggaagagcag cgttccgata gcctgcagag ccaactgatc caggcagagg      1620
acccagagct gggtgctggt acttctaaga gctggcaaat caaccgtgac attggcttcg      1680
ttggctgccc acaacgcttc cgcaacgtat ccggtgacca tccggattac tgtgctcacc      1740
gtaacgcgat ctactacgac ggtatctgca ctggtcgtga tggtttcggt atgaccgact      1800
tcgttggcac taacgcgtgt tggcgtcgcg aagttctgaa cgagatcggt ggcttcgttt      1860
atggtagcgt gactgaagac accctgacta gcaacgaagt tcatcgccgt ggctacatta      1920
```

```
gccgctacgc tgacgaagac ctgtgctggg gtgaagcacc agttaccgtt gcagcagctc    1980
tgctgcagcg tcaacgttgg gctaaaggtg ccatcatgaa cggtatgcgt atcttcaaag    2040
gtgctgctaa agaacgcaaa gaaatgctgc tgagccgtga gaaaccgtct gaactgtctg    2100
agttctacgc atatcgtcgt cagcagcgta aaccaaacaa cactttcgtt tctaccatgt    2160
tctggctgga ttctactctg tacccactgc tggggttgggg tgctttcggt tacgtgttct    2220
gtgctatctt ccacctgatc accgctcagg caccgatctc tccgacctct actcagagcc    2280
tggctggtgc gtttgtgacc tactatctga ttcgttacgg tgcattcttc tctgccttct    2340
atgaagtgaa catgaccgac gttctgcgct ctcagcagtg ttggttctct tactccttcg    2400
cccacactgt gggtgtatgg gatgctctgt ttggtggtgc caagtttggc tgggttgcta    2460
acactggcca acgtcatcgc cgtagctggc tggaatggtt caacatcctg actctgggtg    2520
ctctgctgtc cggcattgtg tggcgtctgt tcgcgttcat tgttatcgaa gaagcgtgtt    2580
ctccgtacga gaacttcggt gctgttgcat tcggcggtta cgtagcgtgg atgatggctc    2640
cagttgctct ggttagcctg aacgaacgcc tgtcttccgc tgacgaatcc gagcgtgaag    2700
gtaaaccgat gccagtgccg actccgatca tcgctgctgc cctgactatc ctgggtgttg    2760
tgttcctgtc tggttgggca aacgctcgtt gtggtatcga agctcgcggt taaggtacct    2820
catgtaatta gttatgtcac gcttacattc acgccctccc cccacatccg ctctaaccga    2880
aaaggaagga gttagacaac ctgaagtcta ggtccctatt tatttttta tagttatgtt    2940 agtattaaga acgttattta tatttcaaat ttttctttt tttctgtaca gacgcgtgta    3000
cgcatgtaac attatactga aaaccttgct tgagaaggtt ttgggacgct cgaaggcttt    3060
aatttgccgg attagaagcc gccgagcggg tgacagccct ccgaaggaag actctcctcc    3120
gtgcgtcctc gtcttcaccg gtcgcgttcc tgaaacgcag atgtgcctcg cgccgcactg    3180
ctccgaacaa taagagattct acaatactag ctttatggt tatgaagagg aaaaattggc    3240
agtaacctgg ccccacaaac cttcaaatga acgaatcaaa ttaacaacca taggatgata    3300
atgcgattag tttttttagcc ttatttctgg ggtaattaat cagcgaagcg atgattttg    3360 atctattaac agatatataa atgcaaaaac tgcataacca cttaactaa tactttcaac    3420 atttcggtt tgtattactt cttattcaaa tgtaataaaa gtatcaacaa aaaattgtta    3480
atatacctct atactttaac gtcaaggagg atccatggc gaagtttggt agccgtaata    3540
agtctccgaa gtggatctct aacggctgct gcttcctgct gggtgccttt actgctctgc    3600
tgctgctgtg gggtctgtgc tcctttatta tcccgattcc gaacaccgat ccgaagctga    3660
actctgtagc gacctctctg cgttctctga acttcccgaa gaacccagca gctaccctgc    3720
caccgaacct gcagcatgat ccaccggata ctactttcta cgacgatccg gaaacctctt    3780
atactatgga taaaccgatg aagaactggg acgagaaacg taaggaatgg ctgctgcatc    3840
acccgtcctt cggcgcagct gctcgtgaca agatcctgct ggtaaccggt tcccagccga    3900
aacgctgtca caacccgatt ggtgatcacc tgctgctgcg tttctttaag aacaaagtgg    3960
attactgccg tctgcataat tacgatatca tctataacaa cgcactgctg cacccgaaaa    4020
tgaactccta ttgggctaag tacccagtga tccgtgctgc aatgatggct catccggaag    4080
ttgaatgggt gtggtgggtt gactctgacg ctgtattcac tgacatggag tttaaactgc    4140
cactgaaacg ctataagaac cacaatctgg tggtgcatgg ttgggaaggt ctggtacgtc    4200
tgaaccactc ctggactggt ctgaacgcag gtgtattcct gatccgtaat tgccaatgga    4260
gcctggagtt catggatgta tgggttagca tgggtccaca aactccagaa tacgagaaat    4320
```

| | |
|---|---|
| ggggtgagcg tctgcgcgaa accttcaaag ataaagttct gccagactct gatgaccaga | 4380 |
| ctgcactggc atacctgatc gcaaccgata acaaagacac ctggcgtgag aaatcttcc | 4440 |
| tggaaagcga gtactacttc gaaggctatt ggctggaaat cgtaaagact tacgagaaca | 4500 |
| tctccgaacg ttacgatgaa gttgaacgca agtagaagg tctgcgtcgt cgccacgctg | 4560 |
| agaaggttag cgagaaatac ggtgcaatgc gtgaagaata cctgaaagat aacaaacgtc | 4620 |
| gtccgttcat cacccatttc actggttgcc agccgtgcaa cggtcaccat aacccagcat | 4680 |
| acaatgcgaa cgactgttgg aatggtatgg aacgtgcact gaactttgca gataaccaga | 4740 |
| tcctgcgtac ctacgttac catcgtcaga atctgctgga caagtccgtt tctccactgc | 4800 |
| cgttcggtta ccagcagct aagaattct catgtaatta gttatgtcac gcttacattc | 4860 |
| acgccctccc cccacatccg ctctaaccga aaggaagga gttagacaac ctgaagtcta | 4920 |
| ggtccctatt tatttttta tagttatgtt agtattaaga cgttattta tatttcaaat | 4980 |
| tttcttttt tttctgtaca gacgcgtgta cgcatgtaac attatactga aaaccttgct | 5040 |
| tgagaaggtt ttgggacgct cgaaggcttt aatttgccgg attagaagcc gccgagcggg | 5100 |
| tgacagccct ccgaaggaag actctcctcc gtgcgtcctc gtcttcaccg gtcgcgttcc | 5160 |
| tgaaacgcag atgtgcctcg cgccgcactg ctccgaacaa taaagattct acaatactag | 5220 |
| cttttatggt tatgaagagg aaaaattggc agtaacctgg ccccacaaac cttcaaatga | 5280 |
| acgaatcaaa ttaacaacca taggatgata atgcgattag tttttttagcc ttatttctgg | 5340 |
| ggtaattaat cagcgaagcg atgattttg atctattaac agatatataa atgcaaaaac | 5400 |
| tgcataacca ctttaactaa tactttcaac attttcggtt tgtattactt cttattcaaa | 5460 |
| tgtaataaaa gtatcaacaa aaattgtta atatacctct atactttaac gtcaaggagg | 5520 |
| cggccgccat ggtgagcaag ggcgaggagc tgttcaccgg ggtggtgccc atcctggtcg | 5580 |
| agctggacgg cgacgtaaac ggccacaagt tcagcgtgtc cggcgagggc gagggcgatg | 5640 |
| ccacctacgg caagctgacc ctgaagttca tctgcaccac cggcaagctg cccgtgccct | 5700 |
| ggcccaccct cgtgaccacc ttcggctacg gcctgcaatg cttcgcccgc tacccgacc | 5760 |
| acatgaagct gcacgacttc ttcaagtccg ccatgcccga aggctacgtc caggagcgca | 5820 |
| ccatcttctt caaggacgac ggcaactaca agacccgcgc cgaggtgaag ttcgagggcg | 5880 |
| acaccctggt gaaccgcatc gagctgaagg gcatcgactt caaggaggac ggcaacatcc | 5940 |
| tggggcacaa gctggagtac aactacaaca gccacaacgt ctatatcatg gccgacaagc | 6000 |
| agaagaacgg catcaaggtg aacttcaaga tccgccacaa catcgaggac ggcagcgtgc | 6060 |
| agctcgccga ccactaccag cagaacaccc ccatcggcga cggccccgtg ctgctgcccg | 6120 |
| acaaccacta cctgagctac cagtccgccc tgagcaaaga ccccaacgag aagcgcgatc | 6180 |
| acatggtcct gctggagttc gtgaccgccg ccgggatcac tctcggcatg gacgagctgt | 6240 |
| acaagtaata atctagaggg ccgcatcatg taattagtta tgtcacgctt acattcacgc | 6300 |
| cctccccca catccgctct aaccgaaaag gaaggagtta caacctga agtctaggtc | 6360 |
| cctatttatt tttttatagt tatgttagta ttaagaacgt tatttatatt tcaaattttt | 6420 |
| cttttttttc tgtacagacg cgtgtacgca tgtaacatta tactgaaaac cttgcttgag | 6480 |
| aaggttttgg gacgctcgaa ggctttaatt tgcggccctg cattaatgaa tcggccaacg | 6540 |
| cgcggggaga ggcggtttgc gtattgggcg ctcttccgct tcctcgctca ctgactcgct | 6600 |
| gcgctcggtc gttcggctgc ggcgagcggt atcagctcac tcaaaggcgg taatacggtt | 6660 |

```
atccacagaa tcagggggata acgcaggaaa gaacatgtga gcaaaaggcc agcaaaagcc    6720
caggaaccgt aaaaaggccg cgttgctggc gttttttccat aggctccgcc ccctgacga    6780 gcatcacaaa aatcgacgct caagtcagag gtggcgaaac ccgacaggac tataaagata    6840
ccaggcgttt ccccctggaa gctccctcgt gcgctctcct gttccgaccc tgccgcttac    6900
cggatacctg tccgcctttc tcccttcggg aagcgtggcg ctttctcata gctcacgctg    6960
taggtatctc agttcggtgt aggtcgttcg ctccaagctg ggctgtgtgc acgaaccccc    7020
cgttcagccc gaccgctgcg ccttatccgg taactatcgt cttgagtcca acccggtaag    7080
acacgactta tcgccactgg cagcagccac tggtaacagg attagcagag cgaggtatgt    7140
aggcggtgct acagagttct tgaagtggtg gcctaactac ggctacacta aaggacagt     7200 atttggtatc tgcgctctgc tgaagccagt taccttcgga aaaagagttg gtagctcttg    7260
atccggcaaa caaaccaccg ctggtagcgg tggttttttt gtttgcaagc agcagattac    7320
gcgcagaaaa aaaggatctc aagaagatcc tttgatcttt tctacggggt ctgacgctca    7380
gtggaacgaa aactcacgtt aagggatttt ggtcatgaga ttatcaaaaa ggatcttcac    7440
ctagatcctt ttaaattaaa aatgaagttt taaatcaatc taaagtatat atgagtaaac    7500
ttggtctgac agttaccaat gcttaatcag tgaggcacct atctcagcga tctgtctatt    7560
tcgttcatcc atagttgcct gactccccgt cgtgtagata actacgatac gggagcgctt    7620
accatctggc cccagtgctg caatgatacc gcgagaccca cgctcaccgg ctccagattt    7680
atcagcaata aaccagccag ccggaagggc cgagcgcaga agtggtcctg caactttatc    7740
cgcctccatc cagtctatta attgttgccg ggaagctaga gtaagtagtt cgccagttaa    7800
tagtttgcgc aacgttgttg gcattgctac aggcatcgtg gtgtcactct cgtcgtttgg    7860
tatggcttca ttcagctccg gttcccaacg atcaaggcga gttacatgat cccccatgtt    7920
gtgcaaaaaa gcggttagct ccttcggtcc tccgatcgtt gtcagaagta agttggccgc    7980
agtgttatca ctcatggtta tggcagcact gcataattct cttactgtca tgccatccgt    8040
aagatgcttt tctgtgactg gtgagtactc aaccaagtca ttctgagaat agtgtatgcg    8100
gcgaccgagt tgctcttgcc cggcgtcaat acgggataat agtgtatcac atagcagaac    8160
tttaaaagtg ctcatcattg gaaaacgttc ttcggggcga aaactctcaa ggatcttacc    8220
gctgttgaga tccagttcga tgtaacccac tcgtgcaccc aactgatctt cagcatcttt    8280
tactttcacc agcgtttctg ggtgagcaaa aacaggaagg caaaatgccg caaaaaaggg    8340
aataagggcg acacggaaat gttgaatact catactcttc cttttcaat gggtaataac    8400 tgatataatt aaattgaagc tctaatttgt gagtttagta tacatgcatt tacttataat    8460 acagttttt agttttgctg gccgcatctt ctcaaatatg cttcccagcc tgcttttctg    8520
taacgttcac cctctacctt agcatccctt ccctttgcaa atagtcctct tccaacaata    8580
ataatgtcag atcctgtaga gaccacatca tccacggttc tatactgttg acccaatgcg    8640
tctcccttgt catctaaacc cacaccgggt gtcataatca accaatcgta accttcatct    8700
cttccaccca tgtctctttg agcaataaag ccgataacaa atctttgtc gctcttcgca    8760 atgtcaacag tacccttagt atattctcca gtagatagggg agcccttgca tgacaattct    8820
gctaacatca aaaggcctct aggttccttt gttacttctt ctgccgcctg cttcaaaccg    8880
ctaacaatac ctgggcccac cacaccgtgt gcattcgtaa tgtctgccca ttctgctatt    8940
ctgtatacac ccgcagagta ctgcaatttg actgtattac caatgtcagc aaatttttctg    9000 tcttcgaaga gtaaaaaatt gtacttggcg gataatgcct ttagcggctt aactgtgccc    9060
```

```
tccatggaaa aatcagtcaa gatatccaca tgtgttttta gtaaacaaat tttgggacct   9120
aatgcttcaa ctaactccag taattccttg gtggtacgaa catccaatga agcacacaag   9180
tttgtttgct tttcgtgcat gatattaaat agcttggcag caacaggact aggatgagta   9240
gcagcacgtt ccttatatgt agctttcgac atgatttatc ttcgtttcct gcaggttttt   9300
gttctgtgca gttgggttaa gaatactggg caatttcatg tttcttcaac actacatatg   9360
cgtatatata ccaatctaag tctgtgctcc ttccttcgtt cttccttctg ttcggagatt   9420
accgaatcaa aaaaatttca agaaaccga aatcaaaaaa aagaataaaa aaaaaatgat   9480
gaattgaatt gaaaagctag cttatcgatg ataagctgtc aaagatgaga attaattcca   9540
cggactatag actatactag atactccgtc tactgtacga tacacttccg ctcaggtcct   9600
tgtcctttaa cgaggcctta ccactctttt gttactctat tgatccagct cagcaaaggc   9660
agtgtgatct aagattctat cttcgcgatg tagtaaaact agctagaccg agaaagagac   9720
tagaaatgca aaaggcactt ctacaatggc tgccatcatt attatccgat gtgacgctgc   9780
agcttctcaa tgatattcga atacgctttg aggagataca gcctaatatc cgacaaactg   9840
ttttacagat ttacgatcgt acttgttacc catcattgaa ttttgaacat ccgaacctgg   9900
gagttttccc tgaaacagat agtatatttg aacctgtata ataatatata gtctagcgct   9960
ttacggaaga caatgtatgt atttcggttc ctggagaaac tattgcatct attgcatagg  10020
taatcttgca cgtcgcatcc ccggttcatt ttctgcgttt ccatcttgca cttcaatagc  10080
atatctttgt taacgaagca tctgtgcttc attttgtaga acaaaaatgc aacgcgagag  10140
cgctaatttt tcaaacaaag aatctgagct gcatttttac agaacagaaa tgcaacgcga  10200
aagcgctatt ttaccaacga agaatctgtg cttcatttt gtaaaacaaa aatgcaacgc  10260
gacgagagcg ctaatttttc aaacaaagaa tctgagctgc attttacag aacagaaatg  10320 caacgcgaga gcgctatttt accaacaaag aatctatact tcttttttgt tctacaaaaa  10380
tgcatcccga gagcgctatt tttctaacaa agcatcttag attactttt ttctcctttg  10440 tgcgctctat aatgcagtct cttgataact ttttgcactg taggtccgtt aaggttagaa  10500
gaaggctact ttggtgtcta ttttctcttc cataaaaaaa gcctgactcc acttcccgcg  10560
tttactgatt actagcgaag ctgcgggtgc attttttcaa gataaaggca tccccgatta  10620
tattctatac cgatgtggat tgcgcatact ttgtgaacag aaagtgatag cgttgatgat  10680
tcttcattgg tcagaaaatt atgaacggtt tcttctattt tgtctctata tactacgtat  10740
aggaaatgtt tacattttcg tattgttttc gattcactct atgaatagtt cttactacaa  10800 ttttttttgtc taaagagtaa tactagagat aaacataaaa aatgtagagg tcgagtttag  10860
atgcaagttc aaggagcgaa aggtggatgg gtaggttata tagggatata gcacagagat  10920
atatagcaaa gagatacttt tgagcaatgt ttgtggaagc ggtattcgca atgggaagct  10980
ccaccccggt tgataatcag aaaagcccca aaaacaggaa gattgtataa gcaaatattt  11040
aaattgtaaa cgttaatatt ttgttaaaat tcgcgttaaa tttttgttaa atcagctcat  11100
tttttaacga atagcccgaa atcggcaaaa tcccttataa atcaaaagaa tagaccgaga  11160
tagggttgag tgttgttcca gtttccaaca agagtccact attaagaac gtggactcca  11220 acgtcaaagg gcgaaaaagg gtctatcagg gcgatggccc actacgtgaa ccatcaccct  11280
aatcaagttt ttggggtcg aggtgccgta aagcagtaaa tcggaagggt aaacggatgc  11340 ccccattag agcttgacgg gggaaagccgg cgaacgtggc gagaaaggaa gggaagaaag  11400
```

```
cgaaaggagc gggggctagg gcggtgggaa gtgtaggggt cacgctgggc gtaaccacca    11460
cacccgccgc gcttaatggg gcgctacagg gcgcgtgggg atgatccact agt           11513

<210> SEQ ID NO 21
<211> LENGTH: 13440
<212> TYPE: DNA
<213> ORGANISM: Artificial sequence
<220> FEATURE:
<223> OTHER INFORMATION: Synthetic construct

<400> SEQUENCE: 21
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttgcca ccatggtgtt tatcgtcaat cttttctcct     540
gcaccttatc tgaaaccacg gttagctcaa taaaatctga agctacggtt agctcaacat     600
ttactgccgt cacggccctg caattggtgg ctgagggtaa gttgcagtcg gcgaagggtt     660
tcggtggtgg tacgattcac tacccaaccc tcgcggccga agcaccctgg tggacgccgg     720
gccaaggcca tggttacgag gcgatcacct acggctggct ggtcggcgaa ctgctgcgcc     780
gcgccgatgg gcgtgggcct ggtctgttag gcgctattgc cgtggttcct ggttacgttt     840
cttacgagaa ctctatcaag tggtggggac cgcgtctggc ttcttgggc tttgtcgttg      900 cacggccgtt gggcctggac tttcatgtgg gcctggcgga tgaagagttt tatcgtgttg     960
cccatatagc gcgcagcaaa gccaatgcag cactagataa cattgctgat gacaccgtcg    1020
gcagtataga tcctaagcgg ttgggcgcta ttggctggtc aggtggcggc ggcgcgctta    1080
aactggcaac ggagcgcagc acagtacgag ccattttgac cagtactaat aaacctgaat    1140
ggcgacgctt cgataaattc ttatgtgcct gcgaggatga ccggattgct gagactaaga    1200
aatatgccaa cgcgttttat aaaaatgccg acatgctcga agagttgacc cgtgaacaca    1260
gtatcgggcc ggataaaaca ttattgacac aaactcggtt tggcttgggg tgcttggatc    1320
aaccgcaagc aggggttaaa attcattttg aagagtacct tgatcaaacc catggattta    1380
tcaatttgac gccagtttca cataaggcga gagcaaatct gattcagatg cctaatgcca    1440
cattcggcct tggcccgcgt gcttttgggc atcctggtgc aggtggatcg gtaggttttg    1500
ccgaccccga acacgatgta gcgtttggtt tcgtgactaa tacattgggg ccttatgtag    1560
ttgagtttaa aagccgtcat ccctcatttt atgcatataa agatggattg gtgctgactg    1620
gaaatgacgt cgactatgtg actgattact atgcaacaaa gcatgctgta catttagatg    1680
atccacgtgc acagaagttg gtcggaatat tggccggttg tctgtaaccc gggtaatcat    1740
gtaattagtt atgtcacgct tacattcacg ccctccccc acatccgctc taaccgaaaa     1800 ggaaggagt agacaacctg aagtctaggt ccctatttat ttttttatag ttatgttagt    1860
attaagaacg ttatttatat ttcaaatttt tcttttttt ctgtacagac gcgtgtacgc     1920
atgtaacatt atactgaaaa ccttgcttga gaaggttttg ggacgctcga aggctttaat    1980
```

```
ttgccggatt agaagccgcc gagcgggtga cagccctccg aaggaagact ctcctccgtg    2040
cgtcctcgtc ttcaccggtc gcgttcctga aacgcagatg tgcctcgcgc cgcactgctc    2100
cgaacaataa agattctaca atactagctt ttatggttat gaagaggaaa aattggcagt    2160
aacctggccc cacaaacctt caaatgaacg aatcaaatta acaaccatag gatgataatg    2220
cgattagttt tttagcctta tttctggggt aattaatcag cgaagcgatg atttttgatc    2280
tattaacaga tatataaatg caaaaactgc ataaccactt taactaatac tttcaacatt    2340
ttcggtttgt attacttctt attcaaatgt aataaaagta tcaacaaaaa attgttaata    2400
tacctctata ctttaacgtc aaggaggcgc gccaccatgg agactgttcg tccaggttgt    2460
tttcgtgctg ttgtttctgt tccactgggt cgtctgactt actctttcct ggtggacggt    2520
cagccgaagt acaacccgga ctgtccgact ctggttaacg aagctggcgt gcgtgtgaac    2580
gtacgccacg gtggttctga cggtgattgc gacggtgaag ctgacgaaga atggggtaaa    2640
ggtcgtccaa gccgtgctcg tcgcgtgctg agccaggttt ctggcctgga cctgtactct    2700
cagcactcca ccagcgacat cgtttctatg ctggtgttcc gtttcttcta cctggctatg    2760
attccagctg gtgcctacta cttcttctgg ctgagcgttc gtggtggtaa tcgccaggct    2820
ccagtttgct gggtggtgtt cgttatgagc gaaatcctgt ctttcgttag cgcgctgatt    2880
tccctgtttg gcatgtggaa gccgatcaaa cgtcgttggc gctctctgga cgctctgcgt    2940
ccagctctgc cagttgcaga ttggccaact gtagacgtga tcatttgcca ctacaaagag    3000
gacaccgaac agctgcgtca gactattcgt gcagcgatga aactggatta cccagcccat    3060
ctgctgcaca ttctgattgc cgacgatggc ttcttcccaa cctccaagat ggtagagcgt    3120
tctgatattg gtctggctct gtaccagacc tgtgttgagg aagcgggtta tgatccgctg    3180
ctggaagaaa ccatgaatga acgtggtctg gttgaacact atactgttaa ggcaggtgac    3240
gacctgccgc gtcatgattg cgcggttgaa gctcaccagt tcgagtttgg tccgtatggt    3300
gcggacatgt acggtccagg tgccctgcca cgtctgtccc tggttgctcg tgtgaagccg    3360
gctgacgctc acaacaaggc aggcaacatc aacaacgtac tgtccaactc taacgcagaa    3420
ggtaagattg ttctgttcct ggatgctgac atgaagccgg tagaatctta cctgctgcgt    3480
gttctgccac tgatgctgga agagcagcgt tccgatagcc tgcagagcca actgatccag    3540
gcagaggacc cagagctggg tgctggtact tctaagagct ggcaaatcaa ccgtgacatt    3600
ggcttcgttg ctgcccaca acgcttcgcg aacgtatccg gtgaccatcc ggattactgt    3660
gctcaccgta acgcgatcta ctacgacggt atctgcactg tcgtgatgg tttcggtatg    3720 accgacttcg ttggcactaa cgcgtgttgg cgtcgcgaag ttctgaacga gatcggtggc    3780
ttcgtttatg gtagcgtgac tgaagacacc ctgactagca acgaagttca tcgccgtggc    3840
tacattagcc gctacgctga cgaagacctg tgctggggtg aagcaccagt taccgttgca    3900
gcagctctgc tgcagcgtca acgttgggct aaaggtgcca tcatgaacgg tatgcgtatc    3960
ttcaaaggtg ctgctaaaga acgcaaagaa atgctgctga ccgtgagaa accgtctgaa    4020 ctgtctgagt ctctacgcata tcgtcgtcag cagcgtaaac caaacaacac tttcgtttct    4080
accatgttct ggctggattc tactctgtac ccactgctgg gttggggtgc tttcggttac    4140
gtgttctgtg ctatcttcca cctgatcacc gctcaggcac cgatctctcc gacctctact    4200
cagagcctgg ctggtcgtt tgtgacctac tatctgattc gttacggtgc attcttctct    4260
gccttctatg aagtgaacat gaccgacgtt ctgcgctctc agcagtgttg gttctcttac    4320
```

```
tccttcgccc acactgtggg tgtatgggat gctctgtttg gtggtgccaa gtttggctgg      4380
gttgctaaca ctggccaacg tcatcgccgt agctggctgg aatggttcaa catcctgact      4440
ctgggtgctc tgctgtccgg cattgtgtgg cgtctgttcg cgttcattgt tatcgaagaa      4500
gcgtgttctc cgtacgagaa cttcggtgct gttgcattcg gcggttacgt agcgtggatg      4560
atggctccag ttgctctggt tagcctgaac gaacgcctgt cttccgctga cgaatccgag      4620
cgtgaaggta aaccgatgcc agtgccgact ccgatcatcg ctgctgccct gactatcctg      4680
ggtgttgtgt tcctgtctgg ttgggcaaac gctcgttgtg gtatcgaagc tcgcggttaa      4740
ggtacctcat gtaattagtt atgtcacgct tacattcacg ccctcccccc acatccgctc      4800
taaccgaaaa ggaaggagtt agacaacctg aagtctaggt ccctatttat ttttttatag      4860
ttatgttagt attaagaacg ttatttatat ttcaaatttt tctttttttt ctgtacagac      4920
gcgtgtacgc atgtaacatt atactgaaaa ccttgcttga aaggttttg ggacgctcga       4980 aggctttaat ttgccggatt agaagccgcc gagcgggtga cagccctccg aaggaagact      5040
ctcctccgtg cgtcctcgtc ttcaccggtc gcgttcctga aacgcagatg tgcctcgcgc      5100
cgcactgctc cgaacaataa agattctaca atactagctt ttatggttat gaagaggaaa      5160
aattggcagt aacctggccc cacaaacctt caaatgaacg aatcaaatta caaccatag       5220 gatgataatg cgattagttt tttagcctta tttctggggt aattaatcag cgaagcgatg      5280 attttttgatc tattaacaga tatataaatg caaaaactgc ataaccactt taactaatac     5340
tttcaacatt ttcggtttgt attacttctt attcaaatgt aataaaagta tcaacaaaaa      5400
attgttaata tacctctata ctttaacgtc aaggagggat ccatggcgaa gtttggtagc      5460
cgtaataagt ctccgaagtg gatctctaac ggctgctgct tcctgctggg tgcctttact      5520
gctctgctgc tgctgtgggg tctgtgctcc tttattatcc cgattccgaa caccgatccg      5580
aagctgaact ctgtagcgac ctctctgcgt tctctgaact tcccgaagaa cccagcagct      5640
accctgccac cgaacctgca gcatgatcca ccggatacta cttctacga cgatccggaa       5700 acctcttata ctatggataa accgatgaag aactgggacg agaaacgtaa ggaatggctg      5760
ctgcatcacc cgtccttcgg cgcagctgct cgtgacaaga tcctgctggt aaccggttcc      5820
cagccgaaac gctgtcacaa cccgattggt gatcacctgc tgctgcgttt ctttaagaac      5880
aaagtggatt actgccgtct gcataattac gatatcatct ataacaacgc actgctgcac      5940
ccgaaaatga actcctattg ggctaagtac ccagtgatcc gtgctgcaat gatggctcat      6000
ccggaagttg aatgggtgtg gtgggttgac tctgacgctg tattcactga catggagttt      6060
aaactgccac tgaaacgcta taagaaccac aatctggtgg tgcatggttg ggaaggtctg      6120
gtacgtctga ccactcctg gactggtctg aacgcaggtg tattcctgat ccgtaattgc      6180
caatggagcc tggagttcat ggatgtatgg gttagcatgg gtccacaaac tccagaatac      6240
gagaaatggg gtgagcgtct gcgcgaaacc ttcaaagata agttctgcc agactctgat      6300 gaccagactg cactggcata cctgatcgca accgataaca aagacacctg gcgtgagaaa      6360
atcttcctgg aaagcgagta ctacttcgaa ggctattggc tggaaatcgt aaagacttac      6420
gagaacatct ccgaacgtta cgatgaagtt gaacgcaaag tagaaggtct gcgtcgtcgc      6480
cacgctgaga aggttagcga gaaatacggt gcaatgcgtg aagaatacct gaaagataac      6540
aaacgtcgtc cgttcatcac ccatttcact ggttgccagc cgtgcaacgg tcaccataac      6600
ccagcataca atgcgaacga ctgttggaat ggtatggaac gtgcactgaa cttgcagat       6660 aaccagatcc tgcgtaccta cggttaccat cgtcagaatc tgctggacaa gtccgtttct      6720
```

```
ccactgccgt tcggttatcc agcagcttaa gaattctcat gtaattagtt atgtcacgct    6780
tacattcacg ccctccccc acatccgctc taaccgaaaa ggaaggagtt agacaacctg     6840
aagtctaggt ccctatttat tttttatag ttatgttagt attaagaacg ttatttatat    6900
ttcaaatttt tcttttttt ctgtacagac gcgtgtacgc atgtaacatt atactgaaaa    6960
ccttgcttga aaggttttg ggacgctcga aggctttaat ttgccggatt agaagccgcc    7020
gagcgggtga cagccctccg aaggaagact ctcctccgtg cgtcctcgtc ttcaccggtc    7080
gcgttcctga aacgcagatg tgcctcgcgc cgcactgctc cgaacaataa agattctaca    7140
atactagctt ttatggttat gaagaggaaa aattggcagt aacctggccc acaaaacctt    7200
caaatgaacg aatcaaatta acaaccatag gatgataatg cgattagttt tttagcctta    7260
tttctggggt aattaatcag cgaagcgatg atttttgatc tattaacaga tatataaatg    7320
caaaaactgc ataaccactt taactaatac tttcaacatt ttcggtttgt attacttctt    7380
attcaaatgt aataaaagta tcaacaaaaa attgttaata tacctctata ctttaacgtc    7440
aaggaggcgg ccgccatggt gagcaagggc gaggagctgt tcaccggggt ggtgcccatc    7500
ctggtcgagc tggacggcga cgtaaacggc cacaagttca gcgtgtccgg cgagggcgag    7560
ggcgatgcca cctacggcaa gctgaccctg aagttcatct gcaccaccgg caagctgccc    7620
gtgccctggc ccaccctcgt gaccaccttc ggctacggcc tgcaatgctt cgcccgctac    7680
cccgaccaca tgaagctgca cgacttcttc aagtccgcca tgcccgaagg ctacgtccag    7740
gagcgcacca tcttcttcaa ggacgacggc aactacaaga cccgcgccga ggtgaagttc    7800
gagggcgaca ccctggtgaa ccgcatcgag ctgaagggca tcgacttcaa ggaggacggc    7860
aacatcctgg ggcacaagct ggagtacaac tacaacagcc acaacgtcta tatcatggcc    7920
gacaagcaga agaacggcat caaggtgaac ttcaagatcc gccacaacat cgaggacggc    7980
agcgtgcagc tcgccgacca ctaccagcag aacacccca tcggcgacgg ccccgtgctg    8040
ctgcccgaca accactacct gagctaccag tccgccctga gcaaagaccc caacgagaag    8100
cgcgatcaca tggtcctgct ggagttcgtg accgccgccg ggatcactct cggcatggac    8160
gagctgtaca agtaataatc tagagggccg catcatgtaa ttagttatgt cacgcttaca    8220
ttcacgccct ccccccacat ccgctctaac cgaaaaggaa ggagttagac aacctgaagt    8280
ctaggtccct atttattttt ttatagttat gttagtatta agaacgttat ttatatttca    8340 aattttctt tttttctgt acagacgcgt gtacgcatgt aacattatac tgaaaaccctt    8400 gcttgagaag gttttgggac gctcgaaggc tttaatttgc ggccctgcat taatgaatcg    8460
gccaacgcgc ggggagaggc ggtttgcgta ttgggcgctc ttccgcttcc tcgctcactg    8520
actcgctgcg ctcggtcgtt cggctgcggc gagcggtatc agctcactca aaggcggtaa    8580
tacggttatc cacagaatca ggggataacg caggaaagaa catgtgagca aaaggccagc    8640
aaaagcccag gaaccgtaaa aaggccgcgt tgctggcgtt ttccataggc tccgcccccc    8700
ctgacgagca tcacaaaaat cgacgctcaa gtcagaggtg gcgaaacccg acaggactat    8760
aaagatacca ggcgtttccc cctggaagct ccctcgtgcg ctctcctgtt ccgaccctgc    8820
cgcttaccgg atacctgtcc gcctttctcc cttcgggaag cgtggcgctt tctcatagct    8880
cacgctgtag gtatctcagt tcggtgtagg tcgttcgctc caagctgggc tgtgtgcacg    8940
aaccccccgt tcagcccgac cgctgcgcct tatccggtaa ctatcgtctt gagtccaacc    9000
cggtaagaca cgacttatcg ccactggcag cagccactgg taacaggatt agcagagcga    9060
```

```
ggtatgtagg cggtgctaca gagttcttga agtggtggcc taactacggc tacactagaa    9120
ggacagtatt tggtatctgc gctctgctga agccagttac cttcggaaaa agagttggta    9180
gctcttgatc cggcaaacaa accaccgctg gtagcggtgg ttttttttgtt tgcaagcagc   9240 agattacgcg cagaaaaaaa ggatctcaag aagatccttt gatcttttct acggggtctg    9300
acgctcagtg gaacgaaaac tcacgttaag ggattttggt catgagatta tcaaaaagga    9360
tcttcaccta gatcctttta aattaaaaat gaagttttaa atcaatctaa agtatatatg    9420
agtaaacttg gtctgacagt taccaatgct taatcagtga ggcacctatc tcagcgatct    9480
gtctatttcg ttcatccata gttgcctgac tccccgtcgt gtagataact acgatacggg    9540
agcgcttacc atctggcccc agtgctgcaa tgataccgcg agacccacgc tcaccggctc    9600
cagatttatc agcaataaac cagccagccg gaagggccga gcgcagaagt ggtcctgcaa    9660
ctttatccgc ctccatccag tctattaatt gttgccggga agctagagta agtagttcgc    9720
cagttaatag tttgcgcaac gttgttggca ttgctacagg catcgtggtg tcactctcgt    9780
cgtttggtat ggcttcattc agctccggtt cccaacgatc aaggcgagtt acatgatccc    9840
ccatgttgtg caaaaaagcg gttagctcct tcggtcctcc gatcgttgtc agaagtaagt    9900
tggccgcagt gttatcactc atggttatgg cagcactgca taattctctt actgtcatgc    9960
catccgtaag atgcttttct gtgactggtg agtactcaac caagtcattc tgagaatagt    10020
gtatgcggcg accgagttgc tcttgcccgg cgtcaatacg ggataatagt gtatcacata    10080
gcagaacttt aaaagtgctc atcattggaa aacgttcttc ggggcgaaaa ctctcaagga    10140
tcttaccgct gttgagatcc agttcgatgt aacccactcg tgcacccaac tgatcttcag    10200
catcttttac tttcaccagc gtttctgggt gagcaaaaac aggaaggcaa aatgccgcaa    10260
aaaagggaat aagggcgaca cggaaatgtt gaatactcat actcttcctt tttcaatggg    10320
taataactga tataattaaa ttgaagctct aatttgtgag tttagtatac atgcatttac    10380
ttataataca gttttttagt tttgctggcc gcatcttctc aaatatgctt cccagcctgc    10440
ttttctgtaa cgttcaccct ctaccttagc atcccttccc tttgcaaata gtcctcttcc    10500
aacaataata atgtcagatc ctgtagagac cacatcatcc acggttctat actgttgacc    10560
caatgcgtct cccttgtcat ctaaacccac accgggtgtc ataatcaacc aatcgtaacc    10620
ttcatctctt ccacccatgt ctctttgagc aataaagccg ataacaaaat ctttgtcgct    10680
cttcgcaatg tcaacagtac ccttagtata ttctccagta gatagggagc ccttgcatga    10740
caattctgct aacatcaaaa ggcctctagg ttcctttgtt acttcttctg ccgcctgctt    10800
caaaccgcta acaatacctg ggcccaccac accgtgtgca ttcgtaatgt ctgcccattc    10860
tgctattctg tatacacccg cagagtactg caatttgact gtattaccaa tgtcagcaaa    10920
ttttctgtct tcgaagagta aaaaattgta cttggcggat aatgcctttta gcggcttaac    10980 tgtgccctcc atggaaaaat cagtcaagat atccacatgt gttttagta aacaaatttt     11040 gggacctaat gcttcaacta actccagtaa ttccttggtg gtacgaacat ccaatgaagc    11100
acacaagttt gtttgctttt cgtgcatgat attaaatagc ttggcagcaa caggactagg    11160
atgagtagca gcacgttcct tatatgtagc tttcgacatg atttatcttc gtttcctgca    11220
ggtttttgtt ctgtgcagtt gggttaagaa tactgggcaa tttcatgttt cttcaacact    11280
acatatgcgt atatatacca atctaagtct gtgctccttc cttcgttctt ccttctgttc    11340
ggagattacc gaatcaaaaa aatttcaaag aaaccgaaat caaaaaaaag aataaaaaaa    11400
aaatgatgaa ttgaattgaa aagctagctt atcgatgata agctgtcaaa gatgagaatt    11460
```

```
aattccacgg actatagact atactagata ctccgtctac tgtacgatac acttccgctc    11520
aggtccttgt cctttaacga ggccttacca ctcttttgtt actctattga tccagctcag    11580
caaaggcagt gtgatctaag attctatctt cgcgatgtag taaaactagc tagaccgaga    11640
aagagactag aaatgcaaaa ggcacttcta caatggctgc catcattatt atccgatgtg    11700
acgctgcagc ttctcaatga tattcgaata cgctttgagg agatacagcc taatatccga    11760
caaactgttt tacagattta cgatcgtact tgttacccat cattgaattt tgaacatccg    11820
aacctgggag ttttccctga aacagatagt atatttgaac ctgtataata atatatagtc    11880
tagcgcttta cggaagacaa tgtatgtatt tcggttcctg gagaaactat tgcatctatt    11940
gcataggtaa tcttgcacgt cgcatccccg gttcattttc tgcgtttcca tcttgcactt    12000
caatagcata tctttgttaa cgaagcatct gtgcttcatt ttgtagaaca aaaatgcaac    12060
gcgagagcgc taatttttca aacaaagaat ctgagctgca tttttacaga acagaaatgc    12120
aacgcgaaag cgctatttta ccaacgaaga atctgtgctt cattttgta aaacaaaaat    12180 gcaacgcgac gagagcgcta atttttcaaa caaagaatct gagctgcatt tttacagaac    12240
agaaatgcaa cgcgagagcg ctattttacc aacaaagaat ctatacttct tttttgttct    12300
acaaaaatgc atcccgagag cgctattttt ctaacaaagc atcttagatt acttttttc    12360 tcctttgtgc gctctataat gcagtctctt gataactttt tgcactgtag gtccgttaag    12420
gttagaagaa ggctactttg gtgtctattt tctcttccat aaaaaaagcc tgactccact    12480
tcccgcgttt actgattact agcgaagctg cgggtgcatt ttttcaagat aaaggcatcc    12540
ccgattatat tctataccga tgtggattgc gcatactttg tgaacagaaa gtgatagcgt    12600
tgatgattct tcattggtca gaaaattatg aacggtttct tctattttgt ctctatatac    12660
tacgtatagg aaatgtttac attttcgtat tgttttcgat tcactctatg aatagttctt    12720
actacaattt ttttgtctaa agagtaatac tagagataaa cataaaaaat gtagaggtcg    12780
agtttagatg caagttcaag gagcgaaagg tggatgggta ggttatatag ggatatagca    12840
cagagatata tagcaaagag atactttga gcaatgtttg tggaagcggt attcgcaatg    12900
ggaagctcca ccccggttga taatcagaaa agccccaaaa acaggaagat tgtataagca    12960
aatatttaaa ttgtaaacgt taatattttg ttaaaattcg cgttaaattt ttgttaaatc    13020
agctcatttt ttaacgaata gcccgaaatc ggcaaaatcc cttataaatc aaaagaatag    13080
accgagatag ggttgagtgt tgttccagtt tccaacaaga gtccactatt aaagaacgtg    13140
gactccaacg tcaagggcg aaaaagggtc tatcagggcg atggcccact acgtgaacca    13200
tcaccctaat caagtttttt ggggtcgagg tgccgtaaag cagtaaatcg aagggtaaa    13260 cggatgcccc catttagagc ttgacgggga aagccggcga acgtggcgag aaaggaaggg    13320
aagaaagcga aaggagcggg ggctagggcg gtgggaagtg taggggtcac gctgggcgta    13380
accaccacac ccgccgcgct taatgggggcg ctacagggcg cgtggggatg atccactagt    13440
```

<210> SEQ ID NO 22
<211> LENGTH: 10123
<212> TYPE: DNA
<213> ORGANISM: Artificial sequence
<220> FEATURE:
<223> OTHER INFORMATION: Synthetic construct

<400> SEQUENCE: 22

```
ggggaattgt gagcggataa caattcccct ctagaaataa ttttgtttaa ctttaagaag      60
```

-continued

```
gagatatacc atggtgttta tcgtcaatct tttctcctgc accttatctg aaaccacggt    120
tagctcaata aaatctgaag ctacggttag ctcaacattt actgccgtca cggccctgca    180
attggtggct gagggtaagt tgcagtcggc gaagggtttc ggtggtggta cgattcacta    240
cccaaccctc gcggccgaag caccctggtg gacgccgggc caaggccatg gttacgaggc    300
gatcacctac ggctggctgg tcggcgaact gctgcgccgc gccgatgggc gtgggcctgg    360
tctgttaggc gctattgccg tggttcctgg ttacgtttct tacgagaact ctatcaagtg    420
gtggggaccg cgtctggctt cttggggctt tgtcgttgca cggccgttgg gcctggactt    480
tcatgtgggc ctggcggatg aagagtttta tcgtgttgcc catatagcgc gcagcaaagc    540
caatgcagca ctagataaca ttgctgatga caccgtcggc agtatagatc ctaagcggtt    600
gggcgctatt ggctggtcag gtggcggcgg cgcgcttaaa ctggcaacgg agcgcagcac    660
agtacgagcc attttgacca gtactaataa acctgaatgg cgacgcttcg ataaattctt    720
atgtgcctgc gaggatgacc ggattgctga gactaagaaa tatgccaacg cgttttataa    780
aaatgccgac atgctcgaag agttgacccg tgaacacagt atcgggccgg ataaaacatt    840
attgacacaa actcggtttg gcttggggtg cttggatcaa ccgcaagcag gggttaaaat    900
tcattttgaa gagtaccttg atcaaaccca tggatttatc aatttgacgc cagtttcaca    960
taaggcgaga gcaaatctga ttcagatgcc taatgccaca ttcggccttg gcccgcgtgc   1020
ttttgggcat cctggtgcag gtggatcggt aggttttgcc gaccccgaac gatgtagc    1080 gtttggtttc gtgactaata cattggggcc ttatgtagtt gagtttaaaa gccgtcatcc   1140
ctcattttat gcatataaag atggattggt gctgactgga aatgacgtcg actatgtgac   1200
tgattactat gcaacaaagc atgctgtaca tttagatgat ccacgtgcac agaagttggt   1260
cggaatattg gccggttgtc tgtaaggatc cgaattcgag ctcggcgcgc ctgcaggtcg   1320
acaagcttgc ggccgcataa tgcttaagtc gaacagaaag taatcgtatt gtacacggcc   1380
gcataatcga aattaatacg actcactata ggggaattgt gagcggataa caattcccca   1440
tcttagtata ttagttaagt ataagaagga gatatacata tggagactgt tcgtccaggt   1500
tgttttcgtg ctgttgtttc tgttccactg ggtcgtctga cttactcttt cctggtggac   1560
ggtcagccga agtacaaccc ggactgtccg actctggtta acgaagctgg cgtgcgtgtg   1620
aacgtacgcc acggtggttc tgacggtgat tgcgacggtg aagctgacga agaatggggt   1680
aaaggtcgtc aagccgtgc tcgtcgcgtg ctgagccagg tttctggcct ggacctgtac   1740
tctcagcact ccaccagcga catcgtttct atgctggtgt tccgtttctt ctacctggct   1800
atgattccag ctggtgccta ctacttcttc tggctgagcg ttcgtggtgg taatcgccag   1860
gctccagttt gctgggtggt gttcgttatg agcgaaatcc tgtctttcgt tagcgcgctg   1920
atttccctgt ttggcatgtg gaagccgatc aaacgtcgtt ggcgctctct ggacgctctg   1980
cgtccagctc tgccagttgc agattggcca actgtagacg tgatcatttg ccactacaaa   2040
gaggacaccg aacagctgcg tcagactatt cgtgcagcga tgaaactgga ttacccagcc   2100
catctgctgc acattctgat tgccgacgat ggcttcttcc caacctccaa gatggtagag   2160
cgttctgata ttggtctggc tctgtaccag acctgtgttg aggaagcggg ttatgatccg   2220
ctgctggaag aaaccatgaa tgaacgtggt ctggttgaac actatactgt taaggcaggt   2280
gacgacctgc cgcgtcatga ttgcgcggtt gaagctcacc agttcgagtt tggtccgtat   2340
ggtgcggaca tgtacggtcc aggtgccctg ccacgtctgt ccctggttgc tcgtgtgaag   2400
ccggctgacg ctcacaacaa ggcaggcaac atcaacaacg tactgtccaa ctctaacgca   2460
```

```
gaaggtaaga ttgttctgtt cctggatgct gacatgaagc cggtagaatc ttacctgctg    2520
cgtgttctgc cactgatgct ggaagagcag cgttccgata gcctgcagag ccaactgatc    2580
caggcagagg acccagagct gggtgctggt acttctaaga gctggcaaat caaccgtgac    2640
attggcttcg ttggctgccc acaacgcttc gcgaacgtat ccggtgacca tccggattac    2700
tgtgctcacc gtaacgcgat ctactacgac ggtatctgca ctggtcgtga tggtttcggt    2760
atgaccgact tcgttggcac taacgcgtgt tggcgtcgcg aagttctgaa cgagatcggt    2820
ggcttcgttt atggtagcgt gactgaagac accctgacta gcaacgaagt tcatcgccgt    2880
ggctacatta ccgctacgc tgacgaagac ctgtgctggg gtgaagcacc agttaccgtt    2940
gcagcagctc tgctgcagcg tcaacgttgg gctaaaggtg ccatcatgaa cggtatgcgt    3000
atcttcaaag gtgctgctaa agaacgcaaa gaaatgctgc tgagccgtga gaaaccgtct    3060
gaactgtctg agttctacgc atatcgtcgt cagcagcgta aaccaaacaa cactttcgtt    3120
tctaccatgt tctggctgga ttctactctg tacccactgc tgggttgggg tgctttcggt    3180
tacgtgttct gtgctatctt ccacctgatc accgctcagg caccgatctc tccgacctct    3240
actcagagcc tggctggtgc gtttgtgacc tactatctga ttcgttacgg tgcattcttc    3300
tctgccttct atgaagtgaa catgaccgac gttctgcgct ctcagcagtg ttggttctct    3360
tactccttcg cccacactgt gggtgtatgg gatgctctgt ttggtggtgc caagtttggc    3420
tgggttgcta acactggcca acgtcatcgc cgtagctggc tggaatggtt caacatcctg    3480
actctgggtg ctctgctgtc cggcattgtg tggcgtctgt tcgcgttcat tgttatcgaa    3540
gaagcgtgtt ctccgtacga gaacttcggt gctgttgcat tcggcggtta cgtagcgtgg    3600
atgatggctc cagttgctct ggttagcctg aacgaacgcc tgtcttccgc tgacgaatcc    3660
gagcgtgaag gtaaaccgat gccagtgccg actccgatca tcgctgctgc cctgactatc    3720
ctgggtgttg tgttcctgtc tggttgggca aacgctcgtt gtggtatcga agctcgcggt    3780
taaggtacca gaaataattt tgtttaactt taagaaggag actcgagatg gcgaagtttg    3840
gtagccgtaa taagtctccg aagtggatct ctaacggctg ctgcttcctg ctgggtgcct    3900
ttactgctct gctgctgctg tggggtctgt gctccttat tatcccgatt ccgaacaccg    3960
atccgaagct gaactctgta gcgacctctc tgcgttctct gaacttcccg aagaacccag    4020
cagctaccct gccaccgaac ctgcagcatg atccaccgga tactactttc tacgacgatc    4080
cggaaacctc ttatactatg gataaaccga tgaagaactg ggacgagaaa cgtaaggaat    4140
ggctgctgca tcacccgtcc ttcggcgcag ctgctcgtga caagatcctg ctggtaaccg    4200
gttcccagcc gaaacgctgt cacaacccga ttggtgatca cctgctgctg cgtttctta    4260 agaacaaagt ggattactgc cgtctgcata attacgatat catctataac aacgcactgc    4320
tgcacccgaa aatgaactcc tattgggcta agtacccagt gatccgtgct gcaatgatgg    4380
ctcatccgga agttgaatgg gtgtggtggg ttgactctga cgctgtattc actgacatgg    4440
agtttaaact gccactgaaa cgctataaga accacaatct ggtggtgcat ggttgggaag    4500
gtctggtacg tctgaaccac tcctggactg gtctgaacgc aggtgtattc ctgatccgta    4560
attgccaatg gagcctggag ttcatggatg tatgggttag catgggtcca caaactccag    4620
aatacgagaa atgggggag cgtctgcgcg aaaccttcaa agataaagtt ctgccagact    4680
ctgatgacca gactgcactg gcatacctga tcgcaaccga taacaaagac cctggcgtg    4740 agaaaatctt cctggaaagc gagtactact tcgaaggcta ttggctggaa atcgtaagga    4800
```

```
cttacgagaa catctccgaa cgttacgatg aagttgaacg caaagtagaa ggtctgcgtc    4860
gtcgccacgc tgagaaggtt agcgagaaat acggtgcaat gcgtgaagaa tacctgaaag    4920
ataacaaacg tcgtccgttc atcacccatt tcactggttg ccagccgtgc aacggtcacc    4980
ataacccagc atacaatgcg aacgactgtt ggaatggtat ggaacgtgca ctgaactttg    5040
cagataacca gatcctgcgt acctacggtt accatcgtca gaatctgctg gacaagtccg    5100
tttctccact gccgttcggt tatccagcag cttaacctag gctgctgcca ccgctgagca    5160
ataactagca taacccttg gggcctctaa acgggtcttg agggggtttt tgctgaaagg     5220
aggaactata tccggattgg cgaatgggac gcgccctgta gcggcgcatt aagcgcggcg    5280
ggtgtggtgg ttacgcgcag cgtgaccgct acacttgcca gcgccctagc gcccgctcct    5340
ttcgctttct tcccttcctt tctcgccacg ttcgccggct ttccccgtca gctctaaat     5400 cgggggctcc ctttagggtt ccgatttagt gctttacggc acctcgaccc caaaaaactt    5460
gattagggtg atggttcacg tagtgggcca tcgccctgat agacggtttt tcgccctttg    5520
acgttggagt ccacgttctt taatagtgga ctcttgttcc aaactggaac aacactcaac    5580
cctatctcgg tctattcttt tgatttataa gggattttgc cgatttcggc ctattggtta    5640
aaaaatgagc tgatttaaca aaaatttaac gcgaatttta acaaaatatt aacgtttaca    5700
atttctggcg gcacgatggc atgagattat caaaaaggat cttcacctag atccttttaa    5760
attaaaaatg aagttttaaa tcaatctaaa gtatatatga gtaaacttgg tctgacagtt    5820
accaatgctt aatcagtgag gcacctatct cagcgatctg tctatttcgt tcatccatag    5880
ttgcctgact ccccgtcgtg tagataacta cgatacggga gggcttacca tctggcccca    5940
gtgctgcaat gataccgcga gacccacgct caccggctcc agatttatca gcaataaacc    6000
agccagccgg aagggccgag cgcagaagtg gtcctgcaac tttatccgcc tccatccagt    6060
ctattaattg ttgccgggaa gctagagtaa gtagttcgcc agttaatagt ttgcgcaacg    6120
ttgttgccat tgctacaggc atcgtggtgt cacgctcgtc gtttggtatg gcttcattca    6180
gctccggttc ccaacgatca aggcgagtta catgatcccc catgttgtgc aaaaaagcgg    6240
ttagctcctt cggtcctccg atcgttgtca gaagtaagtt ggccgcagtg ttatcactca    6300
tggttatggc agcactgcat aattctctta ctgtcatgcc atccgtaaga tgcttttctg    6360
tgactggtga gtactcaacc aagtcattct gagaatagtg tatgcggcga ccgagttgct    6420
cttgcccggc gtcaatacgg gataataccg cgccacatag cagaacttta aaagtgctca    6480
tcattggaaa acgttcttcg ggcgaaaac tctcaaggat cttaccgctg ttgagatcca    6540
gttcgatgta acccactcgt gcacccaact gatcttcagc atcttttact ttcaccagcg    6600
tttctgggtg agcaaaaaca ggaaggcaaa atgccgcaaa aaagggaata agggcgacac    6660
ggaaatgttg aatactcata ctcttccttt ttcaatcatg attgaagcat ttatcagggt    6720
tattgtctca tgagcggata catatttgaa tgtatttaga aaataaaca aataggtcat      6780 gaccaaaatc ccttaacgtg agttttcgtt ccactgagcg tcagaccccg tagaaaagat    6840
caaaggatct tcttgagatc cttttttct gcgcgtaatc tgctgcttgc aaacaaaaaa    6900
accaccgcta ccagcggtgg tttgtttgcc ggatcaagag ctaccaactc tttttccgaa    6960
ggtaactggc ttcagcagag cgcagatacc aaatactgtc cttctagtgt agccgtagtt    7020
aggccaccac ttcaagaact ctgtagcacc gcctacatac ctcgctctgc taatcctgtt    7080
accagtggct gctgccagtg gcgataagtc gtgtcttacc gggttggact caagacgata    7140
gttaccggat aaggcgcagc ggtcgggctg aacggggggt tcgtgcacac agcccagctt    7200
```

-continued

```
ggagcgaacg acctacaccg aactgagata cctacagcgt gagctatgag aaagcgccac    7260
gcttcccgaa gggagaaagg cggacaggta tccggtaagc ggcagggtcg aacaggaga    7320
gcgcacgagg gagcttccag ggggaaacgc ctggtatctt tatagtcctg tcgggtttcg    7380
ccacctctga cttgagcgtc gattttgtg atgctcgtca gggggcgga gcctatggaa     7440
aaacgccagc aacgcggcct ttttacggtt cctggccttt tgctggcctt ttgctcacat    7500
gttctttcct gcgttatccc ctgattctgt ggataaccgt attaccgcct ttgagtgagc    7560
tgataccgct cgccgcagcc gaacgaccga gcgcagcgag tcagtgagcg aggaagcgga    7620
agagcgcctg atgcggtatt ttctccttac gcatctgtgc ggtatttcac accgcatata    7680
tggtgcactc tcagtacaat ctgctctgat gccgcatagt taagccagta tacactccgc    7740
tatcgctacg tgactgggtc atggctgcgc cccgacaccc gccaacaccc gctgacgcgc    7800
cctgacgggc ttgtctgctc ccggcatccg cttacagaca agctgtgacc gtctccggga    7860
gctgcatgtg tcagaggttt tcaccgtcat caccgaaacg cgcgaggcag ctgcggtaaa    7920
gctcatcagc gtggtcgtga agcgattcac agatgtctgc ctgttcatcc gcgtccagct    7980
cgttgagttt ctccagaagc gttaatgtct ggcttctgat aaagcgggcc atgttaaggg    8040
cggttttttc ctgtttggtc actgatgcct ccgtgtaagg gggatttctg ttcatggggg    8100
taatgatacc gatgaaacga gagaggatgc tcacgatacg ggttactgat gatgaacatg    8160
cccggttact ggaacgttgt gagggtaaac aactggcggt atggatgcgg cgggaccaga    8220
gaaaaatcac tcagggtcaa tgccagcgct tcgttaatac agatgtaggt gttccacagg    8280
gtagccagca gcatcctgcg atgcagatcc ggaacataat ggtgcagggc gctgacttcc    8340
gcgtttccag actttacgaa acacggaaac cgaagaccat tcatgttgtt gctcaggtcg    8400
cagacgtttt gcagcagcag tcgcttcacg ttcgctcgcg tatcggtgat tcattctgct    8460
aaccagtaag gcaaccccgc cagcctagcc gggtcctcaa cgacaggagc acgatcatgc    8520
tagtcatgcc ccgcgcccac cggaaggagc tgactgggtt gaaggctctc aagggcatcg    8580
gtcgagatcc cggtgcctaa tgagtgagct aacttacatt aattgcgttg cgctcactgc    8640
ccgctttcca gtcgggaaac ctgtcgtgcc agctgcatta atgaatcggc caacgcgcgg    8700
ggagaggcgg tttgcgtatt gggcgccagg gtggtttttc ttttcaccag tgagacgggc    8760
aacagctgat tgcccttcac cgcctggccc tgagagagtt gcagcaagcg tccacgctg    8820
gtttgcccca gcaggcgaaa atcctgtttg atggtggtta acggcgggat ataacatgag    8880
ctgtcttcgg tatcgtcgta tcccactacc gagatgtccg caccaacgcg cagcccggac    8940
tcggtaatgg cgcgcattgc gcccagcgcc atctgatcgt tggcaaccag catcgcagtg    9000
ggaacgatgc cctcattcag catttgcatg gtttgttgaa aaccggacat ggcactccag    9060
tcgccttccc gttccgctat cggctgaatt tgattgcgag tgagatattt atgccagcca    9120
gccagacgca gacgcgccga gacagaactt aatgggcccg ctaacagcgc gatttgctgg    9180
tgacccaatg cgaccagatg ctccacgccc agtcgcgtac cgtcttcatg ggagaaaata    9240
atactgttga tgggtgtctg gtcagagaca tcaagaaata cgccggaac attagtgcag    9300
gcagcttcca cagcaatggc atcctggtca tccagcggat agttaatgat cagcccactg    9360
acgcgttgcg cgagaagatt gtgcaccgcc gctttacagg cttcgacgcc gcttcgttct    9420
accatcgaca ccaccacgct ggcacccagt tgatcgcgc gagatttaat cgccgcgaca    9480
atttgcgacg gcgcgtgcag ggccagactg gaggtggcaa cgccaatcag caacgactgt    9540
```

-continued

```
ttgcccgcca gttgttgtgc cacgcggttg ggaatgtaat tcagctccgc catcgccgct    9600
tccacttttt cccgcgtttt cgcagaaacg tggctggcct ggttcaccac gcgggaaacg    9660
gtctgataag agacaccggc atactctgcg acatcgtata acgttactgg tttcacattc    9720
accaccctga attgactctc ttccgggcgc tatcatgcca taccgcgaaa ggttttgcgc    9780
cattcgatgg tgtccgggat ctcgacgctc tcccttatgc gactcctgca ttaggaagca    9840
gcccagtagt aggttgaggc cgttgagcac cgccgccgca aggaatggtg catgcaagga    9900
gatggcgccc aacagtcccc cggccacggg gcctgccacc atacccacgc cgaaacaagc    9960
gctcatgagc ccgaagtggc gagcccgatc ttccccatcg gtgatgtcgg cgatataggc   10020
gccagcaacc gcacctgtgg cgccggtgat gccggccacg atgcgtccgg cgtagaggat   10080
cgagatcgat ctcgatcccg cgaaattaat acgactcact ata                     10123
```

ANTI-MICROBIAL AND UV-PROTECTIVE EXTRACTS AND METHODS OF MAKING AND USING THEREOF

CROSS REFERENCE TO RELATED APPLICATIONS

This application claims priority upon U.S. provisional application Ser. No. 62/634,251, filed Feb. 23, 2018, and 62/754,291, filed on Nov. 1, 2018. These applications are hereby incorporated by reference in their entireties for all of their teachings.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CRF), is hereby incorporated by reference in its entirety.

BACKGROUND

Exposure to UV radiation causes harmful effects in a wide variety of things, both living and non-living. For example, exposure of human skin to UV radiation can cause severe sunburn and skin cancer and exposure of beneficial microorganisms to UV radiation can kill them. UV radiation can also cause materials to degrade prematurely and thus suffer mechanical failure or otherwise become unable to serve their intended purpose.

The harmful effects of UV radiation can generally be prevented or lessened through the simple step of using a compound or composition to absorb all or a portion of the UV radiation before it reaches the item it may harm. For example, chemicals in sunscreen absorb a portion of the UV radiation that would normally reach the skin and, as a result, help protect the skin from sunburn and skin cancer.

Although numerous substances capable of absorbing UV radiation are known, not all of them are suitable for all possible uses. Further, some substances may be expensive to produce or may have harmful side effects, such as toxicity or undesired chemical reactions with a protected material. Other substances simply do not last long enough in the environment in which they are used, or persist long after their period of usefulness.

Microbial contamination of materials and surfaces can also cause a range of problems. Harmful microbes may cause infections in humans or animals. Other undesirable microorganisms can cause materials to degrade prematurely, can cause crop failure (e.g., due to fungal species) or food spoilage, can emit unpleasant odors, and the like. Antibiotics and antiseptic products have traditionally been used to control harmful microbial species; however, microorganisms often acquire antibiotic resistance after a few generations of exposure to these products and compounds. Additionally, many antibiotics have unpleasant side effects and many antiseptic products are particularly harsh to surfaces, such as, for example, human skin, or are toxic to wildlife or aquatic species. Furthermore, antibiotics or antiseptic products applied to the surface layer of an object may eventually wear or wash off, thus losing their effectiveness.

Accordingly, there is a demand for new substances able to absorb UV radiation. Furthermore, there is a demand for new antimicrobial substances. It is particularly desirable if both types of substance are biocompatible and biodegradable and further, if the same substances have simultaneously both anti-microbial and UV-protective properties. Additionally, it would be desirable if these substances could be incorporated to articles intended for consumer use such as, for example, food and beverage containers, thereby imparting their properties to these articles. The present invention addresses these needs.

SUMMARY

Described herein are anti-microbial and UV-protective biological devices and extracts produced therefrom. The biological devices include microbial cells transformed with a DNA construct containing genes for producing proteins such as, for example, zinc-related protein/oxidase, silicatein, silaffin, and alcohol dehydrogenase. In some instances, the biological devices also include a gene for lipase. Methods for producing and using the devices are also described herein. Finally, compositions and methods for using the devices and extracts to kill microbial species or prevent microbial growth and to reduce or prevent UV-induced damage or exposure to materials, items, plants, and human and animal subjects are described herein. Also disclosed are biological devices producing polyactive carbohydrates and carbo sugars, as well as compositions and articles incorporating both extracts from these devices and the anti-microbial and UV-protective extracts.

The advantages to the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

5B shows a schematic of a constructed pYES2 plasmid showing the direction, placement, and size of genetic parts used in one aspect of the DNA device.

Figure 5A:
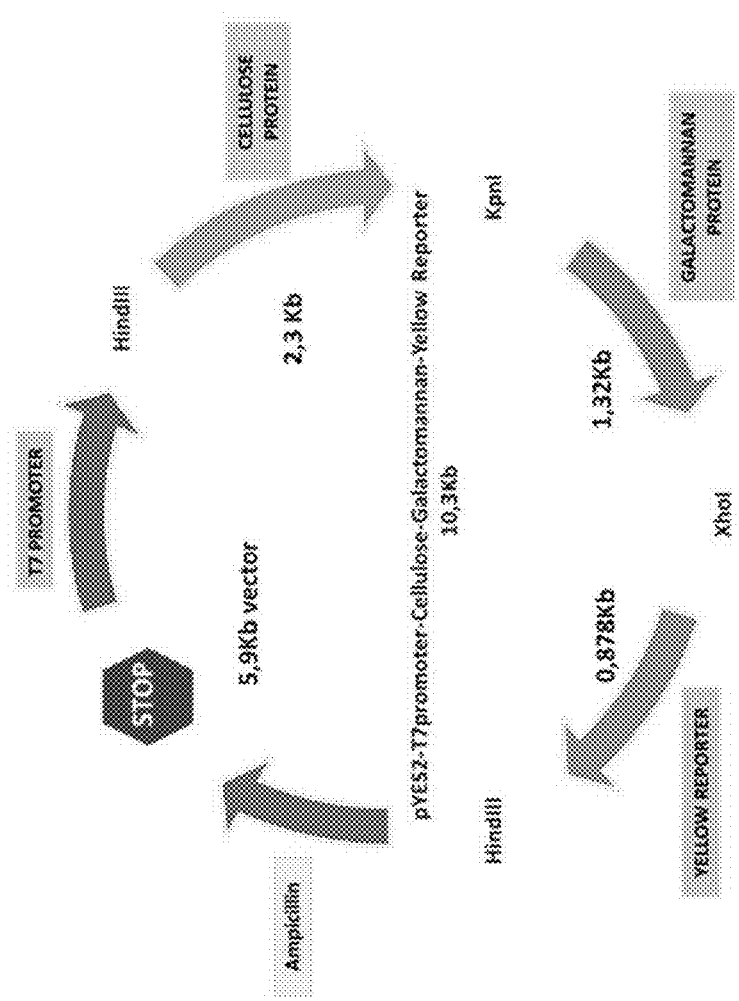
FIG. 5A shows a schematic of a constructed pYES2 plasmid showing the direction, placement, and size of genetic parts used in one aspect of the DNA device.
Figure 5C:
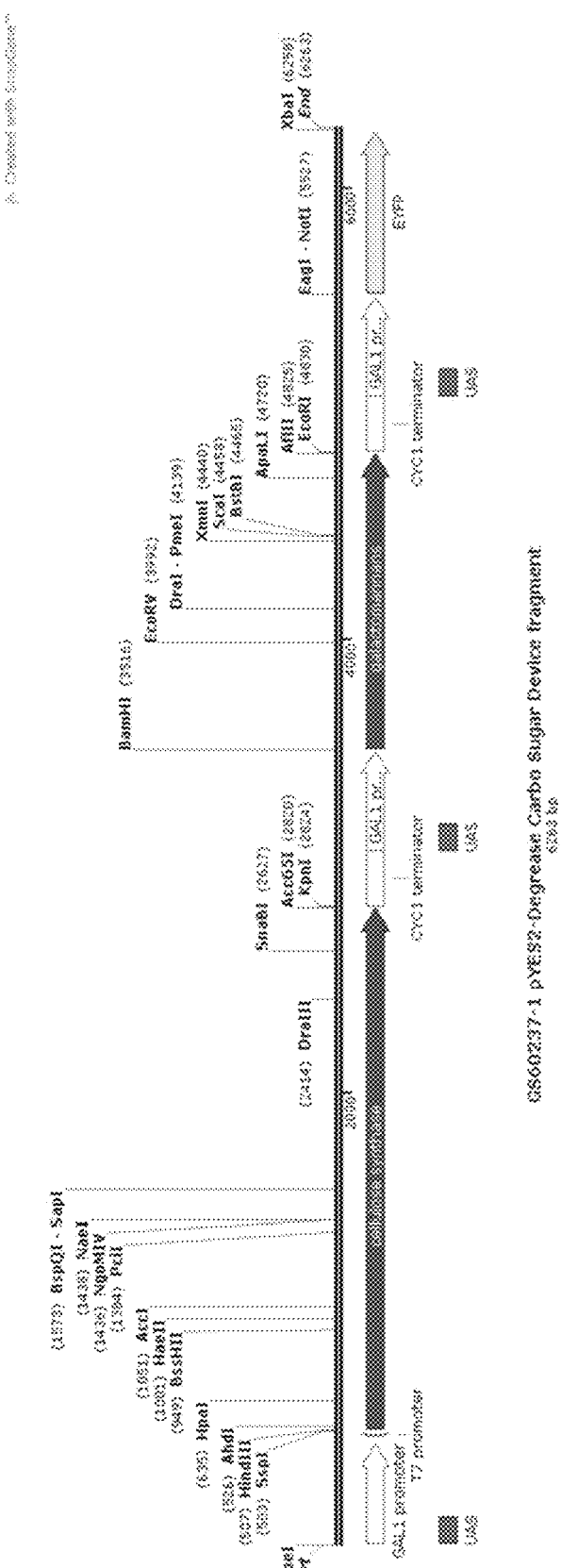
Figure 5D:
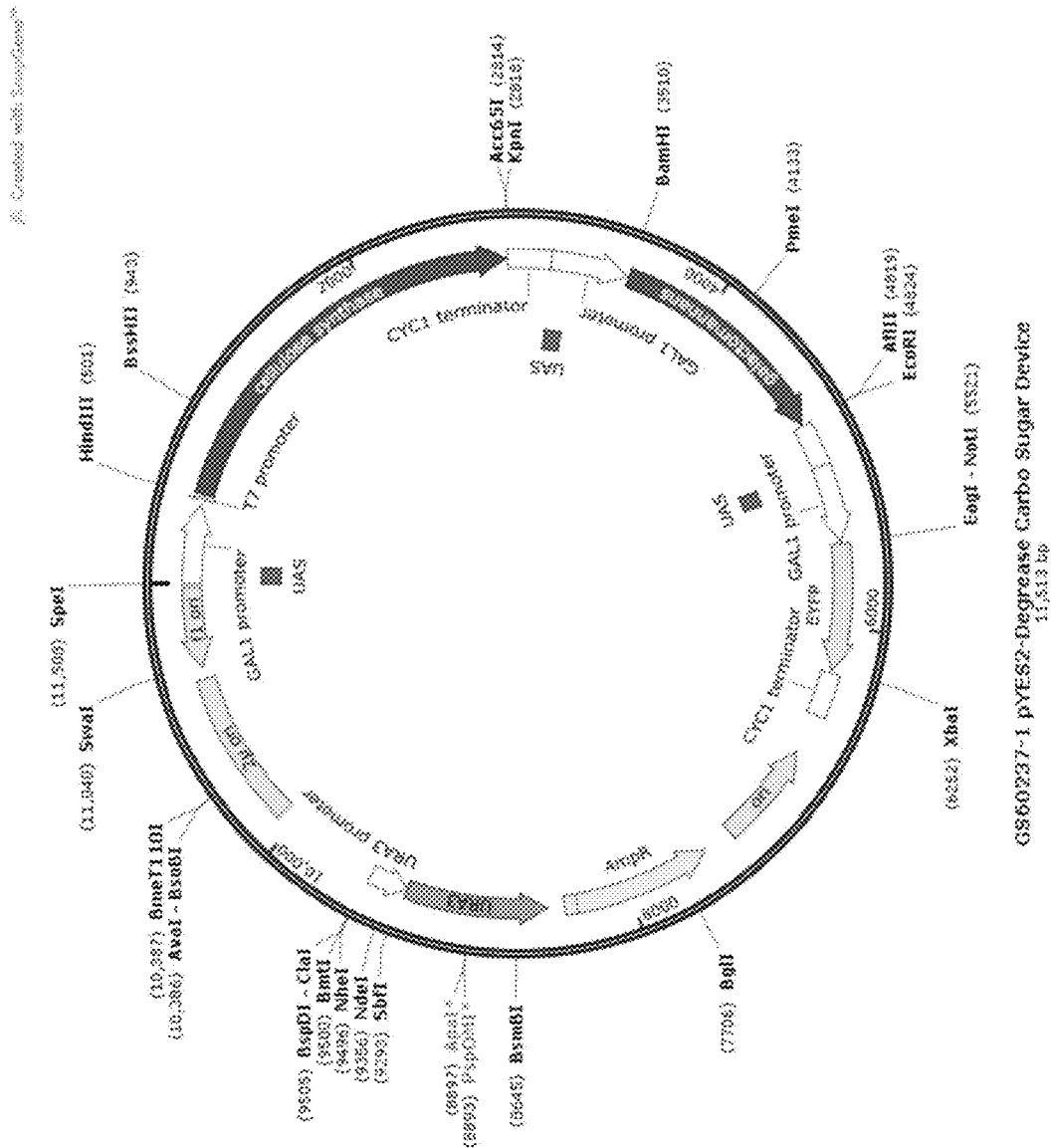

FIGS. 5C and 5D show, respectively, a linear and circular schematic of a constructed pYES2 plasmid showing the direction, placement, and size of genetic parts used of an exemplary DNA device for producing carbo sugars described herein.

Figure 6A:
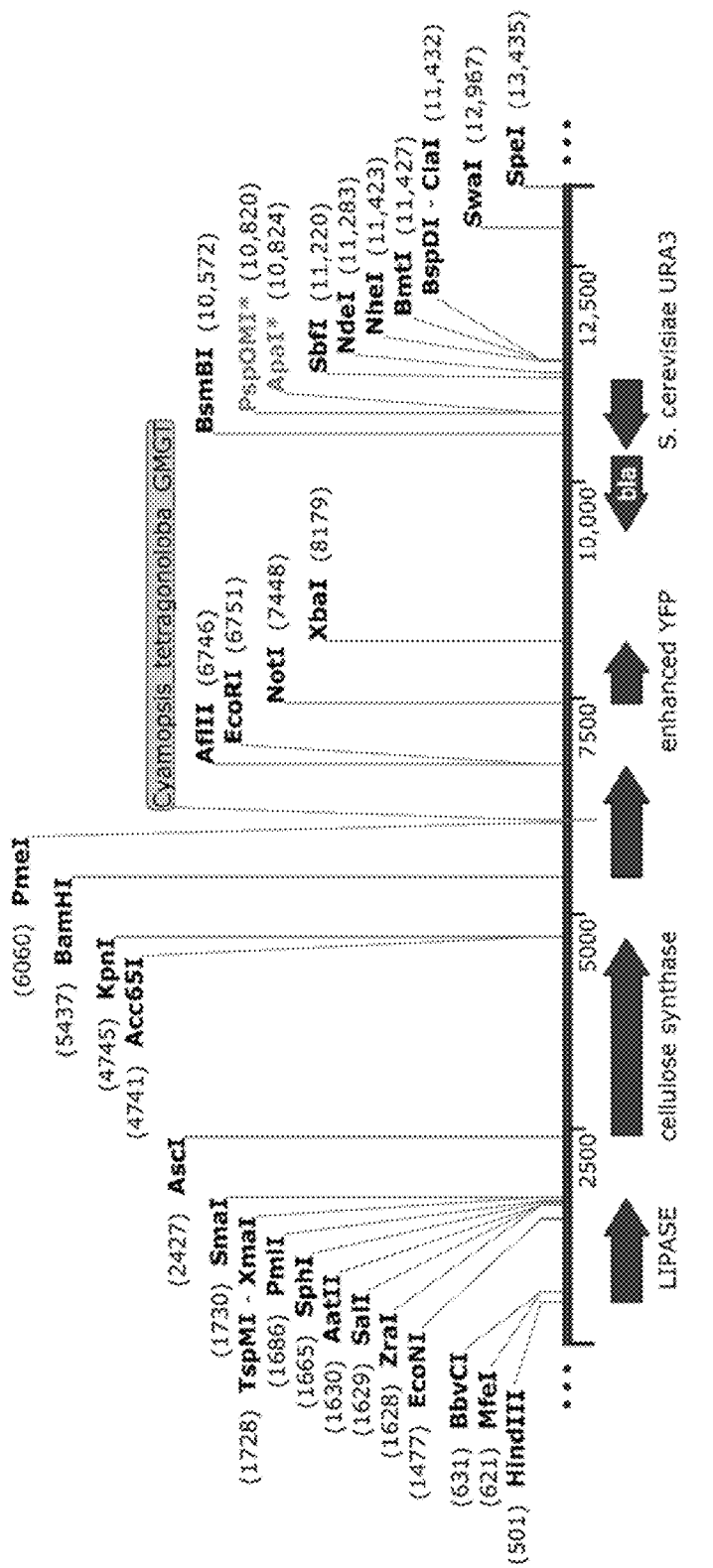
Figure 6B:
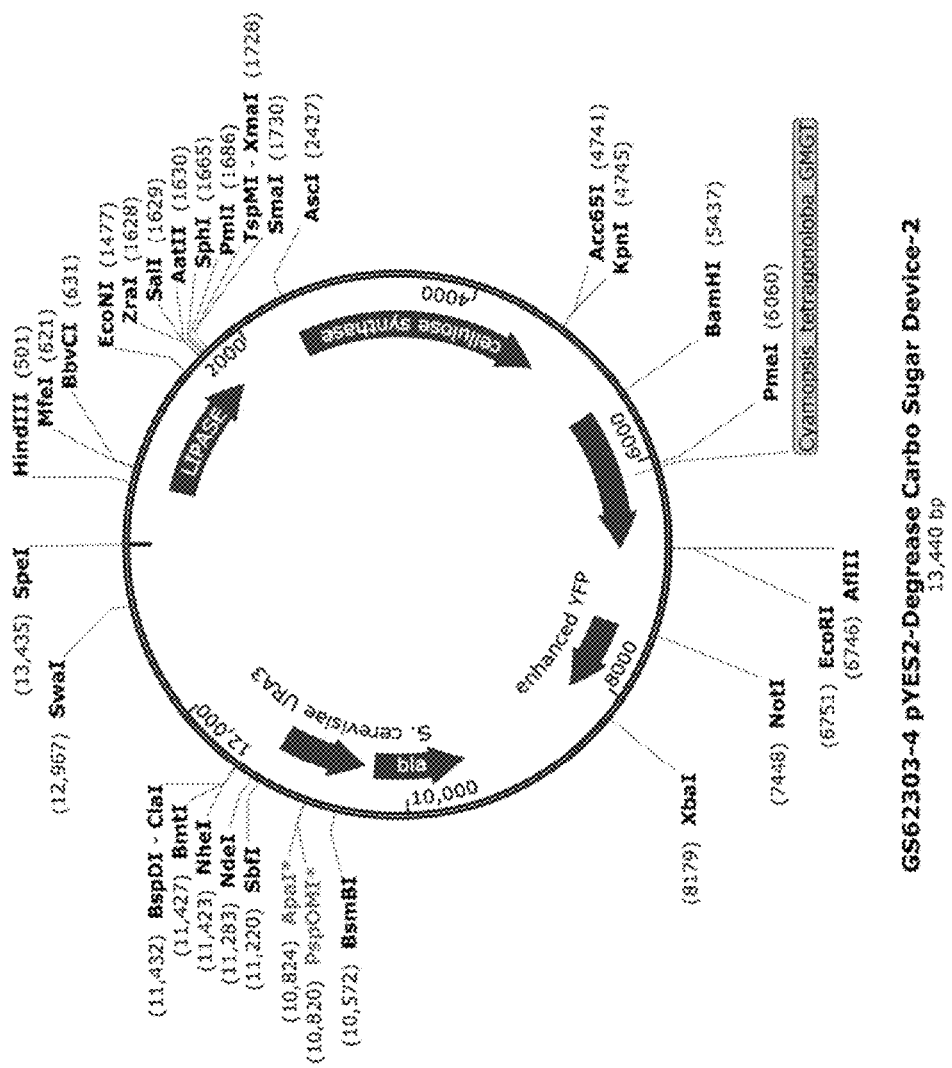

FIGS. 6A and 6B show, respectively, a linear and circular schematic of a constructed plasmid showing the direction, placement, and size of genetic parts used of an alternative exemplary DNA device for producing carbo sugars as described herein.

Figure 7A:
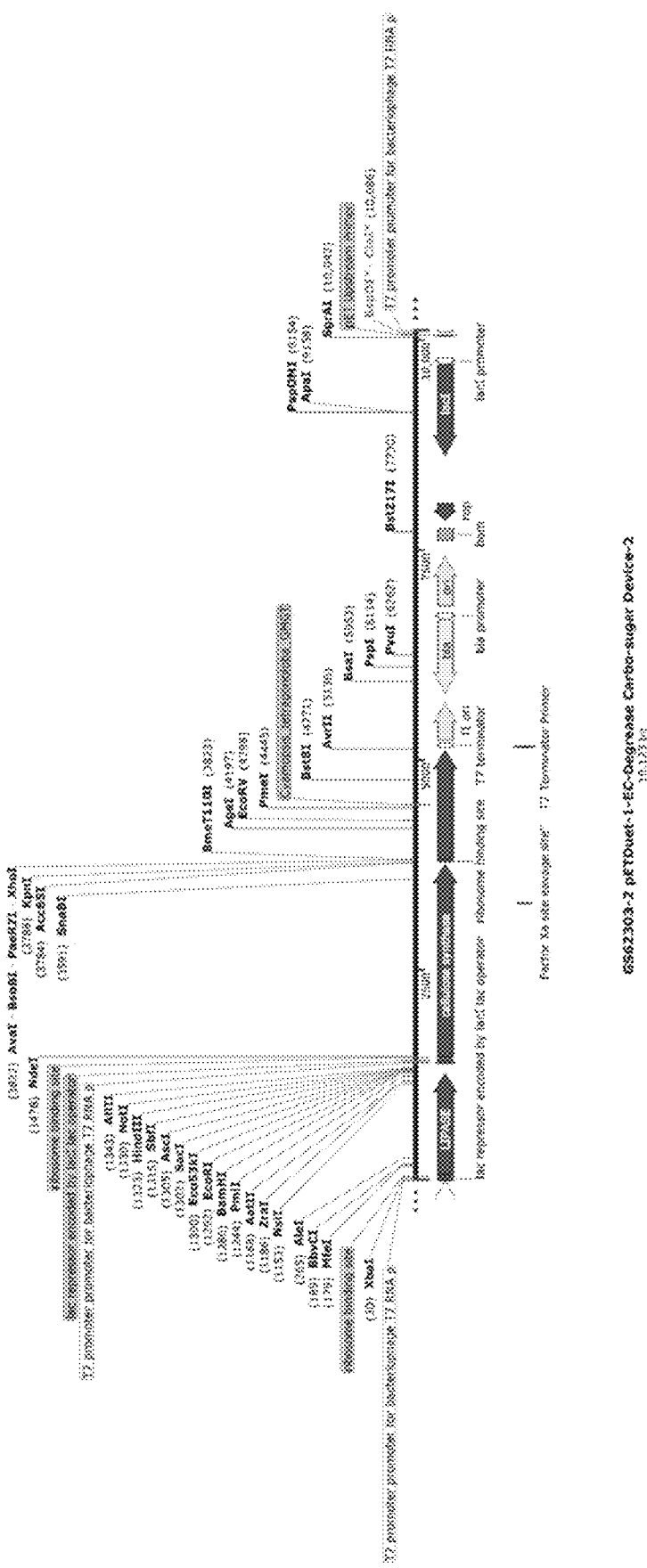
Figure 7B:
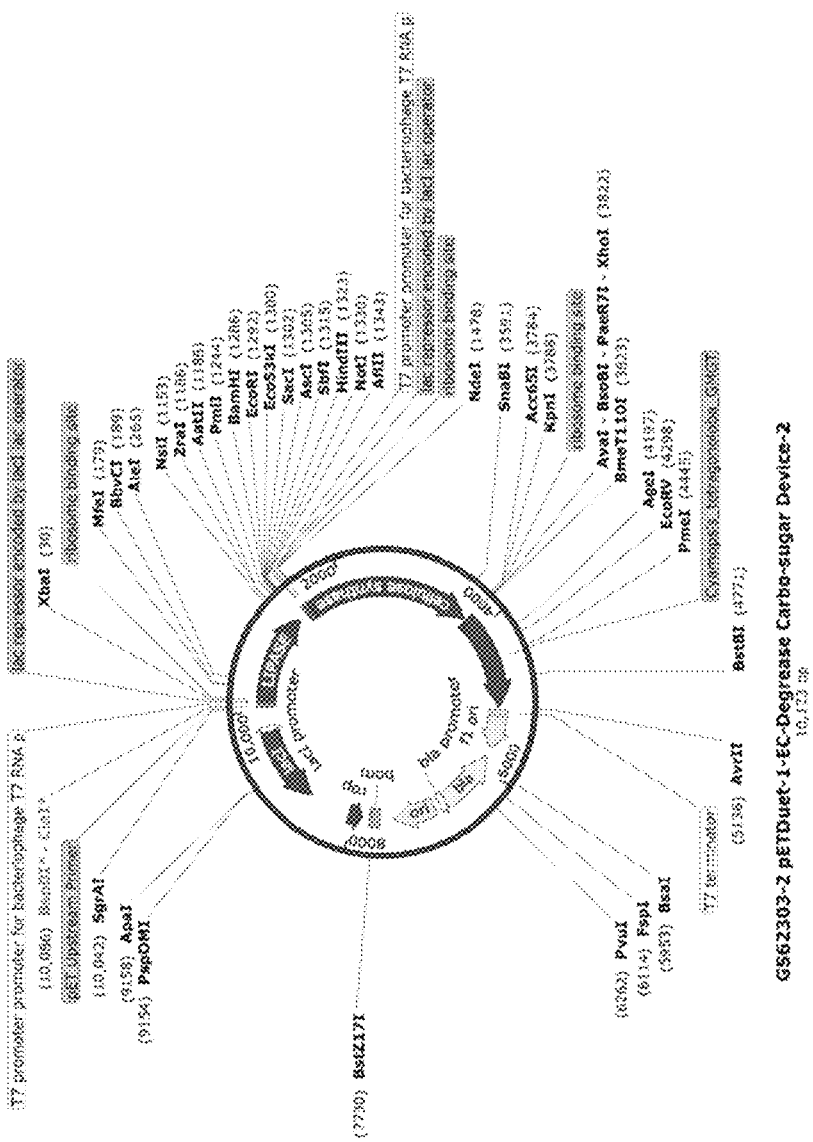

FIGS. 7A and 7B show, respectively, a linear and circular schematic of a constructed plasmid showing the direction, placement, and size of genetic parts used of an alternative exemplary DNA device for producing carbo sugars as described herein.

Figure 8:
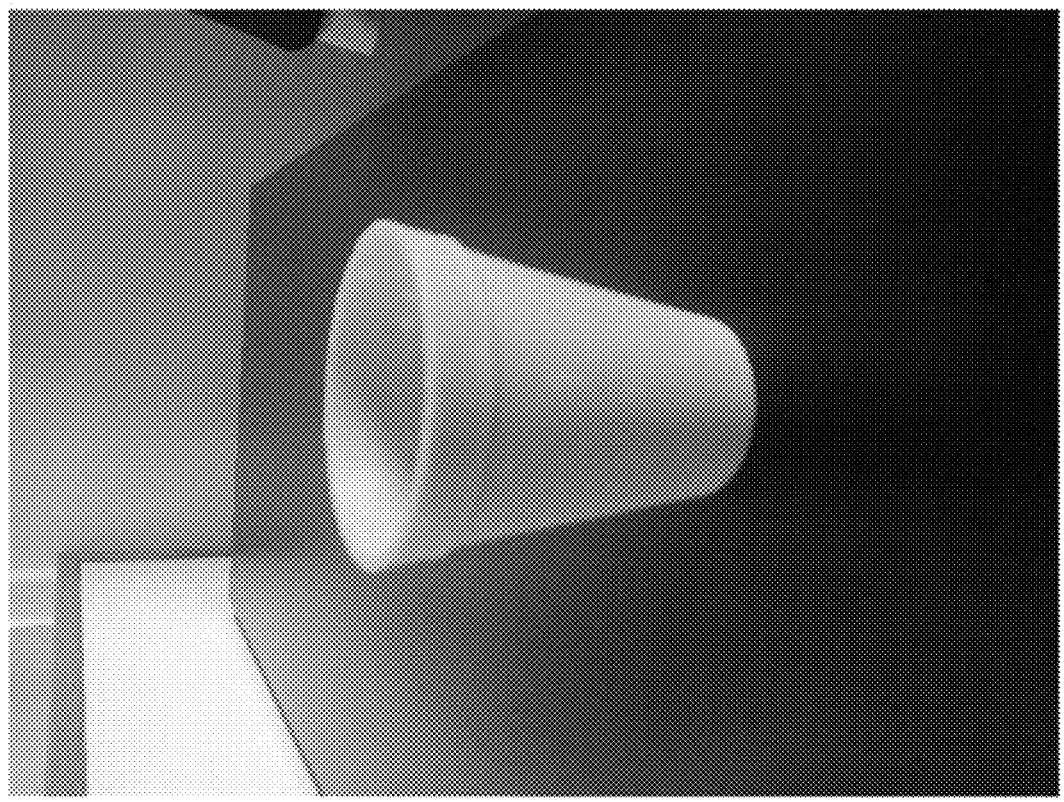

FIG. 8 shows a sample cup prepared from the biofoams disclosed herein.

Figure 9:
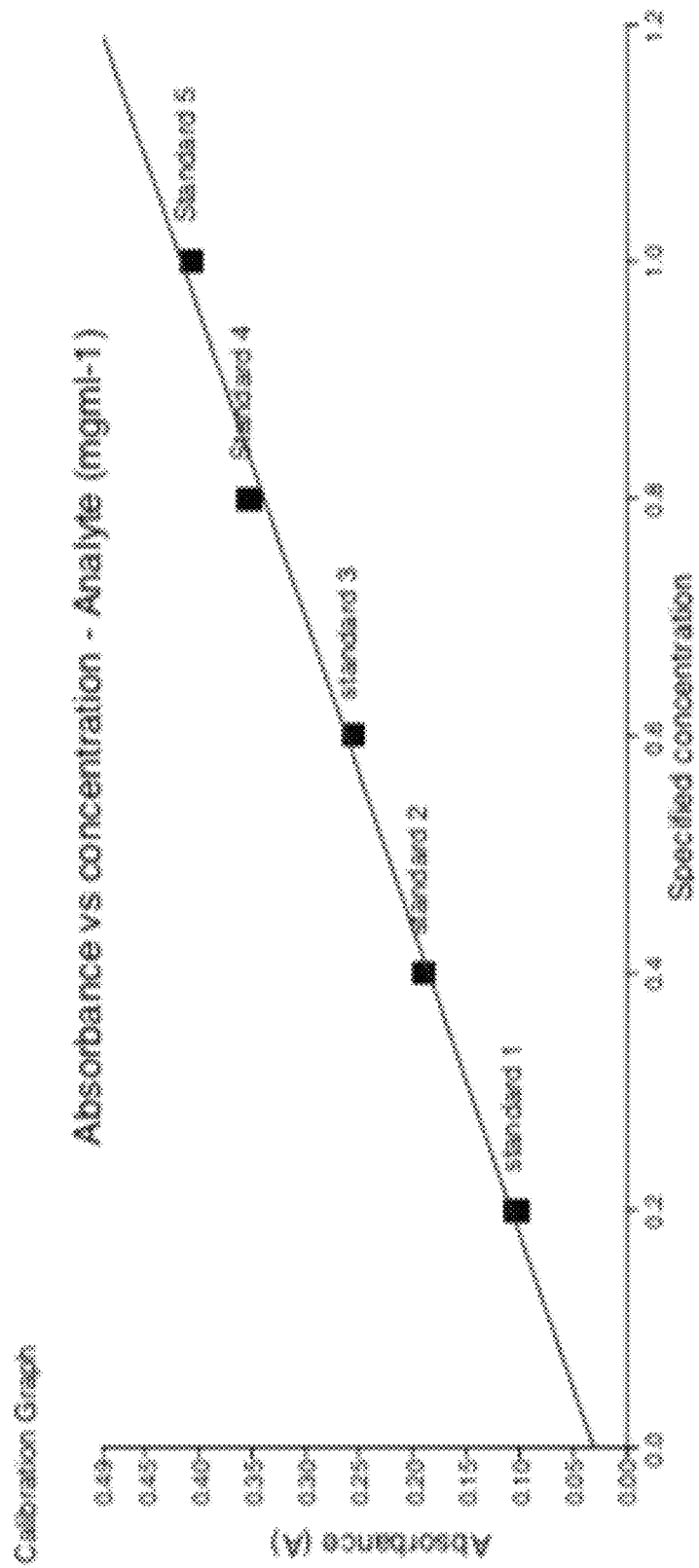

FIG. 9 shows a glucosamine calibration curve used to determine the concentration of polyactive carbohydrate in culture extracts.

Figure 10A:
Figure 10B:
Figure 10C:
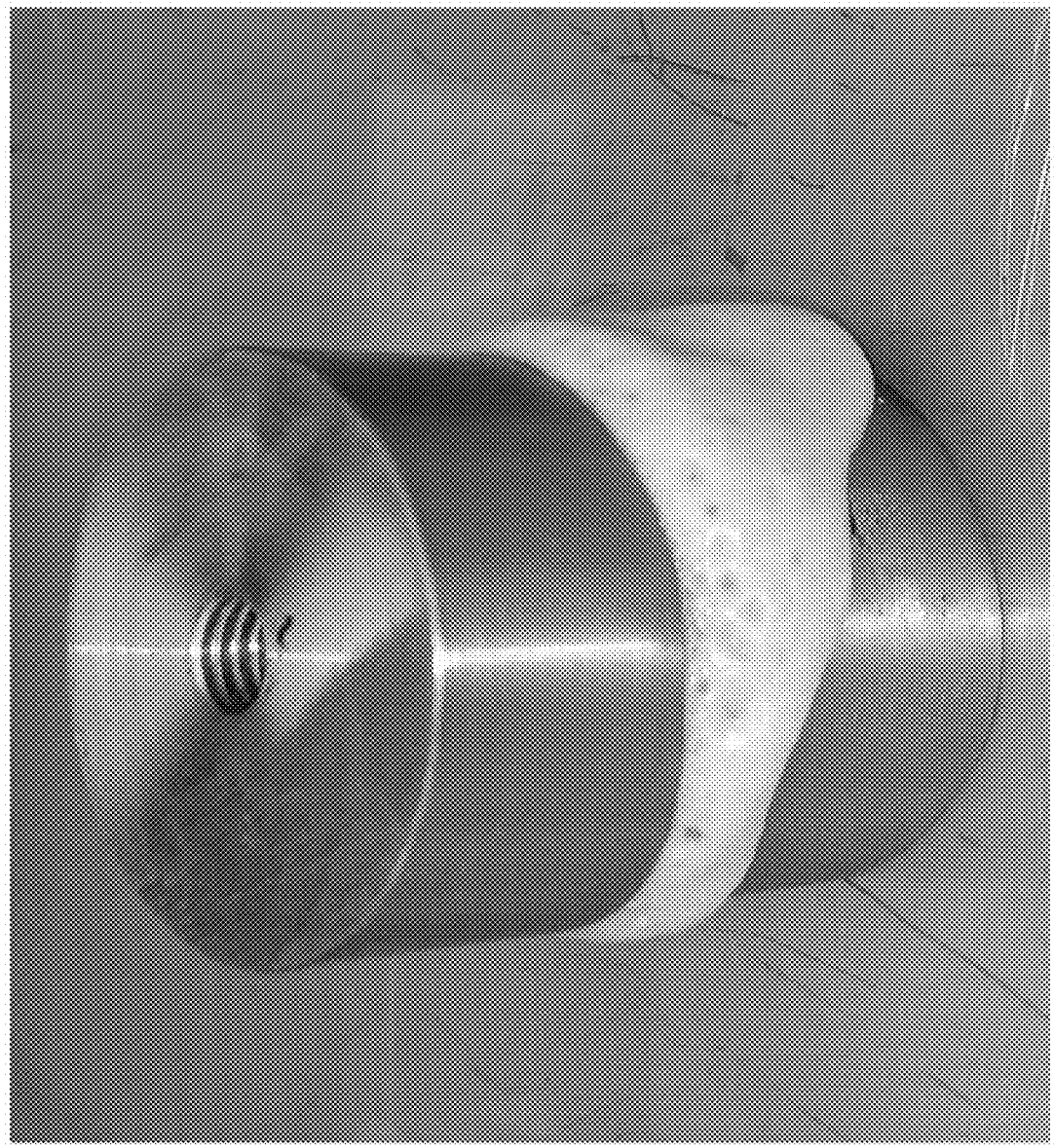

FIGS. 10A, 10B, and 10C show, respectively: plastic glued to plastic, wood glued to wood, metal glued to metal using adhesives produced using the extracts and according to the methods disclosed herein.

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a plasmid" includes mixtures of two or more such plasmids, and the like.

"Optional" or "optionally" means that the subsequently described event or circumstance can or cannot occur, and that the description includes instances where the event or circumstance occurs and instances where it does not. For example, the phrase "optionally includes a reporter protein" means that the reporter protein may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if a yeast is disclosed and discussed and a number of different compatible yeast plasmids are discussed, each and every combination and permutation of yeast and yeast plasmid that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein is a process for producing anti-microbial and/or UV-protective extracts that includes (a) making a DNA construct containing genes for a zinc related protein/oxidase, silicatein, silaffin, alcohol dehydrogenase II, and, optionally, lipase; (b) introducing the DNA construct into host microbial cells via transformation or transfection; and (c) culturing the microbial cells to produce anti-microbial and UV-protective extracts. Also described herein are processes for producing carbo sugars that include (a) making a DNA construct containing genes for cellulose synthase, galactomannan galactosyltransferase, and, optionally, lipase; (b) introducing the DNA construct into host microbial cells via transformation or transfection; and (c) culturing the microbial cells to produce carbo sugars. Further, described herein are processes for producing polyactive carbohydrates that include (a) making a DNA construct containing genes for chitin synthase, chitosanase, chitin deacetylase, and, optionally, lipase; (b) introducing the DNA construct into host microbial cells via transformation or transfection; and (c) culturing the microbial cells to produce polyactive carbohydrates.

I. DNA Constructs

DNA constructs are provided herein for the production of anti-microbial and UV-protective proteins, polyactive carbohydrates, carbo sugars, extracts, and other components. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed according to published algorithms (see Zuker, M., *Science*, 244:48-52, 1989; Jaeger et al., *Proc. Natl. Acad. Sci. USA*, 86:7706-7710, 1989; Jaeger et al., *Methods Enzymol.*, 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, provided herein is a DNA construct comprising the following genetic components:
a) a gene that expresses zinc-related protein/oxidase;
b) a gene that expresses silicatein;
c) a gene that expresses silaffin; and
d) a gene that expresses alcohol dehydrogenase II.

In one aspect, provided herein is a DNA construct comprising the following genetic components:
a) a gene that expresses zinc-related protein/oxidase;
b) a gene that expresses silicatein;
c) a gene that expresses silaffin; and
d) a gene that expresses alcohol dehydrogenase II; and
e) a gene that expresses lipase.

In another aspect, provided herein is a DNA construct comprising the following genetic components:
a) a gene that expresses chitin synthase;
b) a gene that expresses chitosanase; and
c) a gene that expresses chitin deacetylase.

In still another aspect, provided herein is a DNA construct comprising the following genetic components:
a) a gene that expresses chitin synthase;
b) a gene that expresses chitosanase;
c) a gene that expresses chitin deacetylase; and
d) a gene that expresses lipase.

In yet another aspect, provided herein is a DNA construct comprising the following genetic components:
a) a gene that expresses cellulose synthase; and
b) a gene that expresses galactomannan galactosyltransferase.

Each component of the DNA construct is described in detail below.

In one aspect, the nucleic acids (e.g., genes that express zinc-related protein/oxidase, silicatein, silaffin, alcohol dehydrogenase II, lipase, chitin synthase, chitosanase, chitin deacetylase, cellulose synthase, and galactomannan galactosyltransferase) used in the DNA constructs described herein can be amplified using polymerase chain reaction (PCR) prior to being ligated into a plasmid or other vector. Typically, PCR-amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or genes. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the zinc-related protein/oxidase is a member of or is related to the family of proteins known as FAD/NAD(P)-binding oxidoreductases. In a further aspect, activation of zinc-related protein can occur in times of oxidative stress to cells. In another aspect, the zinc-related protein/oxidase is calmodulin or another zinc-binding protein, or a homolog thereof. In one aspect, the zinc-related protein binds zinc (e.g., zinc metal or ions). In another aspect, the zinc-related protein is involved in the oxidation of zinc metal to zinc ions (e.g., $Zn^{+2}$).

In one aspect, the gene that expresses zinc-related protein is isolated from an animal. In a further aspect, the animal is a fish such as, for example, Atlantic salmon. In an alternative aspect, the gene that expresses zinc-related protein is isolated from a bacterium. In one aspect, the bacterium is a *Streptomyces, Polaribacter, Kitasatospora, Actinobacter, Azospirillum, Clostridium, Collimonas*, or *Micromonospora* species. In a still further aspect, the gene that expresses zinc-related protein is isolated from an alga. In one aspect, the alga is *Guillardia theta*. In a further aspect, the gene that expresses zinc-related protein/oxidase has SEQ ID NO. 1 or at least 70% homology thereto, at least 75% homology thereto, at least 80% homology thereto, at least 85% homology thereto, at least 90% homology thereto, or at least 95% homology thereto. In one aspect, the gene that expresses zinc-related protein/oxidase is isolated from *Streptomyces zinciresistens* and can be found in GenBank with GI number EGX59011.1.

Other sequences expressing zinc-related protein/oxidase or related or homologous genes can be identified in a database such as, for example, GenBank. In one aspect, sequences useful herein include those with the GI numbers listed in Table 1.

TABLE 1

Zinc-Related Protein/Oxidase Genes

| Source Organism | Sequence Description | GI Number |
| --- | --- | --- |
| *Streptomyces lincolnensis* | genomic DNA | CP016438.1 |
| *Streptomyces* sp. 4F | genomic DNA | CP013142.1 |
| *Streptomyces collinus* | genomic DNA | CP006259.1 |
| *Streptomyces avermitilis* | genomic DNA | BA000030.4 |
| *Streptomyces* sp. 3124.6 | genomic DNA | LT670819.1 |
| *Streptomyces* sp. 1H-SSA4 | genomic DNA | CP022161.1 |
| *Streptomyces parvulus* | genomic DNA | CP015866.1 |
| *Streptomyces ambofaciens* | genomic DNA | CP012949.1 |
| *Streptomyces ambofaciens* | genomic DNA | CP012382.1 |
| *Streptomyces scabiei* | genomic DNA | FN554889.1 |

TABLE 1-continued

Zinc-Related Protein/Oxidase Genes

| Source Organism | Sequence Description | GI Number |
| --- | --- | --- |
| *Streptomyces davawensis* | genomic DNA | HE971709.1 |
| *Polaribacter* sp. SA4-12 | genomic DNA | CP019334.1 |
| *Streptomyces* sp. 11-1-2 | genomic DNA | CP022545.1 |
| *Streptomyces* sp. CdTB01 | genomic DNA | CP013743.1 |
| *Kitasatospora setae* | genomic DNA | AP010968.1 |
| *Streptomyces pluripotens* | genomic DNA | CP022433.1 |
| *Streptomyces pluripotens* | genomic DNA | CP021080.1 |
| *Streptomyces pactum* | genomic DNA | CP019724.1 |
| *Polaribacter* sp. Hel1_33_78 | genomic DNA | LT629794.1 |
| *Streptomyces* sp. TLI 053 | genomic DNA | LT629775.1 |
| *Streptomyces pactum* | genomic DNA | CP016795.1 |
| *Streptomyces puniscabiei* | genomic DNA | CP017248.1 |
| *Streptomyces griseochromogenes* | genomic DNA | CP016279.1 |
| *Streptomyces incarnatus* | genomic DNA | CP011497.1 |
| *Kitasatospora aureofaciens* | genomic DNA | CP020567.1 |
| *Streptomyces* sp. S10(2016) | genomic DNA | CP015098.1 |
| *Streptomyces reticuli* | genomic DNA | LN997842.1 |
| *Actinobacteria bacterium* IMCC25003 | genomic DNA | CP015603.1 |
| *Polaribacter* sp. KT25b | genomic DNA | LT629752.1 |
| *Streptomyces hygroscopicus* subsp. *limoneus* | genomic DNA | CP013219.1 |
| *Streptomyces* sp. Mg1 | genomic DNA | CP011664.1 |
| *Azospirillum brasilense* | genomic DNA | CP007796.1 |
| *Streptomyces hygroscopicus* subsp. *Jinggangensis* | genomic DNA | CP003720.1 |
| *Streptomyces hygroscopicus* subsp. *Jinggangensis* | genomic DNA | CP003275.1 |
| *Streptomyces* sp. 2323.1 | genomic DNA | LT907981.1 |
| *Clostridium cochlearium* | genomic DNA | LT906477.1 |
| *Collimonas arenae* | genomic DNA | CP009962.1 |
| *Polaribacter* sp. MED152 | genomic DNA | CP004349.1 |
| *Streptomyces* sp. S8 | genomic DNA | CP015362.1 |
| *Micromonospora echinofusca* | genomic DNA | LT607733.1 |
| *Streptomyces* sp. PBH53 | genomic DNA | CP011799.1 |
| *Streptomyces fidvissimus* | genomic DNA | CP005080.1 |
| *Streptomyces katrae* | genomic DNA | CP020042.1 |
| *Streptomyces silaceus* | genomic DNA | CP015588.1 |
| *Streptomyces venezuelae* | genomic DNA | CP018074.1 |
| *Salmo salar* | putative calmodulin | XM_014213459.1 |
| *Streptomyces venezuelae* | genomic DNA | FR845719.1 |
| *Salmo salar* | putative calmodulin | BT059493.1 |
| *Salmo salar* | putative calmodulin | BT045544.1 |
| *Streptomyces albireticuli* | genomic DNA | CP021744.1 |
| *Streptomyces* sp. 3211 | genomic DNA | CP020039.1 |
| *Clostridium sporogenes* | genomic DNA | CP011663.1 |
| *Clostridium sporogenes* | genomic DNA | CP009225.1 |
| *Clostridium botulinum* | genomic DNA | CP006902.1 |
| *Guillardia theta* | genomic DNA | XM_005830304.1 |

Silicateins are biosilica-forming enzymes. A typical silicatein uses a monomeric silicon compound as substrate. Silicateins further display proteolytic activity similar to that of cathepsin L, a lysosomal endopeptidase found in humans and other mammals, birds, fish, and invertebrates such as sponges.

In one aspect, the gene that expresses silicatein is isolated from a freshwater or marine sponge such as, for example, *Suberites domuncula, Hymneniacidon perlevis, Tethya aurantium, Latrunculia oparinae, Mycale phyllophila, Ephydatia fluviatilis, Geodia cydonium, Spongilla lacustris, Lubomirskia baicalensis, Baikalospongia intermedia, Halochondria okadai, Ephydatia muelleri*, or another sponge. In another aspect, the gene that expresses silicatein also has cathepsin L activity. Further in this aspect, the gene is isolated from a coral such as, for example, *Orbicella faveolata*. In another aspect, the gene is isolated from an echinoderm such as *Acanthaster planci* or a mollusk such as *Crassotrea gigas* or *Crassotrea virginica*. In yet another aspect, the gene is isolated from a fish such as, for example,

*Ictalurus furcatus*. In one aspect, the gene that expresses silicatein is isolated from *Suberites domuncula* and can be found in GenBank with GI number AJ272013.1.

In another aspect, the gene that expresses silicatein has SEQ ID NO. 2 or at least 70% homology thereto, at least 75% homology thereto, at least 80% homology thereto, at least 85% homology thereto, at least 90% homology thereto, or at least 95% homology thereto.

Other sequences expressing silicatein or related or homologous genes can e identified in a database such as, for example, GenBank. In one aspect, sequences useful herein include those with the GI numbers listed in Table 2.

TABLE 2

Silicatein Genes

| Source Organism | Sequence Description | GI Number |
|---|---|---|
| Suberites domuncula | silicatein | AJ272013.1 |
| Suberites domuncula | silicatein | HG964669.1 |
| Hymeniacidon perlevis | silicatein | DQ364228.1 |
| Tethya aurantium | silicatein | FR748155.1 |
| Tethya aurantium | silicatein | FR748154.1 |
| Suberites domuncula | silicatein | AJ877017.1 |
| Tethya aurantia | silicatein | AF032117.1 |
| Suberites domuncula | silicatein | HG964668.1 |
| Latrunculia oparinae | silicatein | EU888269.1 |
| Tethya aurantia | silicatein | AF098670.1 |
| Hymeniacidon perlevis | silicatein | EF174599.1 |
| Latrunculia oparinae | silicatein | EU909156.1 |
| Mycale phyllophila | silicatein | KX197954.1 |
| Ephydatia fluviatilis | silicatein | AB370207.1 |
| Latrunculia oparinae | silicatein | EU909155.1 |
| Geodia cydonium | silicatein | AM500857.1 |
| Spongilla lacustris | silicatein | AM941430.1 |
| Ephydatia fluviatilis | silicatein | AB370210.1 |
| Lubomirskia baicalensis | silicatein | AJ968947.1 |
| Autosaccus sp. GV-2009 | silicatein-like protein | GQ387054.1 |
| Spongilla lacustris | silicatein | AM941429.1 |
| Ephydatia sp. n. 1 PW-2008 | silicatein | FM160557.1 |
| Ephydatia fluviatilis | silicatein | AB370206.1 |
| Lubomirskia baicalensis | silicatein | AJ872183.1 |
| Ephydatia sp. n. 2 PW-2008 | silicatein | FM160562.1 |
| Baikalospongia intermedia | silicatein | FM160556.1 |
| Lubomirskia baicalensis | silicatein | AJ968945.1 |
| Spongilla lacustris | silicatein | AM941431.1 |
| Halichondira okadai | silicatein | AB071667.1 |
| Ephydatia muelleri | silicatein | FM160558.1 |
| Ephydatia fluviatilis | silicatein | AB219573.1 |
| Latrunculia oparinae | silicatein | EU909158.1 |
| Ephydatia sp. n. 2 PW-2008 | silicatein | FM160561.1 |
| Ephydatia muelleri | silicatein | FM160559.1 |
| Ephydatia fluviatilis | silicatein | AB370208.1 |
| Amphimedon queenslandica | cathepsin L1-like | XM_003383678.3 |
| Latrunculia oparinae | silicatein | EU909157.1 |
| Acanthodendrilla sp. Vietnam | silicatein | FJ013044.1 |
| Discodermia japonica | silicatein | FR748157.1 |
| Anoplophora glabripennis | cathepsin L1-like | XM_018720387.1 |
| Baikalospongia intermedia | silicatein | FM160555.1 |
| Lubomirskia baicalensis | silicatein | AJ968946.1 |
| Ephydatia muelleri | silicatein | FM160560.1 |
| Ephydatia fluviatilis | silicatein | AM167901.1 |
| Lubomirskia baicalensis | silicatein | AJ786771.1 |
| Swartschewskia papyracea | silicatein | FM160565.1 |
| Ephydatia fluviatilis | silicatein | AM167900.1 |
| Spongilla lacustris | silicatein | GU289406.1 |
| Orbicella faveolata | cathepsin L1-like | XM_020775559.1 |
| Ictalurus furcatus | cathepsin L | GU588322.1 |
| Acanthaster planci | cathepsin L1-like | XM_022226328.1 |

TABLE 2-continued

Silicatein Genes

| Source Organism | Sequence Description | GI Number |
|---|---|---|
| Amphimedon queenslandica | cathepsin L1-like | XM_003383677.3 |
| Crassostrea gigas | cathepsin L1 | XM_011448189.2 |
| Apostichopus japonicas | cathepsin L | KM523550.1 |
| Acanthodendrilla sp. Vietnam | silicatein | FJ013043.1 |
| Crassostrea virginica | cathepsin L1-like | XM_022469675.1 |
| Crassostrea virginica | cathepsin L1-like | XM_022469674.1 |
| Crassostrea virginica | cathepsin L1-like | XM_022469673.1 |
| Crassostrea virginica | cathepsin L1-like | XM_022469672.1 |
| Branchiostoma floridae | hypothetical protein | XM_002611705.1 |
| Oreochromis niloticus | digestive cysteine proteinase 2-like | XM_019348535.1 |
| Oreochromis niloticus | cathepsin L1 | XM_019348480.1 |
| Oreochromis niloticus | cathepsin L1 | XM_019348479.1 |
| Branchiostoma floridae | hypothetical protein | XM_002611707.1 |
| Astyanax mexicanus | cathepsin L1-like | XM_007241546.3 |
| Crassostrea virginica | cathepsin L1-like | XM_022471536.1 |
| Crassostrea virginica | cathepsin L1-like | XM_022471535.1 |
| Meriones unquiculatus | cathepsin L1-like | XM_021650453.1 |
| Branchiostoma belcheri | cathepsin L1-like | XM_019767779.1 |
| Pygocentrus nattereri | digestive cysteine proteinase 2-like | XM_017688979.1 |
| Vigna angularis | senescence-specific cysteine protease SAG39-like | XM_017577302.1 |
| Ictalurus punctatus | cathepsin L1-like | XM_017475948.1 |
| Ictalurus punctatus | cathepsin L1-like | XM_017475947.1 |
| Baikalospongia fungiformis | silicatein | HQ668149.1 |
| Lubomirskia baicalensis | silicatein | GU222667.1 |
| Crassostrea virginica | cathepsin L1-like | XM_022464354.1 |
| Cricetulus griseus | cathepsin L1 | XM_007621048.2 |
| Cricetulus griseus | cathepsin L1 | XM_007607734.2 |
| Biomphalaria glabrata | cathepsin L1-like | XM_013205493.1 |
| Fragaria vesca | senescence-specific cysteine protease SAG39-like | XM_004305390.2 |
| Crassostrea virginica | cathepsin L1-like | XM_022466099.1 |
| Crassostrea virginica | cathepsin L1-like | XM_022466098.1 |
| Chrysochloris asiatica | cathepsin L1-like | XM_006872586.1 |
| Ephydatia fluviatilis | silicatein | GU289405.1 |
| Acanthamoeba castellanii | cysteine protease | EF053509.1 |
| Branchiostoma lanceolatum | cathepsin | AY333297.1 |
| Orbicella faveolata | cathepsin L1-like | XM_020776462.1 |
| Pygocentrus nattereri | cathepsin L1-like | XM_017723497.1 |
| Pygocentrus nattereri | cathepsin L1-like | XM_017723496.1 |
| Lubomirskia baicalensis | silicatein | GU222669.1 |
| Ephydatia muelleri | silicatein | GU289408.1 |
| N. norvegicus | cathepsin L | X80990.1 |
| Lubomirskia baikalensis | silicatein | AJ877018.1 |
| Mizuhopecten yessoensis | cathepsin L1-like | XM_021491465.1 |
| Bactrocera dorsalis | cathepsin L | XM_019992690.1 |
| Branchiostoma belcheri | cathepsin L1-like | XM_019767758.1 |
| Branchiostoma belcheri | cathepsin L1-like | XM_019767757.1 |
| Branchiostoma belcheri | cathepsin L1-like | XM_019767756.1 |
| Branchiostoma belcheri | cathepsin L1-like | XM_019767755.1 |
| Anoplophora glabripennis | cathepsin L1-like proteinase | XM_018720390.1 |

Silaffins are proteins expressed by diatoms and are involved in cell wall formation in those organisms. Silaffins can precipitate silica in various forms on the nano- and micro-scales. Silaffins may act as organic matrices for the genesis of biosilica and the structure, including pore size, of the resultant biosilica can be affected by the presence of other molecules such as phosphate, nitrogen, polyamines, peptides, and so forth.

In one aspect, the gene that expresses a silaffin is isolated from a diatom such as, for example, *Cylindrotheca fusiformis*, In another aspect, the gene that expresses a silaffin is isolated from a fungus such as, for example, *Kazachstania naganishii, Cyberlindnera jadinii, Verticilium dahliae*. In yet another aspect, the gene that expresses a silaffin is isolated from a bacterium such as, for example, *Streptomyces hygroscopicus* or a *Pseudomonas* species or another unicellular organism such as *Capsaspora owczarzaki*. In an alternative aspect, the gene is isolated from an insect such as, for example, *Drosophila navojoa* or *Drosophila busckii*. In one aspect, the gene that expresses a silaffin is isolated from a plant such as *Citrus sinensis* or *Citrus clementina*. In still another aspect, the gene that expresses a silaffin is isolated from a fish such as, for example, *Kryptolebias marmoratus, Austrufundulus limnaeus*, or *Oryzias latipes* or from a mammal such as the bighorn sheep (*Ovis canadensis canadensis*), leopard (*Panthera pardus*), Siberian tiger (*Panthera tigris altaica*), cheetah (*Acinonyx jubatus*), rat (*Rattus norvegicus*), alpaca (*Vicugna pacos*), or domestic cat (*Felis catus*).

In a further aspect, the gene that expresses silaffin has SEQ ID NO. 3 or at least 70% homology thereto, at least 75% homology thereto, at least 80% homology thereto, at least 85% homology thereto, at least 90% homology thereto, or at least 95% homology thereto.

Other sequences expressing silaffin or related or homologous genes can e identified in a database such as, for example, GenBank. In one aspect, sequences useful herein include those with the GI numbers listed in Table 3.

TABLE 3

Silaffin Genes

| Source Organism | Sequence Description | GI Number |
|---|---|---|
| Cylindrotheca fusiformis | silaffin | AF191634.1 |
| Kazachstania naganishii | hypothetical protein | XM_022610325.1 |
| Kryptolebias marmoratus | involucrin-like | XM_017428128.1 |
| Kazachstania naganishii | chromosome 11 sequence | HE978324.1 |
| Cyberlindnera jadinii | hypothetical protein | XM_020217246.1 |
| Streptomyces hygroscopicus | genomic DNA | CP018627.1 |
| Ovis canadensis canadensis | chromosome 5 sequence | CP011890.1 |
| Verticillium dahlia | chromosome 2 sequence | CP010981.1 |
| Capsaspora owczarzaki | proprotein convertase subtilisin/kexin type 1 | XM_011272068.1 |
| Capsaspora owczarzaki | proprotein convertase subtilisin/kexin type 1 | XM_004347923.2 |
| Verticilium dahlia | hypothetical protein | XM_009652892.1 |
| Verticilium dahlia | chromosome 1 sequence | CP009075.1 |
| Oryzias latipes | chromosome 1 sequence | CP020621.1 |
| Kryptolebias marmoratus | myeloid/lymphoid or mixed-lineage leukemia | XM_017431390.1 |
| Austrofundulus limnaeus | afadin-like | XM_013999827.1 |
| Austrofundulus limnaeus | afadin-like | XM_013999825.1 |
| Austrufundulus limnaeus | afadin-like | XM_014026841.1 |
| Felis catus | CD48 transcript variant | XM_019822316.1 |
| Felis catus | CD48 transcript variant | XM_006943036.3 |
| Felis catus | CD48 transcript variant | XM_019822315.1 |
| Panthera pardus | CD48 transcript variant | XM_019433348.1 |
| Panthera pardus | CD48 transcript variant | XM_019433346.1 |
| Panthera pardus | CD48 transcript variant | XM_019433345.1 |
| Drosophila navojoa | condensing complex subunit 1 | XM_018106778.1 |
| Panthera tigris altaica | CD48 molecule | XM_007092375.2 |
| Citrus sinensis | DEAD-box ATP-dependent RNA helicase 21 | XM_015529892.1 |
| Citrus sinensis | DEAD-box ATP-dependent RNA helicase 21 | XM_006476625.2 |
| Vicugna pacos | interleukin 4 receptor transcript variant | XM_006201225.2 |
| Vicugna pacos | interleukin 4 receptor transcript variant | XM_015236831.1 |
| Acinonyx jubatus | CD48 molecule | XM_015076211.1 |
| Austrofundulus limnaeus | repetitive proline-rich cell wall protein 2-like | XM_014032218.1 |

TABLE 3-continued

Silaffin Genes

| Source Organism | Sequence Description | GI Number |
|---|---|---|
| Drosophila busckii | chromosome 2R sequence | CP012524.1 |
| Pseudomonas sp. MT-1 | genomic DNA | AP014655.1 |
| Citrus clementina | hypothetical protein | XM_006439663.1 |
| Rattus norvegicus | secretoglobin family 3A | NM_001013180.1 |

In one aspect, the gene that expresses alcohol dehydrogenase II catalyzes the conversion of ethanol to acetaldehyde. In another aspect, alcohol dehydrogenase II can act with any one of a number of primary unbranched aliphatic alcohols. In some aspects, alcohol dehydrogenase II requires at least two $Zn^{2+}$ ions per subunit to function. In other aspects, one molecule of $NAD^+$ is required to convert an alcohol to an aldehyde or ketone using alcohol dehydrogenase II.

In one aspect, the gene that expresses alcohol dehydrogenase II is isolated from a fungus. In a further aspect, the fungus is a yeast such as, for example, *Saccharomyces cerevisiae*. In a still further aspect, the *S. cerevisiae* is from strain S288c, N85, Y12, YSR127, AHYO914, YJM451, YJM470, YJM554, YJM555, YJM682, YJM689, YJM972, YJM975, YJM978, YJM996, YJM1083, YJM1133, YJM1190, YJM1208, YJM1250, YJM1307, YJM1356, YJM1381, YJM1383, YJM1385, YJM1386, YJM1388, YJM1389, YJM1419, YJM1433, YJM1456, YJM1460, YJM1526, YJM1592, or YJM1615. In an alternative aspect, the *S. cerevisiae* is a wild-type strain. In a further aspect, the gene that expresses alcohol dehydrogenase II has SEQ ID NO. 4 or at least 70% homology thereto, at least 75% homology thereto, at least 80% homology thereto, at least 85% homology thereto, at least 90% homology thereto, or at least 95% homology thereto. In one aspect, the gene that expresses alcohol dehydrogenase II is isolated from *Saccharomyces cerevisiae* and can be found in GENBank with GI number J0314.1.

In a further aspect, the gene that expresses alcohol dehydrogenase II has SEQ ID NO. 4 or at least 70% homology thereto, at least 75% homology thereto, at least 80% homology thereto, at least 85% homology thereto, at least 90% homology thereto, or at least 95% homology thereto.

Other sequences expressing alcohol dehydrogenase or related or homologous genes can e identified in a database such as, for example, GenBank. In one aspect, sequences useful herein include those with the GI numbers listed in Table 4.

TABLE 4

Alcohol Dehydrogenase Genes

| Source Organism | Sequence Description | GI Number |
|---|---|---|
| Saccharomyces cerevisiae | alcohol dehydrogenase II | J01314.1 |
| Saccharomyces cerevisiae | chromosome XIII sequence | CP005453.2 |
| Saccharomyces cerevisiae | chromosome XIII sequence | CP020135.1 |
| Saccharomyces cerevisiae | chromosome XIII sequence | CP005452.2 |
| Saccharomyces cerevisiae | chromosome XIII sequence | CP005450.2 |
| Saccharomyces cerevisiae | chromosome XIII sequence | BK006946.2 |
| Saccharomyces cerevisiae | alcohol dehydrogenase II | NM_001182812.1 |
| Saccharomyces cerevisiae | chromosome XIII sequence | Z49212.1 |
| Saccharomyces cerevisiae | synthetic construct | EF059086.1 |
| Saccharomyces cerevisiae | alcohol dehydrogenase | M38457.1 |
| Saccharomyces cerevisiae | chromosome XIII sequence | CP005464.2 |
| Saccharomyces cerevisiae | chromosome XIII sequence | CP005483.2 |
| Saccharomyces cerevisiae | chromosome XIII sequence | CP005432.2 |
| Saccharomyces cerevisiae | chromosome XIII sequence | CP005482.2 |

TABLE 4-continued

Alcohol Dehydrogenase Genes

| Source Organism | Sequence Description | GI Number |
|---|---|---|
| Saccharomyces cerevisiae | chromosome XIII sequence | LN907796.1 |
| Saccharomyces cerevisiae | chromosome XIII sequence | CP005456.1 |
| Saccharomyces cerevisiae | chromosome XIII sequence | CP005455.1 |
| Saccharomyces cerevisiae | chromosome XIII sequence | CP005440.1 |
| Saccharomyces cerevisiae | chromosome XIII sequence | CP020203.1 |
| Saccharomyces cerevisiae | chromosome XIII sequence | CP005403.2 |
| Saccharomyces cerevisiae | chromosome XIII sequence | CP005472.2 |
| Saccharomyces cerevisiae | chromosome XIII sequence | CP005465.2 |
| Saccharomyces cerevisiae | chromosome XIII sequence | CP005405.2 |
| Saccharomyces cerevisiae | chromosome XIII sequence | CP005414.2 |
| Saccharomyces cerevisiae | chromosome XIII sequence | CP005412.2 |
| Saccharomyces cerevisiae | chromosome XIII sequence | CP005451.2 |
| Saccharomyces cerevisiae | chromosome XIII sequence | CP011559.1 |
| Saccharomyces cerevisiae | chromosome XIII sequence | CP005436.1 |
| Saccharomyces cerevisiae | chromosome XIII sequence | CP005426.1 |
| Saccharomyces cerevisiae | chromosome XIII sequence | CP005406.1 |
| Saccharomyces cerevisiae | glucose-repressible alcohol dehydrogenase II | KJ137141.1 |
| Saccharomyces cerevisiae | alcohol dehydrogenase | JX901290.1 |
| Saccharomyces cerevisiae | chromosome XIII sequence | CP008010.1 |
| Saccharomyces cerevisiae | chromosome XIII sequence | CP020169.1 |
| Saccharomyces cerevisiae | chromosome XIII sequence | CP005449.2 |
| Saccharomyces cerevisiae | chromosome XIII sequence | CP005429.2 |
| Saccharomyces cerevisiae | chromosome XIII sequence | CP005419.2 |
| Saccharomyces cerevisiae | chromosome XIII sequence | CP005409.2 |
| Saccharomyces cerevisiae | chromosome XIII sequence | CP005428.2 |
| Saccharomyces cerevisiae | chromosome XIII sequence | CP005418.2 |
| Saccharomyces cerevisiae | chromosome XIII sequence | CP005408.2 |
| Saccharomyces cerevisiae | chromosome XIII sequence | CP005477.2 |
| Saccharomyces cerevisiae | chromosome XIII sequence | CP005417.2 |
| Saccharomyces cerevisiae | chromosome XIII sequence | CP005425.2 |
| Saccharomyces cerevisiae | chromosome XIII sequence | CP008265.1 |
| Saccharomyces cerevisiae | chromosome XIII sequence | CP008367.1 |
| Saccharomyces cerevisiae | chromosome XIII sequence | CP008554.1 |
| Saccharomyces cerevisiae | chromosome XIII sequence | CP008537.1 |
| Saccharomyces cerevisiae | chromosome XIII sequence | CP008520.1 |
| Saccharomyces cerevisiae | chromosome XIII sequence | CP008129.1 |
| Saccharomyces cerevisiae | chromosome XIII sequence | CP007993.1 |
| Saccharomyces cerevisiae | chromosome XIII sequence | CP005444.2 |
| Saccharomyces cerevisiae | chromosome XIII sequence | CP005434.2 |
| Saccharomyces cerevisiae | chromosome XIII sequence | CP005424.2 |
| Saccharomyces cerevisiae | chromosome XIII sequence | CP005404.2 |
| Saccharomyces cerevisiae | chromosome XIII sequence | CP005423.2 |
| Saccharomyces cerevisiae | chromosome XIII sequence | CP005422.2 |
| Saccharomyces cerevisiae | chromosome XIII sequence | CP005402.2 |
| Saccharomyces cerevisiae | chromosome XIII sequence | CP005421.2 |
| Saccharomyces cerevisiae | chromosome XIII sequence | CP005411.2 |
| Saccharomyces cerevisiae | chromosome XIII sequence | CP005420.2 |
| Saccharomyces cerevisiae | chromosome XIII sequence | CP005427.1 |
| Saccharomyces cerevisiae | chromosome XIII sequence | CP005416.1 |
| Saccharomyces cerevisiae | chromosome XIII sequence | CP005475.2 |
| Saccharomyces cerevisiae | chromosome XIII sequence | CP008401.1 |
| Saccharomyces cerevisiae | chromosome XIII sequence | CP008503.1 |
| Saccharomyces cerevisiae | chromosome XIII sequence | CP005398.2 |
| Saccharomyces cerevisiae | chromosome XIII sequence | CP005478.2 |
| Saccharomyces cerevisiae | chromosome XIII sequence | CP005437.2 |
| Saccharomyces cerevisiae | chromosome XIII sequence | CP005407.2 |
| Saccharomyces cerevisiae | chromosome XIII sequence | CP005454.2 |
| Saccharomyces cerevisiae | chromosome XIII sequence | CP005462.2 |
| Saccharomyces cerevisiae | chromosome XIII sequence | CP005461.2 |
| Saccharomyces cerevisiae | chromosome XIII sequence | CP005401.2 |
| Saccharomyces cerevisiae | chromosome XIII sequence | CP005396.1 |
| Saccharomyces cerevisiae | glucose-repressible alcohol dehydrogenase II | KJ137139.1 |
| Saccharomyces cerevisiae | chromosome XIII sequence | CP005479.2 |
| Saccharomyces cerevisiae | chromosome XIII sequence | CP005469.2 |
| Saccharomyces cerevisiae | chromosome XIII sequence | CP005399.2 |
| Saccharomyces cerevisiae | chromosome XIII sequence | CP005397.2 |
| Saccharomyces cerevisiae | chromosome XIII sequence | CP005415.2 |
| Saccharomyces cerevisiae | chromosome XIII sequence | CP005395.2 |
| Saccharomyces cerevisiae | chromosome XIII sequence | CP008248.1 |
| Saccharomyces cerevisiae | chromosome XIII sequence | CP008333.1 |
| Saccharomyces cerevisiae | chromosome XIII sequence | CP008316.1 |
| Saccharomyces cerevisiae | chromosome XIII sequence | CP008299.1 |
| Saccharomyces cerevisiae | chromosome XIII sequence | CP008282.1 |
| Saccharomyces cerevisiae | chromosome XIII sequence | CP008231.1 |
| Saccharomyces cerevisiae | chromosome XIII sequence | CP008418.1 |
| Saccharomyces cerevisiae | chromosome XIII sequence | CP008384.1 |
| Saccharomyces cerevisiae | chromosome XIII sequence | CP008350.1 |
| Saccharomyces cerevisiae | chromosome XIII sequence | CP008486.1 |
| Saccharomyces cerevisiae | chromosome XIII sequence | CP008469.1 |
| Saccharomyces cerevisiae | chromosome XIII sequence | CP008435.1 |
| Saccharomyces cerevisiae | chromosome XIII sequence | CP008588.1 |
| Saccharomyces cerevisiae | chromosome XIII sequence | CP008571.1 |
| Saccharomyces cerevisiae | chromosome XIII sequence | CP008656.1 |
| Saccharomyces cerevisiae | chromosome XIII sequence | CP008639.1 |
| Saccharomyces cerevisiae | chromosome XIII sequence | CP008605.1 |
| Saccharomyces cerevisiae | chromosome XIII sequence | CP008214.1 |

A lipase is an esterase that catalyzes the hydrolysis of fats, oils, and lipids. In one aspect, the gene that expresses lipase is isolated from a bacterium. In a further aspect, the bacterium is a *Micrococcus* species, a *Pseudomonas* species, a *Moraxella* species, or an *Acinetobacter* species. In a further aspect, the gene that expresses lipase has SEQ ID NO. 7 or at least 70% homology thereto, at least 75% homology thereto, at least 80% homology thereto, at least 85% homology thereto, at least 90% homology thereto, or at least 95% homology thereto. In one aspect, the gene that expresses lipase can be positioned anywhere in the DNA construct disclosed herein. In one aspect, the gene that expresses lipase is positioned 5' (i.e., prior) to the gene that expresses zinc related protein/oxidase.

Other sequences expressing lipase or related or homologous genes can be identified in a database such as, for example, GenBank. In one aspect, sequences useful herein include those with the GI numbers listed in Table 5:

TABLE 5

Lipase Genes

| Source Organism | Sequence Description | GI Number |
|---|---|---|
| *Micrococcus* sp. HL-2003 | lipase gene | AY268069.1 |
| *Pseudomonas* sp. | esterase gene | M68491.1 |
| *Moraxella* L1 | lipase 1 | X53053.1 |
| *A. calcoaceticus* | carboxylesterase and peptidyl prolyl-cis-trans-isomerase | X74839.1 |
| *Acinetobacter* sp. ADP1 | genomic DNA | CR543861.1 |
| *A. calcoaceticus* | esterase | X71598.1 |
| *Pseudomonas trivialis* | genomic DNA | CP011507.1 |
| *Pseudomonas azotoformans* | genomic DNA | CP019856.1 |
| *Pseudomonas extremaustralis* | genomic DNA | LT629689.1 |
| *Pseudomonas fluorescens* | genomic DNA | CP005975.1 |
| *Pseudomonas fluorescens* | genomic DNA | CP010896.1 |
| *Pseudomonas fluorescens* | genomic DNA | AF228666.1 |
| *Pseudomonas simiae* | genomic DNA | CP007637.1 |
| *Pseudomonas fluorescens* | genomic DNA | AM181176.4 |
| *Pseudomonas Antarctica* | genomic DNA | CP015600.1 |
| *Pseudomonas fluorescens* | genomic DNA | CP015639.1 |
| *Pseudomonas azotoformans* | genomic DNA | LT907842.1 |
| *Pseudomonas* sp. NS1 | genomic DNA | CP022960.1 |
| *Pseudomonas poae* | genomic DNA | LT629706.1 |
| *Pseudomonas poae* | genomic DNA | CP004045.1 |
| *Pseudomonas rhodesiae* | genomic DNA | LT629801.1 |
| *Pseudomonas trivialis* | genomic DNA | LT629760.1 |
| *Pseudomonas azotoformans* | genomic DNA | LT629702.1 |
| *Pseudomonas Antarctica* | genomic DNA | LT629704.1 |
| *Pseudomonas fluorescens* | genomic DNA | CP012400.1 |
| *Pseudomonas azotoformans* | genomic DNA | CP014546.1 |
| *Pseudomonas yamanorum* | genomic DNA | LT629793.1 |
| *Pseudomonas prosekii* | genomic DNA | LT629762.1 |
| *Pseudomonas koreensis* | genomic DNA | CP014947.1 |
| *Pseudomonas libanensis* | genomic DNA | LT629699.1 |

TABLE 5-continued

Lipase Genes

| Source Organism | Sequence Description | GI Number |
|---|---|---|
| Pseudomonas sp. GR 6-02 | genomic DNA | CP011567.1 |
| Pseudomonas fluorescens | genomic DNA | CP014868.1 |
| Pseudomonas fluorescens | genomic DNA | CP011117.1 |
| Pseudomonas fluorescens | genomic DNA | S69066.1 |
| Pseudomonas cedrina | genomic DNA | LT629753.1 |
| Pseudomonas sp. bs2935 | genomic DNA | LT629744.1 |
| Pseudomonas fluorescens | genomic DNA | CP017296.1 |
| Pseudomonas sp. WCS374 | genomic DNA | CP007638.1 |
| Pseudomonas fluorescens | genomic DNA | CP003041.1 |
| Pseudomonas corrugate | genomic DNA | LT629798.1 |
| Pseudomonas corrugate | genomic DNA | CP014262.1 |
| Pseudomonas mediterranea | genomic DNA | LT629790.1 |
| Pseudomonas tolaasii | genomic DNA | CP020369.1 |
| Pseudomonas fluorescens | genomic DNA | CP015638.1 |
| Pseudomonas fluorescens | genomic DNA | CP015637.1 |
| Pseudomonas sp. TKP | genomic DNA | CP006852.1 |
| Synthetic construct | carboxylesterase | HM212419.1 |
| Synthetic construct | carboxylesterase | FJ213454.1 |
| Pseudomonas sp. FDAARGOS 380 | genomic DNA | CP023969.1 |
| Pseudomonas synxantha | genomic DNA | LT629786.1 |
| Pseudomonas orientalis | genomic DNA | LT629782.1 |
| Pseudomonas sp. URMO17WK12:I11 | genomic DNA | LN854573.1 |

Chitin synthase is a glycosyltransferase enzyme that catalyzes the following reaction:

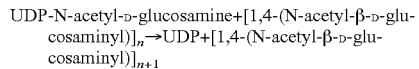

where UDP is uridine diphosphate and N-acetyl-D-glucosamine units are added to the growing chitin chain one residue at a time.

In one aspect, the gene that expresses chitin synthase is isolated from yeast. In a further aspect, the yeast can be *Saccharomyces cerevisiae*. In a still further aspect, the *S. cerevisiae* strain that is the source of chitin synthase can be strain S288c, BSPX042, ySR127, DBVPG6765, YJM1526, YJM972, YJM969, YJM470, YJM248, YJM1478, YJM996, YJM244, YJM1477, YJM1387, YJM993, YJM1332, YJM1242, YJM990, T63, T52, or any other commonly cultured experimental strain of yeast. In another aspect, the *S. cerevisiae* is a wild type strain. In a further aspect, the gene that expresses chitin synthase has SEQ ID NO. 6 or at least 70% homology thereto, at least 75% homology thereto, at least 80% homology thereto, at least 85% homology thereto, at least 90% homology thereto, or at least 95% homology thereto. In one aspect, the gene that expresses chitin synthase is isolated from *Saccharomyces cerevisiae* and can be found in GenBank with GI number NC_001146.8.

Other sequences expressing chitin synthase or related or homologous genes can be identified in a database such as, for example, GenBank. In one aspect, sequences useful herein include those with the GI numbers listed in Table 6.

TABLE 6

Chitin Synthase Genes

| Source Organism | Sequence Description | GI Number |
|---|---|---|
| Saccharomyces cerevisiae | synthetic construct | DQ331902.1 |
| Saccharomyces cerevisiae | chromosome XIV sequence | CP020136.1 |
| Saccharomyces cerevisiae | chromosome XIV sequence | CP014729.1 |
| Saccharomyces cerevisiae | chromosome XIV sequence | CP011560.1 |
| Saccharomyces cerevisiae | chromosome XIV sequence | BK006947.3 |

TABLE 6-continued

Chitin Synthase Genes

| Source Organism | Sequence Description | GI Number |
|---|---|---|
| Saccharomyces cerevisiae | chitin synthase | NM_001183030.2 |
| Saccharomyces cerevisiae | chromosome XIV sequence | Z71468.1 |
| Saccharomyces cerevisiae | chitin synthase | M14045.1 |
| Saccharomyces cerevisiae | chromosome XIV sequence | CP020170.1 |
| Saccharomyces cerevisiae | chromosome XIV sequence | CP005579.2 |
| Saccharomyces cerevisiae | chromosome XIV sequence | CP005519.2 |
| Saccharomyces cerevisiae | chromosome XIV sequence | CP005518.2 |
| Saccharomyces cerevisiae | chromosome XIV sequence | CP005508.2 |
| Saccharomyces cerevisiae | chromosome XIV sequence | CP005498.2 |
| Saccharomyces cerevisiae | chromosome XIV sequence | CP005577.2 |
| Saccharomyces cerevisiae | chromosome XIV sequence | CP005527.2 |
| Saccharomyces cerevisiae | chromosome XIV sequence | CP005497.2 |
| Saccharomyces cerevisiae | chromosome XIV sequence | CP005576.2 |
| Saccharomyces cerevisiae | chromosome XIV sequence | CP005556.2 |
| Saccharomyces cerevisiae | chromosome XIV sequence | CP005526.2 |
| Saccharomyces cerevisiae | chromosome XIV sequence | CP005545.2 |
| Saccharomyces cerevisiae | chromosome XIV sequence | CP005535.2 |
| Saccharomyces cerevisiae | chromosome XIV sequence | CP005525.2 |
| Saccharomyces cerevisiae | chromosome XIV sequence | CP008334.1 |
| Saccharomyces cerevisiae | chromosome XIV sequence | CP008317.1 |
| Saccharomyces cerevisiae | chromosome XIV sequence | CP008351.1 |
| Saccharomyces cerevisiae | chromosome XIV sequence | CP008470.1 |
| Saccharomyces cerevisiae | chromosome XIV sequence | CP008572.1 |
| Saccharomyces cerevisiae | chromosome XIV sequence | CP008674.1 |
| Saccharomyces cerevisiae | chromosome XIV sequence | CP008657.1 |
| Saccharomyces cerevisiae | chromosome XIV sequence | CP008623.1 |
| Saccharomyces cerevisiae | chromosome XIV sequence | CP008181.1 |
| Saccharomyces cerevisiae | chromosome XIV sequence | CP008147.1 |
| Saccharomyces cerevisiae | chromosome XIV sequence | CP008045.1 |
| Saccharomyces cerevisiae | chromosome XIV sequence | CP008028.1 |
| Saccharomyces cerevisiae | chromosome XIV sequence | CP008011.1 |
| Saccharomyces cerevisiae | chromosome XIV sequence | CP007926.1 |
| Saccharomyces cerevisiae | chromosome XIV sequence | CP007892.1 |
| Saccharomyces cerevisiae | chromosome XIV sequence | CP007875.1 |
| Saccharomyces cerevisiae | chromosome XIV sequence | CP007858.1 |
| Saccharomyces cerevisiae | chromosome XIV sequence | CP007824.1 |
| Saccharomyces cerevisiae | chromosome XIV sequence | CP005494.2 |
| Saccharomyces cerevisiae | chromosome XIV sequence | CP005583.2 |
| Saccharomyces cerevisiae | chromosome XIV sequence | CP005573.2 |
| Saccharomyces cerevisiae | chromosome XIV sequence | CP005533.2 |
| Saccharomyces cerevisiae | chromosome XIV sequence | CP005523.2 |
| Saccharomyces cerevisiae | chromosome XIV sequence | CP005503.2 |
| Saccharomyces cerevisiae | chromosome XIV sequence | CP005552.2 |
| Saccharomyces cerevisiae | chromosome XIV sequence | CP005542.2 |
| Saccharomyces cerevisiae | chromosome XIV sequence | CP005532.2 |
| Saccharomyces cerevisiae | chromosome XIV sequence | CP005522.2 |
| Saccharomyces cerevisiae | chromosome XIV sequence | CP005521.2 |
| Saccharomyces cerevisiae | chromosome XIV sequence | CP005550.2 |
| Saccharomyces cerevisiae | chromosome XIV sequence | CP005520.2 |
| Saccharomyces cerevisiae | chromosome XIV sequence | CP005500.2 |
| Saccharomyces cerevisiae | chromosome XIV sequence | CP005524.1 |
| Saccharomyces cerevisiae | chromosome XIV sequence | CP005516.1 |
| Saccharomyces cerevisiae | chromosome XIV sequence | CP004112.1 |
| Saccharomyces cerevisiae | chromosome XIV sequence | CP008266.1 |
| Saccharomyces cerevisiae | chromosome XIV sequence | CP008453.1 |
| Saccharomyces cerevisiae | chromosome XIV sequence | CP008521.1 |
| Saccharomyces cerevisiae | chromosome XIV sequence | CP008640.1 |
| Saccharomyces cerevisiae | chromosome XIV sequence | CP008079.1 |
| Saccharomyces cerevisiae | chromosome XIV sequence | CP005529.2 |
| Saccharomyces cerevisiae | chromosome XIV sequence | CP005499.2 |
| Saccharomyces cerevisiae | chromosome XIV sequence | CP005548.2 |
| Saccharomyces cerevisiae | chromosome XIV sequence | CP005547.2 |
| Saccharomyces cerevisiae | chromosome XIV sequence | CP005546.2 |
| Saccharomyces cerevisiae | chromosome XIV sequence | CP005536.2 |
| Saccharomyces cerevisiae | chromosome XIV sequence | CP005506.2 |
| Saccharomyces cerevisiae | chromosome XIV sequence | CP008283.1 |
| Saccharomyces cerevisiae | chromosome XIV sequence | CP008232.1 |
| Saccharomyces cerevisiae | chromosome XIV sequence | CP008487.1 |
| Saccharomyces cerevisiae | chromosome XIV sequence | CP008436.1 |
| Saccharomyces cerevisiae | chromosome XIV sequence | CP008589.1 |
| Saccharomyces cerevisiae | chromosome XIV sequence | CP008555.1 |
| Saccharomyces cerevisiae | chromosome XIV sequence | CP008538.1 |
| Saccharomyces cerevisiae | chromosome XIV sequence | CP008606.1 |
| Saccharomyces cerevisiae | chromosome XIV sequence | CP008198.1 |
| Saccharomyces cerevisiae | chromosome XIV sequence | CP008164.1 |
| Saccharomyces cerevisiae | chromosome XIV sequence | CP008691.1 |

TABLE 6-continued

Chitin Synthase Genes

| Source Organism | Sequence Description | GI Number |
|---|---|---|
| Saccharomyces cerevisiae | chromosome XIV sequence | CP008130.1 |
| Saccharomyces cerevisiae | chromosome XIV sequence | CP008113.1 |
| Saccharomyces cerevisiae | chromosome XIV sequence | CP008096.1 |
| Saccharomyces cerevisiae | chromosome XIV sequence | CP007977.1 |
| Saccharomyces cerevisiae | chromosome XIV sequence | CP007960.1 |
| Saccharomyces cerevisiae | chromosome XIV sequence | CP005564.2 |
| Saccharomyces cerevisiae | chromosome XIV sequence | CP005544.2 |
| Saccharomyces cerevisiae | chromosome XIV sequence | CP005563.2 |
| Saccharomyces cerevisiae | chromosome XIV sequence | CP005581.2 |
| Saccharomyces cerevisiae | chromosome XIV sequence | CP005551.2 |
| Saccharomyces cerevisiae | chromosome XIV sequence | CP005531.2 |
| Saccharomyces cerevisiae | chromosome XIV sequence | CP005580.2 |
| Saccharomyces cerevisiae | chromosome XIV sequence | CP005530.2 |
| Saccharomyces cerevisiae | chromosome XIV sequence | CP005510.2 |
| Saccharomyces cerevisiae | chromosome XIV sequence | FN393086.1 |
| Saccharomyces cerevisiae | chromosome XIV sequence | CP008504.1 |
| Saccharomyces cerevisiae | chromosome XIV sequence | CP007909.1 |
| Saccharomyces cerevisiae | chromosome XIV sequence | CP005549.2 |
| Saccharomyces cerevisiae | chromosome XIV sequence | CP005539.2 |

Chitosanase is any one of a class of enzymes that perform hydrolysis of β-(1→4)-linkages between D-glucosamine residues in a partially acetylated chitosan molecule. The hydrolysis carried out by chitosanase typically occurs in the middle of the chitosan rather than at the ends.

In one aspect, the gene that expresses chitosanase is isolated from yeast. In a further aspect, the yeast can be *Saccharomyces cerevisiae*. In another aspect, the *S. cerevisiae* strain can be S288c, BSPX042, ySR127, YJM683, YJM682, YJM554, YJM541, YJM456, YJM326, YJM1615, YJM1208, YJM1133, NCIM3107, NCIM3186, T52, T63, YJM1573, YJM1402, YJM1401, another commonly cultured experimental strain, or can be a wild type strain. In a further aspect, the gene that expresses chitosanase has SEQ ID NO. 7 or at least 70% homology thereto, at least 75% homology thereto, at least 80% homology thereto, at least 85% homology thereto, at least 90% homology thereto, or at least 95% homology thereto. In one aspect, the gene that expresses chitosanase is isolated from *Saccharomyces cerevisiae* and can be found in GenBank with GI number AAB67331.1.

Other sequences expressing chitosanase or related or homologous genes can be identified in a database such as, for example, GenBank. In one aspect, sequences useful herein include those with the GI numbers listed in Table 7.

TABLE 7

Chitosanase Genes

| Source Organism | Sequence Description | GI Number |
|---|---|---|
| Saccharomyces cerevisiae | chromosome XII sequence | CP020134.1 |
| Saccharomyces cerevisiae | chromosome XII sequence | CP014727.1 |
| Saccharomyces cerevisiae | chromosome XII sequence | CP011558.1 |
| Saccharomyces cerevisiae | chromosome XII sequence | CP006456.1 |
| Saccharomyces cerevisiae | chromosome XII sequence | CP006455.1 |
| Saccharomyces cerevisiae | chromosome XII sequence | CP006451.1 |
| Saccharomyces cerevisiae | chromosome XII sequence | CP006450.1 |
| Saccharomyces cerevisiae | chromosome XII sequence | CP006448.1 |
| Saccharomyces cerevisiae | chromosome XII sequence | CP006443.1 |
| Saccharomyces cerevisiae | chromosome XII sequence | CP006434.1 |
| Saccharomyces cerevisiae | chromosome XII sequence | CP006383.1 |
| Saccharomyces cerevisiae | chromosome XII sequence | CP006379.1 |
| Saccharomyces cerevisiae | chromosome XII sequence | BK006945.2 |
| Saccharomyces cerevisiae | genomic DNA | NM_001182173.1 |
| Saccharomyces cerevisiae | chromosome XII sequence | U17243.1 |
| Saccharomyces cerevisiae | endochitinase | M74070.1 |
| Saccharomyces cerevisiae | chromosome XII sequence | CP009950.1 |
| Saccharomyces cerevisiae | chromosome XII sequence | CP011821.1 |
| Saccharomyces cerevisiae | chromosome XII sequence | CP008196.1 |
| Saccharomyces cerevisiae | chromosome XII sequence | CP008553.1 |
| Saccharomyces cerevisiae | chromosome XII sequence | CP008536.1 |
| Saccharomyces cerevisiae | chromosome XII sequence | CP008519.1 |
| Saccharomyces cerevisiae | chromosome XII sequence | CP008655.1 |
| Saccharomyces cerevisiae | chromosome XII sequence | CP008213.1 |
| Saccharomyces cerevisiae | chromosome XII sequence | CP008315.1 |
| Saccharomyces cerevisiae | chromosome XII sequence | CP008264.1 |
| Saccharomyces cerevisiae | chromosome XII sequence | CP008145.1 |
| Saccharomyces cerevisiae | chromosome XII sequence | CP006431.1 |
| Saccharomyces cerevisiae | chromosome XII sequence | CP006411.1 |
| Saccharomyces cerevisiae | chromosome XII sequence | CP006410.1 |
| Saccharomyces cerevisiae | chromosome XII sequence | CP008247.1 |
| Saccharomyces cerevisiae | chromosome XII sequence | CP008366.1 |
| Saccharomyces cerevisiae | chromosome XII sequence | CP008349.1 |
| Saccharomyces cerevisiae | chromosome XII sequence | CP008485.1 |
| Saccharomyces cerevisiae | chromosome XII sequence | CP008604.1 |
| Saccharomyces cerevisiae | chromosome XII sequence | CP008179.1 |
| Saccharomyces cerevisiae | chromosome XII sequence | CP008162.1 |
| Saccharomyces cerevisiae | chromosome XII sequence | CP008128.1 |
| Saccharomyces cerevisiae | chromosome XII sequence | CP008026.1 |
| Saccharomyces cerevisiae | chromosome XII sequence | CP007975.1 |
| Saccharomyces cerevisiae | chromosome XII sequence | CP007958.1 |
| Saccharomyces cerevisiae | chromosome XII sequence | CP007941.1 |
| Saccharomyces cerevisiae | chromosome XII sequence | CP007873.1 |
| Saccharomyces cerevisiae | chromosome XII sequence | CP007856.1 |
| Saccharomyces cerevisiae | chromosome XII sequence | CP007839.1 |
| Saccharomyces cerevisiae | chromosome XII sequence | CP008400.1 |
| Saccharomyces cerevisiae | chromosome XII sequence | CP020219.1 |
| Saccharomyces cerevisiae | chromosome XII sequence | CP008451.1 |
| Saccharomyces cerevisiae | chromosome XII sequence | CP006417.1 |
| Saccharomyces cerevisiae | chromosome XII sequence | CP006398.1 |
| Saccharomyces cerevisiae | chromosome XII sequence | CP006389.1 |
| Saccharomyces cerevisiae | chromosome XII sequence | CP008332.1 |
| Saccharomyces cerevisiae | chromosome XII sequence | CP008298.1 |
| Saccharomyces cerevisiae | chromosome XII sequence | CP008417.1 |
| Saccharomyces cerevisiae | chromosome XII sequence | CP008434.1 |
| Saccharomyces cerevisiae | chromosome XII sequence | CP008587.1 |
| Saccharomyces cerevisiae | chromosome XII sequence | CP008638.1 |
| Saccharomyces cerevisiae | chromosome XII sequence | CP008689.1 |
| Saccharomyces cerevisiae | chromosome XII sequence | CP008111.1 |
| Saccharomyces cerevisiae | chromosome XII sequence | CP008094.1 |
| Saccharomyces cerevisiae | chromosome XII sequence | CP008077.1 |
| Saccharomyces cerevisiae | chromosome XII sequence | CP008043.1 |
| Saccharomyces cerevisiae | chromosome XII sequence | CP007924.1 |
| Saccharomyces cerevisiae | chromosome XII sequence | CP007907.1 |
| Saccharomyces cerevisiae | chromosome XII sequence | CP007890.1 |
| Saccharomyces cerevisiae | chromosome XII sequence | CP007822.1 |
| Saccharomyces cerevisiae | chromosome XII sequence | CP008281.1 |
| Saccharomyces cerevisiae | chromosome XII sequence | CP006429.1 |
| Saccharomyces cerevisiae | chromosome XII sequence | CP006419.1 |
| Saccharomyces cerevisiae | chromosome XII sequence | CP008230.1 |
| Saccharomyces cerevisiae | chromosome XII sequence | CP008468.1 |
| Saccharomyces cerevisiae | chromosome XII sequence | CP008672.1 |
| Saccharomyces cerevisiae | chromosome XII sequence | CP008502.1 |
| Saccharomyces cerevisiae | chromosome XII sequence | CP006454.1 |
| Saccharomyces cerevisiae | chromosome XII sequence | CP006445.1 |
| Saccharomyces cerevisiae | chromosome XII sequence | CP006427.1 |
| Saccharomyces cerevisiae | chromosome XII sequence | CP006420.1 |
| Saccharomyces cerevisiae | chromosome XII sequence | CP006409.1 |
| Saccharomyces cerevisiae | chromosome XII sequence | CP006390.1 |
| Saccharomyces cerevisiae | chromosome XII sequence | CP008621.1 |
| Saccharomyces cerevisiae | chromosome XII sequence | CP008009.1 |
| Saccharomyces cerevisiae | chromosome XII sequence | CP006452.1 |
| Saccharomyces cerevisiae | chromosome XII sequence | CP006430.1 |
| Saccharomyces cerevisiae | chromosome XII sequence | CP006401.1 |
| Saccharomyces cerevisiae | chromosome XII sequence | CP006393.1 |
| Saccharomyces cerevisiae | chromosome XII sequence | CP007992.1 |
| Saccharomyces cerevisiae | chromosome XII sequence | CP006414.1 |
| Saccharomyces cerevisiae | chromosome XII sequence | CP008570.1 |
| Saccharomyces cerevisiae | chromosome XII sequence | CP008383.1 |
| Saccharomyces cerevisiae | chromosome XII sequence | CP020236.1 |
| Saccharomyces cerevisiae | chromosome XII sequence | CP006421.1 |
| Saccharomyces cerevisiae | chromosome XII sequence | CP008060.1 |

TABLE 7-continued

Chitosanase Genes

| Source Organism | Sequence Description | GI Number |
|---|---|---|
| Saccharomyces cerevisiae | chromosome XII sequence | CP020151.1 |
| Saccharomyces cerevisiae | chromosome XII sequence | CP006453.1 |
| Saccharomyces cerevisiae | chromosome XII sequence | CP006418.1 |
| Saccharomyces cerevisiae | chromosome XII sequence | CP006386.1 |
| Saccharomyces cerevisiae | chromosome XII sequence | CP006449.1 |
| Saccharomyces cerevisiae | chromosome XII sequence | CP006404.1 |
| Saccharomyces cerevisiae | chromosome XII sequence | LN907795.1 |
| Saccharomyces cerevisiae | chromosome XII sequence | CP006387.1 |

Chitin deacetylase is an enzyme that catalyzes the hydrolysis of chitin to chitosan and acetate. In one aspect, the chitin deacetylase reaction can proceed to completion. In an alternative aspect, the hydrolysis is incomplete, leaving some acetate groups attached to glucosamine residues in the polymer backbone.

In one aspect, the gene that expresses chitin deacetylase is isolated from yeast. In a further aspect, the yeast can be *Saccharomyces cerevisiae*. In another aspect, the *S. cerevisiae* strain can be Y12, S288c, BSPX042, N85, YJM470, YJM456, YJM1615, YJM1592, YJM1549, YJM1460, YJM1389, YJM1388, YJM1387, YJM1304, YJM1208, YJM689, YJM1202, YJM1199, YJM1133, YJM1381, YPS128, another commonly cultured experimental strain, or can be a wild type strain. In a further aspect, the gene that expresses chitin deacetylase has SEQ ID NO. 8 or at least 70% homology thereto, at least 75% homology thereto, at least 80% homology thereto, at least 85% homology thereto, at least 90% homology thereto, or at least 95% homology thereto. In one aspect, the gene that expresses chitin deacetylase is isolated from *Saccharomyces cerevisiae* and can be found in GenBank with accession number NM_001182196.

Other sequences expressing chitin deacetylase or related or homologous genes can be identified in a database such as, for example, GenBank. In one aspect, sequences useful herein include those with the GI numbers listed in Table 8.

TABLE 8

Chitin Deacetylase Genes

| Source Organism | Sequence Description | GI Number |
|---|---|---|
| Saccharomyces cerevisiae | chromosome XII sequence | CP020202.1 |
| Saccharomyces cerevisiae | chromosome XII sequence | CP020134.1 |
| Saccharomyces cerevisiae | chromosome XII sequence | CP014727.1 |
| Saccharomyces cerevisiae | chromosome XII sequence | LN907795.1 |
| Saccharomyces cerevisiae | chromosome XII sequence | CP006449.1 |
| Saccharomyces cerevisiae | chromosome XII sequence | CP006448.1 |
| Saccharomyces cerevisiae | chromosome XII sequence | CP006434.1 |
| Saccharomyces cerevisiae | chromosome XII sequence | CP006433.1 |
| Saccharomyces cerevisiae | chromosome XII sequence | CP006430.1 |
| Saccharomyces cerevisiae | chromosome XII sequence | CP006423.1 |
| Saccharomyces cerevisiae | chromosome XII sequence | CP006407.1 |
| Saccharomyces cerevisiae | chromosome XII sequence | CP006406.1 |
| Saccharomyces cerevisiae | chromosome XII sequence | CP006405.1 |
| Saccharomyces cerevisiae | chromosome XII sequence | CP006390.1 |
| Saccharomyces cerevisiae | chromosome XII sequence | CP006383.1 |
| Saccharomyces cerevisiae | chromosome XII sequence | BK006945.2 |
| Saccharomyces cerevisiae | chitin deacetylase | NM_001182196.1 |
| Saccharomyces cerevisiae | chromosome XII sequence | U17247.1 |
| Saccharomyces cerevisiae | chromosome XII sequence | CP006457.1 |
| Saccharomyces cerevisiae | chromosome XII sequence | CP006382.1 |
| Saccharomyces cerevisiae | chromosome XII sequence | CP006381.1 |
| Saccharomyces cerevisiae | chromosome XII sequence | CP006379.1 |
| Saccharomyces cerevisiae | chromosome XII sequence | CP006401.1 |
| Saccharomyces cerevisiae | chromosome XII sequence | CP020219.1 |
| Saccharomyces cerevisiae | chromosome XII sequence | CP006427.1 |
| Saccharomyces cerevisiae | chromosome XII sequence | CP006426.1 |
| Saccharomyces cerevisiae | chromosome XII sequence | CP006422.1 |
| Saccharomyces cerevisiae | chromosome XII sequence | CP006419.1 |
| Saccharomyces cerevisiae | chromosome XII sequence | CP006417.1 |
| Saccharomyces cerevisiae | chromosome XII sequence | CP006409.1 |
| Saccharomyces cerevisiae | chromosome XII sequence | CP006389.1 |
| Saccharomyces cerevisiae | chromosome XII sequence | CP006377.1 |
| Saccharomyces cerevisiae | chromosome XII sequence | CP020236.1 |
| Saccharomyces cerevisiae | chromosome XII sequence | CP006429.1 |
| Saccharomyces cerevisiae | chromosome XII sequence | CP006421.1 |
| Saccharomyces cerevisiae | chromosome XII sequence | CP006420.1 |
| Saccharomyces cerevisiae | chromosome XII sequence | CP006414.1 |
| Saccharomyces cerevisiae | chromosome XII sequence | CP006410.1 |
| Saccharomyces cerevisiae | chromosome XII sequence | CP011821.1 |
| Saccharomyces cerevisiae | chromosome XII sequence | CP006458.1 |
| Saccharomyces cerevisiae | chromosome XII sequence | CP006456.1 |
| Saccharomyces cerevisiae | chromosome XII sequence | CP006455.1 |
| Saccharomyces cerevisiae | chromosome XII sequence | CP006451.1 |
| Saccharomyces cerevisiae | chromosome XII sequence | CP006450.1 |
| Saccharomyces cerevisiae | chromosome XII sequence | CP006446.1 |
| Saccharomyces cerevisiae | chromosome XII sequence | CP006445.1 |
| Saccharomyces cerevisiae | chromosome XII sequence | CP006443.1 |
| Saccharomyces cerevisiae | chromosome XII sequence | CP006442.1 |
| Saccharomyces cerevisiae | chromosome XII sequence | CP006404.1 |
| Saccharomyces cerevisiae | chromosome XII sequence | CP006436.1 |
| Saccharomyces cerevisiae | chromosome XII sequence | CP006431.1 |
| Saccharomyces cerevisiae | chromosome XII sequence | CP006415.1 |
| Saccharomyces cerevisiae | chromosome XII sequence | CP006411.1 |
| Saccharomyces cerevisiae | chromosome XII sequence | CP006408.1 |
| Saccharomyces cerevisiae | chromosome XII sequence | CP009950.1 |
| Saccharomyces cerevisiae | chromosome XII sequence | CP008196.1 |
| Saccharomyces cerevisiae | chromosome XII sequence | CP020151.1 |
| Saccharomyces cerevisiae | chromosome XII sequence | CP008247.1 |
| Saccharomyces cerevisiae | chromosome XII sequence | CP008332.1 |
| Saccharomyces cerevisiae | chromosome XII sequence | CP008315.1 |
| Saccharomyces cerevisiae | chromosome XII sequence | CP008298.1 |
| Saccharomyces cerevisiae | chromosome XII sequence | CP008281.1 |
| Saccharomyces cerevisiae | chromosome XII sequence | CP008264.1 |
| Saccharomyces cerevisiae | chromosome XII sequence | CP008230.1 |
| Saccharomyces cerevisiae | chromosome XII sequence | CP008417.1 |
| Saccharomyces cerevisiae | chromosome XII sequence | CP008383.1 |
| Saccharomyces cerevisiae | chromosome XII sequence | CP008366.1 |
| Saccharomyces cerevisiae | chromosome XII sequence | CP008349.1 |
| Saccharomyces cerevisiae | chromosome XII sequence | CP008502.1 |
| Saccharomyces cerevisiae | chromosome XII sequence | CP008485.1 |
| Saccharomyces cerevisiae | chromosome XII sequence | CP008468.1 |
| Saccharomyces cerevisiae | chromosome XII sequence | CP008451.1 |
| Saccharomyces cerevisiae | chromosome XII sequence | CP008434.1 |
| Saccharomyces cerevisiae | chromosome XII sequence | CP008587.1 |
| Saccharomyces cerevisiae | chromosome XII sequence | CP008570.1 |
| Saccharomyces cerevisiae | chromosome XII sequence | CP008553.1 |
| Saccharomyces cerevisiae | chromosome XII sequence | CP008536.1 |
| Saccharomyces cerevisiae | chromosome XII sequence | CP008519.1 |
| Saccharomyces cerevisiae | chromosome XII sequence | CP008672.1 |
| Saccharomyces cerevisiae | chromosome XII sequence | CP008655.1 |
| Saccharomyces cerevisiae | chromosome XII sequence | CP008638.1 |
| Saccharomyces cerevisiae | chromosome XII sequence | CP008621.1 |
| Saccharomyces cerevisiae | chromosome XII sequence | CP008604.1 |
| Saccharomyces cerevisiae | chromosome XII sequence | CP008213.1 |
| Saccharomyces cerevisiae | chromosome XII sequence | CP008179.1 |
| Saccharomyces cerevisiae | chromosome XII sequence | CP008162.1 |
| Saccharomyces cerevisiae | chromosome XII sequence | CP008689.1 |
| Saccharomyces cerevisiae | chromosome XII sequence | CP008145.1 |
| Saccharomyces cerevisiae | chromosome XII sequence | CP008128.1 |
| Saccharomyces cerevisiae | chromosome XII sequence | CP008111.1 |
| Saccharomyces cerevisiae | chromosome XII sequence | CP008094.1 |
| Saccharomyces cerevisiae | chromosome XII sequence | CP008077.1 |
| Saccharomyces cerevisiae | chromosome XII sequence | CP008060.1 |
| Saccharomyces cerevisiae | chromosome XII sequence | CP008043.1 |
| Saccharomyces cerevisiae | chromosome XII sequence | CP008026.1 |
| Saccharomyces cerevisiae | chromosome XII sequence | CP008009.1 |
| Saccharomyces cerevisiae | chromosome XII sequence | CP007975.1 |
| Saccharomyces cerevisiae | chromosome XII sequence | CP007958.1 |
| Saccharomyces cerevisiae | chromosome XII sequence | CP007941.1 |
| Saccharomyces cerevisiae | chromosome XII sequence | CP007924.1 |

In one aspect, the gene that expresses cellulose synthase is isolated from plants. In a different aspect, the gene that expresses cellulose synthase is isolated from algae. In one aspect, the algal species is a red algal species such as, for example, *Pyropia yezoensis* (also known as *Porphyra yezoensis*) or *Griffithsia monilis*. In a further aspect, the gene that expresses cellulose synthase has SEQ ID NO. 9 or at least 70% homology thereto, at least 75% homology thereto, at least 80% homology thereto, at least 85% homology thereto, at least 90% homology thereto, or at least 95% homology thereto. In a further aspect, the cellulose synthase is able to use mannose as a substrate instead of or in addition to glucose.

Other sequences expressing cellulose synthase or related or homologous genes can be identified in a database such as, for example, GenBank. In one aspect, sequences useful herein include those with the GI numbers listed in Table 9:

TABLE 9

Cellulose Synthase Genes

| Source Organism | Sequence Description | GI Number |
|---|---|---|
| Porphyra vezoensis | cellulose synthase | EU279853.1 |
| Porphyra vezoensis | cellulose synthase | EU279861.1 |
| Porphyra vezoensis | cellulose synthase pseudogene | EU279857.1 |
| Porphyra vezoensis | cellulose synthase pseudogene | EU279858.1 |
| Porphyra vezoensis | cellulose synthase pseudogene | EU279854.1 |
| Porphyra vezoensis | cellulose synthase pseudogene | EU279855.1 |
| Chondrus crispus | cellulose synthase family | XM_005715532.1 |
| Porphyra vezoensis | cellulose synthase pseudogene | EU279859.1 |
| Porphyra vezoensis | cellulose synthase pseudogene | EU279856.1 |
| Porphyra vezoensis | cellulose synthase pseudogene | EU279860.1 |
| Gelidiella liqulata | cellulose synthase catalytic subunit A | KT920245.1 |
| Gelidiella acerosa | cellulose synthase catalytic subunit A | KT920242.1 |
| Parviphycus albertanoae | cellulose synthase catalytic subunit A | KT920246.1 |
| Parviphycus felicinii | cellulose synthase catalytic subunit A | KT920247.1 |
| Gelidiella incrassata | cellulose synthase catalytic subunit A | KT920244.1 |
| Pterocladiella melanoidea | cellulose synthase catalytic subunit A | KT920254.1 |
| Grffithsia monilis | cellulose synthase A | GU563823.1 |
| Gelidiella fanii | cellulose synthase catalytic subunit A | KT920243.1 |
| Pterocladia rectangularis | cellulose synthase catalytic subunit A | KT920196.1 |
| Ptilophora mediterranea | cellulose synthase catalytic subunit A | KT920238.1 |
| Gelidium pacificum | cellulose synthase catalytic subunit A | KT920227.1 |
| Gelidium microdon | cellulose synthase catalytic subunit A | KT920223.1 |
| Gelidium johnstonii | cellulose synthase catalytic subunit A | KT920222.1 |
| Pterocladella bartletti | cellulose synthase catalytic subunit A | KT920250.1 |
| Pterocladia lucida | cellulose synthase catalytic subunit A | KT920248.1 |
| Gelidium declerckii | cellulose synthase catalytic subunit A | KT920214.1 |
| Ptilophora pterocladioides | cellulose synthase catalytic subunit A | KT920240.1 |
| Pterocladia lucida | cellulose synthase catalytic subunit A | KT920249.1 |
| Gelidium madagascariense | cellulose synthase catalytic subunit A | KT920195.1 |
| Gelidium sp. GHB-2012 | cellulose synthase catalytic subunit A | KT920237.1 |
| Gelidium crinate | cellulose synthase catalytic subunit A | KT920212.1 |
| Ptilophora scalaramosa | cellulose synthase catalytic subunit A | KT920241.1 |
| Gelidium robustum | cellulose synthase catalytic subunit A | KT920234.1 |
| Gelidium purpurascens | cellulose synthase catalytic subunit A | KT920231.1 |
| Gelidium pusillum | cellulose synthase catalytic subunit A | KT920232.1 |
| Gelidium indonesianum | cellulose synthase catalytic subunit A | KT920218.1 |
| Callophyllis japonica | cellulose synthase catalytic subunit A | KT920257.1 |
| Gelidium nudifrons | cellulose synthase catalytic subunit A | KT920225.1 |
| Gelidium isabelae | cellulose synthase catalytic subunit A | KT920219.1 |
| Pterocladiella beachiae | cellulose synthase catalytic subunit A | KT920251.1 |
| Gelidium spinosum | cellulose synthase catalytic subunit A | KT920235.1 |
| Gelidium prostratum | cellulose synthase catalytic subunit A | KT920229.1 |
| Geladium minimum | cellulose synthase catalytic subunit A | KT920224.1 |
| Gelidium sp. SMB-2011a | cellulose synthase catalytic subunit A | KT920216.1 |
| Gelidium elegans | cellulose synthase catalytic subunit A | KT920215.1 |
| Gelidium coulteri | cellulose synthase catalytic subunit A | KT920211.1 |
| Gracilaria textorii | cellulose synthase catalytic subunit A | KT920258.1 |
| Gelidium corneum | cellulose synthase catalytic subunit A | KT920210.1 |
| Gelidium bernabei | cellulose synthase catalytic subunit A | KT920207.1 |
| Gelidium abbottiorum | cellulose synthase catalytic subunit A | KT920204.1 |
| Grateloupia asiatica | cellulose synthase catalytic subunit A | KT920259.1 |
| Ptilophora prolifera | cellulose synthase catalytic subunit A | KT920239.1 |
| Gelidium crispum | cellulose synthase catalytic subunit A | KT920213.1 |
| Chondrus crispus | cellulose synthase family | XM_005711895.1 |
| Gelidium rex | cellulose synthase catalytic subunit A | KT920233.1 |
| Gelidium pulchellum | cellulose synthase catalytic subunit A | KT920230.1 |
| Gelidium coreanum | cellulose synthase catalytic subunit A | KT920209.1 |
| Gelidium capense | cellulose synthase catalytic subunit A | KT920208.1 |
| Rhodymenia intricata | cellulose synthase catalytic subunit A | KT920260.1 |
| Gelidium asperum | cellulose synthase catalytic subunit A | KT920205.1 |
| Aphanta pachyrrhiza | cellulose synthase catalytic subunit A | KT920193.1 |
| Pterocladella nana | cellulose synthase catalytic subunit A | KT920255.1 |
| Gelidium ornamense | cellulose synthase catalytic subunit A | KT920226.1 |
| Gelidium hommersandii | cellulose synthase catalytic subunit A | KT920217.1 |
| Gelidium australe | cellulose synthase catalytic subunit A | KT920206.1 |
| Pterocladiella caerulescens | cellulose synthase catalytic subunit A | KT920252.1 |

TABLE 9-continued

Cellulose Synthase Genes

| Source Organism | Sequence Description | GI Number |
|---|---|---|
| Gelidium jejuense | cellulose synthase catalytic subunit A | KT920221.1 |
| Gelidium japonicum | cellulose synthase catalytic subunit A | KT920220.1 |
| Acanthopeltis longiramulosa | cellulose synthase catalytic subunit A | KT920200.1 |
| Capreolia implexa | cellulose synthase catalytic subunit A | KT920201.1 |
| Acanthopeltis japonica | cellulose synthase catalytic subunit A | KT920199.1 |
| Acanthopeltis hirsuta | cellulose synthase catalytic subunit A | KT920198.1 |
| Acanthopeltis hirsuta | cellulose synthase catalytic subunit A | KT920197.1 |
| Gelidium vagum | cellulose synthase catalytic subunit A | KT920236.1 |
| Aphanta sp. GHB-2016 | cellulose synthase catalytic subunit A | KT920194.1 |
| Pterocladelia capillacea | cellulose synthase catalytic subunit A | KT920253.1 |
| Gelidium pristoides | cellulose synthase catalytic subunit A | KT920228.1 |
| Pterocladelia tenuis | cellulose synthase catalytic subunit A | KT920256.1 |
| Gelidium divaricatum | cellulose synthase catalytic subunit A | KT920202.1 |
| Aphanomyces astaci | hypothetical protein | XM_009832014.1 |
| Aphanomyces invadans | hypothetical protein | XM_008862896.1 |
| Acanthamoeba castellanii str. Neff | putative cellulose synthase | XM_004335119.1 |
| Phytophthora sojae | hypothetical protein | XM_009526171.1 |
| Phytophthora parasitica | hypothetical protein | XM_008915779.1 |
| Aphanomyces invadans | hypothetical protein | XM_008862899.1 |
| Saprolegnia diclina | hypothetical protein | XM_008616683.1 |
| Phytophthora infestans | putative cellulose synthase catalytic subunit | XM_002897169.1 |
| Phytophthora sojae | cellulose synthase 1 | EF563997.1 |
| Phytophthora infestans | cellulose synthase 3 | EF563995.1 |
| Jatropha curcas | sucrose transport protein | XM_012212213.2 |
| Jatropah curcas | sucrose transport protein | XM_012212212.2 |
| Jatropha curcas | sucrose transport protein | XM_012212211.2 |
| Jatropha curcas | sucrose transport protein | XM_012212210.2 |
| Jatropha curcas | sucrose transport protein | NM_001319920.1 |
| Saprolegnia parasitica | hypothetical protein | XM_012347851.1 |
| Protopolystoma xenopodis | unidentified | LM730806.1 |
| Aphanomyces invadans | hypothetical protein | XM_008869048.1 |
| Uncultured bacterium A1Q1 | unidentified | JX649872.1 |
| Plasmopara viticola | cellulose synthase 1 | GQ258973.1 |
| Pyrus x bretschneideri | H2 finger protein ATL20-like | XM_009348167.2 |

In one aspect, the gene that expresses galactomannan galactosyltransferase is isolated from a plant. In one aspect, the galactomannan galactosyltransferase is able to catalyze the synthesis of bonds between an oligo- or poly-mannose backbone and pendant galactose moieties to produce carbo sugars. In a further aspect, the plant is *Oryza japonica, Medicago truncatula, Glycine max, Trigonella foenum-graecum, Lotus japonicus, Senna occidentalis, Cucumis sativus, Fragaria vesca*, or *Cyamopsis tetragonoloba*. In a further aspect, the galactomannan galactosyltransferase has SEQ ID NOs. 10-12 or at least 70% homology thereto. In a further aspect, the gene that expresses galactomannan galactosyltransferase has SEQ ID NO. 12 or at least 70% homology thereto, at least 75% homology thereto, at least 80% homology thereto, at least 85% homology thereto, at least 90% homology thereto, or at least 95% homology thereto.

Other sequences expressing galactomannan galactosyltransferase or related or homologous genes can be identified in a database such as, for example, GenBank. In one aspect, sequences useful herein include those with the GI numbers listed in Table 10:

TABLE 10

Galactomannan Galactosyltransferase Genes

| Source Organism | Sequence Description | GI Number |
|---|---|---|
| Cyamopsis tetragonoloba | galactomannan galactosyltransferase | AJ938067.1 |
| Glycine max | galactomannan galactosyltransferase 1-like | XM_003525821.3 |
| Medicago truncatula | unidentified | AC140720.21 |
| Medicago truncatula | galactosyl transferase | XM_003608493.2 |
| Lotus japonicus | galactomannan galactosyltransferase | AJ567668.1 |
| Lupinus angustifolius | galactomannan galactosyltransferase 1-like | XM_019567307.1 |
| Lupinus angustifolius | galactomannan galactosyltransferase 1-like | XM_019567302.1 |
| Trigonella foenum-graecum | alpha galactosyltransferase | AJ245478.1 |
| Arachis ipaensis | galactomannan galactosyltransferase 1 | XM_016346122.2 |
| Arachis ipaensis | galactomannan galactosyltransferase 1 | XM_016346121.2 |
| Ziziphus jujuba | galactomannan galactosyltransferase 1-like | XM_016034856.1 |
| Ziziphus jujuba | galactomannan galactosyltransferase 1-like | XM_016034855.1 |
| Arachis duranensis | galactomannan galactosyltransferase 1 | XM_016108311.2 |
| Arachis duranensis | galactomannan galactosyltransferase 1 | XM_016108310.2 |
| Glycine max | galactomannan galactosyltransferase 1-like | XM_003539215.3 |
| Glycine max | galactomannan galactosyltransferase 1-like | XM_006590559.2 |
| Glycine max | unidentified | AC235306.1 |
| Glycine max | unidentified | AK245471.1 |
| Senna occidentalis | galactomannan galactosyltransferase | AJ938068.1 |
| Phaseolus vulgaris | hypothetical protein | XM_007156638.1 |
| Glycine max | galactomannan galactosyltransferase | XM_003517306.3 |
| Juglans regia | putative glycosyltransferase 7 | XM_018958015.1 |
| Prunus mume | galactomannan galactosyltransferase 1-like | XM_008239498.2 |
| Prunus mume | galactomannan galactosyltransferase 1-like | XM_008239489.2 |
| Prunus persica | galactomannan galactosyltransferase 1 | XM_007205133.2 |
| Iponoea nil | glycosyltransferase 6-like | XM_019317795.1 |
| Vigna radiata var. radiata | galactomannan galactosyltransferase 1-like | XM_014665934.1 |
| Lupinus angustifolius | galactomannan galactosyltransferase 1-like | XM_019589398.1 |
| Lupinus angustifolius | galactomannan galactosyltransferase 1-like | XM_019589395.1 |
| Lupinus angustifolius | galactomannan galactosyltransferase 1-like | XM_019589394.1 |
| Nelumbo nucifera | putative glycosyltransferase 7 | XM_010274767.2 |
| Vigna angularis | galactomannan galactosyltransferase 1-like | XM_017570547.1 |
| Vigna angularis var. angularis | unidentified | AP015043.1 |

TABLE 10-continued

Galactomannan Galactosyltransferase Genes

| Source Organism | Sequence Description | GI Number |
|---|---|---|
| Pyrus x bretschneideri | galactomannan galactosyltransferase | XM_009364320.2 |
| Vitis vinifera | unidentified | AM447747.2 |
| Morus notabilis | galactomannan galactosyltransferase 1 | XM_O10108622.1 |
| Mattis domestica | galactomannan galactosyltransferase 1-like | NM_001328775.1 |
| Mattis x domestica | galactomannan galactosyltransferase 1-like | XM_008363913.2 |
| Mattis x domestica | unidentified | AB627270.1 |
| Mattis x domestica | unidentified | HM122522.1 |
| Cucumis sativus | galactomannan galactosyltransferase 1-like | XM_004141806.2 |
| Mattis x domestica | galactomannan galactosyltransferase 1-like | XM_008349663.1 |
| Cajanus cajan | galactomannan galactosyltransferase 1-like | XM_020374857.1 |
| Cajanus cajan | galactomannan galactosyltransferase 1-like | XM_020374856.1 |
| Capsicum annum | putative glycosyltransferase 7 | XM_016705445.1 |
| Mattis x domestica | unidentified | HM122524.1 |
| Fragaria vesca | galactomannan galactosyltransferase 1-like | XM_004288217.2 |
| Solanum tuberosum | putative glycosyltransferase 7 | XM_006363751.2 |
| Solanum tuberosum | putative glycosyltransferase 7 | XM_006363750.2 |
| Medicago truncatula | galactosyl transferase | XM_003611508.2 |
| Medicago truncatula | unidentified | CT573500.2 |
| Solanum lycopersicum | putative glycosyltransferase 7 | XM_004231889.3 |
| Solanum lycopersicum | unidentified | AC226502.1 |
| Lycopersicon esculentum | unidentified | BT013963.1 |
| Sesamum indicum | glycosyltransferase 6-like | XM_011101097.2 |
| Cucumis melo | galactomannan galactosyltransferase 1-like | XM_008442195.2 |
| Cucumis melo | unidentified | LN713262.1 |
| Cucumis melo | unidentified | LN681875.1 |
| Solanum lycopersicum | unidentified | HG975514.1 |
| Solanum pennellii | putative glycosyltransferase 7 | XM_015208067.1 |
| Solanum pennellii | unidentified | HG975441.1 |
| Sesamum indicum | glycosyltransferase 6 | XM_011075379.2 |
| Coffea arabica | galactomannan galactosyltransferase | EU568117.1 |
| Cicer arietinum | galactomannan galactosyltransferase 1-like | XM_012718954.1 |
| Theobroma cacao | putative glycosyltransferase 7 | XM_007047507.2 |
| Theobroma cacao | unidentified | LT594788.1 |
| Erythranthe guttatus | glycosyltransferase 6-like | XM_012998642.1 |
| Populus trichocarpa | galactosyltransferase family protein | XM_002310854.2 |
| Prunus persica | glycosyltransferase 6 | XM_007208119.2 |
| Nicotiana attenuata | putative glycosyltransferase 7 | XM_019380314.1 |
| Gossypium arboreum | putative glycosyltransferase 7 | XM_017765398.1 |
| Gossypium arboreum | putative glycosyltransferase 7 | XM_017765397.1 |
| Gossypium hirsutum | putative glycosyltransferase 7 | XM_016879483.1 |
| Gossypium hirsutum | putative glycosyltransferase 7 | XM_016879482.1 |
| Gossypium raimondii | putative glycosyltransferase 7 | XM_012581704.1 |
| Gossypium raimondii | putative glycosyltransferase 7 | XM_012581703.1 |
| Nicotiana tomentosiformis | putative glycosyltransferase 7 | XM_009626576.2 |
| Prunus mume | glycosyltransferase 6-like | XM_008239940.2 |
| Populus euphratica | putative glycosyltransferase 7 | XM_011033007.1 |
| Populus euphratica | putative glycosyltransferase 7 | XM_011017963.1 |
| Musa acuminata subsp. malaccensis | probable glycosyltransferase 7 | XM_009396086.2 |
| Daucus carota subsp. sativus | putative glycosyltransferase 7 | XM_017387245.1 |
| Daucus carota subsp. sativus | putative glycosyltransferase 7 | XM_017387244.1 |
| Gossypium hirsutum | putative glycosyltransferase 7 | XM_016818092.1 |
| Gossypium raimondii | putative glycosyltransferase 7 | XM_012614197.1 |
| Arabis alpina | unidentified | LT669794.1 |
| Eucalyptus grandis | putative glycosyltransferase 7 | XM_010029779.2 |
| Nicotiana tabacum | putative glycosyltransferase 7 | XM_016593700.1 |
| Nicotiana sylvestris | putative glycosyltransferase 7 | XM_009763295.1 |
| Gossypium hirsutum | putative glycosyltransferase 7 | XM_016864575.1 |
| Gossypium arboreum | galactomannan galactosyltransferase 1 | XM_017774502.1 |
| Gossypium hirsutum | putative glycosyltransferase 7 | XM_016850999.1 |
| Gossypium hirsutum | glycosyltransferase 6-like | XM_016841848.1 |
| Gossypium raimondii | glycosyltransferase 6-like | XM_012636540.1 |
| Gossypium arboreum | putative glycosyltransferase 7 | XM_017768866.1 |
| Raphanus sativus | glycosyltransferase 6-like | XM_018611230.1 |
| Jatropha curcas | galactomannan galactosyltransferase 1 | XM_012232035.2 |
| Ricinus communis | galactomannan galactosyltransferase 1 | XM_002513376.2 |
| Raphanus sativus | glycosyltransferase 6 | XM_018626243.1 |
| Prunus mume | putative glycosyltransferase 7 | XM_008227859.1 |

In one aspect, the DNA construct has the following genetic components: a) a gene that expresses zinc-related protein/oxidase, b) a gene that expresses silicatein, c) a gene that expresses silaffin, and d) a gene that expresses alcohol dehydrogenase II. In an alternative aspect, the DNA construct further has e) a gene that expresses lipase.

In another aspect, the DNA construct has the following genetic components: a) a gene that expresses chitin synthase, b) a gene that expresses chitosanase, and c) a gene that expresses chitin deacetylase. In a further aspect, the DNA construct further has d) a gene that expresses lipase.

In still another aspect, the DNA construct has the following genetic components: a) a gene that expresses cellulose synthase and b) a gene that expresses galactomannan galactosyltransferase. In an alternative aspect, the DNA construct further has c) a gene that expresses lipase.

In another aspect, said construct further includes a) a promoter, b) a terminator or stop sequence, c) a gene that confers resistance to an antibiotic (a "selective marker"), d) a reporter protein, or a combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is an operon such as, for example, the LAC operon. As used herein, an "operon" is a segment of DNA containing a group of genes wherein the group is controlled by a single promoter. Genes included in an operon are all transcribed together. In a further aspect, the operon is a LAC operon and can be induced when lactose crosses the cell membrane of the biological device.

In one aspect, the regulatory sequence is a promoter. The term "promoter" refers to a DNA sequence capable of controlling the expression of a coding sequence. In another aspect, the coding sequence to be controlled is located 3' to the promoter. In still another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In a further aspect, the promoter is a native part of the vector used herein. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides from a ribosomal binding site. In another aspect, the promoter is positioned before the gene that expresses zinc-related protein/oxidase, the gene that expresses silicatein, the gene that expresses silaffin, the gene that expresses alcohol dehydrogenase II, the gene that expresses lipase, the gene that expresses chitin synthase, the gene that expresses chitosanase, the gene that expresses chitin deacetylase, the gene that expresses cellulose synthase, the gene that expresses galactomannan galactosyltransferase, or any combination thereof.

In one aspect, the promoter is a GAL1 promoter. In another aspect, the GAL1 promoter is native to the plasmid used to create the vector. In another aspect, a GAL1 promoter is positioned before the gene that expresses zinc-related protein/oxidase, the gene that expresses silicatein, the gene that expresses silaffin, the gene that expresses alcohol dehydrogenase II, or any combination thereof. In another aspect, the promoter is a GAL1 promoter obtained from or native to the pYES2 plasmid.

In another aspect, the promoter is a T7 promoter. In a further aspect, the T7 promoter is native to the plasmid used to create the vector. In still another aspect, the T7 promoter is positioned before any or all of the genes in the construct, or is positioned before the LAC operon. In yet another aspect, the promoter is a T7 promoter obtained from or native to the pETDuet-1 plasmid. In one aspect, the promoter has SEQ ID NO. 13 or a derivative or variant thereof.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. In one aspect, the terminator is a T7 terminator. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting, that is, located on the same molecule of DNA whose expression they affect.

In certain aspects, the DNA construct includes a ribosomal binding site. In one aspect, the ribosomal binding site in the DNA construct is AGGAGG or a derivative or variant thereof. In one aspect, the ribosomal binding site is native to the vector used herein. In certain aspects, when the DNA construct further includes a ribosomal switch. In one aspect, the ribosomal switch has SEQ ID NO. 14 or at least 70% homology thereto. In some aspects, the ribosomal binding site and optional ribosomal switch are positioned after the gene for galactomannan galactosyltransferase from 5' to 3'.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasBI, NotI, XhoI, XphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA at a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, the incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and commercially available. Such vectors include, but are not limited to, pWLnco, pSV2cat, pOG44, pXT1, pSG, pSVK3, pBSK, pYES, pYES2, pBSKII, pUC, pUC19, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the skilled artisan to select host cells that have been successfully transfected with the plasmids (for example, by growing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector, which confers antibiotic resistance, can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 15 or at least 70% homology thereto. The amount of fluorescence that is produced can be correlated to the amount of DNA incorporated into the transfected cells. The fluorescence produced can be detected and quantified using techniques known in the art. For example, spectrofluorometers are typically used to measure fluorescence.

The DNA construct described herein can be part of a vector. In one aspect, the vector is a plasmid, a phagemid, a cosmid, a yeast artificial chromosome, a bacterial artificial chromosome, a virus, a phage, or a transposon.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

In one aspect, the construct includes from 5' to 3' the following genetic components in the following order: (1) a gene that expresses zinc-related protein/oxidase, (2) a gene that expresses silicatein, (3) a gene that expresses silaffin, and (4) a gene that expresses alcohol dehydrogenase II.

In another aspect, the construct comprises from 5' to 3' the following genetic components in the following order: (1) a gene that expresses zinc-related protein/oxidase, (2) a CYC1 terminator, (3) a GAL1 promoter, (4) a gene that expresses silicatein, (5) a CYC1 terminator, (6) a GAL1 promoter, (7) a gene that expresses silaffin, (8) a CYC1 terminator, (9) a GAL1 promoter, (10) a gene that expresses alcohol dehydrogenase II, and (11) a CYC1 terminator.

In another aspect, the construct includes from 5' to 3' the following genetic components in the following order: a gene that expresses zinc-related protein/oxidase having SEQ ID NO. 1 or at least 70% homology thereto, a gene that expresses silicatein having SEQ ID NO. 2 or at least 70% homology thereto, a gene that expresses silaffin having SEQ ID NO. 3 or at least 70% homology thereto, and a gene that expresses alcohol dehydrogenase II having SEQ ID NO. 4 or at least 70% homology thereto.

In one aspect, the construct includes from 5' to 3' the following genetic components in the following order: a gene that expresses zinc-related protein/oxidase having SEQ ID NO. 1 or at least 90% homology thereto, a gene that expresses silicatein having SEQ ID NO. 2 or at least 90% homology thereto, a gene that expresses silaffin having SEQ ID NO. 3 or at least 90% homology thereto, and a gene that expresses alcohol dehydrogenase II having SEQ ID NO. 4 or at least 90% homology thereto.

In another aspect, the construct includes from 5' to 3' the following genetic components in the following order: a) a gene that expresses zinc-related protein/oxidase having SEQ ID NO. 1 or at least 90% homology thereto, b) a CYC1 terminator, c) a GAL1 promoter, d) a gene that expresses silicatein having SEQ ID NO. 2 or at least 90% homology thereto, e) a CYC1 terminator, f) a GAL1 promoter, g) a gene that expresses silaffin having SEQ ID NO. 3 or at least 90% homology thereto, h) a CYC1 terminator, i) a GAL1 promoter, a gene that expresses alcohol dehydrogenase II having SEQ ID NO. 4 or at least 90% homology thereto, and j) a CYC1 terminator.

In another aspect, the construct is a pYES2 plasmid having from 5' to 3' the following genetic components in the following order: a) a gene that expresses zinc-related protein/oxidase having SEQ ID NO. 1 or at least 70% homology thereto, b) a CYC1 terminator, c) a GAL1 promoter, d) a gene that expresses silicatein having SEQ ID NO. 2 or at least 70% homology thereto, e) a CYC1 terminator, f) a GAL1 promoter, g) a gene that expresses silaffin having SEQ ID NO. 3 or at least 70% homology thereto, h) a CYC1 terminator, i) a GAL1 promoter, and j) a gene that expresses alcohol dehydrogenase II having SEQ ID NO. 4 or at least 70% homology thereto, k) and a CYC1 terminator.

In another aspect, the DNA construct is SEQ ID NO. 16 or has at least 90% homology thereto. In a further aspect, the DNA construct is the vector depicted in FIGS. 1A and 1B.

In one aspect, the construct includes from 5' to 3' the following genetic components in the following order: (1) a gene that expresses lipase, (2) a gene that expresses zinc-related protein/oxidase, (3) a gene that expresses silicatein, (4) a gene that expresses silaffin, and (5) a gene that expresses alcohol dehydrogenase II.

In another aspect, the construct includes from 5' to 3' the following genetic components in the following order: (1) a gene that expresses lipase, (2) a CYC1 terminator, (3) a GAL1 promoter, (4) a gene that expresses zinc-related protein/oxidase, (5) a CYC1 terminator, (6) a GAL1 promoter, (7) a gene that expresses silicatein, (8) a CYC1 terminator, (9) a GAL1 promoter, (10) a gene that expresses silaffin, (11) a CYC1 terminator, (12) a GAL1 promoter, (13) a gene that expresses alcohol dehydrogenase II, and (14) a CYC1 terminator.

In one aspect, the construct includes from 5' to 3' the following genetic components in the following order: (1) a gene that expresses lipase having SEQ ID NO. 5 or at least 70% homology thereto, (2) a gene that expresses zinc-related protein/oxidase having SEQ ID NO. 1 or at least 70% homology thereto, (3) a gene that expresses silicatein having SEQ ID NO. 2 or at least 70% homology thereto, (4) a gene that expresses silaffin having SEQ ID NO. 3 or at least 70% homology thereto, and (5) a gene that expresses alcohol dehydrogenase II having SEQ ID NO. 4 or at least 70% homology thereto.

In one aspect, the construct includes from 5' to 3' the following genetic components in the following order: (1) a gene that expresses lipase having SEQ ID NO. 5 or at least 90% homology thereto, (2) a gene that expresses zinc-related protein/oxidase having SEQ ID NO. 1 or at least 90% homology thereto, (3) a gene that expresses silicatein having SEQ ID NO. 2 or at least 90% homology thereto, (4) a gene that expresses silaffin having SEQ ID NO. 3 or at least 90% homology thereto, and (5) a gene that expresses alcohol dehydrogenase II having SEQ ID NO. 4 or at least 90% homology thereto.

In another aspect, the construct is a pYES2 plasmid having from 5' to 3' the following genetic components in the following order: (a) a gene that expresses lipase having SEQ ID NO. 5 or at least 70% homology thereto, (b) a CYC1 terminator, (c) a gene that expresses zinc-related protein/oxidase having SEQ ID NO. 1 or at least 70% homology thereto, (d) a CYC1 terminator, (e) a GAL1 promoter, (f) a gene that expresses silicatein having SEQ ID NO. 2 or at least 70% homology thereto, (g) a CYC1 terminator, (h) a GAL1 promoter, (i) a gene that expresses silaffin having SEQ ID NO. 3 or at least 70% homology thereto, (j) a CYC1 terminator, (k) a GAL1 promoter, (1) a gene that expresses alcohol dehydrogenase II having SEQ ID NO. 4 or at least 70% homology thereto, and (m) a CYC1 terminator.

In another aspect, the DNA construct is SEQ ID NO. 17 or has at least 90% homology thereto. In a further aspect, the DNA construct is the vector depicted in FIGS. 2A and 2B.

In one aspect, the construct for producing the polyactive carbohydrate includes from 5' to 3' the following genetic components in the following order: (1) a gene that expresses chitin synthase, (2) a gene that expresses chitosanase, and (3) a gene that expresses chitin deacetylase.

In another aspect, the construct for producing the polyactive carbohydrate includes from 5' to 3' the following genetic components in the following order: (1) a gene that expresses chitin synthase, (2) a CYC1 terminator, (3) a GAL1 promoter, (4) a gene that expresses chitosanase, (5) a CYC1 terminator, (6) a GAL1 promoter, (7) a gene that expresses chitin deacetylase, and (8) a CYC1 terminator.

In another aspect, the construct for producing the polyactive carbohydrate includes from 5' to 3' the following genetic components in the following order: (1) a gene that expresses chitin synthase having SEQ ID NO. 6 or at least 70% homology thereto, (2) a gene that expresses chitosanase having SEQ ID NO. 7 or at least 70% homology thereto, and (3) a gene that expresses chitin deacetylase having SEQ ID NO. 8 or at least 70% homology thereto.

In another aspect, the construct for producing the polyactive carbohydrate includes from 5' to 3' the following genetic components in the following order: (1) a gene that expresses chitin synthase having SEQ ID NO. 6 or at least 90% homology thereto, (2) a gene that expresses chitosanase having SEQ ID NO. 7 or at least 90% homology thereto, and (3) a gene that expresses chitin deacetylase having SEQ ID NO. 8 or at least 90% homology thereto.

In another aspect, the construct for producing the polyactive carbohydrate is a pYES2 plasmid having from 5' to 3' the following genetic components in the following order: (a) a gene that expresses chitin synthase having SEQ ID NO. 6 or at least 70% homology thereto, (b) a CYC1 terminator, (c) a GAL1 promoter, (d) a gene that expresses chitosanase having SEQ ID NO. 7 or at least 70% homology thereto, (e) a CYC1 terminator, (f) a GAL1 promoter, (g) a gene that expresses chitin deacetylase having SEQ ID NO. 8 or at least 70% homology thereto, and (h) a CYC1 terminator.

In another aspect, the DNA construct for producing the polyactive carbohydrate is SEQ ID NO. 18 or has at least 90% homology thereto. In a further aspect, the DNA construct is the vector depicted in FIGS. 3A and 3B.

In one aspect, the construct for producing the polyactive carbohydrate includes from 5' to 3' the following genetic components in the following order: (1) a gene that expresses lipase, (2) a gene that expresses chitin synthase, (3) a gene that expresses chitosanase, and (4) a gene that expresses chitin deacetylase.

In another aspect, the construct for producing the polyactive carbohydrate includes from 5' to 3' the following genetic components in the following order: (1) a gene that expresses lipase, (2) a CYC1 terminator, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, and (11) a CYC1 terminator.

In another aspect, the construct for producing the polyactive carbohydrate includes from 5' to 3' the following genetic components in the following order: (1) a gene that expresses lipase having SEQ ID NO. 5 or at least 70% homology thereto, (2) a gene that expresses chitin synthase having SEQ ID NO. 6 or at least 70% homology thereto, (3) a gene that expresses chitosanase having SEQ ID NO. 7 or at least 70% homology thereto, and (4) a gene that expresses chitin deacetylase having SEQ ID NO. 8 or at least 70% homology thereto.

In another aspect, the construct for producing the polyactive carbohydrate includes from 5' to 3' the following genetic components in the following order: (1) a gene that expresses lipase having SEQ ID NO. 5 or at least 90% homology thereto, (2) a gene that expresses chitin synthase having SEQ ID NO. 6 or at least 90% homology thereto, (3) a gene that expresses chitosanase having SEQ ID NO. 7 or at least 90% homology thereto, and (4) a gene that expresses chitin deacetylase having SEQ ID NO. 8 or at least 90% homology thereto.

In another aspect, the construct for producing the polyactive carbohydrate is a pYES2 plasmid having from 5' to 3' the following genetic components in the following order: (a) a gene that expresses lipase having SEQ ID NO. 5 or at least 70% homology thereto, (b) a CYC1 terminator, (c) a GAL1 promoter, (d) a gene that expresses chitin synthase having SEQ ID NO. 6 or at least 70% homology thereto, (e) a CYC1 terminator, (f) a GAL1 promoter, (g) a gene that expresses chitosanase having SEQ ID NO. 7 or at least 70% homology thereto, (h) a CYC1 terminator, (i) a GAL1 promoter, (j) a gene that expresses chitin deacetylase having SEQ ID NO. 8 or at least 70% homology thereto, and (k) a CYC1 terminator.

In another aspect, the DNA construct for producing the polyactive carbohydrate is SEQ ID NO. 19 or has at least 90% homology thereto. In a further aspect, the DNA construct is the vector depicted in FIGS. 4A and 4B.

In one aspect, the construct for producing the carbo sugar includes from 5' to 3' the following genetic components in the following order: (1) a gene that expresses cellulose synthase and (2) a gene that expresses galactomannan galactosyltransferase.

In another aspect, the construct for producing the carbo sugar includes from 5' to 3' the following genetic components in the following order: (1) a gene that expresses cellulose synthase, (2) a CYC1 terminator, (3) a GAL1 promoter, (4) a gene that expresses galactomannan galactosyltransferase, and (5) a CYC1 terminator.

In one aspect, the construct for producing the carbo sugar includes from 5' to 3' the following genetic components in the following order: (1) a gene that expresses cellulose synthase having SEQ ID NO. 9 or at least 70% homology thereto and (2) a gene that expresses galactomannan galactosyltransferase having SEQ ID NO. 10 or at least 70% homology thereto.

In one aspect, the construct for producing the carbo sugar includes from 5' to 3' the following genetic components in the following order: (1) a gene that expresses cellulose synthase having SEQ ID NO. 9 or at least 90% homology thereto and (2) a gene that expresses galactomannan galactosyltransferase having SEQ ID NO. 10 or at least 90% homology thereto.

In another aspect, the construct for producing the carbo sugar is a pYES2 plasmid having from 5' to 3' the following genetic components in the following order: (a) a gene that expresses cellulose synthase having SEQ ID NO. 9 or at least 70% homology thereto, (b) a CYC1 terminator, (c) a GAL1 promoter, (d) a gene that expresses galactomannan galactosyltransferase having SEQ ID NO. 10 or at least 70% homology thereto, and (5) a CYC1 terminator.

In another aspect, the DNA construct for producing the carbo sugar is SEQ ID NO. 20 or has at least 90% homology thereto. In a further aspect, the DNA construct is the vector depicted in FIGS. 5A-5D.

In one aspect, the construct for producing the carbo sugar includes from 5' to 3' the following genetic components in the following order: (1) a gene that expresses lipase, (2) a gene that expresses cellulose synthase and (3) a gene that expresses galactomannan galactosyltransferase.

In another aspect, the construct for producing the carbo sugar includes from 5' to 3' the following genetic components in the following order: (1) a gene that expresses lipase, (2) a CYC1 terminator, (3) a GAL1 promoter, (4) a gene that expresses cellulose synthase, (5) a CYC1 terminator, (6) a GAL1 promoter, (7) a gene that expresses galactomannan galactosyltransferase, and (8) a CYC1 terminator.

In one aspect, the construct for producing the carbo sugar includes from 5' to 3' the following genetic components in the following order: (1) a gene that expresses lipase having SEQ ID NO. 5 or at least 70% homology thereto, (2) a gene that expresses cellulose synthase having SEQ ID NO. 9 or at least 70% homology thereto, and (3) a gene that expresses galactomannan galactosyltransferase having SEQ ID NO. 10 or at least 70% homology thereto.

In one aspect, the construct for producing the carbo sugar includes from 5' to 3' the following genetic components in the following order: (1) a gene that expresses lipase having SEQ ID NO. 5 or at least 90% homology thereto, (2) a gene that expresses cellulose synthase having SEQ ID NO. 9 or at least 90% homology thereto, and (3) a gene that expresses galactomannan galactosyltransferase having SEQ ID NO. 10 or at least 90% homology thereto.

In another aspect, the construct for producing the carbo sugar is a pYES2 plasmid having from 5' to 3' the following genetic components in the following order: (a) a gene that expresses cellulose synthase having SEQ ID NO. 9 or at least 70% homology thereto, (b) a CYC1 terminator, (c) a GAL1 promoter, (d) a gene that expresses galactomannan galactosyltransferase having SEQ ID NO. 10 or at least 70% homology thereto, and (5) a CYC1 terminator.

In another aspect, the DNA construct for producing the carbo sugar is SEQ ID NO. 21 or has at least 90% homology thereto. In a further aspect, the DNA construct is the vector depicted in FIGS. 6A-6B.

In one aspect, the construct for producing the carbo sugar includes from 5' to 3' the following genetic components in the following order: (1) a gene that expresses lipase, (2) a gene that expresses cellulose synthase, and (3) a gene that expresses galactomannan galactosyltransferase.

In another aspect, the construct for producing the carbo sugar includes from 5' to 3' the following genetic components in the following order: (1) a gene that expresses lipase, (2) a T7 promoter, (3) a LAC operon, (4) a riboswitch, (5) a gene that expresses cellulose synthase, (6) a riboswitch, and (7) a gene that expresses galactomannan galactosyltransferase.

In one aspect, the construct for producing the carbo sugar includes from 5' to 3' the following genetic components in the following order: (1) a gene that expresses lipase having SEQ ID NO. 5 or at least 70% homology thereto, (2) a gene that expresses cellulose synthase having SEQ ID NO. 9 or at least 70% homology thereto, and (3) a gene that expresses galactomannan galactosyltransferase having SEQ ID NO. 10 or at least 70% homology thereto.

In one aspect, the construct for producing the carbo sugar includes from 5' to 3' the following genetic components in the following order: (1) a gene that expresses lipase having SEQ ID NO. 5 or at least 90% homology thereto, (2) a gene that expresses cellulose synthase having SEQ ID NO. 9 or at least 90% homology thereto, and (3) a gene that expresses galactomannan galactosyltransferase having SEQ ID NO. 10 or at least 90% homology thereto.

In another aspect, the construct for producing the carbo sugar is a pETDuet-1 plasmid having from 5' to 3' the following genetic components in the following order: (a) a gene that expresses lipase having SEQ ID NO. 5 or at least 70% homology thereto, (b) a T7 promoter, (c) a LAC operon, (d) a riboswitch having SEQ ID NO. 14 or at least 70% homology thereto, (e) a gene that expresses cellulose synthase having SEQ ID NO. 9 or at least 70% homology thereto, (f) a riboswitch having SEQ ID NO. 14 or at least 70% homology thereto, and (e) a gene that expresses galactomannan galactosyltransferase having SEQ ID NO. 10 or at least 70% homology thereto.

In another aspect, the DNA construct for producing the carbo sugar is SEQ ID NO. 22 or has at least 90% homology thereto. In a further aspect, the DNA construct is the vector depicted in FIGS. 7A-7B.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce an anti-microbial and UV-protective extract. "Heterologous" genes and proteins are genes and proteins that have been experimentally inserted into a cell that are not normally expressed by the cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which an exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a bacteria such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing the yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Devices and Extracts

The biological devices described herein are useful in the production of anti-microbial and UV-protective extracts as well as in the production of adhesives and hard and soft biofoams. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells can be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated and include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the method involves growing the biological devices described herein for a sufficient time to produce anti-microbial and UV-protective extracts. The ordinary artisan will be able to choose a culture medium and optimum culture conditions based on the biological identity of the host cells.

In one aspect, the UV protective extract can be prepared by exposing a culture of a biological device such as those disclosed herein to UV radiation, then extracting components from the culture. In one aspect, the components are extracted via centrifugation. The UV radiation can be of any wavelength, but in one aspect, it can be shortwave radiation (i.e., ultraviolet C having a wavelength of approximately 100 to 280 nm), medium wave radiation (i.e., ultraviolet B, having a wavelength of approximately 280 to 315 nm), or longwave radiation (i.e., ultraviolet A having a wavelength of 315 to 400 nm). In one aspect, the culture of the biological device can be irradiated with a 254 nm shortwave UV source. In another aspect, the culture of the biological device can be irradiated with a 365 nm longwave UV source. In still another aspect, the culture of the biological device can be irradiated with both a 254 nm and a 365 nm UV source. In yet another aspect, the culture of the biological device can be irradiated with a natural UV source such as, for example, the sun, providing a range of wavelengths for irradiation.

In one aspect, culture of the biological device may proceed until the culture is dense, but not so dense as to trigger deleterious responses (e.g., a response triggered by lack of a food source) and not so dense as to prevent UV radiation from reaching a substantial portion of cells in the culture. Once the desired culture density has been reached, the culture can then be irradiated with UV radiation. Prior to irradiation, in one aspect, the culture is transferred to one or more vessels designed to allow a substantial portion of the biological device to be irradiated.

In one aspect, the irradiation continues for the length of time needed to induce a radiation response in the biological devices and ends at or before a time at which a substantial portion of the biological devices are fatally irradiated. In a further aspect, the extract can be collected after exposing a culture of a biological device to UV irradiation for a period of time ranging from about 12 hours to about 72 hours, or about 12, 24, 36, 48, 60, or 72 hours. In an alternative aspect, the biological devices may continue to be cultured for a time after UV exposure at least sufficient to allow some radiation response in the biological devices. In a further aspect, if irradiation did not cause the death of a substantial portion of the organisms in culture, culture may continue until the radiation response has ceased in a majority of the organisms.

In one aspect, radiation response can include upregulation of at least one of the following: a lipase, a zinc-related protein/oxidase, a silicatein, a silaffin, an alcohol dehydrogenase, or a combination thereof.

It will be understood that up-regulation or down-regulation of one or more of these proteins may not be directly responsible for UV-protective properties, such that increased or decreased amounts of these proteins in the extract may have little or no effect on the UV-protective properties of the extract. Further in this aspect, up-regulation or down-regulation of one of these proteins may have downstream effects that ultimately produce a UV-protective effect. In an alternative aspect, up-regulation or down-regulation of one or more of these proteins may be directly responsible for the UV-protective properties of the extract.

In one aspect, the extract is prepared in a manner able to isolate at least one UV-protective component. In some aspects, the extract can include centrifuged bacterial or yeast components. In one aspect, the extract is formulated at a variety of concentrations in any acceptable carrier to allow its use for a particular purpose. In some aspects, the extract is formulated in an evaporable carrier, such as water or alcohol, to allow the extract to dry on the surface of the material to be protected from UV radiation. In an alternative aspect, the extract is formulated in a lotion, gel, oil, or cream for application to human or animal skin.

In one aspect, the extract can be prepared by centrifuging the culture of biological devices in a manner able to precipitate most proteins, including UV-resistant and/or UV-protective proteins, then discarding the supernatant while retaining the pellet as the extract. Further in this aspect, the pellet can be used as-is or dried. Still further in this aspect, the pelleted material can be diluted to a given concentration using any acceptable carrier, such as water, alcohol, lotion, gel, oil, or cream. In one aspect, the carrier is non-denaturing. In an alternative aspect, the carrier is denaturing. In a still further aspect, the carrier also includes materials to inhibit further bacterial growth and/or protein degradation.

In an alternative aspect, the supernatant contains UV-protective compounds and is not discarded. In yet another aspect, the UV-protective and/or UV-resistant compounds and proteins are extracted by another method known in the art for isolating proteins and/or metabolites.

In a further aspect, the biological device culture may not be pelletized but instead may be killed, for example by lysis or exposure to lethal levels of UV radiation, and the culture medium can be used as-is or in an evaporated form. Further in this aspect, materials to inhibit further microorganism growth and/or protein degradation can also be introduced.

In another aspect, cells from any of the cultures described above can be isolated with or without extraction and/or lysis and used in wet or dry form.

In another aspect, isolated proteins from the biological device culture can be used in place of a more general extract to produce a UV-protective effect. Such proteins can be isolated by techniques known in the art.

In certain aspects, after culturing the biological device to produce the anti-microbial and UV-protective extracts, the host cells of the device can be lysed with one or more enzymes. For example, when the host cells are yeast, the yeast cells can be lysed with lyticase. In one aspect, the lyticase concentration can be 500, 600, 600, 800, 900, or 1000 µL per liter of culture, where any value can be the lower or upper endpoint of a range (e.g., 500 to 900 µL, 600 to 800 µL, etc.).

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from 60% to about 100%, 80% to 90%, 75% to 85%, or about 80% acetylated. The molecular weight of the chitosan can vary, as well. For example, the chitosan can comprise about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, chitosan can be added until a concentration of 0.0015, 0.0025, 0.005, 0.0075, 0.01, 0.015, 0.02, 0.03, 0.04, or 0.05% (where any value can be a lower or upper endpoint of a range, e.g., 0.005 to 0.02%, 0.0075 to 0.015%, etc.) is achieved in the culture. Still further in this aspect, the chitosan is present at a concentration of 0.01%.

In an alternative aspect, some or all of the chitosan can be replaced with the polyactive carbohydrate described herein.

In a further aspect, the anti-microbial and UV-protective extracts can be chemically-modified to produce additional desirable properties. Alternatively, compositions composed of the anti-microbial and UV-protective extracts with lysed and/or intact host cells (e.g., yeast) can be used herein, where it is not necessary to separate the host cells and other components from the anti-microbial and UV-protective extracts.

IV. Applications of UV-Protective Extracts

The extract may be applied to any material that may benefit from a reduction in UV radiation. The exact formulation of the extract plus any carriers can be adjusted based on the desired use. In one aspect, the extract is formulated with only non-toxic components if it is to be used on a human or animal or with another microorganism, such as in a fermentation process or on an agricultural product. In another aspect, the extract can be mixed with other substances to provide UV-protective properties to the overall composition. In still another aspect, if coated on the material to be protected, the extract itself can be covered with a further protective coating to project, for example, against mechanical wear and damage.

In the case when the extract is applied to the surface of an article, it can be applied using techniques known in the art such as spraying or coating. In other aspects, the extract can be intimately mixed with a substance or material that ultimately produces the article. For example, the extract can be mixed with molten glass so that the extract is dispersed throughout the final glass product.

In one aspect, the extract is formulated or applied in such a manner as to block approximately 50%, 60%, 70%, 80%, 90%, 95%, or 99% of the UV radiation that encounters the extract, where any value can be a lower and upper end-point of a range (e.g., 60% to 95%). In a further aspect, the extract can also be formulated to block these percentages of particular UV wavelengths, or, more generally, to block these percentages of UVA, UVB, or UVC radiation.

Extracts according to the present disclosure can be used for a variety of purposes. These purposes include, but are not limited to, the following:

1. blocking UV radiation or other types of radiation;
2. protecting human skin against damage and/or skin cancer induced by UV radiation or other types of radiation;
3. protecting against side effects of radiation used in cancer treatments;
4. protecting animals from deleterious effects of UV radiation or other radiation;
5. protecting plastic, fiberglass, glass, rubber, or other solid surfaces from UV radiation or other radiation;
6. providing a UV radiation screen or screen for other types of radiation;
7. protecting astronauts and/or other persons or organisms as well as equipment during space trips;
8. enhancement of industrial fermentation processes or other processes requiring energy by allowing the use of UV radiation in connection with the process to supply additional energy and thus to increase the ultimate energy-requiring output of the cells without substantially killing the fermenting organism;

9. protection of experimentation, fermentation, biochemical, and/or biological processes under the presence of UV radiation, for example in extraterrestrial conditions such as on the moon or Mars; and 10. protection of agricultural plants, particularly agricultural plants in which the revenue-producing part of the plant is above ground, such as fruits, vine vegetables, beans and peas, and leaf vegetables.

In one particular embodiment, an extract prepared according to the procedure described above can be applied to an agricultural plant. In one aspect, the plant can be one that produces a fruit or vegetable, such as, for example, a watermelon or a tomato. Further in this aspect, the extract can be applied during at least a part of the plant's growth to increase the amounts of one or more nutrients of the fruit or vegetable, such as a vitamin, mineral, or other recommended dietary component. In one specific aspect, the amount of lycopene can be increased (which may be accompanied by a decrease in carotene or other less-valuable nutrients formed by competing pathways). In another aspect, the amount of a flavor-enhancing component, such as glucose, can be increased. Further in this aspect, an increase in glucose can help protect against water loss.

In one aspect, the extract can be applied for about 25%, 50%, 75%, 90%, 95%, or 99% of the fruit or vegetable's on-plant life, where the on-plant life includes the time span from the formation of a separate body that will constitute the fruit or vegetable (in some aspects, excepting flowers) until the fruit or vegetable is harvested. In one aspect, the extract can be first applied when the fruit or vegetable is sufficiently large to no longer be substantially protected from UV radiation by leaves. In another aspect, the extract can first be applied five days, one week, or two weeks prior to harvest. Further in this aspect, application at this later stage can be particularly useful with fruits or vegetables in which an increase in a nutrient or flavor-enhancing component can be obtained by protecting the fruit or vegetable from UV radiation later in its on-plant life.

In one aspect, the extract can be applied once or multiple times to each fruit or vegetable. In another aspect, it can be applied weekly, or it can be reapplied after the fruit or vegetable is exposed to rain or after a turning process. In another aspect, the agricultural plant can be another food crop that grows above ground and is exposed to natural UV radiation, wherein the agricultural product produced can be a fruit, leaf, seed, flower, grain, nut, stem, vegetable, or mushroom.

In another aspect, it is desirable for agricultural plants that do not produce parts typically consumed by humans to be protected from UV irradiation. In a further aspect, these other agricultural plants can includes sources of fibers such as, for example, cotton and linen (flax), of cork, of wood or lumber, of feedstocks for producing ethanol or biodiesel (including, but not limited to, sugar beet, sugarcane, cassava, sorghum, corn, wheat, oil palm, coconut, rapeseed, peanut, sunflower, soybean, and the like), of animal feedstocks or fodder, or of decorative or horticultural plants.

In one aspect, any part of the plant can be coated, including, but not limited to, the part of the plant that is collected during harvest. In an alternative aspect, the harvested part of the plant is not coated, but another part can be coated with the extracts disclosed herein. In addition to the aspects already described, in one aspect, coating a plant with the extracts described herein can prolong the life of the plant, increase production capacity of a desired product, can increase the growth rate of the plant relative to an untreated plant of the same type, can increase production of a desired metabolite that might otherwise decrease due to UV-induced stress, can increase yield of a crop of such plants, and the like.

In a further aspect, application can be accomplished with a commercial sprayer. In another aspect, application can be only on the upper portions of the fruit or vegetable, which are exposed to substantially greater amounts of UV radiation than the lower portions of the fruit or vegetable.

In another aspect, provided herein is a pharmaceutical composition containing the extracts produced by the biological devices described herein. In one aspect, the pharmaceutical composition can be applied to a subject, wherein the subject is exposed to radiation. In one aspect, the radiation is applied as a strategy to treat cancer. In another aspect, the pharmaceutical composition is used to prevent radiation-induced cellular and DNA damage. In another aspect, dosage ranges of the extract in the pharmaceutical composition can vary from 0.01 g extract/mL of pharmaceutical composition to 1 g extract/mL of pharmaceutical composition, or can be 0.01, 0.02, 0.025, 0.05, 0.075, or 1 g extract/mL of pharmaceutical composition. In an alternative aspect, provided herein is a cosmetic composition containing the extracts produced by the biological devices described herein. Further in this aspect, the cosmetic composition can be a cleanser, lotion, cream, shampoo, hair treatment, makeup, lip treatment, nail treatment, or related composition. In still a further aspect, the compositions containing the extracts can have both pharmaceutical and cosmetic applications. In yet another aspect, the compositions containing the extracts can be used in veterinary medicine.

The cosmetic compositions can be formulated in any physiologically acceptable medium typically used to formulate topical compositions. The cosmetic compositions can be in any galenic form conventionally used for a topical application such as, for example, in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/VV or O/W/O), microemulsions, vesicular dispersions of ionic and/or non-ionic type, or wax/aqueous phase dispersions. These compositions are prepared according to the usual methods.

The cosmetic compositions can also contain one or more additives commonly used in the cosmetics field, such as emulsifiers, preservatives, sequestering agents, fragrances, thickeners, oils, waxes or film-forming polymers. In one aspect, in any of the above scenarios, the pharmaceutical, cosmetic, or veterinary composition also includes additional UV-protective compounds or UV-blocking agents such as, for example, zinc oxide, titanium dioxide, carotenoids, oxybenzone, octinoxate, homosalate, octisalate, octocrylene, avobenzone, or a combination thereof.

In one aspect, the composition is a sunscreen. A sunscreen can be formulated with any of the extracts produced herein. In addition to the extract, the sunscreen in certain aspects can be formulated with one or more UV-protective compounds or UV-blocking agents listed above. The sunscreen can be formulated as a paste, lotion, cream, aerosol, or other suitable formulations for topical use. In certain aspects, the sunscreen can be formulated as a transparent composition.

In one aspect, the cosmetic composition can be a film composed of the extracts produced herein that can be directly applied to the skin. For example, the film can be composed of a biocompatible material such as a protein or oligonucleotide, where the extract is coated on one or more surfaces of the film or, in the alternative dispersed throughout the film. For example, the film can be composed of DNA. In this application, the films can be used as a wound covering and provide protection from UV photodamage. The films can also be prepared so that they are optically transparent. Here, it is possible to view the wound without removing the covering and exposing the wound. The films can also include other components useful in cosmetic applications such as, for example, compounds to prevent or reduce wrinkles.

In one aspect, the pharmaceutical, cosmetic, or veterinary compositions described herein are applied to subjects. In one aspect, the subject is a human, another mammal, or a bird. In a further aspect, the mammal is a pet such as a dog or cat or is livestock such as horses, goats, cattle, sheep, and the like. In an alternative aspect, the bird is a pet bird or is poultry such as, for example, a chicken or turkey. In any of these aspects, the compositions can be applied to skin, fur, feathers, wool, hooves, horns, or hair as appropriate and applicable.

In another aspect, provided herein is a paint, dye, stain, or ink containing the UV-protective and/or UV-resistant extract disclosed herein. In one aspect, there are several benefits to having a paint that is resistant to UV irradiation. In a further aspect, imparting UV resistance to a paint slows or stops photodegradation, bleaching, or color fading. In another aspect, a paint with UV resistance prevents chemical modification of exposed paint surfaces. Further in this aspect, chemical modification of exposed paint surfaces includes change in finish, structural changes in binders, flaking, chipping, and the like. In one aspect, the paint provided herein resists these changes.

When the paint, ink, dye, or stain is applied to a surface, the anti-microbial and UV-protective extract can impart antifungal properties to the surface. In one aspect, applying a paint, ink, dye, or stain containing the anti-microbial and UV-protective extracts to the hull of a boat or other surface exposed to water can prevent or reduce the growth of barnacles. In another aspect, the anti-microbial and UV-protective extracts can be applied along with chitosan to the surface exposed to water.

In still another aspect, provided herein is an article coated with the extracts disclosed herein. In one aspect, the article is made of glass, plastic, metal, wood, fabric, or any combination thereof. In one aspect, the article is a construction material such as, for example, steel, concrete or cement, brick, wood, window or door glass, fiberglass, siding, wallboard, a flooring material, masonry, mortar, grout, stone, artificial stone, stucco, shingles, roofing materials, and the like. In a further aspect, the items and articles may be used in the construction and building industries in such applications as building materials, wood preservation, drywall, flooring, roofing materials and roofing membranes, artificial wood, plastic lumber, wood-filled plastics, decking, mobile homes, carpet, awnings, swimming pool liners, and related applications. In any of these applications, whether used as a coating or incorporated throughout the items and articles, the anti-microbial and UV-protective extracts can help preserve the items by reducing or eliminating the growth of fungus and/or other microbes.

In still another aspect, the items and articles may be home goods or consumer goods such as, for example, garments and textiles, leather, footwear and shoe soles, security documents, art and décor, cushions, mattresses, bath and/or kitchen mats, shower curtains, leisure furniture, plastic mulch, and the like.

In yet another aspect, the items and articles can be used in the transportation and automotive industries including upholstery for vehicles such as automobiles, trucks, trains, buses, and boats. In a further aspect, the items and articles can be used in various applications in the shipping industry such as packaging materials, crates, and pallets that are resistant to fungal colonization.

In an alternative aspect, the material is an aeronautical or aerospace material such as, for example, the metal or metal alloy body of an aircraft or spacecraft, paint on the body of an aircraft or spacecraft, glass windows on an aircraft or spacecraft, carbon fiber composite, titanium or aluminum, a ceramic heat absorbing tile, and the like. In still another aspect, the article is a fabric article such as, for example, clothing, drapes, outdoor upholstery, a tent or outdoor pavilion, a flag or banner, or the like. In another aspect, the extract can be applied to the article to fine artwork, solid pieces (e.g., vases), and historical documents in order to preserve them. In another aspect, the extract can be applied to outdoor signs such as highway billboards and advertising.

In other aspects, the extract can be incorporated within or throughout the article. In one aspect, the extract can be mixed with molten glass to produce glass article that are UV resistant such as, for example, sunglasses, car windshields, window glass, and eyeglasses. In another aspect, the glass article can be a bottle for storing a beverage or food container in order to increase the shelf-life of the beverage or food. It is contemplated that the extract can be applied externally to the glass articles as well.

In another aspect, the extract can be mixed with fiberglass or plastics in order to reduce negative effects to aircraft, watercraft, boats, jet skis, decking, house siding, motor homes, sunroofs, and moon roofs that are constantly exposed to UV radiation. It is contemplated that the extract can be applied externally to the fiberglass or plastic articles as well.

In another aspect, the extract can be mixed with rubber, silicone, or latex used to make a variety of articles such as water hoses, tires, and the like. It is contemplated that the extract can be applied externally to the rubber, silicone, or latex articles as well.

In another aspect, the extract can be mixed with foams used to make a variety of articles such as automotive dashboard padding, seat cushions, and the like. It is contemplated that the extract can be applied externally to the foam articles as well.

In another aspect, the extracts described herein can be incorporated into an optical film. In one aspect, the extract is applied to at least one surface of the film. In another aspect, the extract can be dispersed throughout the film. The film can be transparent, translucent or opaque. The film can be composed of, but not limited to, polyolefin resin, such as polyethylene (PE) or polypropylene (PP); polyester resin, such as polyethylene terephthalate (PET); polyacrylate resin, such as polymethyl (meth)acrylate (PMMA); polycarbonate resin; polyurethane resin or a mixture thereof. The optical film can be applied to any substrate where it is desirable to reduce or prevent UV exposure or damage. For example, the optical film can be applied to windows to reduce or prevent UV radiation from entering a structure (e.g., building, vehicle, etc.).

In still another aspect, the items and articles can be materials used in the manufacture of other goods. In this aspect, the items and articles can be plastic, coated fabrics, flexible films, foils or sheet, flexible extrusion products, products produced by injection molding, vinyl, gaskets, vinyl films or sheeting, plastisols, molded goods, or organosols. In yet another aspect, the items and articles can be artificial turf, parts such as, for example, filters used in air conditioning units, or materials intended for use in the oil and gas industries.

In another aspect, provided herein is a method of reducing or preventing the exposure of an item to UV radiation by applying the extracts described herein to the item or incorporating the extract within/throughout the article. Further in this aspect, "reducing" is defined relative to an untreated control. That is, if two like items are exposed to equal amounts of UV radiation for an equal amount of time, but one has been treated with the UV-resistant extracts and the other has not, and some objective response is measured (e.g., color fading, structural degradation, plant size or yield, etc.), the treated item will appear to have been exposed to a lower amount of UV (for example, the color of the treated item will have faded less and will remain closer to the original, or a treated plant will appear larger and more vigorous and will have a greater yield, etc.). In some aspects, treatment with the extracts disclosed herein will prevent UV exposure from occurring. As used herein, "prevent" indicates that a treated item will not be affected, changed, or altered by UV exposure.

In one aspect, the extract blocks from 50% to 100% of UV radiation from contacting the item. Further in this aspect, the extract blocks at least 50%, 55%, 60%, 65%, 70%, 75%, 80%, 85%, 90%, 95%, 99%, or 100% of UV radiation from contacting the item. In another aspect, the extract blocks from 50% to 100% of longwave UV radiation from contacting the item. Further in this aspect, the extract blocks at least 50%, 55%, 60%, 65%, 70%, 75%, 80%, 85%, 90%, 95%, 99%, or 100% of longwave UV radiation from contacting the item. In one aspect, the extract blocks from 50% to 100% of shortwave UV radiation from contacting the item. Further in this aspect, the extract blocks at least 50%, 55%, 60%, 65%, 70%, 75%, 80%, 85%, 90%, 95%, 99%, or 100% of shortwave UV radiation from contacting the item.

Depending upon the application, the extract can prevent or reduce damage cause by UV radiation from limited to extended periods of time. By varying the amount of extract that is applied as well as the number of times the extract is applied, the degree of UV protection can be varied. In certain aspects, it may be desirable for the article to be protected from UV damage for a short period of time then subsequently biodegrade.

In another aspect, the extracts produced herein can be used to reduce or prevent the growth of barnacles on boats and other water vehicles. In one aspect, the extract can be admixed with a paint that is typically applied to water vehicles, where the paint also includes chitosan. In one aspect, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. In one aspect, chitosan isolated from the shells of crab, shrimp, lobster, and/or krill is useful herein. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units.

In all of the above aspects, incorporation of the antimicrobial and UV-protective extracts prevents or inhibits fungal growth, thereby reducing odors, improving and maintaining the appearance of the items and articles, reducing decomposition, and maintaining a microbe-free environment.

V. UV-Resistant Plants

In one aspect, provided herein is a plant that is resistant to UV radiation. As used herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of a plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refers to differentiated and undifferentiated tissues of plants including those present in any of the tissues described above, as well as to cells in culture such as, for example, single cells, protoplasts, embryos, calluses, etc. It is contemplated that any cell from which a fertile plant can be regenerated is useful as a recipient cell. Type I, Type II, and Type III callus can be initiated from tissue sources including, but not limited to, immature embryos, immature inflorescences, seedling apical meristems, microspores, and the like. Those cells that are capable of proliferating as callus are also useful herein. Methods for growing plant cells are known in the art (see U.S. Pat. No. 7,919,679).

In one aspect, plant calluses grown from 2 to 4 weeks can be used herein. The plant cells can be derived from plants varying in age. The plant cells can be contacted with the biological device in a number of different ways. In one aspect, the device can be added to a medium containing the plant cells. In another aspect, the device can be injected into the plant cells via syringe. The amount of device and the duration of exposure to the device can vary as well. In one aspect, the concentration of the device is about $10^1$, $10^4$, $10^5$, $10^6$, $10^7$, $10^8$, or $10^9$ cells/mL of water. In one aspect, when the host cell is a bacterium, the concentration of the device is about $10^6$. In another aspect, when the host cell is yeast, the concentration of the device is about $10^9$. Different volumes of the biological device can be used as well, ranging from 5 μL to 500 μL.

In certain aspects, any of the biological devices described above can be used in combination with a polysaccharide to enhance one or more physiological properties of the plant. In one aspect, the plant cells are first contacted with the biological device, then subsequently contacted with the polysaccharide. In another aspect, the plant cells are first contacted with the polysaccharide and subsequently contacted with the biological device. In a further aspect, the plant cells are simultaneously contacted with the polysaccharide and the biological device.

In one aspect, the polysaccharide includes chitosan, glucosamine (GlcN), N-acetylglucosamine (NAG), or any combination thereof. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. In one aspect, chitosan isolated from the shells of crab, shrimp, lobster, and/or krill is useful herein.

The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the chitosan is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.1% to 0.01% by weight, from 0.075% to 0.025% by weight, or is about 0.05% by weight. The polysaccharides used herein are generally natural polymers and thus present no environmental concerns. Additionally, the polysaccharide can be used in acceptably low concentrations.

In an alternative aspect, the polyactive carbohydrate and/or carbo sugars disclosed herein can be used in place of some or all of the polysaccharide.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of the callus can vary depending upon the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue cultures can grow for extended periods of time ranging from days to several weeks. Moreover, tissue culturing with the polysaccharide can occur in the dark and/or light. As discussed above, the plant cells can be contacted with any of the biological devices described above. Thus, the use of the polysaccharides and biological devices described herein is a versatile way to culture and grow plant cells—and ultimately, plants of interest—with enhanced physiological properties.

In one aspect, a plant callus such as described above can be planted and allowed to grow and mature into a plant bearing fruit and leaves.

In a further aspect, provided herein is a plant grown by the process of contacting plant gamete cells, a plant reproductive organ, or a plant callus with the biological devices disclosed herein. Also provided herein is a method for producing such a plant. In one aspect, the method includes the steps of:

(a) contacting a plant callus with the biological device;
(b) culturing the plant callus; and
(c) growing a plant from the plant callus.

In some aspects, the plant callus is cultured with chitosan. In a further aspect, the chitosan is from 60%, 65%, 70%, 75%, 80%, 85%, 90%, 95%, or 100% acetylated and has 3, 4, 5, 6, 7, 8, 9, 10, 11, 12, 13, 14, 15, 16, 17, 18, 19, or 20 glucosamine units, N-acetylglucosamine units, or a combination thereof, where any value can be a lower and upper end-point of a range (e.g., 60% to 80% acetylation).

In another aspect, provided herein is a method for increasing the UV-resistance of a plant, the method involving growing a plant from plant cells that have been contacted with the biological devices disclosed herein. In one aspect, increased UV-resistance can be measured by growing plants from a treated and an untreated callus alongside one another and comparing UV-induced damage after a period of time. In a further aspect, an agricultural product harvested from a UV-resistant plant will also be more UV-resistant. Further in this aspect, for example, cotton from a cotton plant grown with the biological devices will be more UV-resistant than cotton grown from an untreated plant.

VI. Production of Hard and Soft Biofoams and Articles Made Therefrom

In another aspect, the anti-microbial and UV-protective extracts described herein can be used to produce polyurethane compositions that have numerous applications.

In one aspect, the polyurethane composition is produced by:
a) admixing a polyactive carbohydrate and a natural oil polyol to produce a first admixture; and
b) admixing the first admixture with a polyisocyanate to produce the polyurethane composition.

In another aspect, the polyurethane composition is produced by:
a) admixing a carbo sugar and a natural oil polyol to produce a first admixture; and
b) admixing the first admixture with a polyisocyanate to produce the polyurethane composition.

In still another aspect, the polyurethane composition is produced by:
a) admixing a polyactive carbohydrate, a carbo sugar, and a natural oil polyol to produce a first admixture; and
b) admixing the first admixture with a polyisocyanate to produce the polyurethane composition.

In another aspect, the polyurethane composition produced by:
a) admixing the extract with a polyactive carbohydrate, and a natural oil polyol to produce a first admixture; and
b) admixing the first admixture with a polyisocyanate and a carbo sugar to produce the polyurethane composition.

In one aspect, the polyurethane composition is produced by:
a) admixing the extract with a polyactive carbohydrate and castor oil to produce a first admixture; and
b) admixing the first admixture with a polyisocyanate, a carbo sugar, and beeswax to produce the polyurethane composition,
where the polyactive carbohydrate comprises an extract produced from host cells comprising a DNA construct comprising the following genetic components: (a) a gene that expresses chitin synthase, (b) a gene that expresses chitosanase, and (c) a gene that expresses chitin deacetylase and the carbo sugar comprises an extract produced from host cells comprising the following genetic components: (1) a gene that expresses cellulose synthase and (2) a gene that expresses galactomannan galactosyltransferase, and
the polyisocyanate is an aromatic diisocyanate such as, for example, 4,4'-methylene diphenyl diisocyanate.

In one aspect, the anti-microbial and UV-protective extracts disclosed herein can be added at any step in the method for producing the polyurethane compositions. Further in this aspect, the extracts can be added at the time of mixing the polyactive carbohydrate and/or carbo sugar and natural oil polyol, or can be present in the solutions of polyactive carbohydrate, carbo sugar, and/or natural oil polyol prior to mixing, or can be added at the time of mixing the first admixture with the polyisocyanate. In an alternative aspect, the extracts can be used to coat items or articles made from the polyurethane compositions.

As used herein, a "carbo sugar" is a polymer with an oligo- or poly-mannose backbone that is fully or partially galactosylated. In one aspect, the carbo sugar can be chemically or enzymatically fully or partially hydrolyzed prior to use in order to fine tune the molecular weight and associated properties of the carbo sugar. In one aspect, the carbo sugar is produced by a biological. In another aspect, the carbo sugar can be produced by DNA constructs shown in FIGS. 5A-5D transformed in host cells (e.g., yeast, bacteria) and subsequently cultured to yield a carbo sugar extract. The carbo sugar extract can then be isolated using the techniques described herein.

As used herein, a "polyactive carbohydrate" is a polymer composed of individual monosaccharide units. In one aspect, the polyactive carbohydrate is partially or fully acetylated. In another aspect, an enzymatic or chemical deacetylation process can be used on the polyactive carbohydrate or any precursors to alter the degree of acetylation. In still another aspect, the polyactive carbohydrate can be chemically or enzymatically fully or partially hydrolyzed prior to use in order to fine tune the properties of the polyactive carbohydrate as they relate to molecular weight. In one aspect, the polyactive carbohydrate is produced by a biological device. In another aspect, the polyactive carbohydrate can be produced by DNA constructs shown in FIGS. 3A-3B and 4A-4B transformed in host cells (e.g., yeast, bacteria) and subsequently cultured to yield the polyactive carbohydrate. The polyactive carbohydrate extract can then be isolated using the techniques described herein.

A "natural oil" as used herein is any oil extracted from a living organism. In one aspect, the living organism is a plant or alga. In a further aspect, the plant is the castor bean or castor oil plant (*Ricinus communis*). In another aspect, the living organism is an animal. In an alternative aspect, the living organism is a fungus. Natural oils can additionally contain triglycerides, fatty acids, fatty acid esters, sterols, isoprenoid or terpenoid compounds, alkaloids, phenols, and other metabolites.

"Natural oil polyols" are compounds that include at least one free hydroxyl group and are derived from or present in natural oils. A natural oil polyol may be naturally occurring, as with the ricinoleic acid in castor oil, or it may be chemically synthesized from an oil or fat containing one or more carbon-carbon double bonds. In one aspect, a natural fatty acid or triglyceride containing a carbon-carbon double bond is subjected to ozonolysis to cleave the double bond, followed by treatment with another molecule such as, for example, ethylene glycol, to form an alcohol. In another aspect, a natural fatty acid or triglyceride containing a carbon-carbon double bond can be formylated in the presence of carbon monoxide and hydrogen gas, followed by hydrogenation to produce a hydroxyl group. Other methods of producing natural oil polyols are also contemplated. Natural oils can be used as extracted or can optionally be purified. In one aspect, the natural oil polyol is or is derived from soy, a chemically-modified vegetable oil, a carbohydrate, lignin, cork, cashew nutshell liquid, *Lesquerella* oil, or a combination thereof. In one aspect, the natural oil polyol is castor oil. In another aspect, the natural oil polyol is ricinoleic acid. In still another aspect, the natural oil polyol is coriolic acid or a chemically-modified fatty acid.

"Castor oil" can optionally be extracted from the seeds of the castor oil plant. The primary component of castor oil is ricinoleic acid; minor components include oleic acid, linoleic acid, linolenic acid, stearic acid, palmitic acid, dihydroxystearic acid, and other trace fatty acids.

In one aspect, the natural oil polyol can include one or more hydroxyl fatty acids, which are defined herein as fatty acids having at least one free hydroxyl group. The hydroxyl fatty acid has the general formula R'C(O)OH, wherein R' is a saturated or unsaturated hydrocarbon chain having from 10 to 25 carbon atoms, and at least one hydroxyl group is covalently attached to a carbon atom of the hydrocarbon chain. The hydrocarbon can be linear or branched. In the case where the hydrocarbon is unsaturated, the hydrocarbon can have one carbon-carbon double bond or multiple carbon-carbon double bonds. Examples of monohydroxy fatty acids (i.e., one hydroxyl group present on the fatty acid) include, but are not limited to, hydroxynervonic acid, cerebronic acid, 10-hydroxy-20-decenoic acid, hydroxyl-2-decenoic acid 10-phoshpate, strophantus acid, lesquerolic acid, densipolic acid, auricolic acid, α-dimorphecolic acid, kamlolenic acid, 8-hydroxyoctadeca-9,11-diynoic acid, 8-hydroxyoctadeca-17-en-9,11-diynoic acid (isanolic), or 8-hydroxyoctadeca-13,17-dien-9,11-diynoic acid. Examples of polyhydroxy fatty acids (i.e., two or more hydroxyl groups) include, but are not limited to, axillarenic acid, tetrapedic acid, byrsonic acid, 9,10-dihydroxyoctadecanoic acid, phaseolic acid, phloionolic acid, Resolvin D1, 10,18S-docosatriene, or Resolvin E1. The hydroxyl fatty acids can be used as is in the natural oil (e.g., castor oil), isolated from a natural oil, or synthesized accordingly.

In certain aspects, a surfactant can be used to produce the polyurethane compositions described herein, where the surfactant is admixed with the polyactive carbohydrate and/or carbo sugar and a natural oil polyol to produce a first admixture. The anti-microbial and UV-protective extracts may be added to the admixture during this step or to one of the reagents prior to admixing to produce the first admixture. A "surfactant" is an organic compound that may be derived from a natural product, or may result from chemical modification of a natural product, or may be completely chemically synthesized. Surfactants typically contain hydrophilic head groups and hydrophobic tails. In one aspect, the head group is anionic, cationic, non-ionic, or zwitterionic. In another aspect, the tail is composed of a hydrocarbon or a glucoside. Surfactants alter the surface tension of liquids and may form micelles or bilayers in aqueous solution. Many applications of surfactants are known in the art. Surfactants are, for example, commonly employed as emulsifiers, detergents, wetting agents, and the like.

Numerous cationic surfactants can be used in the compositions described herein. In one aspect, the cationic surfactant can be a quaternary ammonium salt.

Numerous zwitterionic surfactants can be used in the compositions described herein. In one aspect, the zwitterionic surfactant can be a lecithin such as soy lecithin; in another aspect, the zwitterionic surfactant can be a hydroxysultaine, a betaine, a sulfobetaine, or a mixture thereof. Among betaines, surfactants may be selected from the group comprising high alkyl betaines such as cetyl dimethyl carboxymethyl betaine, cocamidopropyl betaine, cocobetaine, coco dimethyl carboxymethyl betaine, lauryl amidopropyl betaine, lauryl bis-(2-hydroxyethyl) carboxymethyl betaine, lauryl bis-(2-hydroxypropyl)alpha-carboxyethyl betaine, lauryl dimethyl alphacarboxyethyl betaine, lauryl dimethyl carboxymethyl betaine, oleyl betaine, oleyl dimethyl gamma-carboxypropyl betaine, stearyl bis-(2-hydroxypropyl) carboxymethyl betaine, and mixtures thereof. Among sulfobetaines, surfactants may be selected from the group comprising coco dimethyl sulfopropyl betaine, lauryl bis-(2-hydroxyethyl) sulfopropyl betaine, lauryl dimethyl sulfoethyl betaine, stearyl dimethyl sulfopropyl betaine, and mixtures thereof. Amidobetaines and amidosulfobetaines are also contemplated.

Numerous nonionic surfactants can be used in the compositions described herein. Nonionic surfactants useful in the compositions described herein include alkoxylated fatty acid esters, alkyl glucosides, alkyl polyglucosides, amine oxides, alcohol ethoxylates, cocoamine oxide, glyceryl monohydroxystearate, glyceryl stearate, hydroxyl stearic acid, lauramine oxide, laureth-2, polyhydroxy fatty acid amides, polyoxyalkylene stearates, propylene glycol stearate, sorbitan monostearate, sucrose cocoate, sucrose esters, sucrose laurate, steareth-2, PEG-40 hydrogenated castor oil, and mixtures thereof. Preferred nonionic surfactants include those based on polyethoxylated sorbitan and oleic acid such as, for example, polysorbate 80 and polysorbate 20, both of which are available under a variety of trade names.

Further nonionic surfactants contemplated include, in one aspect, the condensation products of a higher aliphatic alcohol, such as a fatty alcohol, containing about 8 to 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from IC. Tergitol™ 15-S surfactants include $C_{11}$-$C_{13}$ secondary alcohol polyethylene glycol ethers, Brij™97 surfactant is polyoxyethylene(10) oleyl ether; Brij™58 surfactant is polyoxyethylene(20) cetyl ether; and Brij™76 surfactant is polyoxyethylene(10) stearyl ether.

In another aspect, a useful class of nonionic surfactants includes the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy)ethanols. Igepal™ CA surfactants include octylphenoxy poly(ethyleneoxy)ethanols. Still another useful class of hydrocarbon nonionic surfactants includes block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. In other aspects, the nonionic surfactants include sorbitan fatty acid esters, polyoxyethylene sorbitan fatty acid esters and polyoxyethylene stearates having HLBs of about 6 to about 19, about 9 to about 18, and about 10 to about 16. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates. In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Numerous anionic surfactants can be used herein. In one aspect, the anionic surfactant can be alcohol phosphates and phosphonates, alkyl alkoxy carboxylates, alkyl aryl sulfates, alkyl aryl sulfonates, alkyl carboxylates, alkyl ether carboxylates, alkyl ether sulfates, alkyl ether sulfonates, alkyl phosphates, alkyl polyethoxy carboxylates, alkyl polyglucosides, alkyl polyglucoside sulfates, alkyl polyglucoside sulfonates, alkyl succinamates, alkyl sulfates, alkyl sulfonates, aryl sulfates, aryl sulfonates, fatty taurides, isethionates, N-acyl taurates, nonoxynol phosphates, octoxynol phosphates, sarcosinates, sulfated fatty acid esters, taurates, and mixtures thereof. Useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8)N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt. Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the trade name AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and/or dodecylbenzenesulfonic acid sold under BIO-SOFT© AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates. Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340KL from Clariant Corp., as well as PPG-5 cetyl 10 phosphate available under the trade designation CRODA-PHOS™ SG from Croda Inc., Parsipanny, N.J. Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, a surfactant is chosen based on its ability to form a stable emulsion containing an acidic aqueous solution of a polyactive carbohydrate and/or a carbo sugar, a natural oil polyol, and, in some aspects, the anti-microbial and UV-protective extracts described herein. In other aspects, the anti-microbial and UV-protective extracts are added later and the surfactant is not required to form a stable emulsion containing the anti-microbial and UV-protective extracts. In a further aspect, the concentration of surfactant can be from 0.001% to 1% (v/v), or can be about 0.001%, 0.005%, 0.01%, 0.05%, 0.1%, 0.35%, 0.5%, or 1% (v/v) with respect to the final emulsion volume. In another aspect, 0.35% of polysorbate 80 is used. In a further aspect, emulsion formation can be evaluated as a function of stirring time (e.g., about 1 minute, about 2 minutes, about 4 minutes, about 6 minutes, about 8 minutes, or about 10 minutes) and/or stirring speed (e.g., about 2000 rpm, about 5000 rpm, about 10,000 rpm, or about 20,000 rpm).

In another aspect, beeswax can be used as a component to produce the polyurethane and biofoam. Any type of beeswax can be used in this embodiment (e.g., European, Oriental). Beeswax is typically composed of a mixture of hydrocarbons, esters (mono, di, tri), hydroxy esters and polyesters, free fatty acids, and free fatty alcohols, with one of the main components being triacontanyl palmitate. The beeswax cab e added at any stage during production of the polyurethane composition. In one aspect, the beeswax is admixed with the composition composed of the anti-microbial and UV-protective extracts disclosed herein with the polyactive carbohydrate and/or carbo sugar. In another aspect, the beeswax is admixed with the polyisocyanate.

The order in which the components can be admixed with one another to produce the first admixture can vary. In one aspect, the natural oil polyol can be added to a solution of the polyactive carbohydrate and/or the carbo sugar. In one aspect, the natural oil polyol is added over time (e.g., 2 minutes, 4 minutes, 5 minutes, 6 minutes, 8 minutes, or 10 minutes) with stirring (2000 rpm, 5000 rpm, 10,000 rpm, or 20,000 rpm) to create a final admixture that also incorporates the polyactive carbohydrate and/or the carbo sugar. In one aspect, the natural oil polyol is castor oil and stirring is conducted at 10,000 rpm for 5 minutes. In any of these aspects, the anti-microbial and UV-protective extracts disclosed herein can be added at any step of the process, to any solution or reagent.

In one aspect, the carbo sugar, if used, is from 0.1 to 1% by weight of the first admixture. In another aspect, the amount of carbo sugar is 0.1, 0.2, 0.3, 0.4, 0.5, 0.6, 0.7, 0.8, 0.9, or 1 wt % of the first admixture, where any value can be a lower or upper endpoint of a range (e.g., 0.2 to 0.7, etc.). In another aspect, the carbo sugar can be prepared and used as a solution. In one aspect, the carbo sugar is an aqueous solution of 1% to 5% (w/v), wherein the first admixture includes 20% to 80% (v/v) of the aqueous solution of carbo sugar.

In one aspect, the polyactive carbohydrate is from 0.1 to 1% by weight of the first admixture. In another aspect, the amount of polyactive carbohydrate is 0.1, 0.2, 0.3, 0.4, 0.5, 0.6, 0.7, 0.8, 0.9, or 1 wt % of the first admixture, where any value can be a lower or upper endpoint of a range (e.g., 0.2 to 0.7, etc.). In another aspect, the polyactive carbohydrate can be prepared and used as a solution. In one aspect, the polyactive carbohydrate is an aqueous solution of 1% to 5% (v/v), where the first admixture includes 20% to 80% (v/v) of the aqueous solution of the polyactive carbohydrate.

In one aspect, the natural oil polyol is from 20% to 80% (v/v) of the first admixture. In another aspect, the natural oil polyol is about 20%, 25%, 30%, 35%, 40%, 45%, 50%, 55%, 60%, 70%, 75%, or 80% (v/v) of the first admixture, where any value can be a lower or upper endpoint of a range (e.g., 40% to 60%, etc.).

Prior to the addition of the polyisocyanate, additional components can be added to the first admixture of polyactive carbohydrate and/or carbo sugar and natural oil polyol. In one aspect, a catalyst can be added to the first admixture. A "catalyst" as used herein is any substance that can increase the rate of a chemical reaction. In one aspect, the catalyst is not consumed in the reaction. A single molecule of a catalyst can assist with multiple chemical reactions. Catalysts useful herein include, but are not limited to, tertiary amines such as dimethylethanolamine (DMAE), triethylenediamine (DABCO), 3-aminopropyldimethylamine (DMAPA), dimethylcyclohexylamine (DMCHA); compounds containing hydroxyl groups or secondary amines such as, for example, propylene glycol; metallic compounds including metal carboxylates such as, for example, dibutyltin dilaurate (DBTDL) as well as mercury, lead, bismuth, and zinc carboxylates; and other alkyl tin carboxylates, oxides, and mercaptides. In one aspect, the catalyst is added to an emulsion containing the polyactive carbohydrate, natural oil polyol, and, in some aspects, the anti-microbial and UV resistant extracts at from about 0.05% to about 2% (v/v) with respect to the volume of the emulsion. In another aspect, about 0.05%, 0.1%, 0.15%, 0.2%, 0.25%, 0.4%, 0.6%, 0.7%, 0.8%, 1%, 1.2%, 1.5%, or 2% catalyst is used. In some aspects, a combination of catalysts is used. In one aspect, 0.5% (v/v) dibutyltin dilaurate and 1% (v/v) dimethylethanolamine were used in combination. In a further aspect, stirring is used to incorporate the catalyst throughout an emulsion containing the polyactive carbohydrate and/or the carbo sugar, the natural oil polyol, and, in some aspects, the anti-microbial and UV resistant extracts disclosed herein. In one aspect, different stirring times (e.g., about 1 minute, about 2 minutes, about 3 minutes, about 4 minutes, about 5 minutes, about 8 minutes, or about 10 minutes) and different stirring speeds (about 100 rpm, about 200 rpm, about 300 rpm, about 40 rpm, about 500 rpm, about 600 rpm, or about 700 rpm) are evaluated to determine the minimum stirring time and speed required to fully incorporate the catalyst into the emulsion. In one aspect, the emulsion and added catalyst are stirred at 300 rpm for 3 minutes.

In another aspect, a clay can be added to the first admixture. "Clay" and "clay minerals" as used herein refer to hydrous aluminum phylosilicates. Clays can optionally include oxides and/or chelates of other metals and semimetals such as, for example, silicon, iron, calcium, magnesium, sodium, potassium, and other alkali and alkaline earth metals. "Bentonite" is a category of impure clay that can consist of montmorillonite, kaolinite, and other species; and that can include potassium, sodium, calcium, aluminum, and/or other metals. "Zeolites" are microporous aluminosilicates that can accommodate a variety of cations, including, but not limited to, potassium, calcium, and magnesium. The cations in zeolites can be exchanged in aqueous solutions. Clays, bentonites, and zeolites can be used as sources of trace oxides and/or ions in the practice of the present invention. An "oxide" as used herein refers to a molecule, a network solid, or an ionic compound containing at least one oxygen atom and one other element. In one aspect, clays, bentonites, and zeolites contain chelated metal and semi-metal ions. Not wishing to be bound by theory, the inclusion of the clay can be used to vary the pore size of the final biofoam product produced.

In one aspect, a metal or semimetal oxide or a chelated metal ion can be incorporated into the first admixture. In one aspect, the metal or semimetal oxide includes, for example, $Al_2O_3$, $Fe_2O_3$, MgO, CaO, $Na_2O$, $K_2O$, $SiO_2$, or a combination thereof. In this aspect, the metal or semimetal oxide can be introduced into the polyurethane compositions as a pure compound. In an alternative aspect, ions such as, for example, aluminum, iron (III), magnesium, calcium, sodium, potassium, silicon, and combinations thereof, can be incorporated into the polyurethane compositions described herein through the inclusion of clays or clay minerals. In one aspect, the metal or semimetal oxides or chelated metals are incorporated at concentrations of from about 0.02 nM to about 1.2 mM, or at 0.02 nM, 0.04 nM, 0.06 nM, 0.08 nM, 0.1 nM, 0.15 nM, 0.2 nM, 0.25 nM, 0.3 nM, 0.35 nM, 0.4 nM, 0.45 nM, 0.5 nM, 0.55 nM, 0.2 mM, 0.4 mM, 0.6 mM, 0.8 mM, or 1.2 mM.

In another aspect, one or more water-soluble metal salts can be incorporated into the first admixture. In one aspect, the water-soluble metal salts can include, for example, gallium (III) nitrate hydrate, zinc sulfate, zinc acetate, or a combination thereof. In one aspect, 50 mg/L of gallium (III) nitrate hydrate is incorporated into the emulsion containing the polyactive carbohydrate, natural oil polyol, and the anti-microbial and UV-protective extracts. In another aspect, 100 mg/L of zinc sulfate is incorporated into the emulsion containing the polyactive carbohydrate, natural oil polyol, and in some aspects, the anti-microbial and UV-protective extracts.

After preparation of the first admixture as described above, a polyisocyanate is added to the first admixture. "Polyisocyanates" as used herein are compounds with two or more —N=C=O groups. In one aspect, the polyisocyanate is an aliphatic diisocyanate, a cycloaliphatic diisocyanate, an aromatic diisocyanate, or an isomer thereof. In another aspect, the isocyanate or polyisocyanate is 2,4-toluenediisocyanate, 2,6-toluenediisocyanate, 4,4'-methylene diphenyl diisocyanate (MDI), 4,4'-methylenebis(cyclohexylisocyanate) (H12-MDI), 1-isocyanato-3-isocyanatomethyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, xylylene diisocyanate, dichlorohexamethylene diisocyanate, dicyclohexyl-4,4'-diisocyanate, 1-methyl-2,4-diisocyanato-cyclohexane, 1-methyl-2,6-diisocyanato-cyclohexane, naphthalene-1,5-diisocyanate, p-phenylendiisocyanate, tetramethyl-xylylenediisocyanate (TMXDI), or any combination thereof. The isocyanate or polyisocyanate can exist as one or more structural isomers. Alternatively, the isocyanate or polyisocyanate can be a dimer, trimer, or oligomer. In other aspects, the isocyanate or polyisocyanate can exist as one or more positional isomers. For example, the polyisocyanate can be a mixture of 2,4-toluenediisocyanate and 2,6-toluenediisocyanate. In a further aspect, the polyisocyanate can be a 65:35 mixture of 2,4-TDI and 2,6-TDI (i.e., TDI 65). In a different aspect, the polyisocyanate can be an 80:20 mixture of 2,4-TDI and 2,6-TDI (i.e., TDI 80). In an alternative aspect, the polyisocyanate is a modified MDI or polyphenylmethane polyisocyanate such as one of those sold by Yantai Wanhua Polyurethanes Co. under the trade name WANNATE®.

In one aspect, the polyisocyanate is added to the first admixture at different ratios such as, for example, about 1:1, about 1:2, about 1:3, about 1:4, about 1:5, about 1:6, about 1:7, or about 1:8 with respect to the total emulsion volume, or any range thereof (e.g., 1:1 to 1:8, 1:3 to 1:5, etc.). In this aspect, polymerization reactions can be carried out. Different reaction times (e.g., 8 minutes, 10 minutes, 12 minutes, 15 minutes, or 20 minutes) and stirring speeds (e.g., 500 rpm, 600 rpm, 700 rpm, 800 rpm, 900 rpm, or 1000 rpm) can be evaluated to determine the optimum reaction time and stirring speed. In one aspect, the first admixture is admixed with the polyisocyanate for 10 minutes at 500 rpm. In another aspect, the reaction is conducted at room temperature.

In some aspects, the anti-microbial and UV-protective extracts are added to the second admixture containing the isocyanate, or, alternatively, are already present in the isocyanate solution when it is incorporated into the first admixture.

Upon admixing the components in the first admixture with the polyisocyanate, isocyanate-reactive functional groups present on the polyactive carbohydrate and/or the carbo sugar and/or the natural oil polyol and/or the anti-microbial and UV-protective extracts react with the isocyanate groups on the polyisocyanate to produce a polyurethane. Here, a polymer composed of organic residues joined by urethane linkages is produced. Although the components in the first admixture include hydroxyl groups, other components may be present that can include other isocyanate-reactive functional groups such as amine groups, thiol groups, or other nucleophilic groups capable of reacting with isocyanate groups.

The amount of the carbo sugar, if used, in the final biofoam product can vary. In one aspect, the amount of carbo sugar present in the biofoam is from 0.005% to 0.1% by weight of the biofoam. In another aspect, the amount of carbo sugar present in the biofoam is 0.005%, 0.01%, 0.02%, 0.03%, 0.04%, 0.05%, 0.06%, 0.07%, 0.08%, 0.09%, or 0.1% by weight of the biofoam, where any value can be a lower and/or upper endpoint of a range (e.g., 0.01% to 0.05%). When used to prepare the biofoams, the carbo sugar can be prepared as a stock solution. For example, the carbo sugar in powder form (0.05 g, 0.1 g, 0.2 g, 0.3 g, 0.4 g, 0.5 g, 0.6 g, 0.7 g, 0.8 g, 0.9 g, or 1 g) can be added to water (100 mL to 1 L) to produce a stock solution. The pH of the stock solution can be adjusted with standard buffer solutions. In one aspect, the pH of the carbo sugar stock solution is from 1 to 5, 1.5 to 4, or 2 to 3.

The amount of the polyactive carbohydrate present in the final biofoam product can vary. In one aspect, the amount of polyactive carbohydrate present in the biofoam is from 0.005% to 0.1% by weight of the biofoam. In another aspect, the amount of polyactive carbohydrate present in the biofoam is about 0.005%, 0.01%, 0.02%, 0.03%, 0.04%, 0.05%, 0.06%, 0.07%, 0.08%, 0.09%, or 0.1% by weight of the biofoam, where any value can be a lower or upper endpoint of a range (e.g., 0.01% to 0.05%). When used to prepare the biofoams, the polyactive carbohydrate can be prepared as a stock solution. For example, the polyactive carbohydrate in powder form (0.05, 0.1, 0.2, 0.3, 0.4, 0.5, 0.6, 0.7, 0.8, 0.9, or 1 g) can be added to water (100 mL to 1 L) to produce a stock solution. In some aspects, the anti-microbial and UV-protective extracts are also admixed with this stock solution. The pH of the stock solution can be adjusted as necessary.

The selection and amounts of reactants as well as processing conditions will determine the physical state of the biofoams. In one aspect, when the polyisocyanate is admixed with the first admixture, a solid biofoam is produced. The polyurethane compositions produced herein can be poured into a mold of any desired shape. If necessary, the mold containing the polyurethane composition can be placed in an oven to remove residual solvent and produce the final biofoam.

In other aspects, one or more blowing agents can be incorporated into the polyurethane compositions to produce the biofoams. A blowing agent can be physical or chemical in nature. A "physical blowing agent" is a gas or low boiling point liquid which expands due to heat generated by the polyurethane-forming reaction, thus forming bubbles and creating foam. A "chemical blowing agent" is a compound or substance that reacts to form a gas. In one aspect, the blowing agent is a physical blowing agent. Physical blowing agents include compounds such as, for example, hydrofluorocarbons (HFCs), hydrocarbons (HCs), hydrofluoroolefins, liquid $CO_2$, and other low boiling point liquids. In one aspect, the physical blowing agent is HFC-134a (1,1,1,2-tetrafluoroethane), HFC-245fa (pentafluoropropane), HFC-365mfe (1,1,1,3,3-pentafluorobutane), HFC-152a (1,1-difluoroethane), formic acid, methyl formate, HFO-1234ze (1,3,3,3-tetrafluoropropene), cyclopentane, n-pentane, iso-pentane, iso-butane, acetone, dichloromethane, or a mixture thereof. In another aspect, the blowing agent is a chemical blowing agent. In one aspect, the chemical blowing agent is carbon dioxide produced by the reaction of isocyanate groups with water. In a further aspect, both chemical and physical blowing agents can be used.

In other aspects, the biofoams include additional additives not already described above such as, for example, flame retardants, color additives, release agents, biocides, other additives, or a combination thereof. The additional components can be admixed with a dispersion or emulsion of polyurethane composition in order to incorporate the additives throughout the biofoam. In the alternative, the additives can be applied to the surface of the solid biofoam.

In another aspect, after the preparation of the biofoam, the biofoam can contain residual solvent (e.g., water). In certain aspects, it is desirable to remove all or substantially all (e.g., greater than 70%, greater than 80%, greater than 90%, greater than 95%, greater than 99%, or 100%) of the solvent in the biofoam. In one aspect, drying of the biofoams can be accomplished in an oven at about 20° C., 30° C., 40° C., 50° C., 60° C., or about 70° C. In one aspect, the biofoams are dried in an oven at 50° C. In a further aspect, the biofoams can be dried for from about 0.5 to ab08t 100 hours, or for about 72 hours. In one aspect, removal of water from biofoams is assessed by periodically removing the biofoams from the oven and weighing them. When the biofoams have the same weight at, for example, at least 2 or 3 successive weighings separated by several hours, the biofoams can be considered to be dry and can be removed from the oven.

The biofoams produced herein have several beneficial properties. In one aspect, the biofoams are resistant to discoloration. In another aspect, discoloration of the biofoams can be assessed by exposing the biofoams to an agent known to cause stains. In a further aspect, the agent known to cause stains is, for example, tea, coffee, or red wine. In one aspect, the biofoams can be submersed in coffee for a period of up to about 24 hours. In this aspect, after 24 hours, the biofoams are removed from the coffee and rinsed with water. Discoloration can then be qualitatively assessed as, for example, weak, medium, or strong.

In another aspect, the biofoams are resistant to acid degradation. For example, the biofoam can be assessed by placing a piece of the foam in an aqueous solution of an acid for 24 or 48 hours. In a further aspect, the acid is present at a 0.1N concentration. In another aspect, the acid is an organic acid such as, for example, acetic acid or formic acid. In an alternative aspect, the acid is an inorganic acid such as, for example, nitric acid, hydrochloric acid, phosphoric acid, or sulfuric acid. Resistance to mixtures of acids can also be tested. In a further aspect, photographs of the foam before and after exposure to acid can be compared to qualitatively assess acid resistance. In another aspect, the foam can be weighed before and after acid exposure to assess whether material has been lost.

In one aspect, it is desirable to know the maximum temperature to which the biofoams can be exposed without decomposition. This is known as temperature resistance. In one aspect, decomposition due to heat exposure can be assessed by placing a piece of the foam in an oven at a temperature of from about 50° C. to about 120° C. In a further aspect, temperature resistance is assessed at about 50° C., at about 80° C., or at about 120° C. In certain aspects, pieces of biofoam can be placed in an oven and the internal temperatures of the biofoam pieces can be measured periodically with, for example, a thermometer or a thermocouple. In a further aspect, temperature resistance can be measured every 10 minutes for up to one hour. In one aspect, the biofoam samples can be weighed prior to assessing temperature resistance, and can be weighed periodically to evaluate the level of decomposition. In this aspect, samples can be weighed every 10 minutes for up to one hour, at about the same time the internal temperature of the biofoam pieces is being measured, with weight loss indicating that decomposition has occurred. In an additional aspect, temperature resistance can be qualitatively assessed by, for example, visually noting any discoloration of the biofoam samples that occurs subsequently to heat treatment. In one aspect, if a sample exhibits less than about 20% weight loss, or less than about 10% weight loss, after exposure to a particular temperature, the sample can be said to be temperature resistant. In another aspect, if a sample does not become visibly discolored after exposure to a particular temperature, the sample can be said to be temperature resistant.

In one aspect, it is desirable to assess the biofoams for recovery from deformation. In this aspect, pressure can be applied to the biofoams, causing deformation. Also in this aspect, when pressure is removed from the biofoams, the biofoams can return to their original shapes and/or sizes. In certain aspects, from about 0.5 bars to about 1 bar of pressure are applied. In other aspects, the time required for the biofoams to recover from deformation is measured. In one aspect, the biofoams take up to about 5 seconds to recover from deformation. In another aspect, the biofoams take from about 1 second to about 3 seconds to recover from deformation.

The polyurethane compositions described herein can be used to produce biofoams that have numerous applications. The term "biofoam" as used herein is any substance formed when pockets of gas have been trapped in a solid or liquid.

In one aspect, the biofoams produced herein can exist as an emulsion or dispersion at room temperature. In other aspects, the biofoams produced herein are solid materials at room temperature.

In one aspect, provided herein are articles composed of or including the biofoams described herein. The biofoams produced herein can be used in any application where soft, synthetic polyurethane foams are used. For example, the biofoams can be used in upholstery such as cushions, pillows, furniture, or mattresses, including in automobiles, trains, watercraft and boats, and aircraft. In another aspect, the biofoams can be used to produce equipment for exercise or physical therapy including, for example, yoga mats and other floor mats, padding or upholstery for weight machines and seating for stationary and street bicycles, foam balls for physical therapy, comfort grips for handles for weights, kettlebells, bicycles, and the like, helmet padding and other personal protective equipment, and similar applications. In still another aspect, the biofoams can be used in the construction industry such as for insulation and carpet padding or carpet underlay materials. In another aspect, the biofoams can be used to create packaging materials including antistatic cushioning, case inserts, pads for vibration control, camping pads, and the like.

In another aspect, the biofoams disclosed herein can be used in the medical industry. In one aspect, the biofoams can be used where it is desirable to reduce or minimize blunt force or trauma to a subject. For example, the polyurethane composition can be injected between the skin of the subject and a cast to produce a biofoam that can further prevent any applied force to the broken bone of the subject. In certain aspects, the polyurethane composition can include anti-microbial agents in order to prevent odor.

In one aspect, the biofoams disclosed herein can be used to manufacture disposable cups and other packaging and containers intended for holding, transporting, and/or storing food and beverage items. In one aspect, the cups are impervious to water for a period of time ranging from a few hours to six months. In another aspect, the cups are impervious to hot and cold temperatures ranging from 10° C. to 65° C. In still another aspect, the cups are made from 70% to 100% natural and/or organic ingredients and are biodegradable. In yet another aspect, the food or beverage containers have anti-microbial properties that may delay or inhibit spoilage of food and beverages stored therein.

In one aspect, the biofoams can be formed using molds or 3D printers into construction materials, materials such as seat padding or upholstery foam used in the airplane and automobile industries, as insulation against freezing or heat, or as noise damping or acoustic materials.

VII. Additional Applications of the UV-Protective and Anti-Microbial Extracts

A. Adhesives

In other aspects, the polyurethane compositions described herein can be used as adhesives. For example, the polyurethane composition can be in a sufficient amount of solvent so that it can readily be applied to the surface of a substrate (e.g., spray coating, dipping, brushing). Upon removal of the solvent, a biofoam is produced, which results in the formation of a strong bond between two substrates. In other aspects, the polyurethane compositions can be used to seal cracks and holes. Here, the polyurethane composition is sprayed in a crack or hole and then forms a biofoam.

In another aspect, the adhesives can adhere plastic to plastic, metal to metal, wood to wood, plastic to metal, plastic to wood, and/or metal to wood. In one aspect, the adhesives are biodegradable and are designed break down over time. In an alternative aspect, under appropriate environmental conditions, the adhesives can last for months or even years.

B. Enhanced Plant Growth

In one aspect, the biofoams described herein can be granulated and added to soil in order to enhance plant growth. For example, when the granules are mixed with soil and seeds are planted therein, seedlings exposed to granules in the soil are more robust than seedlings planted in soil without granules (see Examples). In one aspect, the seedlings are taller and/or have broader leaves. In another aspect, the seedlings produce more chlorophyll and/or other pigments. In still another aspect, the granules are biodegradable and break down over time so they do not contaminate the soil with which they are mixed. In one aspect, the seeds planted can be corn, beans, tomatoes, peppers, peas, squash, cucumber, eggplant, radish, beet, turnip, melon, or any other fruit or vegetable commonly grown from seed. In another aspect, the seeds can be ornamental plants or herbs such as, for example, cilantro/coriander, thyme, oregano, basil, rosemary, savory, marjoram, chives, parsley, sage, dill, or other commonly used culinary or medicinal herbs.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions can be used to optimize the product purity and yield obtained from the desired process. Only reasonable and routine experimentation will be required to optimize such processes and conditions.

Example 1: Preparation of DNA Construct for Production of Anti-Microbial and UV-Protective Extracts A. Devices for Production of Anti-Microbial and UV-Protective Extracts The DNA construct was composed of the genetic components described herein and assembled in plasmid vectors (e.g., pYES2, purchased from Invitrogen). Sequences of genes and/or proteins with desired properties were identified in GenBank; these include a gene that expresses zinc-related protein/oxidase, a gene that expresses silicatein, a gene that expresses silaffin, and a gene that expresses alcohol dehydrogenase II. The sequences were synthesized by CloneTex Systems, Inc. (Austin, Tex.). Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes (Asc1 and Kpn1) according to directions and using reagents provided by the enzymes' supplier (New England Biolabs).

Figure 1A:
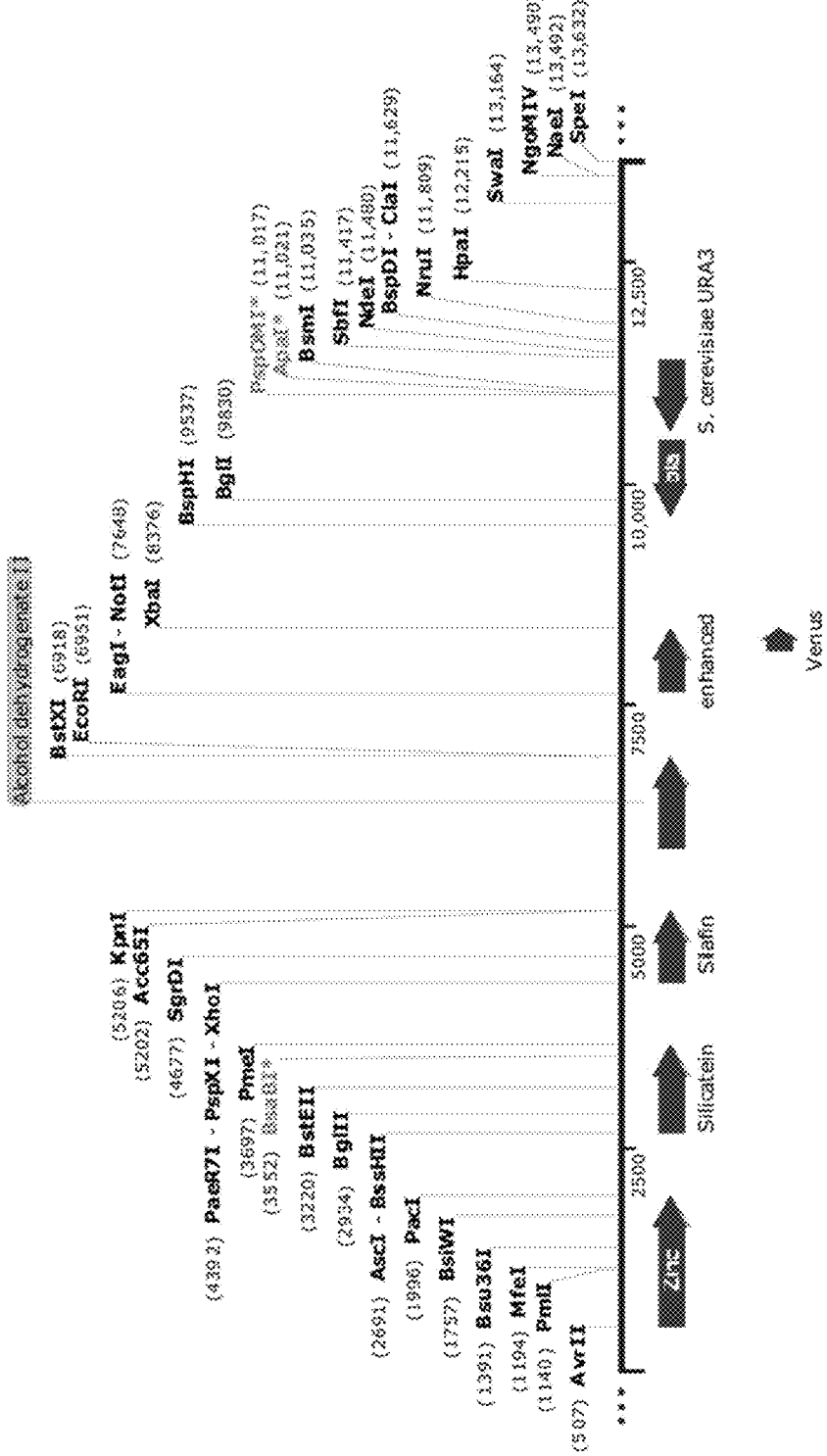
FIGS. 1A and 1B show, respectively, a linear and circular schematic of a constructed plasmid showing the direction, placement, and size of genetic parts used of an exemplary DNA device for producing anti-microbial and UV-protective extracts as described herein.
Figure 1B:
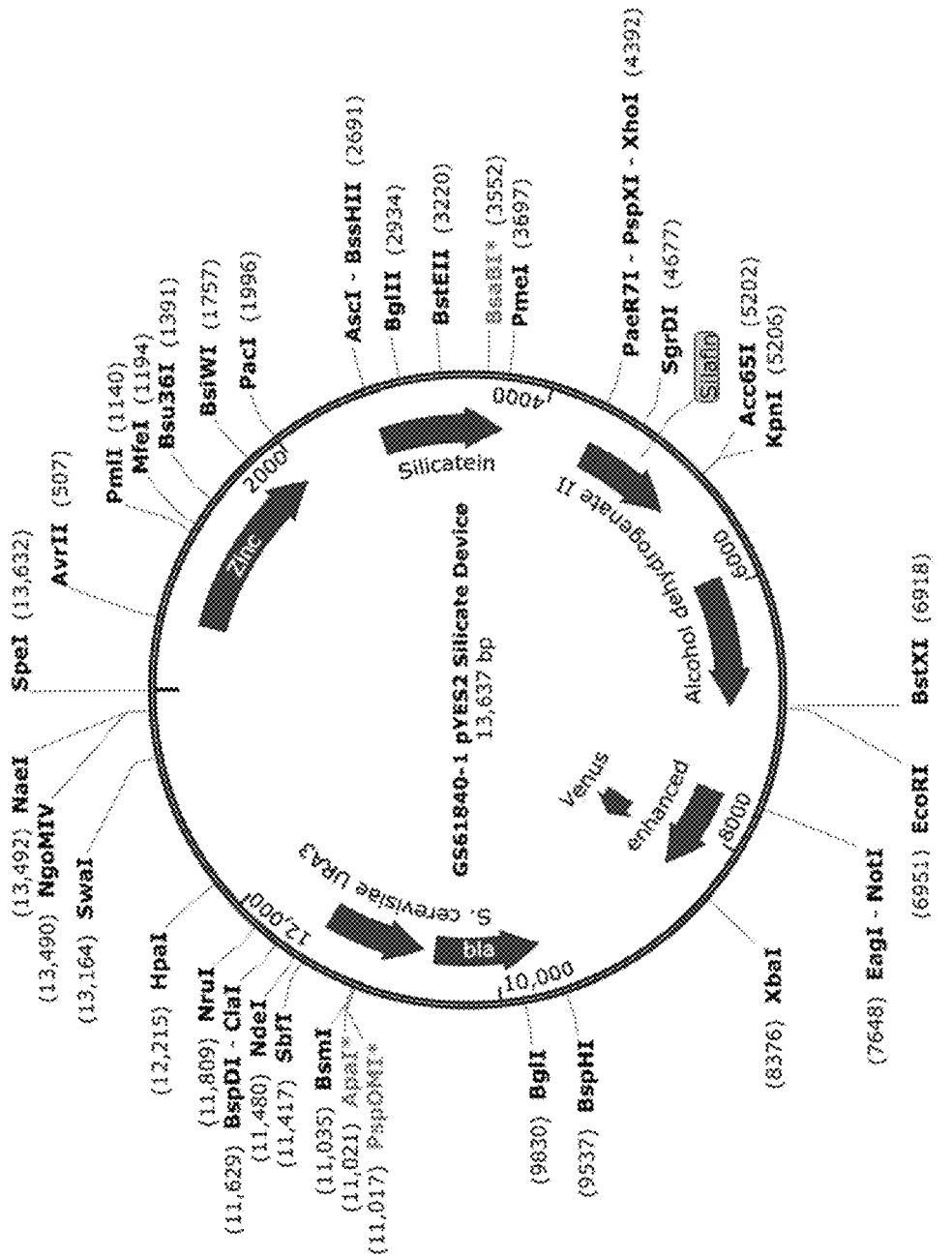

From 5' to 3', the construct includes (a) a gene that expresses zinc-related protein/oxidase, (b) a CYC1 terminator, (c) a GAL1 promoter, (d) a gene that expresses silicatein, (e) a CYC1 terminator, (f) a GAL1 promoter, (g) a gene that expresses silaffin, (h) a CYC1 terminator, (i) a GAL1 promoter, (j) a gene that expresses alcohol dehydrogenase II, (k) a CYC1 terminator, and (l) a yellow fluorescent reporter protein assembled in pYES2 plasmid (SEQ ID NO. 16) (FIGS. 1A and 1B).

Figure 2A:
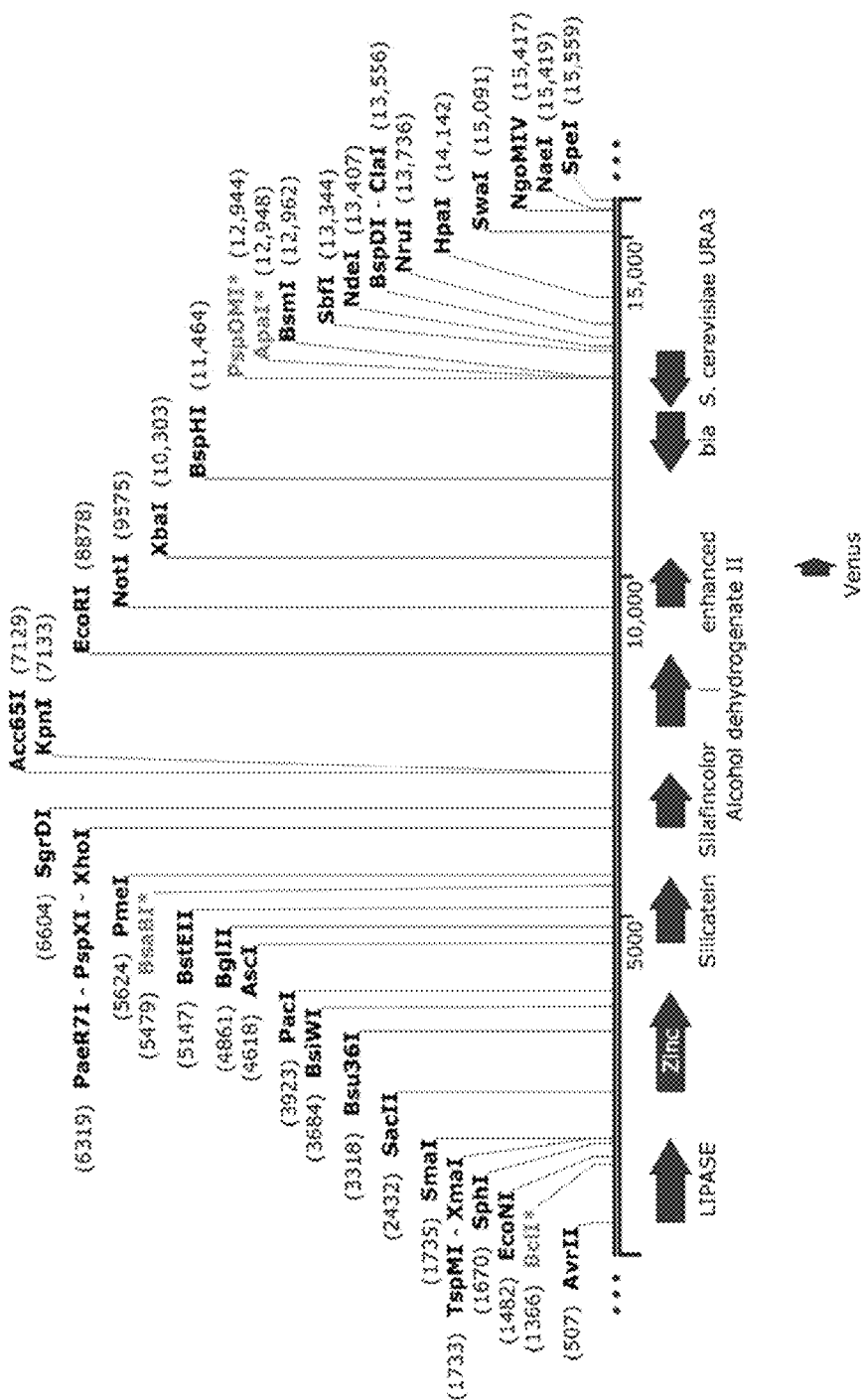
FIGS. 2A and 2B show, respectively, a linear and circular schematic of a constructed plasmid showing the direction, placement, and size of genetic parts used of an alternative exemplary DNA device for producing anti-microbial and UV-protective extracts as described herein.
Figure 2B:
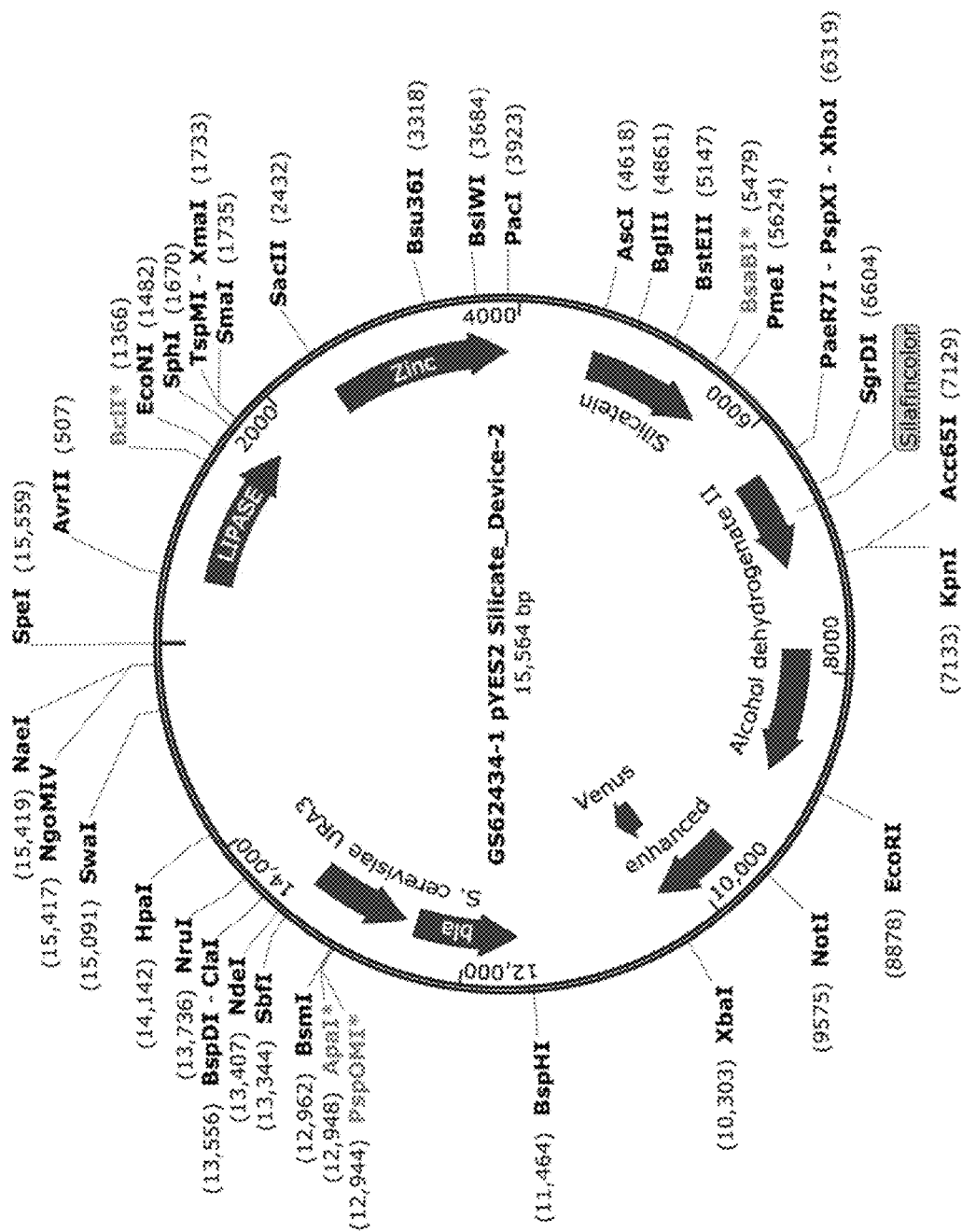

Also prepared was a second construct. From 5' to 3', the second construct includes (a) a gene that expresses lipase, (b) a CYC1 terminator, (c) a GAL1 promoter (d) a gene that expresses zinc-related protein/oxidase, (e) a CYC1 terminator, (f) a GAL1 promoter, (g) a gene that expresses silicatein, (h) a CYC1 terminator, (i) a GAL1 promoter, (j) a gene that expresses silaffin, (k) a CYC1 terminator, (l) a GAL1 promoter, (m) a gene that expresses alcohol dehydrogenase II, (n) a CYC1 terminator, and (o) a yellow fluorescent reporter protein assembled in pYES2 plasmid (SEQ ID NO. 17) (FIGS. 2A and 2B).

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, $2^{nd}$ ed., Vol. 1, Cold Spring Harbor Laboratory Press: Cold Spring Harbor, N.Y.). PCR amplified pieces of all fragments were combined using homologous recombination technology (Gibson Assembly). The complete insert, containing restriction sites on each end, was then ligated into the plasmid. Successful construction of the insert and ligation of the insert into the plasmid were confirmed by gel electrophoresis and DNA sequencing.

Digestion and ligation were used to ensure assembly of synthesized DNA parts using restriction enzymes and reagents (PCR reagents and enzymes were purchased from New England Biolabs). DNA was quantified using a NanoVue spectrophotometer (GE Life Sciences) and a standard UV/Visible spectrophotometer using the ratio of absorbances at 260 nm and 280 nm. In order to verify final ligations, DNA was visualized and purified via electrophoresis using a Thermo EC-150 power supply.

The DNA construct was made with gene parts fundamental for expression of sequences such as, for example, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the method described below.

B. Devices for Production of a Polyactive Carbohydrate

DNA constructs for producing polyactive carbohydrates were constructed in the same manner as for DNA constructs producing UV-protective and anti-microbial extracts as described above. Plasmids used for these constructs included pYES2, pBSK, and pETDuet-1. Sequences of genes and/or proteins with desired properties were identified in GenBank; these included a gene that expresses lipase, a gene that expresses chitin synthase, a gene that expresses chitosanase, and a gene that expresses chitin deacetylase. These sequences were synthesized by CloneTex Systems, Inc. (Austin, Tex.). Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors. Lipase was included in some constructs and was functional at any position in the construct. However, a position 5' of the gene for expressing chitin synthase was preferable when the lipase gene was included.

Figure 3A:
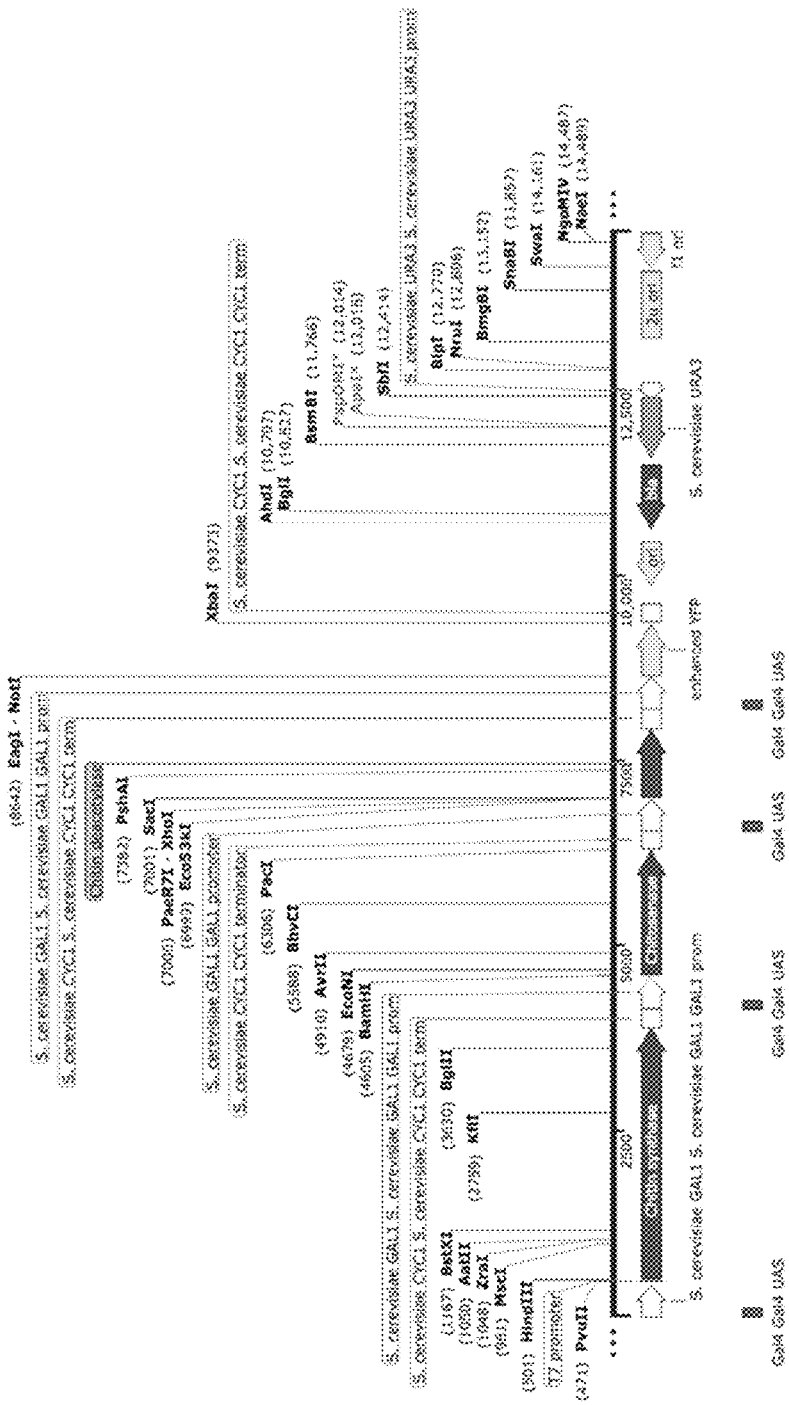
FIGS. 3A and 3B show, respectively, a linear and circular schematic of a constructed plasmid showing the direction, placement, and size of genetic parts used of an exemplary DNA device for producing a polyactive carbohydrate as described herein.
Figure 3B:
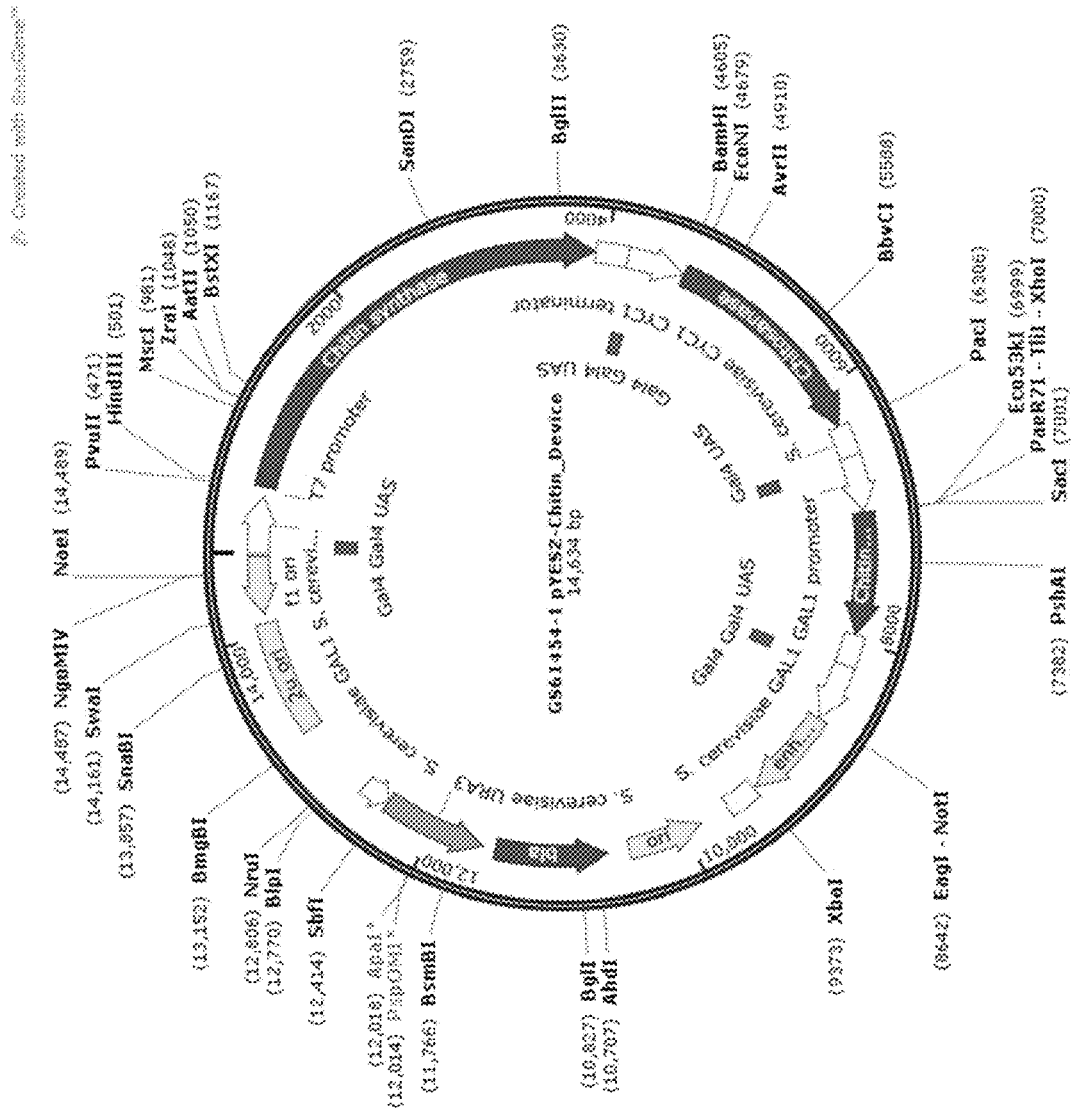

From 5' to 3', one version of the construct includes (a) a gene that expresses chitin synthase, (b) a CYC1 terminator, (c) a GAL1 promoter, (d) a gene that expresses chitosanase, (e) a CYC1 terminator, (f) a GAL1 promoter, (g) a gene that expresses chitin deacetylase, (h) a CYC1 terminator, (i) a GAL1 promoter, and (j) a yellow fluorescent reporter protein (SEQ ID NO. 18) (FIGS. 3A and 3B).

Figure 4A:
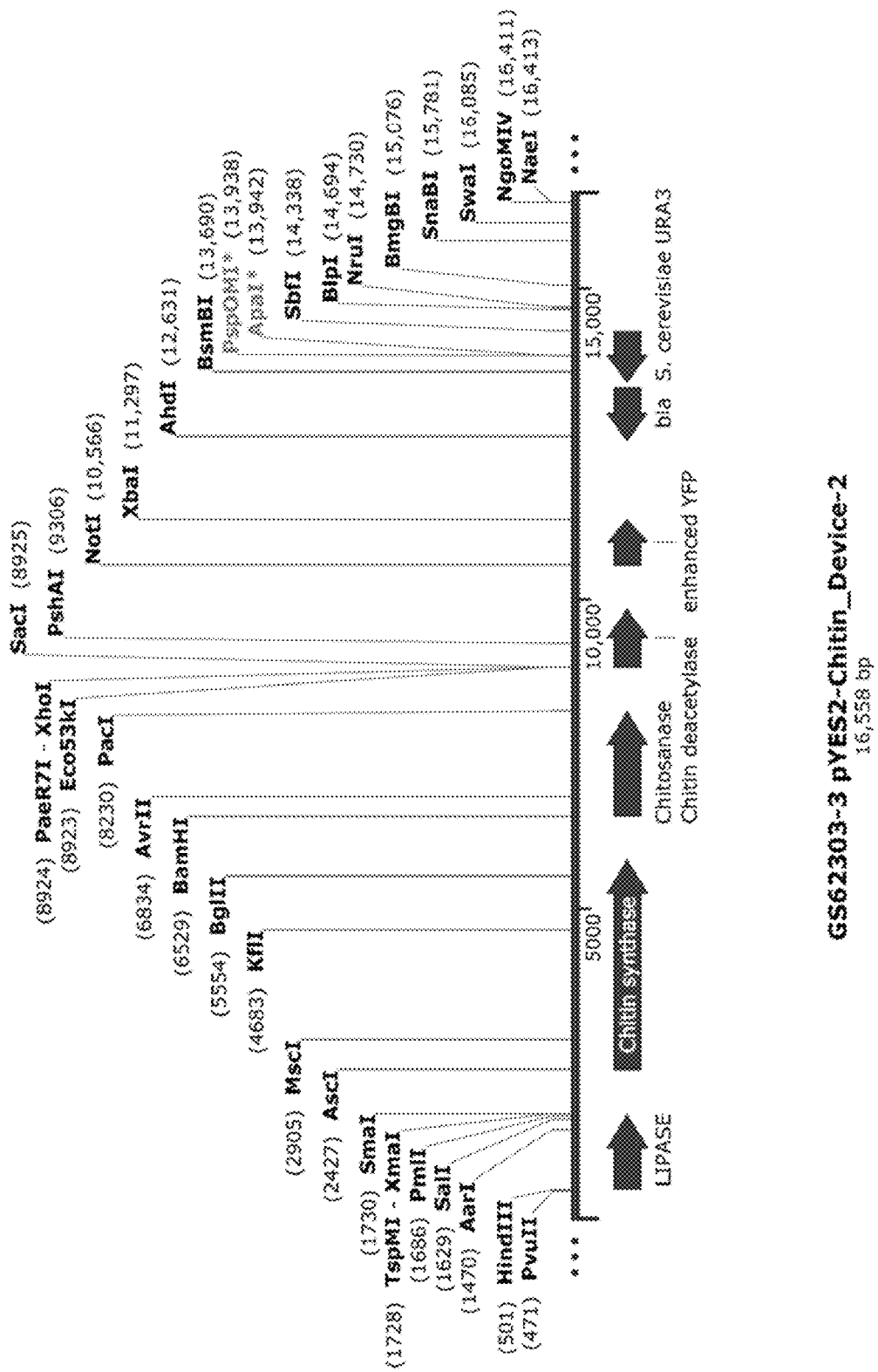
FIGS. 4A and 4B show, respectively, a linear and circular schematic of a constructed plasmid showing the direction, placement, and size of genetic parts used of an alternative exemplary DNA device for producing a polyactive carbohydrate as described herein.
Figure 4B:
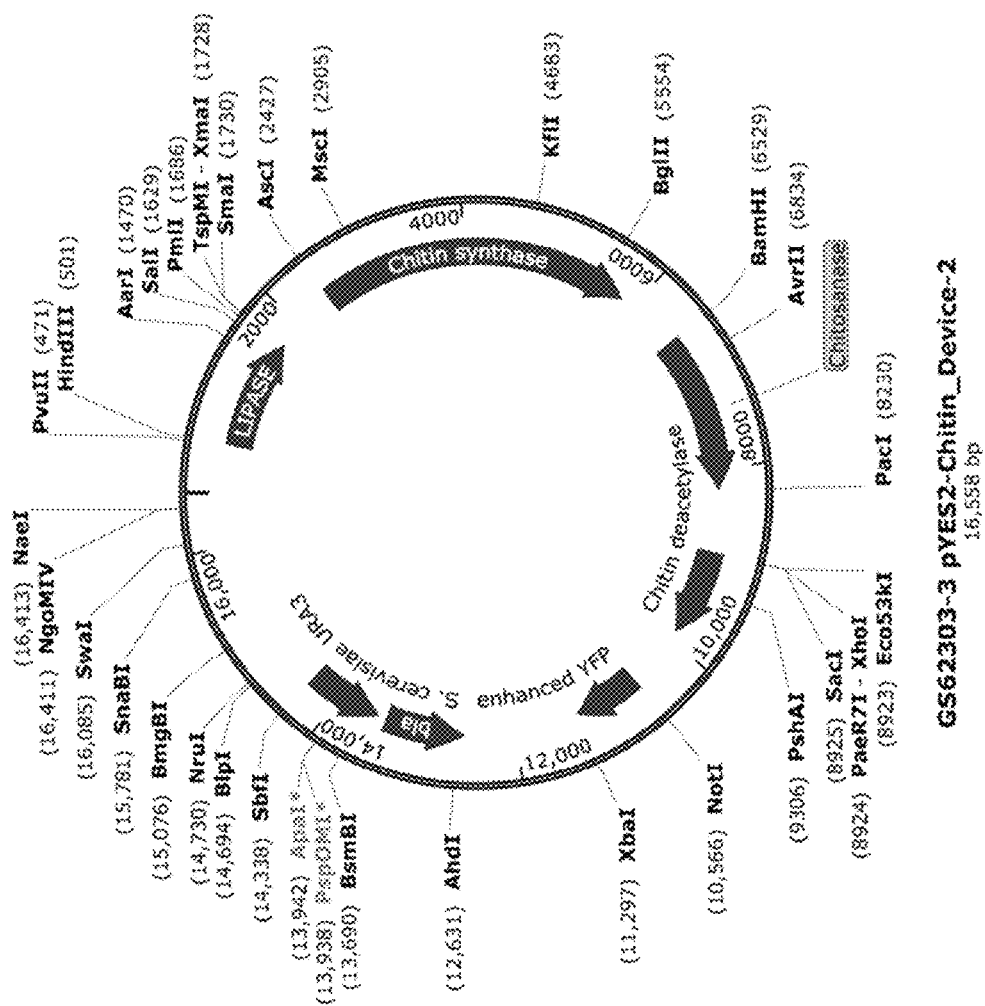

From 5' to 3', a second version of the construct includes (a) a gene that expresses lipase, (b) a CYC1 terminator, (c) a GAL1 promoter, (d) a gene that expresses chitin synthase, (e) a CYC1 terminator, (f) a GAL1 promoter, (g) a gene that expresses chitosanase, (h) a CYC1 terminator, (i) a GAL1 promoter, (j) a gene that expresses chitin deacetylase, (k) a CYC1 terminator, (l) a GAL1 promoter, and (m) a yellow fluorescent reporter protein (SEQ ID NO. 19) (FIGS. 4A and 4B).

Successful construction of the constructs was assessed as described previously for the UV-protective and anti-microbial constructs.

C. Devices for Production of a Carbo Sugar

DNA constructs for producing carbo sugars were constructed in the same manner as for DNA constructs producing UV-protective and anti-microbial extracts as described above. The plasmids used for these constructs was pYES2. Sequences of genes and/or proteins with desired properties were identified in GenBank; these included a gene that expresses lipase, a gene that expresses galactomannan galactosyltransferase, and a gene that expresses cellulose synthase. These sequences were synthesized by CloneTex Systems, Inc. (Austin, Tex.). Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors. Lipase was included in some constructs and was functional at any position in the construct. However, a position 5' of the gene for expressing cellulose synthase was preferable when the lipase gene was included.

From 5' to 3', the construct includes (a) a gene that expresses cellulose synthase, (b) a CYC1 terminator, (c) a GAL1 promoter, (d) a gene that expresses galactomannan galactosyltransferase, (e) a CYC1 terminator, and (f) a yellow fluorescent reporter protein (SEQ ID NO. 20) (FIGS. 5A-5D).

From 5' to 3', the construct includes (a) a gene that expresses lipase, (b) a CYC1 terminator, (c) a GAL1 promoter, (d) a gene that expresses cellulose synthase, (e) a CYC1 terminator, (f) a GAL1 promoter, (g) a gene that expresses galactomannan galactosyltransferase, (h) a CYC1 terminator, and (i) a yellow fluorescent reporter protein (SEQ ID NO. 21) (FIGS. 6A-6B).

From 5' to 3', the construct includes (a) a gene that expresses lipase, (b) a T7 promoter, (c) a LAC operon, (d) a riboswitch, (e) a gene that expresses cellulose synthase, (f) a riboswitch, and (g) a gene that expresses galactomannan galactosyltransferase (SEQ ID NO. 22) (FIGS. 7A-7B).

Successful construction of the constructs was assessed as described previously for the UV-protective and anti-microbial constructs.

Example 2: Selection of Microorganisms

The anti-microbial and UV-protective extract was produced using transfected yeasts (*Saccharomyces cerevisiae*, ATCC® 200892™) and/or bacteria (*Escherichia coli*, ONE-SHOT® Top10 competent cells from Life Technologies™, BL21 (DE3) *E. coli* from Novagen, Inc., or DH5α™ *E. coli* from Thermo Fisher Scientific).

Example 3: Development of Competent Yeast Cells

Yeast cells were made competent by subjecting them to an electrochemical process adapted from Gietz and Schiestl (*Nature Protocols*, 2007, 2:35-37). Briefly, a single yeast colony was inoculated into 100 mL YPD (yeast extract peptone dextrose) growth media. Yeast was grown overnight on a shaker at 30° C. to $OD_{600}$=1.0. (Acceptable results were obtained with $OD_{600}$ values ranging from 0.6 to 1.8.) Cells were centrifuged at 2000 rpm in a tabletop centrifuge and resuspended in 10 mL TEL buffer (10 mM Tris-HCl, 1 mM EDTA, 0.1 M LiAc, pH=7.5) and shaken vigorously overnight at room temperature. Cells were again centrifuged and resuspended in 1 mL TEL buffer. Cells prepared in this manner could be stored in the refrigerator for up to one month.

In other experiments, competent yeast cells (strain INVSc1) were purchased from Invitrogen, Inc. and prepared and transformed using a kit purchased from Sigma-Aldrich, Inc.

Example 4: Transformation of Yeast Cells to Produce Anti-Microbial and UV-Protective Device, Polyactive Carbohydrates, and Carbo Sugars A clone with 100% accuracy in the desired DNA sequence was selected for further processing. The selected clone was used to obtain a high concentration of the plasmid construct at a mid-scale plasmid purification level. Cells containing the plasmid were selected on a synthetic complete (SC) dropout plate deficient in uracil. A well-isolated clone was chosen from the SC plate and preserved in YPD medium containing 15% glycerol for storage at −80° C.

Competent cells were stored in the freezer until needed. Cells were thawed on ice and 100 µL of competent cells in TEL buffer were placed in a sterile 1.5 mL microcentrifuge tube. To this was added 5 µL of a 10 mg/mL solution of salmon sperm DNA (carrier DNA). Transforming DNA was added in various amounts. From 1 to 5 µg was sufficient for plasmids from commercial sources, but more DNA was required when transforming yeast with artificial DNA constructs. 10 µL of the DNA device were added to the microcentrifuge tube containing the competent yeast cells and the contents of the tube were mixed. The DNA-yeast suspension was incubated for 30 min at room temperature. A PLATE solution (consisting of 40% PEG-3350 in 1×TEL buffer) was prepared. 0.7 mL of PLATE solution was added to the DNA-yeast suspension and the contents were mixed thoroughly and incubated for 1 h at room temperature. The mixture was placed in an electromagnetic chamber for 30 minutes. Cells were then heated at 42° C. for 5-10 minutes and 250 µL aliquots were plated on yeast malt agar to which selective growth compounds had been added. Plates were incubated overnight at 30° C.

DNA expression and effectiveness of transformation were determined by fluorescence of the transformed cells expressed in fluorescence units (FSUs) using a 20/20 Luminometer (Promega) according to a protocol provided by the manufacturer. Plasmid DNA extraction, purification, PCR, and gel electrophoresis were also used to confirm transformation. Different transformed devices were obtained. Different types of fluorescent reporter proteins were used (e.g., yellow, red, green, and cyan) for all transformed cells and/or constructs. However, the yellow fluorescent protein was preferred. When no fluorescent reporter protein was assembled, no fluorescence was observed.

*S. cerevisiae* cells were subject to transformation with the modified pYES2 plasmid as described above. Transformed yeast cells were incubated for 30 min at 28-30° C. Colonies of transformed yeast cells were selected, their DNA isolated and subjected to PCR amplification. Two control treatments were also carried out: (1) a negative control involving competent yeast and nuclease free water instead of a plasmid and (2) a positive control involving competent yeast with unmodified pYES2 plasmid.

Alternatively, the pETDuet-1 plasmid-based device was transformed into DH5α and BL21(DE3) *E. coli* using a standard heat shock protocol. Four clones were selected from a transformed plate and processed for full-length DNA sequencing. A clone with 100% DNA sequence accuracy was selected for further processing and was used to obtain a high concentration of plasmid construct at a mid-scale plasmid purification level.

Example 5: Induction and Growth of Device

The following procedure was used to induce production of the extract from the UV-protective and anti-microbial devices described previously. A small sample of yeast device transformed with the construct in FIGS. 1A-1B (SEQ ID NO. 16) was grown in 3-5 mL of yeast malt overnight at 30° C.

1 mL of the device grown overnight was added to 1 L of yeast malt containing at least 2% raffinose sugar and incubated at 30° C. for 2-4 hours until device growth reaches 0.6-0.8 optical density as measured by UV-Vis spectrophotometry. Galactose sugar at 1% based on a 1 L culture is added to the previously described culture, then incubated for at least 48 hours at 30° C.

Example 6: Isolation of Anti-Microbial and UV-Protective Extracts

After 48 hours of culture as described in Example 5, the culture of the UV-protective and anti-microbial device was treated with lyticase (240 µL/L) for 24 hours. The culture was then centrifuged at 9,000 rpm for 15 minutes to obtain a pellet. The supernatant is not discarded. The pellet was resuspended in distilled water at a level of approximately 1 g pellet per 100 mL of water. This mixture was subjected to sonication for 2 minutes, using a 30 seconds on/15 seconds off program at 60% of wavelength amplitude (QSONICA Sonicator, Newtown, Conn.). This procedure was repeated twice.

The supernatant from the centrifugation is again centrifuged to remove dead cells and/or debris. The centrifuged supernatant is then filtered through a 0.45 µm pore filter. The filtrate contains antifungal compounds and metabolites and can be used for antifungal treatment.

Example 7: Antifungal Testing Using the Biological Devices

Antifungal capabilities of the extract produced in Example 6 were evaluated using *Fusarium graminearum* (ATCC 15624). The minimal fungal concentration in culture was $10^4$ cells/mL. Fungal cultures were mixed with the extract produced above (10% of either extract based on total solution volume).

Samples of the above mixture were obtained at 0, 30, and 60 minutes, as well as 24 hours, 48 hours, and 72 hours and fungal growth was determined. At each sampling time, 500 µL aliquots of the fungal culture were taken into PDA agar plates to confirm whether the fungal cells obtained were alive or dead. Antifungal effectiveness was determined by counting fungal colonies; photographic records were also collected. A control experiment with a fungal culture extract and no biological device was also performed.

The extract inhibited growth of the fungus *Fusarium graminearum* after 24 hours of incubation, as compared to control (i.e., fungal culture without treatment with extract), which showed full growth.

Example 8: Production of Soft Biofoams

The following procedures were used to construct soft biofoams from extracts of the devices disclosed herein. These biofoams are 90% natural and 10% synthetic.

A. Polyactive Carbohydrate Extract
1. Yeast transformed with the device depicted in FIGS. 3A and 3B (SEQ ID NO. 18) was fermented in yeast malt medium with 2% raffinose and 1 mg/mL of glucosamine and induced with galactose at 30° C. for 72 hours.
2. The culture medium was centrifuged at 9,000 rpm for 15 minutes to pelletize the culture.
3. The pellet was resuspended at 1 g/50 mL in sterile deionized water.
4. The resuspension was sonicated for two minutes and 30 seconds using a 30 seconds on/15 seconds off protocol.
5. The sonicated mixture was centrifuged at 9,000 rpm for 15 minutes.
6. The supernatant was filtered with a 0.45 µm filter.

B. Anti-Microbial and UV-Protective Extract
1. Yeast transformed with the device depicted in FIGS. 1A and 1B (SEQ ID NO. 16) was fermented in yeast malt medium with 2% raffinose and induced with galactose at 30° C. for 72 hours.
2. The culture medium was centrifuged at 9,000 rpm for 15 minutes to pelletize the culture.
3. The pellet was resuspended at 1 g/50 mL in sterile deionized water.
4. The resuspension was sonicated 3 times for 2 minutes and 30 seconds each time.
5. The sonicated mixture was centrifuged at 9,000 rpm for 15 minutes.
6. The supernatant was filtered with a 0.45 µm filter.

C. Construction of a Soft Biofoam Containing a Polyactive Carbohydrate Extract and an Anti-Microbial and UV-Protective Extract At room temperature, 19 mL of polyactive carbohydrate extract as described above and 19 mL of anti-microbial/UV-protective extract (optical density 2.4) were mixed with 2 mL of polysorbate 80 and stirred for 3 minutes. 50 mL of castor oil were added and the mixture was stirred for an additional 10 minutes.

Separately, also at room temperature, 5 mL of each extract were mixed with 0.5 g of bentonite and vortexed for 5 minutes. This second mixture was added to the above mixture and stirred for an additional 10 minutes.

20 mL of isocyanate (MDI; Geos Quimica S.A.S.) were added to the above mixture over the course of 7 minutes at room temperature; this represented a ratio of approximately 5:1 polyol:isocyanate. Pressurized air (5-15 psi) was injected during the last 2 minutes of this process if required for continued mixing, although in some cases air was not required.

The mixture was allowed to dry overnight at room temperature, then transferred to a mold to complete the final formation of the biofoam. Molds of various shapes and sizes were used, depending on the intended use of the final biofoam product.

After formation of the biofoams, they were removed from the molds and the biofoam objects were transferred to an oven to complete drying at 30-40° C. for 30-60 minutes.

D. Physical Characteristics of the Soft Biofoams Containing a Polyactive Carbohydrate and Anti-Microbial/UV-Protective Extracts The soft biofoams once dried had a soft texture with memory (i.e., would return to the original shape after deformation). For a 7 $cm^3$ cube, the mass of the biofoam was approximately 63 g. These biofoams also exhibited antimicrobial properties.

Example 9: Production of Hard Biofoams

A. Procedure for Making Biofoams Containing a Polyactive Carbohydrate and Anti-Microbial/UV-Protective Extracts The following procedures were used to construct hard biofoams from extracts of the devices disclosed herein. These biofoams are 90% natural and 10% synthetic and the polyactive carbohydrate and anti-microbial/UV-protective extracts were prepared as described in Example 8. In some experiments, carbo sugar extracts were used in place of or in addition to the polyactive carbohydrate extracts.

At room temperature, 24.5 mL of each respective extract were mixed together with 1 mL of polysorbate 80 for 3 minutes. 40 mL of castor oil were added and the mixture was stirred for an additional 10 minutes.

Separately, and also at room temperature, 5 mL of each respective extract were mixed together with 0.5 g of bentonite and vortexed for 5 minutes. This mixture was added to the above solution and stirred for 10 minutes.

20 mL of isocyanate (MDI; Geos Quimica S.A.S.) were added to the above mixture over the course of 7 minutes at room temperature; this represented a ratio of approximately 5:1 polyol:isocyanate. Pressurized air (5-15 psi) was injected during the last 2 minutes of this process if required for continued mixing, although in some cases air was not required.

The mixture was allowed to dry overnight at room temperature, then transferred to a mold to complete the final formation of the biofoam. Molds of various shapes and sizes were used, depending on the intended use of the final biofoam product.

After formation of the biofoams, they were removed from the molds and the biofoam objects were transferred to an oven to complete drying at 30-40° C. for 30-60 minutes.

B. Physical Characteristics of the Hard Biofoams Containing a Polyactive Carbohydrate and Anti-Microbial/UV-Protective Extracts The hard biofoams once dried had a hard texture with no memory (i.e., would not return to the original shape after deformation). For a 7 cm$^3$ cube, the mass of the biofoam was approximately 55 g. These biofoams also exhibited antimicrobial properties.

C. Chemical and Mechanical Properties of Hard Biofoams

The hard biofoams described herein were subjected to various physical and chemical tests. The hard biofoams could be placed into cup-shaped molds and formed into cups.

A piece of hard biofoam was immersed in water for six months and remained floating in the water at the end of that time period. This indicated that the hard biofoam was impermeable to water. A piece of hard biofoam was also immersed in 1% acetic acid for six months. It did not degrade, but remained floating in the solution. This indicated that the hard biofoam was resistant to mild acid.

A hammer was used to strike a block of hard biofoam. The hard biofoam did not break or splinter, indicating resistance to physical impact.

Example 10: Preparation of Biodegradable Cups from Polyactive Carbohydrate Extracts and Anti-Microbial/UV-Protective Extracts The following procedures were used to prepare and optimize the composition of biodegradable cups from extracts of the devices disclosed herein. These cups range from 79-97% natural and 3-21% synthetic and the polyactive carbohydrate and anti-microbial/UV-protective extracts were prepared as described in Example 8. In some experiments, device cultures were allowed to grow for up to 190 hours, but 72 hours was generally sufficient.

At room temperature, a total of 49 mL of extracts from the devices disclosed herein (usually equal volumes of the polyactive carbohydrate extract and the anti-microbial/UV-protective extract produced in Example 8) were added to the surfactant and stirred for 3 minutes. Castor oil was added and stirring was carried out for an additional 10 minutes. Separately, a total of 10 mL of extracts from the devices disclosed herein (again, usually equal volumes) were added to bentonite and the mixture was vortexed for 5 minutes. This second mixture was added to the first and stirring took place for an additional 10 minutes.

Following this, isocyanate (typically MDI from Geos Quimica S.A.S.) was added in a ratio of 4:1 polyol:isocyanate (typically 25 mL isocyanate) and stirred for 10 minutes at room temperature. This mixture was allowed to dry for 3 minutes at room temperature and excess water was removed from the mixture.

The mixture was then transferred to a 60 cc Teflon mold to complete the final formation of the cup. Molds of various sizes can be used depending on the cup size and shape desired.

After 24 hours, the cup was removed from the Teflon mold and transferred to an oven to dry for 30-60 minutes at 30-40° C. (FIG. 8).

Texture, size, and weight of cups varied depending upon the composition. All cups constructed were impermeable to water when tested with water of different temperatures ranging from 10-65° C. A typical cup from a 60 cc mold weighed from 30-35 g and had a hard, smooth texture. Different cup compositions are provided in Table 11.

TABLE 11

Composition of Sample Biofoam Cups

| Component or Property | Cup A | Cup B | Cup C | Cup D |
|---|---|---|---|---|
| % Natural | 78.6 | 86.54 | 94.87 | 96.89 |
| % Synthetic | 21.4 | 13.45 | 5.12 | 3.13 |
| Polyactive carbohydrate extract (mL) | 29.5 | 60 | 70 | 94 |
| Anti-microbial/UV-protective extract (mL) | 29.5 | 60 | 70 | 70 |
| Castor oil (mL) | 40 | 50 | 20 | 10 |
| Beeswax cream (5%, mL) | 0 | 20 | 20 | 10 |
| Polysorbate 80 (mL) | 1 | 2 | 4 | 2 |
| Isocyanate (mL) | 25 | 30 | 10 | 6 |
| Bentonite (g) | 0.5 | 1 | 1 | 1 |
| NaH (drops) | 0 | 3 | 3 | 3 |

Example 11: Preparation of Biodegradable Cups from Polyactive Carbohydrate Extract, Carbosugar Extract, and Anti-Microbial/UV-Protective Extract The following procedure was used to produce a cup. At room temperature, the polyactive carbohydrate extract (65 mL, concentration of 2.5 OD produce from yeast cells transformed with construct in Example 1) and the anti-microbial/UV-protective extract (35 mL, concentration of 2.5 OD produced in Example 8) were added to the surfactant (TWEEN 80, 2 mL) and stirred for 3 minutes. Castor oil (15 mL) was added and stirring was carried out for an additional 5 minutes. Separately, 5 mL each of the polyactive carbohydrate extracts and the anti-microbial/UV-protective extract were added to bentonite and the mixture was vortexed for 5 minutes. This second mixture was added to the mixture above and stirring took place for an additional 10 minutes.

In a separate mixture, polyisocyanate (Geos Química S.A.S—Isocyanate for rigid—MDI) (6 mL), beeswax cream (10 ml at 5 wt %) and carbo sugar extract produce from yeast cells transformed with construct in Example 1 (40 ml) were mixed for 9 minutes at room temperature (250-28° C.). This mixture was admixed with the mixture above and stirred for 10 minutes at room temperature. This mixture was allowed to dry for 3 minutes at room temperature and excess water was removed from the mixture.

The mixture was then transferred to a 60 cc Teflon mold to complete the final formation of the cup. Molds of various sizes can be used depending on the cup size and shape desired.

After 24 hours, the cup was removed from the Teflon mold and transferred to an oven to dry for 30-60 minutes at 30-40° C.

Example 12: Determination of Polyactive Carbohydrate Concentration in Culture Extracts Concentrations of polyactive carbohydrate produced in Example 8 used to produce the cups and in subsequent experiments were determined as follows. Samples from device cultures were obtained and centrifuged at 9,000 rpm for 15 minutes at 15° C. and a pellet was obtained. The pellet was sonicated for two minutes and 30 seconds using a 30 seconds on/15 seconds off protocol. The resulting mixture was centrifuged at 9,000 rpm for 15 minutes and the supernatant was filtered using 0.45 μm filters to obtain an extract.

A standard curve was constructed using a glucosamine standard since the base molecule of the polyactive carbohydrate is glucosamine (see FIG. 9). Table 12 provides the numerical data used to construct the calibration curve:

TABLE 12

Glucosamine Calibration Curve

| Sample | Concentration (as prepared, mg/mL) | Concentration (based on absorbance, mg/mL) | Residual | Absorbance (AU) |
|---|---|---|---|---|
| 1 | 0.2 | 0.1878 | 0.0122 | 0.1034 |
| 2 | 0.4 | 0.4146 | −0.0146 | 0.1907 |
| 3 | 0.6 | 0.5842 | 0.0158 | 0.2560 |
| 4 | 0.8 | 0.8369 | −0.0369 | 0.3533 |
| 5 | 1.0 | 0.9766 | 0.0234 | 0.4071 |

The culture extract prepared as described above had a concentration of 0.7195 mg/mL of polyactive carbohydrate. This was diluted to 0.3688 mg/mL for use in biofoam and cup production experiments.

Example 13: Effect of Biofoam Waste on Plant Growth

The effect of waste from biofoam cup production on plants was assessed as follows. Corn or bean seeds were placed in soil without (control) or with granular waste from cup production. Growth of germinating seeds and leaf/plant color were evaluated over a 2-month period.

Average plant size and color for the treatment and control groups after two months can be seen in Table 13:

TABLE 13

Growth and Coloration of Plants Exposed to Biofoam Production Waste after Two Months

| Plant | | Bean | Corn |
|---|---|---|---|
| Control | Height | 13.5 cm | 33 cm |
| | Color | Light Green | Light Green |
| Treatment | Height | 18 cm | 45 cm |
| | Color | Intense Green | Intense Green |

Intensity of color, as qualitatively assessed in Table 13, is reflective of an increase in chlorophyll content. Both bean and corn plants treated with granules of biofoam waste exhibited increased growth and chlorophyll production as compared to untreated controls.

Example 14: Preparation of Adhesives from Polyactive Carbohydrate Extracts and Anti-Microbial/UV-Protective Extracts The following procedures were used to prepare adhesives from extracts of the devices disclosed herein. These adhesives are 90% natural and 10% synthetic and the polyactive carbohydrate and anti-microbial/UV-protective extracts were prepared as described in Example 8.

At room temperature, 19.5 mL of each respective extract were mixed together with 1 mL of polysorbate 80 for 3 minutes. 40 mL of castor oil were added and the mixture was stirred for an additional 10 minutes.

Separately, and also at room temperature, 5 mL of each respective extract were mixed together with 0.5 g of bentonite and vortexed for 5 minutes. This mixture was added to the above solution and stirred for 9 minutes.

20 mL of isocyanate (MDI; Geos Quimica S.A.S.) were added to the above mixture over the course of 9 minutes at room temperature; this represented a ratio of approximately 4:1 polyol:isocyanate.

The mixture was then applied to the surfaces to be glued together. The adhesive has a drying time of two hours and was able to adhere plastic, wood, and metal (see FIGS. 10A-10C).

Because the adhesives are prepared from 90% natural materials, they are biodegradable.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A biological device comprising microbial host cells transformed with a vector, wherein the vector comprises a DNA construct comprising the following genetic components:
   (a) a gene having the nucleic acid sequence of SEQ ID NO. 1 or at least 90% homology thereto that encodes a zinc-related protein/oxidase,
   (b) a gene having the nucleic acid sequence of SEQ ID NO. 2 or at least 90% homology thereto that encodes a silicatein,
   (c) a gene having the nucleic acid sequence of SEQ ID NO. 3 or at least 90% homology thereto that encodes a silaffin, and
   (d) a gene having the nucleic acid sequence of SEQ ID NO. 4 or at least 90% homology thereto that encodes an alcohol dehydrogenase II.

2. The biological device of claim 1, further comprising (e) a gene having the nucleic acid sequence of SEQ ID NO. 7 or at least 90% homology thereto that encodes a lipase.

3. The DNA biological device of claim 1, wherein the gene that encodes the zinc-related protein/oxidase has the nucleic acid sequence of SEQ ID NO. 1.

4. The biological device of claim 1, wherein the gene that encodes the silicatein has the nucleic acid sequence of SEQ ID NO. 2.

5. The biological device of claim 1, wherein the gene that encodes the silaffin has the nucleic acid sequence of SEQ ID NO. 3.

6. The biological device of claim 1, wherein the gene that encodes the alcohol dehydrogenase II has the nucleic acid sequence of SEQ ID NO. 4.

7. The biological device of claim 2, where in the gene that encodes the lipase has the nucleic acid sequence of SEQ ID NO. 7.

8. The biological device of claim 1, wherein the construct further comprises a promoter.

9. The biological device of claim 8, wherein the promoter comprises a GAL1 promoter, a T7 promoter, or both.

10. The biological device of claim 1, wherein the construct further comprises a terminator.

11. The biological device of claim 10, wherein the terminator is a CYC1 terminator.

12. The biological device of claim 1, wherein the construct further comprises a gene that confers resistance to an antibiotic.

13. The biological device of claim 1, wherein the biological device further comprises a gene that encodes a reporter protein.

14. The biological device of claim 1, wherein the DNA construct comprises from 5' to 3' the following genetic components in the following order: (1) the gene that encodes the zinc-related protein/oxidase, (2) the gene that encodes the silicatein, (3) the gene that encodes the silaffin, and (4) the gene that encodes the alcohol dehydrogenase 11.

15. The biological device of claim 1, wherein the DNA construct comprises from 5' to 3' the following genetic components in the following order: (1) the gene that encodes the zinc-related protein/oxidase, (2) a CYC1 terminator, (3) a GAL1 promoter, (4) the gene that encodes the silicatein, (5) a CYC1 terminator, (6) a GAL1 promoter, (7) the gene that encodes the silaffin, (8) a CYC1 terminator, (9) a GAL1 promoter, (10) the gene that encodes the alcohol dehydrogenase II, and (11) a CYC1 terminator.

16. The biological device of claim 1, wherein the DNA construct comprises from 5' to 3' the following genetic components in the following order: (1) the gene that encodes the zinc-related protein/oxidase has the nucleic acid sequence of SEQ ID NO: 1, (2) the gene that encodes the silicatein has the nucleic acid sequence of SEQ ID NO: 2, (3) the gene that encodes the silaffin has the nucleic acid sequence of SEQ ID NO: 3, and (4) the gene that encodes the alcohol dehydrogenase II has the nucleic acid sequence of SEQ ID NO: 4.

17. The biological device of claim 2, wherein the DNA construct comprises from 5' to 3' the following genetic components in the following order: (1) the gene that encodes the lipase, (2) the gene that encodes the zinc-related protein/oxidase, (3) the gene that encodes the silicatein, (4) the gene that encodes the silaffin, and (5) the gene that encodes the alcohol dehydrogenase II.

18. The biological device of claim 2, wherein the DNA construct comprises from 5' to 3' the following genetic components in the following order: (1) the gene that encodes the lipase, (2) a CYC1 terminator, (3) a GAL1 promoter, (4) the gene that encodes the zinc-related protein/oxidase, (5) a CYC1 terminator, (6) a GAL1 promoter, (7) the gene that encodes the silicatein, (8) a CYC1 terminator, (9) a GAL1 promoter, (10) the gene that encodes the silaffin, (11) a CYC1 terminator, (12) a GAL1 promoter, (13) the gene that encodes the alcohol dehydrogenase II, and (14) a CYC1 terminator.

19. The biological device of claim 2, wherein the DNA construct comprises from 5' to 3' the following genetic components in the following order: (1) the gene that encodes the lipase has the nucleic acid sequence of SEQ ID NO. 7, (2) the gene that encodes the zinc-related protein/oxidase has the nucleic acid sequence of SEQ ID NO: 1, (3) the gene that encodes the silicatein has the nucleic acid sequence of SEQ ID NO: 2, (4) the gene that encodes the silaffin has the nucleic acid sequence of SEQ ID NO: 3, and (5) the gene that encodes the alcohol dehydrogenase II has the nucleic acid sequence of SEQ ID NO: 4.

20. The biological device of claim 1, wherein the vector is a plasmid.

21. The biological device of claim 20, wherein the plasmid is pWLNEO, pSV2CAT, pOG44, pXTI, pSG, pSVK3, pBSK, pBR322, pYES, pYES2, pBSKII, or pUC.

22. The biological device of claim 20, wherein the plasmid is pYES2.

23. The biological device of claim 20, wherein the plasmid is pBSK.

24. The biological device of claim 1, wherein the host cells comprise yeast or bacteria.

25. The biological device of claim 24, wherein the bacteria comprise *Escherichia coli*.

26. The biological device of claim 24, wherein the yeast comprise *Saccharomyces cerevisiae*.

* * * * *